(12) United States Patent
Burnouf et al.

(10) Patent No.: US 7,635,583 B2
(45) Date of Patent: Dec. 22, 2009

(54) PROTEIN CRYSTAL COMPRISING THE PROCESSIVITY CLAMP FACTOR OF DNA POLYMERASE AND A LIGAND, AND ITS USES

(75) Inventors: Dominique Yves Joel Burnouf, Brumath (FR); Jerome Edouard Wagner, Strasbourg (FR); Philippe Dumas, Strasbourg (FR); Shingo Fujii, Strasbourg (FR); Robert Pierre Paul Fuchs, Strasbourg (FR); Vincent Olieric, Strasbourg (FR)

(73) Assignee: Centre National de la Recherche Scientifique, Paris (FR)

( * ) Notice: Subject to any disclaimer, the term of this patent is extended or adjusted under 35 U.S.C. 154(b) by 66 days.

(21) Appl. No.: 10/561,867

(22) PCT Filed: Jun. 25, 2004

(86) PCT No.: PCT/EP2004/006942

§ 371 (c)(1),
(2), (4) Date: Jul. 6, 2006

(87) PCT Pub. No.: WO2005/001084

PCT Pub. Date: Jan. 6, 2005

(65) Prior Publication Data

US 2007/0275898 A1    Nov. 29, 2007

(30) Foreign Application Priority Data

Jun. 27, 2003   (EP)   .................... 03291596

(51) Int. Cl.
    *C12N 9/00*   (2006.01)
    *C07K 14/00*  (2006.01)
    *G01N 33/48*  (2006.01)
(52) U.S. Cl. .................. 435/183; 530/350; 702/19
(58) Field of Classification Search .............. None
    See application file for complete search history.

(56) References Cited

FOREIGN PATENT DOCUMENTS

WO    WO0238596    * 5/2002
WO    WO 03/025004   3/2003

OTHER PUBLICATIONS

Kong et al. (May 1, 1992) Cell, 69(3):425-37.*
Giege et al., Crystallogenesis of Biological Macromolecule: Facts and Perspectives, (1994) Acta Cryst., vol. D50, pp. 339-350.*
Branden et al., Introduction to Protein Structure, Second Edition, Garland Publishing Inc., New York, (1999) pp. 374-375 and 382.*
Drenth, Principles of Protein X-ray Crystallography (1995) Springer, New York, p. 1.*
Kierzek et al., Models of protein crystal growth, (2001) Biophys Chem, 91:1-20.*
Wiencek, New Strategies for Protein Crystal Growth, (1999) Ann Rev Biomed Eng., 1:505-534.*
Kong X-P et al: "The-dimensional structure of the beta subunit of *E. coli* DNA polymerase III holenzyme: a sliding DNA clamp", Cell, Cell Press, Cambridge, NA, US, vol. 69, May 1, 1992, pp. 425-437, XP002968224, ISSN: 0092-8674, the whole document.
Yang Wei:, "Damage repair DNA polymerases Y.", Current Opinion in Structural Biology, vol. 13, No. 1, Feb. 2003, pp. 23-30, XP002262979, ISSN: 0959-440X (ISSN pring) the whole document.
Podobnik Marjetka et al:, "Nucleotide -induced conformational changes in an isolated *Escherichia coli* DNA polymerase III clamp loader subunit.", Structure (Cambridge), vol. 11, No. 3, Mar. 2003, pp. 253-263, XP002262980, ISSN: 0969-2126 (ISSN pring) the whole document.
Jeruzalmi David et al:, "Crystal structure of the processivity clamp loader gamma (gamma) complex of *E. coli* DNA polymerase III", Cell vol. 106, No. 4, Aug. 24, 2001, pp. 429-441, XP002262981, ISSN: 0092-8674, the whole document.

* cited by examiner

*Primary Examiner*—David J Steadman
*Assistant Examiner*—Alexander D Kim
(74) *Attorney, Agent, or Firm*—Young & Thompson

(57) ABSTRACT

A protein crystal having the processivity clamp factor of DNA polymerase that is the β subunit of DNA polymerase III of *Escherichia coli* and a peptide of about 3 to about 30 amino acids, in particular of about 16 amino acids. The peptide includes all or part of the processivity clamp factor binding sequence of a processivity clamp factor interacting protein, such as prokaryotic Pol I, Pol II, Pol III, Pol IV, Pol V, MutS, ligase I, α subunit of DNA polymerase, UmuD or UmuD', or eukaryotic pol ε, pol δ, pol η, pol ι, pol κ.

4 Claims, 68 Drawing Sheets

```
REMARK coordinates from restrained individual B-factor refinement
REMARK refinement resolution: 500.0 - 1.65 A
REMARK starting r= 0.2072 free_r= 0.2361
REMARK final    r= 0.2072 free_r= 0.2361
REMARK B rmsd for bonded mainchain atoms=  1.427  target= 1.5
REMARK B rmsd for bonded sidechain atoms=  2.420  target= 2.0
REMARK B rmsd for angle mainchain atoms=   2.189  target= 2.0
REMARK B rmsd for angle sidechain atoms=   3.637  target= 2.5
REMARK rweight=  0.1000 (with wa= 0.987736)
REMARK target= mlf  steps= 30
REMARK sg= P1 a= 41.23 b= 65.22 c= 73.38 alpha= 73.11 beta= 85.58 gamma= 85.8
REMARK parameter file 1  : CNS_TOPPAR:protein_rep.param
REMARK parameter file 2  : CNS_TOPPAR:water_rep.param
REMARK molecular structure file: amy.mtf
REMARK input coordinates: amy.pdb
REMARK reflection file= amy.cv
REMARK ncs= none
REMARK B-correction resolution: 6.0 - 1.65
REMARK initial B-factor correction applied to fobs :
REMARK   B11=  -3.662 B22=   2.485 B33=   1.177
REMARK   B12=   2.042 B13=   2.748 B23=  -0.502
REMARK B-factor correction applied to coordinate array B:   0.012
REMARK bulk solvent: density level= 0.36444 e/A^3, B-factor= 46.0136 A^2
REMARK reflections with |Fobs|/sigma_F < 0.0 rejected
REMARK reflections with |Fobs| > 10000 * rms(Fobs) rejected
REMARK theoretical total number of refl. in resol. range:   87646 (100.0 %)
REMARK number of unobserved reflections (no entry or |F|=0):  2854 (  3.3 %)
REMARK number of reflections rejected:                            0 (  0.0 %)
REMARK total number of reflections used:                      84792 ( 96.7 %)
REMARK number of reflections in working set:                  80566 ( 91.9 %)
REMARK number of reflections in test set:                      4226 (  4.8 %)
CRYST1   41.230   65.220   73.380   73.11   85.58   85.80 P 1
REMARK FILENAME="/work/olieric/db/db2-5_P1/cns/bindividual.pdb"
REMARK DATE:31-Mar-03  11:57:01       created by user: olieric
REMARK VERSION:1.1
ATOM      1  CB  MET A   1     -14.276 -31.220  16.788  1.00 17.29      A
ATOM      2  CG  MET A   1     -13.562 -30.976  15.453  1.00 19.06      A
ATOM      3  SD  MET A   1     -13.791 -29.325  14.750  1.00 20.01      A
ATOM      4  CE  MET A   1     -12.595 -28.385  15.663  1.00 20.04      A
ATOM      5  C   MET A   1     -12.346 -32.264  17.931  1.00 17.38      A
ATOM      6  O   MET A   1     -12.094 -31.451  18.823  1.00 18.05      A
ATOM      7  N   MET A   1     -14.641 -32.810  18.672  1.00 17.69      A
ATOM      8  CA  MET A   1     -13.789 -32.489  17.479  1.00 17.26      A
ATOM      9  N   LYS A   2     -11.404 -32.959  17.305  1.00 16.63      A
ATOM     10  CA  LYS A   2      -9.951 -32.827  17.687  1.00 17.10      A
ATOM     11  CB  LYS A   2      -9.686 -33.813  18.819  1.00 20.78      A
ATOM     12  CG  LYS A   2      -8.255 -33.915  19.217  1.00 24.62      A
ATOM     13  CD  LYS A   2      -8.095 -34.972  20.295  1.00 28.83      A
ATOM     14  CE  LYS A   2      -6.710 -34.905  20.918  1.00 31.65      A
ATOM     15  NZ  LYS A   2      -6.617 -35.825  22.100  1.00 33.43      A
ATOM     16  C   LYS A   2      -9.119 -33.168  16.483  1.00 17.18      A
ATOM     17  O   LYS A   2      -9.455 -34.064  15.706  1.00 14.51      A
ATOM     18  N   PHE A   3      -8.034 -32.423  16.284  1.00 14.69      A
ATOM     19  CA  PHE A   3      -7.135 -32.762  15.187  1.00 14.50      A
ATOM     20  CB  PHE A   3      -7.652 -32.265  13.810  1.00 16.07      A
ATOM     21  CG  PHE A   3      -7.818 -30.761  13.686  1.00 15.16      A
ATOM     22  CD1 PHE A   3      -9.067 -30.157  13.880  1.00 15.68      A
ATOM     23  CD2 PHE A   3      -6.757 -29.953  13.299  1.00 12.43      A
ATOM     24  CE1 PHE A   3      -9.253 -28.775  13.590  1.00 15.69      A
ATOM     25  CE2 PHE A   3      -6.838 -28.593  13.105  1.00 15.35      A
ATOM     26  CZ  PHE A   3      -8.153 -27.995  13.313  1.00 14.55      A
ATOM     27  C   PHE A   3      -5.783 -32.146  15.480  1.00 15.40      A
ATOM     28  O   PHE A   3      -5.685 -31.234  16.283  1.00 14.89      A
ATOM     29  N   THR A   4      -4.732 -32.697  14.884  1.00 13.77      A
ATOM     30  CA  THR A   4      -3.407 -32.124  15.046  1.00 15.62      A
ATOM     31  CB  THR A   4      -2.486 -32.356  15.948  1.00 17.56      A
ATOM     32  OG1 THR A   4      -3.030 -32.988  17.274  1.00 18.68      A
ATOM     33  OG2 THR A   4      -1.084 -32.288  16.013  1.00 18.01      A
ATOM     34  C   THR A   4      -2.846 -32.111  13.645  1.00 15.42      A
ATOM     35  O   THR A   4      -2.880 -33.120  12.942  1.00 17.97      A
ATOM     36  N   VAL A   5      -2.317 -30.970  13.238  1.00 16.55      A
ATOM     37  CA  VAL A   5      -1.804 -30.886  11.883  1.00 16.64      A
ATOM     38  CB  VAL A   5      -2.948 -30.508  10.930  1.00 18.41      A
ATOM     39  CG1 VAL A   5      -3.416 -29.040  11.181  1.00 18.38      A
ATOM     40  CG2 VAL A   5      -2.514 -30.773   9.468  1.00 19.99      A
ATOM     41  C   VAL A   5      -0.679 -29.886  11.773  1.00 17.93      A
ATOM     42  O   VAL A   5      -0.559 -28.960  12.592  1.00 16.18      A
ATOM     43  N   GLU A   6       0.166 -30.070  10.765  1.00 16.71      A
ATOM     44  CA  GLU A   6       1.253 -29.120  10.579  1.00 18.01      A
ATOM     45  CB  GLU A   6       2.218 -29.605   9.499  1.00 19.85      A
ATOM     46  CG  GLU A   6       3.012 -30.850   9.875  1.00 24.39      A
ATOM     47  CD  GLU A   6       3.999 -31.273   8.780  1.00 30.54      A
ATOM     48  OE1 GLU A   6       4.475 -30.396   8.006  1.00 30.19      A
ATOM     49  OE2 GLU A   6       4.317 -32.484   8.709  1.00 31.65      A
ATOM     50  C   GLU A   6       0.734 -27.751  10.164  1.00 17.50      A
ATOM     51  O   GLU A   6      -0.166 -27.642   9.334  1.00 17.39      A
ATOM     52  N   ARG A   7       1.337 -26.703  10.717  1.00 15.98      A
ATOM     53  CA  ARG A   7       0.975 -25.341  10.359  1.00 16.73      A
ATOM     54  CB  ARG A   7       1.939 -24.375  11.051  1.00 16.92      A
ATOM     55  CG  ARG A   7       1.902 -22.950  10.542  1.00 15.16      A
ATOM     56  CD  ARG A   7       3.010 -22.130  11.223  1.00 15.32      A
ATOM     57  NE  ARG A   7       3.117 -20.745  10.778  1.00 15.48      A
ATOM     58  CZ  ARG A   7       3.906 -20.342   9.787  1.00 19.58      A
ATOM     59  NH1 ARG A   7       4.550 -21.243   9.135  1.00 19.10      A
ATOM     60  NH2 ARG A   7       3.953 -19.063   9.445  1.00 19.15      A
ATOM     61  C   ARG A   7       1.077 -25.168   8.842  1.00 19.33      A
ATOM     62  O   ARG A   7       0.232 -24.536   8.201  1.00 20.23      A
ATOM     63  N   GLU A   8       2.116 -25.777   8.284  1.00 20.57      A
ATOM     64  CA  GLU A   8       2.392 -25.680   6.869  1.00 23.30      A
ATOM     65  CB  GLU A   8       3.869 -26.474   6.585  1.00 25.23      A
```

| | | | | | | | | | | |
|---|---|---|---|---|---|---|---|---|---|---|
|ATOM|66|CG|GLU|A|8|4.958|-25.909|7.259|1.00 29.45|A|
|ATOM|67|CD|GLU|A|8|4.840|-25.478|8.733|1.00 28.90|A|
|ATOM|68|OE1|GLU|A|8|4.512|-26.346|9.633|1.00 28.78|A|
|ATOM|69|OE2|GLU|A|8|5.119|-24.257|8.986|1.00 23.71|A|
|ATOM|70|C|GLU|A|8|1.213|-26.154|6.007|1.00 22.79|A|
|ATOM|71|O|GLU|A|8|0.997|-25.624|4.913|1.00 24.80|A|
|ATOM|72|N|HIS|A|9|0.433|-27.108|6.514|1.00 21.38|A|
|ATOM|73|CA|HIS|A|9|-0.711|-27.627|5.748|1.00 21.73|A|
|ATOM|74|CB|HIS|A|9|-1.034|-29.064|6.157|1.00 23.42|A|
|ATOM|75|CG|HIS|A|9|0.111|-30.021|6.010|1.00 27.55|A|
|ATOM|76|CD2|HIS|A|9|1.279|-29.926|5.335|1.00 29.37|A|
|ATOM|77|ND1|HIS|A|9|0.136|-31.242|6.644|1.00 27.98|A|
|ATOM|78|CE1|HIS|A|9|1.273|-31.856|6.376|1.00 28.44|A|
|ATOM|79|NE2|HIS|A|9|1.986|-31.080|5.583|1.00 30.06|A|
|ATOM|80|C|HIS|A|9|-1.974|-26.796|5.903|1.00 22.06|A|
|ATOM|81|O|HIS|A|9|-2.916|-26.941|5.113|1.00 20.93|A|
|ATOM|82|N|LEU|A|10|-2.007|-25.930|6.909|1.00 20.66|A|
|ATOM|83|CA|LEU|A|10|-3.169|-25.074|7.155|1.00 21.35|A|
|ATOM|84|CB|LEU|A|10|-3.366|-24.857|8.655|1.00 21.25|A|
|ATOM|85|CG|LEU|A|10|-4.041|-25.917|9.494|1.00 22.14|A|
|ATOM|86|CD1|LEU|A|10|-4.016|-25.491|10.958|1.00 22.44|A|
|ATOM|87|CD2|LEU|A|10|-5.499|-26.105|9.002|1.00 19.68|A|
|ATOM|88|C|LEU|A|10|-3.135|-23.595|6.547|1.00 22.26|A|
|ATOM|89|O|LEU|A|10|-4.182|-23.091|6.121|1.00 24.22|A|
|ATOM|90|N|LEU|A|11|-1.935|-23.173|6.349|1.00 22.98|A|
|ATOM|91|CA|LEU|A|11|-1.731|-21.819|5.853|1.00 25.99|A|
|ATOM|92|CB|LEU|A|11|-0.223|-21.587|5.647|1.00 27.18|A|
|ATOM|93|CG|LEU|A|11|0.489|-20.748|6.712|1.00 31.58|A|
|ATOM|94|CD1|LEU|A|11|-0.093|-20.987|8.066|1.00 31.86|A|
|ATOM|95|CD2|LEU|A|11|1.991|-21.058|6.673|1.00 31.87|A|
|ATOM|96|C|LEU|A|11|-2.497|-21.417|4.602|1.00 24.67|A|
|ATOM|97|O|LEU|A|11|-3.300|-20.487|4.638|1.00 24.80|A|
|ATOM|98|N|LYS|A|12|-2.270|-22.122|3.507|1.00 24.14|A|
|ATOM|99|CA|LYS|A|12|-2.949|-21.784|2.263|1.00 25.70|A|
|ATOM|100|CB|LYS|A|12|-2.393|-22.627|1.102|1.00 28.62|A|
|ATOM|101|CG|LYS|A|12|-2.758|-22.084|-0.282|1.00 33.62|A|
|ATOM|102|CD|LYS|A|12|-2.196|-22.974|-1.407|1.00 36.68|A|
|ATOM|103|CE|LYS|A|12|-3.036|-24.242|-1.643|1.00 39.26|A|
|ATOM|104|NZ|LYS|A|12|-3.304|-25.093|-0.433|1.00 38.98|A|
|ATOM|105|C|LYS|A|12|-4.458|-21.963|2.397|1.00 22.87|A|
|ATOM|106|O|LYS|A|12|-5.233|-21.072|2.031|1.00 24.13|A|
|ATOM|107|N|PRO|A|13|-4.906|-23.118|2.922|1.00 21.49|A|
|ATOM|108|CD|PRO|A|13|-4.218|-24.397|3.213|1.00 21.35|A|
|ATOM|109|CA|PRO|A|13|-6.359|-23.257|3.052|1.00 21.39|A|
|ATOM|110|CB|PRO|A|13|-6.521|-24.589|3.774|1.00 20.96|A|
|ATOM|111|CG|PRO|A|13|-5.337|-25.379|3.227|1.00 21.10|A|
|ATOM|112|C|PRO|A|13|-6.972|-22.103|3.836|1.00 20.93|A|
|ATOM|113|O|PRO|A|13|-7.985|-21.545|3.431|1.00 21.33|A|
|ATOM|114|N|LEU|A|14|-6.369|-21.735|4.967|1.00 21.72|A|
|ATOM|115|CA|LEU|A|14|-6.920|-20.646|5.762|1.00 22.99|A|
|ATOM|116|CB|LEU|A|14|-6.111|-20.432|7.048|1.00 22.65|A|
|ATOM|117|CG|LEU|A|14|-6.506|-21.332|8.208|1.00 19.80|A|
|ATOM|118|CD1|LEU|A|14|-5.520|-21.068|9.351|1.00 19.79|A|
|ATOM|119|CD2|LEU|A|14|-7.951|-21.053|8.667|1.00 19.15|A|
|ATOM|120|C|LEU|A|14|-6.892|-19.318|5.041|1.00 26.19|A|
|ATOM|121|O|LEU|A|14|-7.964|-18.577|5.189|1.00 27.05|A|
|ATOM|122|N|GLN|A|15|-5.947|-18.995|4.297|1.00 27.36|A|
|ATOM|123|CA|GLN|A|15|-5.935|-17.742|3.574|1.00 31.46|A|
|ATOM|124|CB|GLN|A|15|-4.608|-17.570|2.842|1.00 33.84|A|
|ATOM|125|CG|GLN|A|15|-4.472|-16.213|2.182|1.00 38.53|A|
|ATOM|126|CD|GLN|A|15|-3.117|-16.025|1.545|1.00 41.36|A|
|ATOM|127|OE1|GLN|A|15|-2.080|-16.062|2.223|1.00 42.71|A|
|ATOM|128|NE2|GLN|A|15|-3.109|-15.827|0.230|1.00 43.79|A|
|ATOM|129|C|GLN|A|15|-7.081|-17.731|2.568|1.00 32.51|A|
|ATOM|130|O|GLN|A|15|-7.813|-16.741|2.440|1.00 32.62|A|
|ATOM|131|N|GLN|A|16|-7.250|-18.852|1.878|1.00 33.52|A|
|ATOM|132|CA|GLN|A|16|-8.284|-18.960|0.862|1.00 33.60|A|
|ATOM|133|CB|GLN|A|16|-8.191|-20.314|0.161|1.00 34.74|A|
|ATOM|134|CG|GLN|A|16|-9.193|-20.486|-0.970|1.00 38.72|A|
|ATOM|135|CD|GLN|A|16|-8.630|-20.088|-2.328|1.00 41.86|A|
|ATOM|136|OE1|GLN|A|16|-8.139|-18.960|-2.519|1.00 42.92|A|
|ATOM|137|NE2|GLN|A|16|-8.701|-21.018|-3.286|1.00 41.57|A|
|ATOM|138|C|GLN|A|16|-9.698|-18.767|1.398|1.00 32.72|A|
|ATOM|139|O|GLN|A|16|-10.502|-18.042|0.808|1.00 33.73|A|
|ATOM|140|N|VAL|A|17|-10.018|-19.396|2.521|1.00 31.34|A|
|ATOM|141|CA|VAL|A|17|-11.371|-19.262|3.041|1.00 32.67|A|
|ATOM|142|CB|VAL|A|17|-11.801|-20.516|3.822|1.00 29.85|A|
|ATOM|143|CG1|VAL|A|17|-11.679|-21.733|2.928|1.00 28.35|A|
|ATOM|144|CG2|VAL|A|17|-10.948|-20.683|5.063|1.00 29.58|A|
|ATOM|145|C|VAL|A|17|-11.608|-18.045|3.917|1.00 35.48|A|
|ATOM|146|O|VAL|A|17|-12.757|-17.663|4.130|1.00 34.98|A|
|ATOM|147|N|SER|A|18|-10.539|-17.448|4.431|1.00 39.01|A|
|ATOM|148|CA|SER|A|18|-10.672|-16.274|5.294|1.00 43.39|A|
|ATOM|149|CB|SER|A|18|-9.520|-16.208|6.292|1.00 43.24|A|
|ATOM|150|OG|SER|A|18|-9.475|-17.366|7.099|1.00 44.08|A|
|ATOM|151|C|SER|A|18|-10.695|-14.990|4.477|1.00 45.76|A|
|ATOM|152|O|SER|A|18|-11.095|-13.932|4.982|1.00 45.88|A|
|ATOM|153|N|GLY|A|19|-10.265|-15.096|3.221|1.00 50.03|A|
|ATOM|154|CA|GLY|A|19|-10.221|-13.953|2.322|1.00 54.68|A|
|ATOM|155|C|GLY|A|19|-11.387|-12.985|2.438|1.00 57.76|A|
|ATOM|156|O|GLY|A|19|-11.234|-11.899|3.011|1.00 58.12|A|
|ATOM|157|N|PRO|A|20|-12.566|-13.333|1.893|1.00 60.08|A|
|ATOM|158|CD|PRO|A|20|-12.947|-14.603|1.250|1.00 60.71|A|
|ATOM|159|CA|PRO|A|20|-13.713|-12.425|1.989|1.00 62.25|A|
|ATOM|160|CB|PRO|A|20|-14.831|-13.208|1.289|1.00 62.05|A|
|ATOM|161|CG|PRO|A|20|-14.434|-14.648|1.497|1.00 61.28|A|
|ATOM|162|C|PRO|A|20|-14.040|-12.092|3.450|1.00 64.35|A|
|ATOM|163|O|PRO|A|20|-14.838|-12.786|4.088|1.00 64.86|A|
|ATOM|164|N|LEU|A|21|-13.420|-11.032|3.976|1.00 66.50|A|
|ATOM|165|CA|LEU|A|21|-13.636|-10.631|5.368|1.00 68.70|A|

Figure 1 (continued 2)

```
ATOM    165  CB  LEU A  21     -13.417 -11.842   6.292  1.00 68.85      A
ATOM    166  CG  LEU A  21     -13.658 -11.701   7.797  1.00 69.20      A
ATOM    167  CD1 LEU A  21     -15.091 -11.257   8.058  1.00 69.44      A
ATOM    168  CD2 LEU A  21     -13.383 -13.037   8.473  1.00 69.17      A
ATOM    169  C   LEU A  21     -12.744  -9.468   5.837  1.00 69.92      A
ATOM    170  O   LEU A  21     -11.823  -9.033   5.133  1.00 70.14      A
ATOM    171  N   GLY A  22     -13.029  -8.981   7.043  1.00 70.90      A
ATOM    172  CA  GLY A  22     -12.270  -7.883   7.608  1.00 72.13      A
ATOM    173  C   GLY A  22     -13.141  -6.650   7.685  1.00 73.06      A
ATOM    174  O   GLY A  22     -13.445  -6.156   8.773  1.00 73.37      A
ATOM    175  N   GLY A  23     -13.556  -6.165   6.518  1.00 73.72      A
ATOM    176  CA  GLY A  23     -14.395  -4.982   6.447  1.00 74.24      A
ATOM    177  C   GLY A  23     -15.796  -5.167   7.006  1.00 74.63      A
ATOM    178  O   GLY A  23     -16.645  -5.826   6.394  1.00 74.77      A
ATOM    179  N   ARG A  24     -16.028  -4.573   8.176  1.00 74.56      A
ATOM    180  CA  ARG A  24     -17.315  -4.624   8.865  1.00 74.14      A
ATOM    181  CB  ARG A  24     -18.178  -3.428   8.440  1.00 75.43      A
ATOM    182  CG  ARG A  24     -19.494  -3.302   9.198  1.00 77.04      A
ATOM    183  CD  ARG A  24     -20.297  -2.119   8.683  1.00 78.78      A
ATOM    184  NE  ARG A  24     -21.576  -1.912   9.373  1.00 80.11      A
ATOM    185  CZ  ARG A  24     -22.483  -1.049   9.068  1.00 80.78      A
ATOM    186  NH1 ARG A  24     -22.251  -0.188   8.084  1.00 81.08      A
ATOM    187  NH2 ARG A  24     -23.623  -0.988   9.744  1.00 81.03      A
ATOM    188  C   ARG A  24     -18.102  -5.919   8.655  1.00 73.74      A
ATOM    189  O   ARG A  24     -19.099  -5.940   7.932  1.00 73.15      A
ATOM    190  N   PRO A  25     -17.659  -7.031   9.280  1.00 71.00      A
ATOM    191  CD  PRO A  25     -16.401  -7.195  10.026  1.00 70.86      A
ATOM    192  CA  PRO A  25     -18.367  -8.297   9.129  1.00 69.14      A
ATOM    193  CB  PRO A  25     -17.526  -9.256   9.967  1.00 69.82      A
ATOM    194  CG  PRO A  25     -16.138  -8.670   9.855  1.00 70.46      A
ATOM    195  C   PRO A  25     -19.787  -8.152   9.673  1.00 67.21      A
ATOM    196  O   PRO A  25     -19.964  -7.852  10.852  1.00 67.34      A
ATOM    197  N   THR A  26     -20.794  -8.355   8.825  1.00 64.60      A
ATOM    198  CA  THR A  26     -22.184  -8.218   9.265  1.00 61.62      A
ATOM    199  CB  THR A  26     -23.179  -8.457   8.100  1.00 62.41      A
ATOM    200  OG1 THR A  26     -22.829  -7.625   6.986  1.00 62.97      A
ATOM    201  CG2 THR A  26     -24.598  -8.102   8.535  1.00 62.89      A
ATOM    202  C   THR A  26     -22.487  -9.199  10.399  1.00 58.62      A
ATOM    203  O   THR A  26     -21.891  -9.105  11.474  1.00 58.71      A
ATOM    204  N   LEU A  27     -23.413 -10.128  10.167  1.00 54.49      A
ATOM    205  CA  LEU A  27     -23.766 -11.123  11.177  1.00 49.96      A
ATOM    206  CB  LEU A  27     -24.522 -12.298  10.546  1.00 50.45      A
ATOM    207  CG  LEU A  27     -25.845 -12.037   9.828  1.00 50.99      A
ATOM    208  CD1 LEU A  27     -25.611 -11.122   8.637  1.00 51.87      A
ATOM    209  CD2 LEU A  27     -26.450 -13.356   9.361  1.00 51.62      A
ATOM    210  C   LEU A  27     -22.461 -11.627  11.791  1.00 46.97      A
ATOM    211  O   LEU A  27     -21.498 -11.909  11.076  1.00 45.78      A
ATOM    212  N   PRO A  28     -22.406 -11.734  13.125  1.00 42.86      A
ATOM    213  CD  PRO A  28     -23.458 -11.471  14.125  1.00 42.50      A
ATOM    214  CA  PRO A  28     -21.179 -12.207  13.770  1.00 39.77      A
ATOM    215  CB  PRO A  28     -21.586 -12.325  15.243  1.00 40.55      A
ATOM    216  CG  PRO A  28     -22.641 -11.263  15.384  1.00 41.64      A
ATOM    217  C   PRO A  28     -20.704 -13.536  13.197  1.00 36.67      A
ATOM    218  O   PRO A  28     -19.502 -13.737  12.978  1.00 35.24      A
ATOM    219  N   ILE A  29     -21.659 -14.434  12.964  1.00 33.25      A
ATOM    220  CA  ILE A  29     -21.389 -15.764  12.440  1.00 31.49      A
ATOM    221  CB  ILE A  29     -22.725 -16.518  12.190  1.00 32.34      A
ATOM    222  CG2 ILE A  29     -23.443 -15.893  11.009  1.00 32.60      A
ATOM    223  CG1 ILE A  29     -22.486 -18.006  11.925  1.00 33.89      A
ATOM    224  CD1 ILE A  29     -23.008 -18.776  13.115  1.00 33.09      A
ATOM    225  C   ILE A  29     -20.600 -15.694  11.137  1.00 29.03      A
ATOM    226  O   ILE A  29     -19.779 -16.569  10.860  1.00 27.06      A
ATOM    227  N   LEU A  30     -20.810 -14.645  10.352  1.00 27.42      A
ATOM    228  CA  LEU A  30     -20.124 -14.555   9.059  1.00 26.34      A
ATOM    229  CB  LEU A  30     -20.837 -13.539   8.153  1.00 27.73      A
ATOM    230  CG  LEU A  30     -22.319 -13.856   7.930  1.00 29.16      A
ATOM    231  CD1 LEU A  30     -22.901 -12.767   7.025  1.00 29.49      A
ATOM    232  CD2 LEU A  30     -22.528 -15.249   7.312  1.00 28.59      A
ATOM    233  C   LEU A  30     -18.640 -14.238   9.154  1.00 24.62      A
ATOM    234  O   LEU A  30     -17.910 -14.362   8.168  1.00 24.88      A
ATOM    235  N   GLY A  31     -18.190 -13.860  10.350  1.00 21.78      A
ATOM    236  CA  GLY A  31     -16.789 -13.553  10.548  1.00 21.58      A
ATOM    237  C   GLY A  31     -16.069 -14.788  11.093  1.00 19.65      A
ATOM    238  O   GLY A  31     -14.889 -14.720  11.414  1.00 21.22      A
ATOM    239  N   ASN A  32     -16.784 -15.895  11.182  1.00 19.33      A
ATOM    240  CA  ASN A  32     -16.221 -17.164  11.678  1.00 17.81      A
ATOM    241  CB  ASN A  32     -17.174 -17.859  12.668  1.00 18.05      A
ATOM    242  CG  ASN A  32     -17.079 -17.275  14.077  1.00 14.39      A
ATOM    243  OD1 ASN A  32     -16.566 -16.193  14.234  1.00 18.82      A
ATOM    244  ND2 ASN A  32     -17.541 -18.018  15.082  1.00 16.05      A
ATOM    245  C   ASN A  32     -16.006 -18.109  10.524  1.00 19.88      A
ATOM    246  O   ASN A  32     -16.554 -17.930   9.426  1.00 20.74      A
ATOM    247  N   LEU A  33     -15.178 -19.116  10.781  1.00 19.03      A
ATOM    248  CA  LEU A  33     -14.924 -20.155   9.804  1.00 18.58      A
ATOM    249  CB  LEU A  33     -13.435 -20.435   9.671  1.00 20.53      A
ATOM    250  CG  LEU A  33     -12.569 -19.411   8.996  1.00 22.72      A
ATOM    251  CD1 LEU A  33     -11.137 -19.964   8.958  1.00 25.09      A
ATOM    252  CD2 LEU A  33     -13.107 -19.134   7.606  1.00 25.02      A
ATOM    253  C   LEU A  33     -15.530 -21.398  10.365  1.00 18.12      A
ATOM    254  O   LEU A  33     -15.430 -21.648  11.578  1.00 17.01      A
ATOM    255  N   LEU A  34     -16.181 -22.175   9.513  1.00 15.99      A
ATOM    256  CA  LEU A  34     -16.733 -23.933   9.951  1.00 16.00      A
ATOM    257  CB  LEU A  34     -17.913 -23.854   9.073  1.00 18.73      A
ATOM    258  CG  LEU A  34     -19.416 -25.301   9.197  1.00 17.56      A
ATOM    259  CD1 LEU A  34     -18.968 -25.610  10.583  1.00 20.61      A
ATOM    260  CD2 LEU A  34     -19.527 -25.480   8.138  1.00 20.63      A
ATOM    261  C   LEU A  34     -15.618 -24.467   9.807  1.00 17.87      A
ATOM    262  O   LEU A  34     -15.009 -24.561   8.723  1.00 18.24      A
ATOM    263  N   LEU A  35     -15.335 -25.196  10.893  1.00 16.38      A
ATOM    264  CA  LEU A  35     -14.346 -26.290  10.903  1.00 16.62      A
```

Figure 1 (continued 3)

| | | | | | | | | | | |
|---|---|---|---|---|---|---|---|---|---|---|
| ATOM | 266 | CB | LEU | A | 35 | -13.301 | -26.110 | 12.029 | 1.00 | 16.55 | A |
| ATOM | 267 | CG | LEU | A | 35 | -12.328 | -24.919 | 11.927 | 1.00 | 20.44 | A |
| ATOM | 268 | CD1 | LEU | A | 35 | -13.026 | -25.564 | 11.887 | 1.00 | 26.52 | A |
| ATOM | 269 | CD2 | LEU | A | 35 | -11.438 | -24.958 | 13.149 | 1.00 | 22.52 | A |
| ATOM | 270 | C | LEU | A | 35 | -15.083 | -27.609 | 11.117 | 1.00 | 16.64 | A |
| ATOM | 271 | O | LEU | A | 35 | -15.859 | -27.763 | 12.066 | 1.00 | 15.83 | A |
| ATOM | 272 | N | GLN | A | 36 | -14.857 | -28.572 | 10.227 | 1.00 | 15.28 | A |
| ATOM | 273 | CA | GLN | A | 36 | -15.520 | -29.866 | 10.344 | 1.00 | 15.61 | A |
| ATOM | 274 | CB | GLN | A | 36 | -16.596 | -29.997 | 9.238 | 1.00 | 17.87 | A |
| ATOM | 275 | CG | GLN | A | 36 | -17.676 | -28.913 | 9.217 | 1.00 | 23.26 | A |
| ATOM | 276 | CD | GLN | A | 36 | -18.504 | -28.948 | 7.921 | 1.00 | 27.12 | A |
| ATOM | 277 | OE1 | GLN | A | 36 | -19.714 | -29.221 | 7.953 | 1.00 | 31.11 | A |
| ATOM | 278 | NE2 | GLN | A | 36 | -17.850 | -28.676 | 6.775 | 1.00 | 26.03 | A |
| ATOM | 279 | C | GLN | A | 36 | -14.507 | -30.996 | 10.156 | 1.00 | 16.00 | A |
| ATOM | 280 | O | GLN | A | 36 | -13.767 | -30.971 | 9.177 | 1.00 | 17.23 | A |
| ATOM | 281 | N | VAL | A | 37 | -14.461 | -31.947 | 11.097 | 1.00 | 14.69 | A |
| ATOM | 282 | CA | VAL | A | 37 | -13.594 | -33.123 | 10.959 | 1.00 | 15.63 | A |
| ATOM | 283 | CB | VAL | A | 37 | -12.796 | -33.403 | 12.236 | 1.00 | 14.73 | A |
| ATOM | 284 | CG1 | VAL | A | 37 | -12.146 | -34.774 | 12.143 | 1.00 | 16.16 | A |
| ATOM | 285 | CG2 | VAL | A | 37 | -11.774 | -32.274 | 12.445 | 1.00 | 14.31 | A |
| ATOM | 286 | C | VAL | A | 37 | -14.508 | -34.322 | 10.684 | 1.00 | 17.15 | A |
| ATOM | 287 | O | VAL | A | 37 | -15.380 | -34.665 | 11.495 | 1.00 | 16.68 | A |
| ATOM | 288 | N | ALA | A | 38 | -14.325 | -34.947 | 9.525 | 1.00 | 18.78 | A |
| ATOM | 289 | CA | ALA | A | 38 | -15.145 | -36.114 | 9.157 | 1.00 | 19.67 | A |
| ATOM | 290 | CB | ALA | A | 38 | -15.359 | -35.571 | 8.293 | 1.00 | 19.20 | A |
| ATOM | 291 | C | ALA | A | 38 | -14.273 | -36.995 | 8.288 | 1.00 | 21.68 | A |
| ATOM | 292 | O | ALA | A | 38 | -13.526 | -36.475 | 7.360 | 1.00 | 20.43 | A |
| ATOM | 293 | N | ASP | A | 39 | -14.380 | -38.312 | 8.476 | 1.00 | 23.51 | A |
| ATOM | 294 | CA | ASP | A | 39 | -13.554 | -39.266 | 7.746 | 1.00 | 27.39 | A |
| ATOM | 295 | CB | ASP | A | 39 | -13.801 | -39.139 | 6.244 | 1.00 | 30.92 | A |
| ATOM | 296 | CG | ASP | A | 39 | -13.805 | -40.490 | 5.533 | 1.00 | 35.17 | A |
| ATOM | 297 | OD1 | ASP | A | 39 | -13.575 | -41.528 | 6.196 | 1.00 | 37.93 | A |
| ATOM | 298 | OD2 | ASP | A | 39 | -14.044 | -40.515 | 4.303 | 1.00 | 38.02 | A |
| ATOM | 299 | C | ASP | A | 39 | -12.136 | -38.837 | 8.140 | 1.00 | 26.49 | A |
| ATOM | 300 | O | ASP | A | 39 | -11.870 | -38.606 | 9.310 | 1.00 | 29.24 | A |
| ATOM | 301 | N | GLY | A | 40 | -11.246 | -38.693 | 7.199 | 1.00 | 26.55 | A |
| ATOM | 302 | CA | GLY | A | 40 | -9.893 | -38.278 | 7.614 | 1.00 | 22.82 | A |
| ATOM | 303 | C | GLY | A | 40 | -9.611 | -36.884 | 7.084 | 1.00 | 20.99 | A |
| ATOM | 304 | O | GLY | A | 40 | -8.488 | -36.548 | 6.730 | 1.00 | 20.13 | A |
| ATOM | 305 | N | THR | A | 41 | -10.640 | -36.059 | 7.061 | 1.00 | 17.70 | A |
| ATOM | 306 | CA | THR | A | 41 | -10.528 | -34.735 | 6.493 | 1.00 | 17.27 | A |
| ATOM | 307 | CB | THR | A | 41 | -11.407 | -34.671 | 5.199 | 1.00 | 19.00 | A |
| ATOM | 308 | OG1 | THR | A | 41 | -11.050 | -35.775 | 4.341 | 1.00 | 23.54 | A |
| ATOM | 309 | CG2 | THR | A | 41 | -11.215 | -33.363 | 4.457 | 1.00 | 22.95 | A |
| ATOM | 310 | C | THR | A | 41 | -10.974 | -33.587 | 7.389 | 1.00 | 16.76 | A |
| ATOM | 311 | O | THR | A | 41 | -11.921 | -33.718 | 8.136 | 1.00 | 18.19 | A |
| ATOM | 312 | N | LEU | A | 42 | -10.251 | -32.483 | 7.332 | 1.00 | 14.51 | A |
| ATOM | 313 | CA | LEU | A | 42 | -10.668 | -31.272 | 8.035 | 1.00 | 13.60 | A |
| ATOM | 314 | CB | LEU | A | 42 | -9.461 | -30.576 | 8.698 | 1.00 | 14.21 | A |
| ATOM | 315 | CG | LEU | A | 42 | -9.719 | -29.130 | 9.112 | 1.00 | 12.61 | A |
| ATOM | 316 | CD1 | LEU | A | 42 | -10.808 | -29.020 | 10.222 | 1.00 | 13.95 | A |
| ATOM | 317 | CD2 | LEU | A | 42 | -8.374 | -28.566 | 9.579 | 1.00 | 15.96 | A |
| ATOM | 318 | C | LEU | A | 42 | -11.170 | -30.377 | 6.914 | 1.00 | 15.92 | A |
| ATOM | 319 | O | LEU | A | 42 | -10.443 | -30.104 | 5.951 | 1.00 | 15.29 | A |
| ATOM | 320 | N | SER | A | 43 | -12.413 | -29.907 | 7.016 | 1.00 | 13.67 | A |
| ATOM | 321 | CA | SER | A | 43 | -12.914 | -28.978 | 6.009 | 1.00 | 14.02 | A |
| ATOM | 322 | CB | SER | A | 43 | -14.287 | -29.408 | 5.481 | 1.00 | 15.11 | A |
| ATOM | 323 | OG | SER | A | 43 | -14.202 | -30.670 | 4.815 | 1.00 | 13.94 | A |
| ATOM | 324 | C | SER | A | 43 | -13.020 | -27.623 | 6.675 | 1.00 | 14.22 | A |
| ATOM | 325 | O | SER | A | 43 | -13.350 | -27.526 | 7.856 | 1.00 | 14.63 | A |
| ATOM | 326 | N | LEU | A | 44 | -12.706 | -26.571 | 5.928 | 1.00 | 13.45 | A |
| ATOM | 327 | CA | LEU | A | 44 | -12.770 | -25.220 | 6.475 | 1.00 | 13.96 | A |
| ATOM | 328 | CB | LEU | A | 44 | -11.379 | -24.576 | 6.501 | 1.00 | 16.23 | A |
| ATOM | 329 | CG | LEU | A | 44 | -10.224 | -25.221 | 7.264 | 1.00 | 19.59 | A |
| ATOM | 330 | CD1 | LEU | A | 44 | -10.661 | -25.513 | 8.708 | 1.00 | 23.82 | A |
| ATOM | 331 | CD2 | LEU | A | 44 | -9.736 | -26.446 | 6.550 | 1.00 | 22.21 | A |
| ATOM | 332 | C | LEU | A | 44 | -13.643 | -24.408 | 5.547 | 1.00 | 17.42 | A |
| ATOM | 333 | O | LEU | A | 44 | -13.411 | -24.421 | 4.336 | 1.00 | 17.59 | A |
| ATOM | 334 | N | THR | A | 45 | -14.634 | -23.682 | 6.087 | 1.00 | 15.58 | A |
| ATOM | 335 | CA | THR | A | 45 | -15.517 | -22.913 | 5.221 | 1.00 | 18.70 | A |
| ATOM | 336 | CB | THR | A | 45 | -16.922 | -23.570 | 5.153 | 1.00 | 18.52 | A |
| ATOM | 337 | OG1 | THR | A | 45 | -16.816 | -24.941 | 4.706 | 1.00 | 18.50 | A |
| ATOM | 338 | CG2 | THR | A | 45 | -17.833 | -22.792 | 4.165 | 1.00 | 18.61 | A |
| ATOM | 339 | C | THR | A | 45 | -15.702 | -21.465 | 5.653 | 1.00 | 19.93 | A |
| ATOM | 340 | O | THR | A | 45 | -15.915 | -21.185 | 6.844 | 1.00 | 20.27 | A |
| ATOM | 341 | N | GLY | A | 46 | -15.617 | -20.555 | 4.687 | 1.00 | 18.64 | A |
| ATOM | 342 | CA | GLY | A | 46 | -15.837 | -19.129 | 4.940 | 1.00 | 20.18 | A |
| ATOM | 343 | C | GLY | A | 46 | -17.022 | -18.683 | 4.090 | 1.00 | 20.92 | A |
| ATOM | 344 | O | GLY | A | 46 | -17.233 | -19.247 | 3.011 | 1.00 | 20.00 | A |
| ATOM | 345 | N | THR | A | 47 | -17.816 | -17.692 | 4.537 | 1.00 | 20.46 | A |
| ATOM | 346 | CA | THR | A | 47 | -18.967 | -17.267 | 3.729 | 1.00 | 22.40 | A |
| ATOM | 347 | CB | THR | A | 47 | -20.188 | -18.213 | 3.916 | 1.00 | 23.17 | A |
| ATOM | 348 | OG1 | THR | A | 47 | -21.242 | -17.858 | 2.999 | 1.00 | 23.27 | A |
| ATOM | 349 | CG2 | THR | A | 47 | -20.745 | -18.108 | 5.349 | 1.00 | 25.43 | A |
| ATOM | 350 | C | THR | A | 47 | -19.440 | -15.864 | 4.085 | 1.00 | 23.68 | A |
| ATOM | 351 | O | THR | A | 47 | -19.201 | -15.400 | 5.200 | 1.00 | 24.49 | A |
| ATOM | 352 | N | ASP | A | 48 | -20.108 | -15.199 | 3.149 | 1.00 | 23.27 | A |
| ATOM | 353 | CA | ASP | A | 48 | -20.664 | -13.857 | 3.407 | 1.00 | 22.37 | A |
| ATOM | 354 | CB | ASP | A | 48 | -19.905 | -12.780 | 2.621 | 1.00 | 24.34 | A |
| ATOM | 355 | CG | ASP | A | 48 | -20.123 | -12.864 | 1.121 | 1.00 | 24.11 | A |
| ATOM | 356 | OD1 | ASP | A | 48 | -20.836 | -13.780 | 0.558 | 1.00 | 22.62 | A |
| ATOM | 357 | OD2 | ASP | A | 48 | -19.586 | -12.901 | 0.107 | 1.00 | 20.57 | A |
| ATOM | 358 | C | ASP | A | 48 | -22.155 | -13.856 | 3.053 | 1.00 | 23.86 | A |
| ATOM | 359 | O | ASP | A | 48 | -22.800 | -12.787 | 2.957 | 1.00 | 22.46 | A |
| ATOM | 360 | N | LEU | A | 49 | -22.690 | -15.069 | 2.911 | 1.00 | 21.60 | A |
| ATOM | 361 | CA | LEU | A | 49 | -24.084 | -15.347 | 2.568 | 1.00 | 23.11 | A |
| ATOM | 362 | CB | LEU | A | 49 | -25.043 | -14.351 | 3.336 | 1.00 | 24.46 | A |
| ATOM | 363 | CG | LEU | A | 49 | -25.225 | -14.479 | 4.744 | 1.00 | 26.70 | A |
| ATOM | 364 | CD1 | LEU | A | 49 | -26.124 | -13.337 | 5.190 | 1.00 | 27.13 | A |
| ATOM | 365 | CD2 | LEU | A | 49 | -25.795 | -15.847 | 5.105 | 1.00 | 26.87 | A |

Figure 1 (continued 4)

```
ATOM    366  C   LEU A  49     -24.325 -15.305   1.067  1.00 20.63           A
ATOM    367  O   LEU A  49     -25.268 -15.928   0.566  1.00 24.38           A
ATOM    368  N   GLU A  50     -23.484 -14.575   0.346  1.00 19.18           A
ATOM    369  CA  GLU A  50     -23.652 -14.494  -1.097  1.00 19.11           A
ATOM    370  CB  GLU A  50     -23.243 -13.110  -1.610  1.00 21.43           A
ATOM    371  CG  GLU A  50     -23.515 -12.896  -3.113  1.00 27.31           A
ATOM    372  CD  GLU A  50     -23.235 -11.458  -3.604  1.00 28.85           A
ATOM    373  OE1 GLU A  50     -22.085 -10.968  -3.454  1.00 31.33           A
ATOM    374  OE2 GLU A  50     -24.168 -10.822  -4.172  1.00 31.83           A
ATOM    375  C   GLU A  50     -22.787 -15.559  -1.758  1.00 20.12           A
ATOM    376  O   GLU A  50     -23.166 -16.124  -2.786  1.00 19.05           A
ATOM    377  N   MET A  51     -21.651 -15.846  -1.127  1.00 18.26           A
ATOM    378  CA  MET A  51     -20.698 -16.832  -1.670  1.00 18.26           A
ATOM    379  CB  MET A  51     -19.643 -16.116  -2.504  1.00 19.67           A
ATOM    380  CG  MET A  51     -18.947 -15.032  -1.780  1.00 22.10           A
ATOM    381  SD  MET A  51     -18.086 -14.041  -2.993  1.00 25.87           A
ATOM    382  CE  MET A  51     -16.514 -14.275  -2.397  1.00 27.36           A
ATOM    383  C   MET A  51     -20.053 -17.576  -0.525  1.00 18.84           A
ATOM    384  O   MET A  51     -20.102 -17.129   0.634  1.00 18.64           A
ATOM    385  N   GLU A  52     -19.428 -18.699  -0.853  1.00 16.68           A
ATOM    386  CA  GLU A  52     -18.839 -19.572   0.152  1.00 19.13           A
ATOM    387  CB  GLU A  52     -19.901 -20.637   0.452  1.00 22.65           A
ATOM    388  CG  GLU A  52     -19.554 -21.806   1.323  1.00 32.13           A
ATOM    389  CD  GLU A  52     -20.803 -22.623   1.650  1.00 34.31           A
ATOM    390  OE1 GLU A  52     -20.682 -23.571   2.335  1.00 38.54           A
ATOM    391  OE2 GLU A  52     -21.913 -22.211   1.238  1.00 36.05           A
ATOM    392  C   GLU A  52     -17.595 -20.188  -0.449  1.00 18.26           A
ATOM    393  O   GLU A  52     -17.555 -20.688  -1.639  1.00 17.91           A
ATOM    394  N   MET A  53     -16.584 -20.356   0.377  1.00 18.60           A
ATOM    395  CA  MET A  53     -15.339 -20.955  -0.074  1.00 17.33           A
ATOM    396  CB  MET A  53     -14.202 -19.930  -0.036  1.00 21.43           A
ATOM    397  CG  MET A  53     -12.851 -20.501  -0.484  1.00 26.15           A
ATOM    398  SD  MET A  53     -12.771 -20.914  -2.256  1.00 32.73           A
ATOM    399  CE  MET A  53     -12.410 -19.257  -2.959  1.00 30.62           A
ATOM    400  C   MET A  53     -15.051 -22.112   0.886  1.00 17.68           A
ATOM    401  O   MET A  53     -15.069 -21.933   2.102  1.00 17.40           A
ATOM    402  N   VAL A  54     -14.786 -23.294   0.338  1.00 15.12           A
ATOM    403  CA  VAL A  54     -14.507 -24.468   1.162  1.00 16.82           A
ATOM    404  CB  VAL A  54     -15.508 -25.612   0.914  1.00 17.64           A
ATOM    405  CG1 VAL A  54     -15.224 -26.754   1.871  1.00 18.47           A
ATOM    406  CG2 VAL A  54     -16.959 -25.117   1.098  1.00 21.00           A
ATOM    407  C   VAL A  54     -13.139 -25.036   0.823  1.00 17.33           A
ATOM    408  O   VAL A  54     -12.814 -25.201  -0.343  1.00 19.27           A
ATOM    409  N   ALA A  55     -12.349 -25.363   1.848  1.00 15.10           A
ATOM    410  CA  ALA A  55     -11.031 -25.973   1.611  1.00 13.30           A
ATOM    411  CB  ALA A  55      -9.923 -25.043   2.056  1.00 15.71           A
ATOM    412  C   ALA A  55     -10.929 -27.286   2.394  1.00 16.85           A
ATOM    413  O   ALA A  55     -11.628 -27.433   3.451  1.00 16.80           A
ATOM    414  N   ARG A  56     -10.138 -28.233   1.895  1.00 15.48           A
ATOM    415  CA  ARG A  56      -9.989 -29.505   2.613  1.00 15.80           A
ATOM    416  CB  ARG A  56     -10.566 -30.677   1.789  1.00 20.20           A
ATOM    417  CG  ARG A  56     -12.018 -30.440   1.349  1.00 23.44           A
ATOM    418  CD  ARG A  56     -12.819 -31.720   1.096  1.00 28.95           A
ATOM    419  NE  ARG A  56     -14.035 -31.591   1.909  1.00 31.67           A
ATOM    420  CZ  ARG A  56     -15.058 -30.787   1.625  1.00 32.95           A
ATOM    421  NH1 ARG A  56     -15.053 -30.038   0.509  1.00 32.56           A
ATOM    422  NH2 ARG A  56     -16.048 -30.566   2.503  1.00 29.00           A
ATOM    423  C   ARG A  56      -8.515 -29.772   2.931  1.00 15.96           A
ATOM    424  O   ARG A  56      -7.623 -29.430   2.131  1.00 15.17           A
ATOM    425  N   VAL A  57      -8.273 -30.354   4.104  1.00 14.32           A
ATOM    426  CA  VAL A  57      -6.913 -30.693   4.567  1.00 12.85           A
ATOM    427  CB  VAL A  57      -6.481 -29.759   5.755  1.00 15.84           A
ATOM    428  CG1 VAL A  57      -5.134 -30.198   6.297  1.00 17.83           A
ATOM    429  CG2 VAL A  57      -6.452 -28.283   5.289  1.00 18.06           A
ATOM    430  C   VAL A  57      -6.966 -32.141   5.049  1.00 13.46           A
ATOM    431  O   VAL A  57      -7.853 -32.534   5.813  1.00 13.57           A
ATOM    432  N   ALA A  58      -6.028 -32.968   4.596  1.00 12.91           A
ATOM    433  CA  ALA A  58      -6.027 -34.351   5.050  1.00 13.63           A
ATOM    434  CB  ALA A  58      -5.328 -35.213   4.062  1.00 16.31           A
ATOM    435  C   ALA A  58      -5.423 -34.471   6.459  1.00 13.81           A
ATOM    436  O   ALA A  58      -4.481 -33.740   6.807  1.00 15.05           A
ATOM    437  N   LEU A  59      -5.997 -35.362   7.269  1.00 15.23           A
ATOM    438  CA  LEU A  59      -5.558 -35.589   8.648  1.00 16.38           A
ATOM    439  CB  LEU A  59      -6.748 -35.439   9.599  1.00 15.55           A
ATOM    440  CG  LEU A  59      -7.384 -34.042   9.562  1.00 14.50           A
ATOM    441  CD1 LEU A  59      -8.607 -34.021  10.509  1.00 15.98           A
ATOM    442  CD2 LEU A  59      -6.364 -32.973   9.991  1.00 14.17           A
ATOM    443  C   LEU A  59      -4.980 -36.986   8.804  1.00 20.00           A
ATOM    444  O   LEU A  59      -5.702 -37.982   8.671  1.00 23.51           A
ATOM    445  N   VAL A  60      -3.700 -37.070   9.138  1.00 20.91           A
ATOM    446  CA  VAL A  60      -3.081 -38.379   9.305  1.00 22.99           A
ATOM    447  CB  VAL A  60      -1.720 -38.472   8.532  1.00 21.30           A
ATOM    448  CG1 VAL A  60      -0.726 -37.522   9.135  1.00 21.15           A
ATOM    449  CG2 VAL A  60      -1.177 -39.910   8.545  1.00 24.79           A
ATOM    450  C   VAL A  60      -2.861 -38.661  10.779  1.00 25.44           A
ATOM    451  O   VAL A  60      -3.801 -39.830  11.197  1.00 26.02           A
ATOM    452  N   GLN A  61      -2.761 -37.596  11.578  1.00 26.01           A
ATOM    453  CA  GLN A  61      -2.551 -37.734  13.014  1.00 26.21           A
ATOM    454  CB  GLN A  61      -1.962 -36.437  13.569  1.00 26.62           A
ATOM    455  CG  GLN A  61      -0.643 -36.050  12.877  1.00 27.26           A
ATOM    456  CD  GLN A  61       0.082 -34.866  13.534  1.00 28.51           A
ATOM    457  OE1 GLN A  61       0.279 -34.851  14.750  1.00 30.47           A
ATOM    458  NE2 GLN A  61       0.498 -33.881  12.726  1.00 28.34           A
ATOM    459  C   GLN A  61      -3.853 -38.063  13.663  1.00 26.03           A
ATOM    460  O   GLN A  61      -4.944 -37.822  13.065  1.00 26.37           A
ATOM    461  N   PRO A  62      -3.878 -38.637  14.883  1.00 26.72           A
ATOM    462  CD  PRO A  62      -2.749 -39.028  15.752  1.00 26.01           A
ATOM    463  CA  PRO A  62      -5.159 -38.969  15.514  1.00 24.46           A
ATOM    464  CB  PRO A  62      -4.758 -39.400  16.929  1.00 26.77           A
ATOM    465  CG  PRO A  62      -3.406 -40.043  16.689  1.00 25.60           A
```

Figure 1 (continued 5)

```
ATOM    466  C   PRO A  62      -6.098 -37.789  15.500  1.00 21.59           A
ATOM    467  O   PRO A  62      -5.693 -36.637  15.713  1.00 20.88           A
ATOM    468  N   HIS A  63      -7.361 -38.082  15.234  1.00 21.18           A
ATOM    469  CA  HIS A  63      -8.371 -37.046  15.179  1.00 17.84           A
ATOM    470  CB  HIS A  63      -8.475 -36.482  13.754  1.00 18.27           A
ATOM    471  CG  HIS A  63      -8.667 -37.536  12.708  1.00 18.43           A
ATOM    472  CD2 HIS A  63      -9.792 -38.061  12.170  1.00 20.08           A
ATOM    473  ND1 HIS A  63      -7.615 -38.203  12.120  1.00 20.69           A
ATOM    474  CE1 HIS A  63      -8.083 -39.097  11.260  1.00 21.51           A
ATOM    475  NE2 HIS A  63      -9.403 -39.030  11.272  1.00 22.48           A
ATOM    476  C   HIS A  63      -9.728 -37.601  15.597  1.00 18.21           A
ATOM    477  O   HIS A  63      -9.933 -38.834  15.643  1.00 20.01           A
ATOM    478  N   GLU A  64     -10.643 -36.686  15.907  1.00 16.87           A
ATOM    479  CA  GLU A  64     -11.993 -37.073  16.308  1.00 19.00           A
ATOM    480  CB  GLU A  64     -12.160 -36.905  17.813  1.00 20.97           A
ATOM    481  CG  GLU A  64     -11.224 -37.788  18.610  1.00 24.05           A
ATOM    482  CD  GLU A  64     -11.335 -37.528  20.090  1.00 29.25           A
ATOM    483  OE1 GLU A  64     -12.050 -36.577  20.463  1.00 30.33           A
ATOM    484  OE2 GLU A  64     -10.710 -38.277  20.873  1.00 32.20           A
ATOM    485  C   GLU A  64     -11.964 -36.181  15.567  1.00 17.16           A
ATOM    486  O   GLU A  64     -12.753 -34.976  15.435  1.00 18.02           A
ATOM    487  N   PRO A  65     -14.070 -36.758  15.084  1.00 17.24           A
ATOM    488  CD  PRO A  65     -14.424 -38.180  15.166  1.00 17.26           A
ATOM    489  CA  PRO A  65     -15.063 -35.988  14.344  1.00 15.23           A
ATOM    490  CB  PRO A  65     -15.932 -37.063  13.753  1.00 15.65           A
ATOM    491  CG  PRO A  65     -15.903 -38.172  14.775  1.00 17.89           A
ATOM    492  C   PRO A  65     -15.825 -34.959  15.143  1.00 16.81           A
ATOM    493  O   PRO A  65     -15.958 -35.076  16.372  1.00 18.43           A
ATOM    494  N   GLY A  66     -16.279 -33.965  14.415  1.00 16.40           A
ATOM    495  CA  GLY A  66     -17.048 -32.905  15.003  1.00 16.58           A
ATOM    496  C   GLY A  66     -16.925 -31.636  14.205  1.00 17.44           A
ATOM    497  O   GLY A  66     -16.181 -31.543  13.219  1.00 18.08           A
ATOM    498  N   ALA A  67     -17.655 -30.628  14.646  1.00 15.76           A
ATOM    499  CA  ALA A  67     -17.660 -29.360  13.998  1.00 16.07           A
ATOM    500  CB  ALA A  67     -18.734 -29.361  12.850  1.00 15.82           A
ATOM    501  C   ALA A  67     -17.946 -28.232  14.919  1.00 17.46           A
ATOM    502  O   ALA A  67     -18.623 -28.416  15.950  1.00 19.40           A
ATOM    503  N   THR A  68     -17.433 -27.070  14.570  1.00 16.43           A
ATOM    504  CA  THR A  68     -17.658 -25.853  15.337  1.00 16.34           A
ATOM    505  CB  THR A  68     -16.788 -25.805  16.626  1.00 16.66           A
ATOM    506  OG1 THR A  68     -17.221 -24.683  17.412  1.00 17.85           A
ATOM    507  CG2 THR A  68     -15.312 -25.634  16.291  1.00 16.50           A
ATOM    508  C   THR A  68     -17.290 -24.675  14.449  1.00 17.50           A
ATOM    509  O   THR A  68     -16.857 -24.867  13.309  1.00 19.15           A
ATOM    510  N   THR A  69     -17.492 -23.453  14.916  1.00 16.80           A
ATOM    511  CA  THR A  69     -17.069 -22.299  14.121  1.00 16.22           A
ATOM    512  CB  THR A  69     -18.267 -21.521  13.810  1.00 19.21           A
ATOM    513  OG1 THR A  69     -18.868 -20.676  14.500  1.00 19.12           A
ATOM    514  CG2 THR A  69     -19.314 -22.481  12.964  1.00 19.28           A
ATOM    515  C   THR A  69     -16.254 -21.394  15.053  1.00 17.37           A
ATOM    516  O   THR A  69     -16.542 -21.318  16.250  1.00 19.10           A
ATOM    517  N   VAL A  70     -15.228 -20.743  14.523  1.00 16.92           A
ATOM    518  CA  VAL A  70     -14.348 -19.854  15.311  1.00 16.96           A
ATOM    519  CB  VAL A  70     -12.994 -20.555  15.682  1.00 18.01           A
ATOM    520  CG1 VAL A  70     -13.223 -21.742  16.630  1.00 20.79           A
ATOM    521  CG2 VAL A  70     -12.305 -21.010  14.414  1.00 18.76           A
ATOM    522  C   VAL A  70     -14.000 -18.592  14.523  1.00 17.58           A
ATOM    523  O   VAL A  70     -14.107 -18.577  13.284  1.00 16.61           A
ATOM    524  N   PRO A  71     -13.676 -17.513  15.220  1.00 16.78           A
ATOM    525  CD  PRO A  71     -13.582 -17.325  16.689  1.00 17.77           A
ATOM    526  CA  PRO A  71     -13.224 -16.275  14.523  1.00 17.44           A
ATOM    527  CB  PRO A  71     -12.701 -15.398  15.633  1.00 19.39           A
ATOM    528  CG  PRO A  71     -13.616 -15.810  16.788  1.00 20.22           A
ATOM    529  C   PRO A  71     -12.184 -16.546  13.451  1.00 17.20           A
ATOM    530  O   PRO A  71     -11.091 -16.993  13.744  1.00 17.02           A
ATOM    531  N   ALA A  72     -12.522 -16.251  12.204  1.00 16.42           A
ATOM    532  CA  ALA A  72     -11.610 -16.566  11.125  1.00 16.85           A
ATOM    533  CB  ALA A  72     -12.325 -16.376   9.776  1.00 18.54           A
ATOM    534  C   ALA A  72     -10.294 -15.813  11.128  1.00 17.52           A
ATOM    535  O   ALA A  72      -9.225 -16.433  10.975  1.00 17.07           A
ATOM    536  N   ARG A  73     -10.342 -14.492  11.276  1.00 16.94           A
ATOM    537  CA  ARG A  73      -9.109 -13.711  11.242  1.00 19.22           A
ATOM    538  CB  ARG A  73      -9.394 -12.209  11.247  1.00 23.69           A
ATOM    539  CG  ARG A  73      -8.138 -11.345  10.965  1.00 28.94           A
ATOM    540  CD  ARG A  73      -7.648 -11.495   9.517  1.00 34.56           A
ATOM    541  NE  ARG A  73      -6.218 -11.192   9.385  1.00 39.05           A
ATOM    542  CZ  ARG A  73      -5.513 -11.337   8.262  1.00 40.82           A
ATOM    543  NH1 ARG A  73      -6.102 -11.781   7.155  1.00 42.67           A
ATOM    544  NH2 ARG A  73      -4.217 -11.044   8.246  1.00 41.48           A
ATOM    545  C   ARG A  73      -8.202 -14.053  12.420  1.00 18.20           A
ATOM    546  O   ARG A  73      -6.988 -14.203  12.260  1.00 17.86           A
ATOM    547  N   LYS A  74      -8.794 -14.201  13.595  1.00 17.94           A
ATOM    548  CA  LYS A  74      -7.998 -14.536  14.762  1.00 17.40           A
ATOM    549  CB  LYS A  74      -8.853 -14.517  16.023  1.00 17.77           A
ATOM    550  CG  LYS A  74      -9.201 -13.129  16.534  1.00 19.95           A
ATOM    551  CD  LYS A  74     -10.300 -13.274  17.579  1.00 20.83           A
ATOM    552  CE  LYS A  74     -10.701 -11.937  18.146  1.00 21.69           A
ATOM    553  NZ  LYS A  74     -11.934 -12.085  18.959  1.00 18.53           A
ATOM    554  C   LYS A  74      -7.364 -15.910  14.608  1.00 15.84           A
ATOM    555  O   LYS A  74      -6.181 -16.077  14.902  1.00 16.97           A
ATOM    556  N   PHE A  75      -8.123 -16.856  14.144  1.00 16.01           A
ATOM    557  CA  PHE A  75      -7.565 -18.241  13.995  1.00 16.50           A
ATOM    558  CB  PHE A  75      -8.567 -19.271  13.653  1.00 15.00           A
ATOM    559  CG  PHE A  75      -8.176 -20.690  13.548  1.00 17.05           A
ATOM    560  CD1 PHE A  75      -7.463 -21.292  14.585  1.00 18.49           A
ATOM    561  CD2 PHE A  75      -8.449 -21.441  12.409  1.00 18.78           A
ATOM    562  CE1 PHE A  75      -7.031 -22.619  14.485  1.00 19.50           A
ATOM    563  CE2 PHE A  75      -8.011 -22.784  12.300  1.00 20.42           A
ATOM    564  CZ  PHE A  75      -7.303 -23.364  13.339  1.00 17.99           A
ATOM    565  C   PHE A  75      -6.451 -18.217  12.947  1.00 15.71           A
```

```
ATOM    566  O   PHE A  75      -5.377 -18.772  13.158  1.00 15.69      A
ATOM    567  N   PHE A  76      -6.671 -17.524  11.821  1.00 15.86      A
ATOM    568  CA  PHE A  76      -5.625 -17.426  10.800  1.00 15.67      A
ATOM    569  CB  PHE A  76      -6.182 -16.680   9.572  1.00 16.48      A
ATOM    570  CG  PHE A  76      -5.186 -16.476   8.472  1.00 20.93      A
ATOM    571  CD1 PHE A  76      -4.368 -17.506   8.049  1.00 20.82      A
ATOM    572  CD2 PHE A  76      -5.108 -15.250   7.830  1.00 25.97      A
ATOM    573  CE1 PHE A  76      -3.481 -17.330   6.996  1.00 22.93      A
ATOM    574  CE2 PHE A  76      -4.219 -15.058   6.761  1.00 27.38      A
ATOM    575  CZ  PHE A  76      -3.407 -16.104   6.348  1.00 24.82      A
ATOM    576  C   PHE A  76      -4.366 -16.709  11.335  1.00 16.51      A
ATOM    577  O   PHE A  76      -3.244 -17.182  11.129  1.00 15.99      A
ATOM    578  N   ASP A  77      -4.544 -15.583  12.027  1.00 14.50      A
ATOM    579  CA  ASP A  77      -3.387 -14.859  12.560  1.00 17.13      A
ATOM    580  CB  ASP A  77      -3.832 -13.526  13.167  1.00 19.74      A
ATOM    581  CG  ASP A  77      -4.223 -12.510  12.107  1.00 23.30      A
ATOM    582  OD1 ASP A  77      -3.860 -12.698  10.926  1.00 23.00      A
ATOM    583  OD2 ASP A  77      -4.897 -11.515  12.465  1.00 24.82      A
ATOM    584  C   ASP A  77      -2.618 -15.695  13.590  1.00 16.29      A
ATOM    585  O   ASP A  77      -1.399 -15.629  13.647  1.00 16.00      A
ATOM    586  N   ILE A  78      -3.325 -16.465  14.414  1.00 15.43      A
ATOM    587  CA  ILE A  78      -2.633 -17.306  15.393  1.00 15.62      A
ATOM    588  CB  ILE A  78      -3.649 -18.030  16.297  1.00 16.32      A
ATOM    589  CG2 ILE A  78      -2.968 -19.174  17.072  1.00 17.56      A
ATOM    590  CG1 ILE A  78      -4.298 -17.015  17.275  1.00 17.30      A
ATOM    591  CD1 ILE A  78      -5.491 -17.573  18.024  1.00 17.54      A
ATOM    592  C   ILE A  78      -1.809 -18.354  14.652  1.00 15.81      A
ATOM    593  O   ILE A  78      -0.531 -18.553  14.949  1.00 16.75      A
ATOM    594  N   CYS A  79      -2.413 -19.013  13.676  1.00 14.73      A
ATOM    595  CA  CYS A  79      -1.665 -20.046  12.938  1.00 15.03      A
ATOM    596  CB  CYS A  79      -2.603 -20.761  11.979  1.00 16.89      A
ATOM    597  SG  CYS A  79      -3.823 -21.817  12.844  1.00 17.54      A
ATOM    598  C   CYS A  79      -0.456 -19.455  12.192  1.00 16.05      A
ATOM    599  O   CYS A  79       0.649 -19.988  12.265  1.00 17.02      A
ATOM    600  N   ARG A  80      -0.669 -18.337  11.512  1.00 16.19      A
ATOM    601  CA  ARG A  80       0.393 -17.690  10.775  1.00 16.85      A
ATOM    602  CB  ARG A  80      -0.188 -16.537   9.946  1.00 20.00      A
ATOM    603  CG  ARG A  80       0.778 -15.991   8.885  1.00 27.92      A
ATOM    604  CD  ARG A  80       0.031 -15.082   7.905  1.00 32.53      A
ATOM    605  NE  ARG A  80      -0.726 -14.049   8.612  1.00 35.79      A
ATOM    606  CZ  ARG A  80      -0.172 -13.067   9.323  1.00 37.31      A
ATOM    607  NH1 ARG A  80       1.152 -12.973   9.420  1.00 38.32      A
ATOM    608  NH2 ARG A  80      -0.944 -12.190   9.956  1.00 37.64      A
ATOM    609  C   ARG A  80       1.494 -17.166  11.704  1.00 15.48      A
ATOM    610  O   ARG A  80       2.671 -17.183  11.330  1.00 16.18      A
ATOM    611  N   GLY A  81       1.126 -16.734  12.920  1.00 13.81      A
ATOM    612  CA  GLY A  81       2.092 -16.185  13.853  1.00 15.77      A
ATOM    613  C   GLY A  81       2.971 -17.205  14.540  1.00 15.13      A
ATOM    614  O   GLY A  81       3.993 -16.858  15.138  1.00 15.06      A
ATOM    615  N   LEU A  82       2.558 -18.463  14.470  1.00 13.35      A
ATOM    616  CA  LEU A  82       3.351 -19.550  15.059  1.00 13.35      A
ATOM    617  CB  LEU A  82       2.525 -20.848  15.156  1.00 12.49      A
ATOM    618  CG  LEU A  82       1.493 -20.791  16.304  1.00 12.47      A
ATOM    619  CD1 LEU A  82       0.486 -21.910  16.176  1.00 12.91      A
ATOM    620  CD2 LEU A  82       2.215 -20.852  17.693  1.00 14.10      A
ATOM    621  C   LEU A  82       4.565 -19.749  14.158  1.00 15.03      A
ATOM    622  O   LEU A  82       4.527 -19.404  12.963  1.00 13.85      A
ATOM    623  N   PRO A  83       5.543 -20.315  14.709  1.00 15.44      A
ATOM    624  CD  PRO A  83       5.747 -20.913  16.057  1.00 16.82      A
ATOM    625  CA  PRO A  83       6.858 -20.533  13.940  1.00 17.95      A
ATOM    626  CB  PRO A  83       7.878 -20.913  15.013  1.00 17.93      A
ATOM    627  CG  PRO A  83       7.049 -21.726  15.978  1.00 17.83      A
ATOM    628  C   PRO A  83       6.792 -21.560  12.827  1.00 19.15      A
ATOM    629  O   PRO A  83       5.974 -22.483  12.842  1.00 16.64      A
ATOM    630  N   GLU A  84       7.647 -21.362  11.834  1.00 18.77      A
ATOM    631  CA  GLU A  84       7.720 -22.297  10.724  1.00 20.63      A
ATOM    632  CB  GLU A  84       8.866 -21.879   9.798  1.00 23.64      A
ATOM    633  CG  GLU A  84       9.092 -22.783   8.594  1.00 31.62      A
ATOM    634  CD  GLU A  84      10.336 -22.356   7.829  1.00 36.15      A
ATOM    635  OE1 GLU A  84      10.445 -21.139   7.504  1.00 39.83      A
ATOM    636  OE2 GLU A  84      11.206 -23.221   7.567  1.00 40.03      A
ATOM    637  C   GLU A  84       7.978 -23.693  11.297  1.00 19.73      A
ATOM    638  O   GLU A  84       8.801 -23.867  12.213  1.00 20.17      A
ATOM    639  N   GLY A  85       7.263 -24.686  10.779  1.00 20.11      A
ATOM    640  CA  GLY A  85       7.432 -26.046  11.263  1.00 19.52      A
ATOM    641  C   GLY A  85       6.582 -26.430  12.465  1.00 19.27      A
ATOM    642  O   GLY A  85       6.600 -27.576  12.919  1.00 21.77      A
ATOM    643  N   ALA A  86       5.825 -25.479  12.996  1.00 16.80      A
ATOM    644  CA  ALA A  86       4.989 -25.776  14.152  1.00 16.45      A
ATOM    645  CB  ALA A  86       4.313 -24.490  14.661  1.00 16.16      A
ATOM    646  C   ALA A  86       3.910 -26.805  13.839  1.00 16.34      A
ATOM    647  O   ALA A  86       3.430 -26.884  12.703  1.00 16.48      A
ATOM    648  N   GLU A  87       3.552 -27.584  14.857  1.00 15.82      A
ATOM    649  CA  GLU A  87       2.479 -28.577  14.792  1.00 16.94      A
ATOM    650  CB  GLU A  87       2.871 -29.867  15.511  1.00 20.12      A
ATOM    651  CG  GLU A  87       3.869 -30.727  14.757  1.00 24.42      A
ATOM    652  CD  GLU A  87       3.204 -31.527  13.643  1.00 29.00      A
ATOM    653  OE1 GLU A  87       1.952 -31.445  13.512  1.00 30.19      A
ATOM    654  OE2 GLU A  87       3.927 -32.242  12.902  1.00 33.75      A
ATOM    655  C   GLU A  87       1.371 -27.989  15.398  1.00 16.68      A
ATOM    656  O   GLU A  87       1.613 -27.315  16.369  1.00 16.47      A
ATOM    657  N   ILE A  88       0.137 -27.956  15.113  1.00 15.53      A
ATOM    658  CA  ILE A  88      -0.964 -27.296  15.783  1.00 14.47      A
ATOM    659  CB  ILE A  88      -1.551 -26.225  14.815  1.00 14.61      A
ATOM    660  CG2 ILE A  88      -2.717 -25.471  15.455  1.00 15.66      A
ATOM    661  CG1 ILE A  88      -0.434 -25.252  14.413  1.00 16.03      A
ATOM    662  CD1 ILE A  88      -0.916 -24.176  13.495  1.00 15.45      A
ATOM    663  C   ILE A  88      -2.026 -28.285  16.215  1.00 13.85      A
ATOM    664  O   ILE A  88      -2.626 -28.982  15.376  1.00 14.57      A
ATOM    665  N   ALA A  89      -2.251 -28.360  17.529  1.00 12.25      A
```

Figure 1 (continued 7)

| | | | | | | | | | | |
|---|---|---|---|---|---|---|---|---|---|---|
|ATOM|666|CA|ALA|A|89|-3.239|-29.289|18.093|1.00 12.02|A|
|ATOM|667|CB|ALA|A|89|-2.659|-29.952|19.353|1.00 13.11|A|
|ATOM|668|C|ALA|A|89|-4.472|-28.479|18.426|1.00 11.71|A|
|ATOM|669|O|ALA|A|89|-4.399|-27.426|19.061|1.00 13.67|A|
|ATOM|670|N|VAL|A|90|-5.626|-28.961|18.000|1.00 10.89|A|
|ATOM|671|CA|VAL|A|90|-6.867|-28.214|18.186|1.00 12.44|A|
|ATOM|672|CB|VAL|A|90|-7.383|-27.710|16.811|1.00 12.40|A|
|ATOM|673|CG1|VAL|A|90|-8.769|-27.064|16.940|1.00 13.53|A|
|ATOM|674|CG2|VAL|A|90|-6.412|-26.706|16.235|1.00 14.45|A|
|ATOM|675|C|VAL|A|90|-7.922|-29.131|18.759|1.00 13.45|A|
|ATOM|676|O|VAL|A|90|-8.095|-30.261|18.298|1.00 15.19|A|
|ATOM|677|N|GLN|A|91|-8.636|-28.655|19.774|1.00 14.36|A|
|ATOM|678|CA|GLN|A|91|-9.735|-29.465|20.314|1.00 14.06|A|
|ATOM|679|CB|GLN|A|91|-9.285|-30.386|21.450|1.00 17.88|A|
|ATOM|680|CG|GLN|A|91|-8.554|-29.714|22.519|1.00 21.85|A|
|ATOM|681|CD|GLN|A|91|-7.719|-30.667|23.362|1.00 28.08|A|
|ATOM|682|OE1|GLN|A|91|-7.236|-31.706|22.883|1.00 32.53|A|
|ATOM|683|NE2|GLN|A|91|-7.514|-30.297|24.610|1.00 28.96|A|
|ATOM|684|C|GLN|A|91|-10.861|-28.572|20.778|1.00 15.88|A|
|ATOM|685|O|GLN|A|91|-10.662|-27.498|21.336|1.00 15.55|A|
|ATOM|686|N|LEU|A|92|-12.076|-29.022|20.506|1.00 15.92|A|
|ATOM|687|CA|LEU|A|92|-13.242|-28.290|20.937|1.00 18.46|A|
|ATOM|688|CB|LEU|A|92|-14.426|-28.669|20.044|1.00 18.53|A|
|ATOM|689|CG|LEU|A|92|-15.797|-28.084|20.379|1.00 19.11|A|
|ATOM|690|CD1|LEU|A|92|-15.815|-26.557|20.190|1.00 17.67|A|
|ATOM|691|CD2|LEU|A|92|-16.801|-28.748|19.451|1.00 19.82|A|
|ATOM|692|C|LEU|A|92|-13.490|-28.723|22.370|1.00 19.94|A|
|ATOM|693|O|LEU|A|92|-13.491|-29.938|22.675|1.00 20.27|A|
|ATOM|694|N|GLU|A|93|-13.692|-27.737|23.242|1.00 21.27|A|
|ATOM|695|CA|GLU|A|93|-13.950|-27.969|24.656|1.00 23.60|A|
|ATOM|696|CB|GLU|A|93|-12.727|-27.593|25.472|1.00 24.28|A|
|ATOM|697|CG|GLU|A|93|-11.502|-28.346|25.001|1.00 25.20|A|
|ATOM|698|CD|GLU|A|93|-10.402|-28.368|26.037|1.00 26.28|A|
|ATOM|699|OE1|GLU|A|93|-10.239|-27.343|26.732|1.00 28.86|A|
|ATOM|700|OE2|GLU|A|93|-9.701|-29.405|26.152|1.00 26.10|A|
|ATOM|701|C|GLU|A|93|-15.122|-27.105|25.061|1.00 24.07|A|
|ATOM|702|O|GLU|A|93|-14.943|-26.031|25.640|1.00 25.47|A|
|ATOM|703|N|GLY|A|94|-16.318|-27.570|24.726|1.00 26.68|A|
|ATOM|704|CA|GLY|A|94|-17.517|-26.822|25.063|1.00 28.20|A|
|ATOM|705|C|GLY|A|94|-17.675|-25.520|24.310|1.00 28.08|A|
|ATOM|706|O|GLY|A|94|-17.807|-25.500|23.080|1.00 30.95|A|
|ATOM|707|N|GLU|A|95|-17.668|-24.409|25.036|1.00 27.27|A|
|ATOM|708|CA|GLU|A|95|-17.840|-23.109|24.405|1.00 26.17|A|
|ATOM|709|CB|GLU|A|95|-18.429|-22.111|25.404|1.00 29.49|A|
|ATOM|710|CG|GLU|A|95|-19.812|-22.514|25.947|1.00 34.68|A|
|ATOM|711|CD|GLU|A|95|-20.819|-22.776|24.829|1.00 37.59|A|
|ATOM|712|OE1|GLU|A|95|-20.860|-21.971|23.871|1.00 39.61|A|
|ATOM|713|OE2|GLU|A|95|-21.568|-23.779|24.915|1.00 40.32|A|
|ATOM|714|C|GLU|A|95|-16.561|-22.524|23.816|1.00 23.92|A|
|ATOM|715|O|GLU|A|95|-16.603|-21.458|23.201|1.00 24.33|A|
|ATOM|716|N|ARG|A|96|-15.429|-23.192|24.031|1.00 19.97|A|
|ATOM|717|CA|ARG|A|96|-14.189|-22.685|23.489|1.00 18.11|A|
|ATOM|718|CB|ARG|A|96|-13.242|-22.189|24.619|1.00 20.61|A|
|ATOM|719|CG|ARG|A|96|-12.680|-23.267|25.616|1.00 22.85|A|
|ATOM|720|CD|ARG|A|96|-11.343|-23.897|25.139|1.00 25.49|A|
|ATOM|721|NE|ARG|A|96|-10.623|-24.711|26.143|1.00 24.91|A|
|ATOM|722|CZ|ARG|A|96|-9.771|-24.241|27.058|1.00 25.23|A|
|ATOM|723|NH1|ARG|A|96|-9.515|-22.942|27.120|1.00 25.05|A|
|ATOM|724|NH2|ARG|A|96|-9.147|-25.086|27.903|1.00 30.77|A|
|ATOM|725|C|ARG|A|96|-13.471|-23.726|22.666|1.00 15.35|A|
|ATOM|726|O|ARG|A|96|-13.740|-24.924|22.790|1.00 15.87|A|
|ATOM|727|N|MET|A|97|-12.609|-23.237|21.781|1.00 14.95|A|
|ATOM|728|CA|MET|A|97|-11.789|-24.134|20.978|1.00 12.81|A|
|ATOM|729|CB|MET|A|97|-11.921|-23.850|19.476|1.00 15.67|A|
|ATOM|730|CG|MET|A|97|-11.205|-24.939|18.666|1.00 13.94|A|
|ATOM|731|SD|MET|A|97|-11.365|-24.789|16.864|1.00 16.92|A|
|ATOM|732|CE|MET|A|97|-9.931|-23.715|16.512|1.00 14.97|A|
|ATOM|733|C|MET|A|97|-10.377|-23.860|21.444|1.00 12.28|A|
|ATOM|734|O|MET|A|97|-9.912|-22.714|21.373|1.00 13.91|A|
|ATOM|735|N|LEU|A|98|-9.697|-24.908|21.922|1.00 11.68|A|
|ATOM|736|CA|LEU|A|98|-8.342|-24.751|22.424|1.00 11.70|A|
|ATOM|737|CB|LEU|A|98|-8.137|-25.671|23.643|1.00 13.52|A|
|ATOM|738|CG|LEU|A|98|-6.728|-25.651|24.249|1.00 15.75|A|
|ATOM|739|CD1|LEU|A|98|-6.406|-24.288|24.856|1.00 16.82|A|
|ATOM|740|CD2|LEU|A|98|-6.635|-26.764|25.314|1.00 17.18|A|
|ATOM|741|C|LEU|A|98|-7.340|-25.091|21.327|1.00 11.06|A|
|ATOM|742|O|LEU|A|98|-7.413|-26.162|20.715|1.00 13.52|A|
|ATOM|743|N|VAL|A|99|-6.429|-24.155|21.081|1.00 11.82|A|
|ATOM|744|CA|VAL|A|99|-5.357|-24.306|20.102|1.00 10.73|A|
|ATOM|745|CB|VAL|A|99|-5.348|-23.106|19.112|1.00 10.91|A|
|ATOM|746|CG1|VAL|A|99|-4.236|-23.307|18.079|1.00 13.86|A|
|ATOM|747|CG2|VAL|A|99|-6.690|-23.022|18.393|1.00 13.77|A|
|ATOM|748|C|VAL|A|99|-4.032|-24.330|20.855|1.00 11.36|A|
|ATOM|749|O|VAL|A|99|-3.735|-23.418|21.637|1.00 12.82|A|
|ATOM|750|N|ARG|A|100|-3.241|-25.378|20.621|1.00 11.29|A|
|ATOM|751|CA|ARG|A|100|-1.951|-25.515|21.299|1.00 10.63|A|
|ATOM|752|CB|ARG|A|100|-2.017|-26.687|22.287|1.00 12.67|A|
|ATOM|753|CG|ARG|A|100|-3.028|-26.536|23.444|1.00 13.82|A|
|ATOM|754|CD|ARG|A|100|-2.999|-27.792|24.309|1.00 18.46|A|
|ATOM|755|NE|ARG|A|100|-3.557|-28.927|23.578|1.00 18.43|A|
|ATOM|756|CZ|ARG|A|100|-2.969|-30.114|23.447|1.00 20.90|A|
|ATOM|757|NH1|ARG|A|100|-1.779|-30.341|24.003|1.00 23.86|A|
|ATOM|758|NH2|ARG|A|100|-3.571|-31.006|22.763|1.00 21.35|A|
|ATOM|759|C|ARG|A|100|-0.818|-25.796|20.348|1.00 12.06|A|
|ATOM|760|O|ARG|A|100|-0.952|-26.607|19.455|1.00 13.88|A|
|ATOM|761|N|SER|A|101|0.319|-25.142|20.560|1.00 10.58|A|
|ATOM|762|CA|SER|A|101|1.500|-25.414|19.734|1.00 12.72|A|
|ATOM|763|CB|SER|A|101|1.457|-24.582|18.448|1.00 14.43|A|
|ATOM|764|OG|SER|A|101|2.562|-24.907|17.600|1.00 14.52|A|
|ATOM|765|C|SER|A|101|2.697|-25.036|20.597|1.00 13.21|A|

Figure 1 (continued 8)

```
ATOM    766  O   SER A 101       2.755 -23.917  21.070  1.00 12.38           A
ATOM    767  N   GLY A 102       3.655 -25.952  20.787  1.00 14.97           A
ATOM    768  CA  GLY A 102       4.787 -25.626  21.655  1.00 15.35           A
ATOM    769  C   GLY A 102       4.234 -25.239  23.022  1.00 14.72           A
ATOM    770  O   GLY A 102       3.396 -25.957  23.566  1.00 15.06           A
ATOM    771  N   ARG A 103       4.715 -24.127  23.580  1.00 14.39           A
ATOM    772  CA  ARG A 103       4.225 -23.632  24.861  1.00 15.53           A
ATOM    773  CB  ARG A 103       5.383 -23.301  25.800  1.00 16.98           A
ATOM    774  CG  ARG A 103       6.122 -24.596  26.170  1.00 18.28           A
ATOM    775  CD  ARG A 103       7.074 -24.407  27.335  1.00 22.26           A
ATOM    776  NE  ARG A 103       8.146 -23.480  27.027  1.00 24.02           A
ATOM    777  CZ  ARG A 103       9.048 -23.096  27.930  1.00 27.13           A
ATOM    778  NH1 ARG A 103       8.986 -23.567  29.177  1.00 28.33           A
ATOM    779  NH2 ARG A 103      10.000 -22.243  27.594  1.00 29.41           A
ATOM    780  C   ARG A 103       3.346 -22.402  24.617  1.00 15.01           A
ATOM    781  O   ARG A 103       3.318 -21.450  25.423  1.00 16.19           A
ATOM    782  N   SER A 104       2.650 -22.424  23.477  1.00 12.66           A
ATOM    783  CA  SER A 104       1.707 -21.349  23.143  1.00 11.12           A
ATOM    784  CB  SER A 104       1.917 -20.857  21.705  1.00 11.60           A
ATOM    785  OG  SER A 104       3.262 -20.458  21.462  1.00 11.97           A
ATOM    786  C   SER A 104       0.313 -21.971  23.254  1.00 13.02           A
ATOM    787  O   SER A 104       0.076 -23.082  22.774  1.00 13.52           A
ATOM    788  N   ARG A 105      -0.608 -21.251  23.895  1.00 11.22           A
ATOM    789  CA  ARG A 105      -1.991 -21.722  24.070  1.00 13.13           A
ATOM    790  CB  ARG A 105      -2.262 -22.132  25.534  1.00 14.88           A
ATOM    791  CG  ARG A 105      -1.481 -23.313  26.011  1.00 14.45           A
ATOM    792  CD  ARG A 105      -1.618 -23.515  27.546  1.00 14.09           A
ATOM    793  NE  ARG A 105      -3.010 -23.510  28.001  1.00 16.53           A
ATOM    794  CZ  ARG A 105      -3.784 -24.593  28.018  1.00 18.83           A
ATOM    795  NH1 ARG A 105      -3.293 -25.743  27.603  1.00 17.38           A
ATOM    796  NH2 ARG A 105      -5.054 -24.513  28.441  1.00 18.17           A
ATOM    797  C   ARG A 105      -2.956 -20.617  23.727  1.00 13.13           A
ATOM    798  O   ARG A 105      -2.750 -19.454  24.098  1.00 13.47           A
ATOM    799  N   PHE A 106      -4.036 -20.973  23.032  1.00 11.95           A
ATOM    800  CA  PHE A 106      -5.055 -19.984  22.687  1.00 12.74           A
ATOM    801  CB  PHE A 106      -4.909 -19.554  21.211  1.00 12.74           A
ATOM    802  CG  PHE A 106      -3.507 -19.127  20.851  1.00 13.12           A
ATOM    803  CD1 PHE A 106      -2.537 -20.086  20.549  1.00 13.32           A
ATOM    804  CD2 PHE A 106      -3.146 -17.791  20.918  1.00 13.88           A
ATOM    805  CE1 PHE A 106      -1.230 -19.724  20.331  1.00 13.59           A
ATOM    806  CE2 PHE A 106      -1.819 -17.406  20.702  1.00 15.45           A
ATOM    807  CZ  PHE A 106      -0.862 -18.385  20.411  1.00 13.62           A
ATOM    808  C   PHE A 106      -6.422 -20.606  22.881  1.00 12.43           A
ATOM    809  O   PHE A 106      -6.666 -21.731  22.464  1.00 13.63           A
ATOM    810  N   SER A 107      -7.322 -19.864  23.519  1.00 12.50           A
ATOM    811  CA  SER A 107      -8.683 -20.348  23.707  1.00 15.61           A
ATOM    812  CB  SER A 107      -9.056 -20.308  25.183  1.00 17.07           A
ATOM    813  OG  SER A 107     -10.401 -20.709  25.398  1.00 20.88           A
ATOM    814  C   SER A 107      -9.551 -19.357  22.940  1.00 14.70           A
ATOM    815  O   SER A 107      -9.596 -18.184  23.304  1.00 15.97           A
ATOM    816  N   LEU A 108     -10.219 -19.841  21.882  1.00 15.80           A
ATOM    817  CA  LEU A 108     -11.072 -19.012  21.039  1.00 15.44           A
ATOM    818  CB  LEU A 108     -10.829 -19.356  19.565  1.00 14.95           A
ATOM    819  CG  LEU A 108      -9.457 -18.953  19.034  1.00 15.14           A
ATOM    820  CD1 LEU A 108      -9.221 -19.543  17.631  1.00 17.32           A
ATOM    821  CD2 LEU A 108      -9.368 -17.437  19.028  1.00 18.64           A
ATOM    822  C   LEU A 108     -12.548 -19.248  21.305  1.00 14.24           A
ATOM    823  O   LEU A 108     -12.949 -20.357  21.612  1.00 14.91           A
ATOM    824  N   SER A 109     -13.347 -18.194  21.121  1.00 15.51           A
ATOM    825  CA  SER A 109     -14.789 -18.290  21.304  1.00 16.32           A
ATOM    826  CB  SER A 109     -15.425 -16.899  21.319  1.00 19.43           A
ATOM    827  OG  SER A 109     -15.108 -16.215  20.106  1.00 24.23           A
ATOM    828  C   SER A 109     -15.367 -19.064  20.138  1.00 17.73           A
ATOM    829  O   SER A 109     -14.799 -19.072  19.056  1.00 18.59           A
ATOM    830  N   THR A 110     -16.485 -19.728  20.364  1.00 16.33           A
ATOM    831  CA  THR A 110     -17.113 -20.485  19.277  1.00 17.92           A
ATOM    832  CB  THR A 110     -17.101 -22.013  19.518  1.00 18.59           A
ATOM    833  OG1 THR A 110     -17.879 -22.330  20.685  1.00 19.81           A
ATOM    834  OG2 THR A 110     -15.654 -22.546  19.697  1.00 17.30           A
ATOM    835  C   THR A 110     -18.572 -20.118  19.136  1.00 19.22           A
ATOM    836  O   THR A 110     -19.167 -19.492  20.023  1.00 17.85           A
ATOM    837  N   LEU A 111     -19.124 -20.499  17.991  1.00 18.88           A
ATOM    838  CA  LEU A 111     -20.553 -20.351  17.716  1.00 19.64           A
ATOM    839  CB  LEU A 111     -20.847 -19.228  16.737  1.00 19.79           A
ATOM    840  CG  LEU A 111     -20.773 -17.810  17.316  1.00 19.24           A
ATOM    841  CD1 LEU A 111     -20.926 -16.832  16.218  1.00 19.44           A
ATOM    842  CD2 LEU A 111     -21.882 -17.599  18.408  1.00 20.76           A
ATOM    843  C   LEU A 111     -20.887 -21.715  17.112  1.00 20.43           A
ATOM    844  O   LEU A 111     -20.073 -22.344  16.402  1.00 18.31           A
ATOM    845  N   PRO A 112     -22.085 -22.222  17.394  1.00 19.50           A
ATOM    846  CD  PRO A 112     -23.083 -21.651  18.318  1.00 20.92           A
ATOM    847  CA  PRO A 112     -22.523 -23.525  16.899  1.00 20.93           A
ATOM    848  CB  PRO A 112     -23.959 -23.605  17.391  1.00 22.46           A
ATOM    849  CG  PRO A 112     -23.884 -22.845  18.660  1.00 21.60           A
ATOM    850  C   PRO A 112     -22.421 -23.751  15.398  1.00 20.94           A
ATOM    851  O   PRO A 112     -22.767 -22.888  14.582  1.00 21.16           A
ATOM    852  N   ALA A 113     -21.904 -24.922  15.040  1.00 22.00           A
ATOM    853  CA  ALA A 113     -21.786 -25.266  13.625  1.00 23.34           A
ATOM    854  CB  ALA A 113     -21.161 -26.665  13.485  1.00 22.78           A
ATOM    855  C   ALA A 113     -23.191 -25.235  13.006  1.00 25.52           A
ATOM    856  O   ALA A 113     -23.369 -24.901  11.826  1.00 24.33           A
ATOM    857  N   ALA A 114     -24.191 -25.575  13.812  1.00 26.80           A
ATOM    858  CA  ALA A 114     -25.576 -25.561  13.345  1.00 29.91           A
ATOM    859  CB  ALA A 114     -26.479 -26.091  14.435  1.00 29.86           A
ATOM    860  C   ALA A 114     -26.049 -24.167  12.904  1.00 31.08           A
ATOM    861  O   ALA A 114     -27.019 -24.040  12.146  1.00 32.98           A
ATOM    862  N   ASP A 115     -25.366 -23.127  13.370  1.00 31.48           A
ATOM    863  CA  ASP A 115     -25.706 -21.738  13.046  1.00 30.69           A
ATOM    864  CB  ASP A 115     -25.221 -20.795  14.150  1.00 32.52           A
ATOM    865  CG  ASP A 115     -25.969 -20.954  15.464  1.00 33.04           A
```

Figure 1 (continued 9)

```
ATOM    866  OD1 ASP A 115     -26.756 -21.906  15.653  1.00 34.66           A
ATOM    867  OD2 ASP A 115     -25.737 -20.092  16.336  1.00 36.15           A
ATOM    868  C   ASP A 115     -25.058 -21.240  11.764  1.00 31.41           A
ATOM    869  O   ASP A 115     -25.450 -20.196  11.235  1.00 30.02           A
ATOM    870  N   PHE A 116     -24.038 -21.951  11.286  1.00 30.62           A
ATOM    871  CA  PHE A 116     -23.315 -21.913  10.102  1.00 31.36           A
ATOM    872  CB  PHE A 116     -22.046 -22.362   9.881  1.00 29.27           A
ATOM    873  CG  PHE A 116     -20.991 -21.658   9.069  1.00 27.56           A
ATOM    874  CD1 PHE A 116     -20.203 -20.570   9.541  1.00 27.11           A
ATOM    875  CD2 PHE A 116     -20.805 -21.958   7.721  1.00 27.95           A
ATOM    876  CE1 PHE A 116     -19.246 -19.982   8.889  1.00 28.16           A
ATOM    877  CE2 PHE A 116     -19.855 -21.280   6.963  1.00 28.67           A
ATOM    878  CZ  PHE A 116     -19.073 -20.288   7.546  1.00 29.11           A
ATOM    879  C   PHE A 116     -24.191 -21.561   8.863  1.00 33.68           A
ATOM    880  O   PHE A 116     -24.650 -22.627   8.463  1.00 33.88           A
ATOM    881  N   PRO A 117     -24.425 -20.397   8.238  1.00 36.47           A
ATOM    882  CD  PRO A 117     -23.799 -19.093   8.500  1.00 37.82           A
ATOM    883  CA  PRO A 117     -25.260 -20.325   7.042  1.00 38.24           A
ATOM    884  CB  PRO A 117     -25.299 -18.826   6.721  1.00 38.61           A
ATOM    885  CG  PRO A 117     -24.854 -18.146   8.000  1.00 38.51           A
ATOM    886  C   PRO A 117     -24.580 -21.093   5.941  1.00 39.42           A
ATOM    887  O   PRO A 117     -25.353 -21.773   5.243  1.00 39.30           A
ATOM    888  N   ASN A 118     -23.258 -21.015   5.823  1.00 41.25           A
ATOM    889  CA  ASN A 118     -22.537 -21.746   4.778  1.00 41.85           A
ATOM    890  CB  ASN A 118     -24.615 -21.596   4.534  1.00 42.76           A
ATOM    891  CG  ASN A 118     -25.954 -24.662   4.699  1.00 46.71           A
ATOM    892  OD1 ASN A 118     -26.693 -24.180   5.564  1.00 48.14           A
ATOM    893  ND2 ASN A 118     -26.242 -25.782   4.049  1.00 47.23           A
ATOM    894  C   ASN A 118     -25.787 -22.308   2.856  1.00 43.69           A
ATOM    895  O   ASN A 118     -27.006 -22.231   3.065  1.00 43.09           A
ATOM    896  N   LEU A 119     -25.242 -22.165   1.655  1.00 41.35           A
ATOM    897  CA  LEU A 119     -26.073 -21.954   0.485  1.00 41.09           A
ATOM    898  CB  LEU A 119     -25.208 -21.818  -0.774  1.00 38.77           A
ATOM    899  CG  LEU A 119     -24.451 -20.490  -0.937  1.00 38.25           A
ATOM    900  CD1 LEU A 119     -23.588 -20.520  -2.192  1.00 37.70           A
ATOM    901  CD2 LEU A 119     -25.453 -19.357  -1.028  1.00 36.82           A
ATOM    902  C   LEU A 119     -27.015 -23.132   0.350  1.00 41.13           A
ATOM    903  O   LEU A 119     -26.623 -24.284   0.577  1.00 41.95           A
ATOM    904  N   ASP A 120     -28.266 -22.833   0.011  1.00 41.01           A
ATOM    905  CA  ASP A 120     -29.263 -23.870  -0.171  1.00 41.25           A
ATOM    906  CB  ASP A 120     -30.624 -23.263  -0.503  1.00 41.00           A
ATOM    907  CG  ASP A 120     -31.197 -22.481   0.649  1.00 43.98           A
ATOM    908  OD1 ASP A 120     -31.099 -22.974   1.794  1.00 45.98           A
ATOM    909  OD2 ASP A 120     -31.745 -21.384   0.411  1.00 45.63           A
ATOM    910  C   ASP A 120     -28.824 -24.775  -1.302  1.00 40.45           A
ATOM    911  O   ASP A 120     -28.073 -24.362  -2.197  1.00 40.20           A
ATOM    912  N   ASP A 121     -29.272 -26.018  -1.253  1.00 38.62           A
ATOM    913  CA  ASP A 121     -28.919 -26.947  -2.299  1.00 36.77           A
ATOM    914  CB  ASP A 121     -29.544 -28.319  -2.034  1.00 39.85           A
ATOM    915  CG  ASP A 121     -28.833 -29.091  -0.944  1.00 43.33           A
ATOM    916  OD1 ASP A 121     -27.587 -29.317  -1.094  1.00 44.66           A
ATOM    917  OD2 ASP A 121     -29.460 -29.472   0.059  1.00 45.13           A
ATOM    918  C   ASP A 121     -29.420 -26.365  -3.614  1.00 33.67           A
ATOM    919  O   ASP A 121     -30.401 -25.623  -3.656  1.00 33.57           A
ATOM    920  N   TRP A 122     -28.715 -26.694  -4.690  1.00 27.14           A
ATOM    921  CA  TRP A 122     -25.923 -26.194  -5.809  1.00 22.15           A
ATOM    922  CB  TRP A 122     -25.321 -24.994  -5.213  1.00 22.15           A
ATOM    923  CG  TRP A 122     -25.383 -24.856  -6.715  1.00 21.27           A
ATOM    924  CD2 TRP A 122     -25.938 -24.939  -7.188  1.00 20.32           A
ATOM    925  CE2 TRP A 122     -24.654 -24.929  -6.609  1.00 20.70           A
ATOM    926  CE3 TRP A 122     -26.052 -25.027  -8.580  1.00 17.91           A
ATOM    927  CD1 TRP A 122     -26.160 -24.786  -4.959  1.00 22.23           A
ATOM    928  NE1 TRP A 122     -24.817 -24.832  -5.249  1.00 20.82           A
ATOM    929  CZ2 TRP A 122     -23.486 -25.000  -7.378  1.00 21.15           A
ATOM    930  CZ3 TRP A 122     -24.899 -25.099  -9.351  1.00 19.53           A
ATOM    931  CH2 TRP A 122     -23.621 -25.083  -8.743  1.00 19.91           A
ATOM    932  C   TRP A 122     -28.636 -27.256  -6.992  1.00 25.27           A
ATOM    933  O   TRP A 122     -28.010 -28.255  -6.618  1.00 24.64           A
ATOM    934  N   GLN A 123     -28.965 -27.064  -8.257  1.00 22.99           A
ATOM    935  CA  GLN A 123     -28.612 -28.050  -9.261  1.00 23.31           A
ATOM    936  CB  GLN A 123     -29.882 -28.686  -9.785  1.00 25.63           A
ATOM    937  CG  GLN A 123     -29.649 -30.014 -10.430  1.00 31.98           A
ATOM    938  CD  GLN A 123     -29.414 -31.110  -9.363  1.00 32.90           A
ATOM    939  OE1 GLN A 123     -28.877 -32.157  -9.681  1.00 36.51           A
ATOM    940  NE2 GLN A 123     -29.836 -30.869  -8.109  1.00 33.21           A
ATOM    941  C   GLN A 123     -27.811 -27.488 -10.441  1.00 21.76           A
ATOM    942  O   GLN A 123     -28.179 -26.467 -10.999  1.00 21.19           A
ATOM    943  N   SER A 124     -26.743 -28.163 -10.855  1.00 22.29           A
ATOM    944  CA  SER A 124     -25.993 -27.635 -11.990  1.00 23.13           A
ATOM    945  CB  SER A 124     -24.548 -28.143 -12.016  1.00 26.37           A
ATOM    946  OG  SER A 124     -24.479 -29.416 -12.593  1.00 30.20           A
ATOM    947  C   SER A 124     -26.706 -28.034 -13.274  1.00 22.74           A
ATOM    948  O   SER A 124     -27.311 -29.119 -13.358  1.00 21.31           A
ATOM    949  N   GLU A 125     -26.627 -27.150 -14.265  1.00 22.78           A
ATOM    950  CA  GLU A 125     -27.261 -27.343 -15.553  1.00 23.65           A
ATOM    951  CB  GLU A 125     -28.368 -26.300 -15.707  1.00 26.17           A
ATOM    952  CG  GLU A 125     -29.141 -26.116 -14.432  1.00 30.15           A
ATOM    953  CD  GLU A 125     -29.837 -24.787 -14.611  1.00 34.19           A
ATOM    954  OE1 GLU A 125     -29.157 -23.802 -14.408  1.00 34.81           A
ATOM    955  OE2 GLU A 125     -31.010 -24.826 -15.017  1.00 36.43           A
ATOM    956  C   GLU A 125     -25.794 -27.394 -15.781  1.00 22.71           A
ATOM    957  O   GLU A 125     -26.561 -27.694 -17.806  1.00 22.51           A
ATOM    958  N   VAL A 126     -25.101 -26.693 -16.427  1.00 20.09           A
ATOM    959  CA  VAL A 126     -24.048 -26.531 -17.411  1.00 21.58           A
ATOM    960  CB  VAL A 126     -24.023 -25.055 -17.937  1.00 22.61           A
ATOM    961  CG1 VAL A 126     -23.060 -24.927 -19.077  1.00 25.78           A
ATOM    962  CG2 VAL A 126     -25.433 -24.627 -18.355  1.00 25.22           A
ATOM    963  C   VAL A 126     -22.730 -26.817 -16.729  1.00 19.60           A
ATOM    964  O   VAL A 126     -22.476 -26.270 -15.676  1.00 19.58           A
ATOM    965  N   GLU A 127     -21.898 -27.661 -17.318  1.00 17.89           A
```

Figure 1 (continued 10)

```
ATOM    966  CA  GLU A 127     -20.602 -27.975 -16.742  1.00 19.23           A
ATOM    967  CB  GLU A 127     -20.643 -29.341 -16.024  1.00 18.90           A
ATOM    968  CG  GLU A 127     -21.759 -29.457 -15.033  1.00 18.41           A
ATOM    969  CD  GLU A 127     -21.797 -30.796 -14.274  1.00 18.10           A
ATOM    970  OE1 GLU A 127     -21.217 -31.797 -14.742  1.00 22.04           A
ATOM    971  OE2 GLU A 127     -22.431 -30.819 -13.209  1.00 19.35           A
ATOM    972  C   GLU A 127     -19.509 -28.013 -17.791  1.00 19.53           A
ATOM    973  O   GLU A 127     -19.741 -28.464 -18.933  1.00 20.65           A
ATOM    974  N   PHE A 128     -18.312 -27.578 -17.403  1.00 17.93           A
ATOM    975  CA  PHE A 128     -17.171 -27.600 -18.304  1.00 18.52           A
ATOM    976  CB  PHE A 128     -17.329 -26.530 -19.409  1.00 19.39           A
ATOM    977  CG  PHE A 128     -17.528 -25.136 -18.885  1.00 18.24           A
ATOM    978  CD1 PHE A 128     -16.423 -24.329 -18.575  1.00 18.53           A
ATOM    979  CD2 PHE A 128     -18.818 -24.640 -18.668  1.00 18.55           A
ATOM    980  CE1 PHE A 128     -16.605 -23.031 -18.044  1.00 18.93           A
ATOM    981  CE2 PHE A 128     -19.014 -23.347 -18.134  1.00 18.45           A
ATOM    982  CZ  PHE A 128     -17.909 -22.541 -17.822  1.00 17.31           A
ATOM    983  C   PHE A 128     -15.900 -27.381 -17.519  1.00 19.63           A
ATOM    984  O   PHE A 128     -15.922 -27.006 -16.335  1.00 16.92           A
ATOM    985  N   THR A 129     -14.785 -27.656 -18.174  1.00 19.01           A
ATOM    986  CA  THR A 129     -13.497 -27.456 -17.561  1.00 21.20           A
ATOM    987  CB  THR A 129     -12.696 -28.761 -17.436  1.00 24.95           A
ATOM    988  OG1 THR A 129     -12.403 -29.263 -18.751  1.00 27.82           A
ATOM    989  CG2 THR A 129     -13.471 -29.800 -16.613  1.00 24.46           A
ATOM    990  C   THR A 129     -12.729 -26.538 -18.479  1.00 21.52           A
ATOM    991  O   THR A 129     -13.035 -26.429 -19.669  1.00 24.36           A
ATOM    992  N   LEU A 130     -11.743 -25.859 -17.923  1.00 21.67           A
ATOM    993  CA  LEU A 130     -10.885 -25.005 -18.716  1.00 21.43           A
ATOM    994  CB  LEU A 130     -11.600 -23.722 -19.161  1.00 21.02           A
ATOM    995  CG  LEU A 130     -11.737 -22.614 -18.130  1.00 21.55           A
ATOM    996  CD1 LEU A 130     -12.246 -21.359 -18.862  1.00 18.68           A
ATOM    997  CD2 LEU A 130     -12.684 -23.045 -17.006  1.00 20.37           A
ATOM    998  C   LEU A 130      -9.666 -24.689 -17.877  1.00 20.77           A
ATOM    999  O   LEU A 130      -9.676 -24.832 -16.645  1.00 21.88           A
ATOM   1000  N   PRO A 131      -8.576 -24.302 -18.535  1.00 21.78           A
ATOM   1001  CD  PRO A 131      -8.433 -24.202 -19.997  1.00 22.11           A
ATOM   1002  CA  PRO A 131      -7.327 -23.970 -17.864  1.00 22.02           A
ATOM   1003  CB  PRO A 131      -6.382 -23.669 -19.023  1.00 21.96           A
ATOM   1004  CG  PRO A 131      -6.975 -24.434 -20.168  1.00 22.46           A
ATOM   1005  C   PRO A 131      -7.468 -22.772 -16.938  1.00 23.06           A
ATOM   1006  O   PRO A 131      -8.194 -21.823 -17.256  1.00 22.79           A
ATOM   1007  N   GLN A 132      -6.767 -22.806 -15.808  1.00 22.91           A
ATOM   1008  CA  GLN A 132      -6.813 -21.686 -14.868  1.00 23.70           A
ATOM   1009  CB  GLN A 132      -5.881 -21.922 -13.678  1.00 25.71           A
ATOM   1010  CG  GLN A 132      -6.311 -23.098 -12.821  1.00 29.70           A
ATOM   1011  CD  GLN A 132      -5.450 -23.279 -11.576  1.00 32.46           A
ATOM   1012  OE1 GLN A 132      -5.308 -22.365 -10.762  1.00 32.13           A
ATOM   1013  NE2 GLN A 132      -4.878 -24.477 -11.425  1.00 33.56           A
ATOM   1014  C   GLN A 132      -6.394 -20.419 -15.581  1.00 22.79           A
ATOM   1015  O   GLN A 132      -6.999 -19.368 -15.380  1.00 21.02           A
ATOM   1016  N   ALA A 133      -5.375 -20.517 -16.424  1.00 21.06           A
ATOM   1017  CA  ALA A 133      -4.897 -19.337 -17.154  1.00 22.13           A
ATOM   1018  CB  ALA A 133      -3.624 -19.681 -17.935  1.00 22.47           A
ATOM   1019  C   ALA A 133      -5.942 -18.757 -18.098  1.00 20.39           A
ATOM   1020  O   ALA A 133      -5.932 -17.559 -18.361  1.00 21.36           A
ATOM   1021  N   THR A 134      -6.833 -19.590 -18.630  1.00 18.88           A
ATOM   1022  CA  THR A 134      -7.853 -19.085 -19.549  1.00 18.20           A
ATOM   1023  CB  THR A 134      -8.512 -20.254 -20.296  1.00 19.77           A
ATOM   1024  OG1 THR A 134      -7.498 -20.911 -21.092  1.00 19.04           A
ATOM   1025  CG2 THR A 134      -9.594 -19.776 -21.214  1.00 18.65           A
ATOM   1026  C   THR A 134      -8.885 -18.288 -18.773  1.00 17.20           A
ATOM   1027  O   THR A 134      -9.341 -17.214 -19.190  1.00 16.08           A
ATOM   1028  N   MET A 135      -9.260 -18.827 -17.627  1.00 17.79           A
ATOM   1029  CA  MET A 135     -10.237 -18.138 -16.786  1.00 18.34           A
ATOM   1030  CB  MET A 135     -10.612 -19.011 -15.579  1.00 18.90           A
ATOM   1031  CG  MET A 135     -11.596 -18.329 -14.623  1.00 21.27           A
ATOM   1032  SD  MET A 135     -13.215 -17.944 -15.348  1.00 25.97           A
ATOM   1033  CE  MET A 135     -13.884 -19.343 -15.539  1.00 21.37           A
ATOM   1034  C   MET A 135      -9.677 -16.800 -16.311  1.00 18.69           A
ATOM   1035  O   MET A 135     -10.386 -15.793 -16.327  1.00 17.86           A
ATOM   1036  N   LYS A 136      -8.409 -16.776 -15.890  1.00 18.69           A
ATOM   1037  CA  LYS A 136      -7.754 -15.553 -15.443  1.00 20.30           A
ATOM   1038  CB  LYS A 136      -6.302 -15.835 -15.024  1.00 23.59           A
ATOM   1039  CG  LYS A 136      -5.351 -14.628 -15.146  1.00 28.29           A
ATOM   1040  CD  LYS A 136      -3.863 -15.004 -14.987  1.00 31.41           A
ATOM   1041  CE  LYS A 136      -3.406 -16.112 -15.975  1.00 35.30           A
ATOM   1042  NZ  LYS A 136      -3.714 -15.883 -17.445  1.00 35.62           A
ATOM   1043  C   LYS A 136      -7.752 -14.531 -16.578  1.00 19.86           A
ATOM   1044  O   LYS A 136      -8.004 -13.352 -16.364  1.00 20.49           A
ATOM   1045  N   ARG A 137      -7.445 -14.988 -17.786  1.00 17.95           A
ATOM   1046  CA  ARG A 137      -7.423 -14.094 -18.915  1.00 16.91           A
ATOM   1047  CB  ARG A 137      -6.931 -14.844 -20.152  1.00 20.63           A
ATOM   1048  CG  ARG A 137      -6.418 -13.923 -21.256  1.00 27.85           A
ATOM   1049  CD  ARG A 137      -7.457 -13.620 -22.307  1.00 32.60           A
ATOM   1050  NE  ARG A 137      -7.054 -12.470 -23.126  1.00 38.30           A
ATOM   1051  CZ  ARG A 137      -7.656 -12.105 -24.254  1.00 39.88           A
ATOM   1052  NH1 ARG A 137      -8.682 -12.806 -24.711  1.00 42.58           A
ATOM   1053  NH2 ARG A 137      -7.255 -11.029 -24.915  1.00 38.76           A
ATOM   1054  C   ARG A 137      -8.819 -13.504 -19.171  1.00 16.74           A
ATOM   1055  O   ARG A 137      -8.950 -12.317 -19.436  1.00 16.26           A
ATOM   1056  N   LEU A 138      -9.846 -14.333 -19.081  1.00 13.43           A
ATOM   1057  CA  LEU A 138     -11.202 -13.848 -19.338  1.00 13.64           A
ATOM   1058  CB  LEU A 138     -12.201 -15.020 -19.290  1.00 14.57           A
ATOM   1059  CG  LEU A 138     -12.160 -15.924 -20.526  1.00 14.17           A
ATOM   1060  CD1 LEU A 138     -12.888 -17.223 -20.219  1.00 17.01           A
ATOM   1061  CD2 LEU A 138     -12.794 -15.194 -21.734  1.00 15.21           A
ATOM   1062  C   LEU A 138     -11.604 -12.799 -18.341  1.00 13.26           A
ATOM   1063  O   LEU A 138     -12.232 -11.788 -18.700  1.00 13.04           A
ATOM   1064  N   ILE A 139     -11.269 -13.036 -17.073  1.00 13.36           A
ATOM   1065  CA  ILE A 139     -11.642 -12.066 -16.049  1.00 14.01           A
```

Figure 1 (continued 11)

```
ATOM   1066  CB   ILE A 139     -11.574 -12.711 -14.631  1.00 14.80       A
ATOM   1067  CG2  ILE A 139     -11.749 -11.612 -13.554  1.00 14.76       A
ATOM   1068  CG1  ILE A 139     -12.657 -13.793 -14.526  1.00 14.38       A
ATOM   1069  CD1  ILE A 139     -12.522 -14.700 -13.259  1.00 15.70       A
ATOM   1070  C    ILE A 139     -10.828 -10.782 -16.115  1.00 15.36       A
ATOM   1071  O    ILE A 139     -11.403  -9.681 -16.129  1.00 15.94       A
ATOM   1072  N    GLU A 140      -9.500 -10.891 -16.185  1.00 14.35       A
ATOM   1073  CA   GLU A 140      -8.663  -9.698 -16.254  1.00 16.18       A
ATOM   1074  CB   GLU A 140      -7.175 -10.107 -16.250  1.00 18.11       A
ATOM   1075  CG   GLU A 140      -6.708 -10.696 -14.927  1.00 24.32       A
ATOM   1076  CD   GLU A 140      -5.209 -11.032 -14.909  1.00 29.34       A
ATOM   1077  OE1  GLU A 140      -4.642 -11.276 -15.995  1.00 31.06       A
ATOM   1078  OE2  GLU A 140      -4.606 -11.069 -13.804  1.00 33.19       A
ATOM   1079  C    GLU A 140      -8.955  -8.832 -17.481  1.00 15.66       A
ATOM   1080  O    GLU A 140      -8.774  -7.613 -17.452  1.00 16.06       A
ATOM   1081  N    ALA A 141      -9.428  -9.456 -18.547  1.00 14.10       A
ATOM   1082  CA   ALA A 141      -9.690  -8.725 -19.785  1.00 12.46       A
ATOM   1083  CB   ALA A 141      -9.921  -9.712 -20.945  1.00 16.01       A
ATOM   1084  C    ALA A 141     -10.893  -7.796 -19.666  1.00 13.15       A
ATOM   1085  O    ALA A 141     -11.005  -6.834 -20.422  1.00 12.75       A
ATOM   1086  N    THR A 142     -11.771  -8.088 -18.726  1.00 12.50       A
ATOM   1087  CA   THR A 142     -13.017  -7.313 -18.635  1.00 10.74       A
ATOM   1088  CB   THR A 142     -14.234  -8.165 -19.093  1.00 11.13       A
ATOM   1089  OG1  THR A 142     -14.408  -9.249 -18.173  1.00 15.23       A
ATOM   1090  CG2  THR A 142     -14.000  -8.750 -20.499  1.00 11.74       A
ATOM   1091  C    THR A 142     -13.397  -6.766 -17.277  1.00 13.68       A
ATOM   1092  O    THR A 142     -14.208  -5.849 -17.229  1.00 12.84       A
ATOM   1093  N    GLN A 143     -12.824  -7.279 -16.193  1.00 12.98       A
ATOM   1094  CA   GLN A 143     -13.218  -6.886 -14.832  1.00 14.94       A
ATOM   1095  CB   GLN A 143     -12.264  -7.548 -13.841  1.00 17.55       A
ATOM   1096  CG   GLN A 143     -12.686  -7.401 -12.422  1.00 23.99       A
ATOM   1097  CD   GLN A 143     -11.760  -8.145 -11.481  1.00 27.58       A
ATOM   1098  OE1  GLN A 143     -12.121  -8.446 -10.332  1.00 31.11       A
ATOM   1099  NE2  GLN A 143     -10.561  -8.434 -11.956  1.00 27.03       A
ATOM   1100  C    GLN A 143     -13.311  -5.398 -14.533  1.00 14.23       A
ATOM   1101  O    GLN A 143     -14.235  -4.946 -13.808  1.00 15.54       A
ATOM   1102  N    PHE A 144     -12.372  -4.641 -15.073  1.00 14.47       A
ATOM   1103  CA   PHE A 144     -12.312  -3.206 -14.848  1.00 14.06       A
ATOM   1104  CB   PHE A 144     -11.028  -2.636 -15.430  1.00 13.76       A
ATOM   1105  CG   PHE A 144     -11.014  -2.621 -16.924  1.00 16.11       A
ATOM   1106  CD1  PHE A 144     -10.537  -3.718 -17.656  1.00 14.91       A
ATOM   1107  CD2  PHE A 144     -11.524  -1.510 -17.611  1.00 15.82       A
ATOM   1108  CE1  PHE A 144     -10.567  -3.701 -19.064  1.00 15.95       A
ATOM   1109  CE2  PHE A 144     -11.558  -1.484 -19.000  1.00 16.83       A
ATOM   1110  CZ   PHE A 144     -11.060  -2.579 -19.730  1.00 18.10       A
ATOM   1111  C    PHE A 144     -13.503  -2.424 -15.388  1.00 15.25       A
ATOM   1112  O    PHE A 144     -13.727  -1.296 -14.957  1.00 14.82       A
ATOM   1113  N    SER A 145     -14.268  -3.019 -16.306  1.00 13.80       A
ATOM   1114  CA   SER A 145     -15.442  -2.334 -16.873  1.00 14.34       A
ATOM   1115  CB   SER A 145     -15.637  -2.720 -18.328  1.00 15.77       A
ATOM   1116  OG   SER A 145     -14.570  -2.200 -19.120  1.00 16.45       A
ATOM   1117  C    SER A 145     -16.737  -2.587 -16.121  1.00 15.00       A
ATOM   1118  O    SER A 145     -17.787  -2.069 -16.526  1.00 15.49       A
ATOM   1119  N    MET A 146     -16.699  -3.407 -15.084  1.00 15.16       A
ATOM   1120  CA   MET A 146     -17.917  -3.660 -14.288  1.00 15.61       A
ATOM   1121  CB   MET A 146     -17.677  -4.746 -13.224  1.00 16.31       A
ATOM   1122  CG   MET A 146     -17.414  -6.142 -13.771  1.00 16.90       A
ATOM   1123  SD   MET A 146     -17.264  -7.426 -12.423  1.00 20.35       A
ATOM   1124  CE   MET A 146     -15.868  -6.822 -11.667  1.00 18.34       A
ATOM   1125  C    MET A 146     -18.290  -2.364 -13.546  1.00 17.87       A
ATOM   1126  O    MET A 146     -17.436  -1.571 -13.177  1.00 17.71       A
ATOM   1127  N    ALA A 147     -19.584  -2.171 -13.302  1.00 18.85       A
ATOM   1128  CA   ALA A 147     -20.000  -0.987 -12.561  1.00 22.61       A
ATOM   1129  CB   ALA A 147     -21.514  -0.786 -12.718  1.00 20.80       A
ATOM   1130  C    ALA A 147     -19.666  -1.181 -11.088  1.00 25.26       A
ATOM   1131  O    ALA A 147     -19.455  -2.315 -10.624  1.00 25.14       A
ATOM   1132  N    HIS A 148     -19.654  -0.068 -10.359  1.00 29.57       A
ATOM   1133  CA   HIS A 148     -19.407  -0.078  -8.916  1.00 32.55       A
ATOM   1134  CB   HIS A 148     -18.185   0.755  -8.530  1.00 35.09       A
ATOM   1135  CG   HIS A 148     -16.886   0.218  -9.025  1.00 38.05       A
ATOM   1136  CD2  HIS A 148     -15.868  -0.390  -8.368  1.00 38.84       A
ATOM   1137  ND1  HIS A 148     -16.477   0.347 -10.336  1.00 39.33       A
ATOM   1138  CE1  HIS A 148     -15.259  -0.151 -10.463  1.00 39.25       A
ATOM   1139  NE2  HIS A 148     -14.867  -0.603  -9.284  1.00 39.69       A
ATOM   1140  C    HIS A 148     -20.588   0.578  -8.210  1.00 32.61       A
ATOM   1141  O    HIS A 148     -20.810   1.781  -8.365  1.00 33.21       A
ATOM   1142  N    GLN A 149     -21.326  -0.203  -7.436  1.00 32.56       A
ATOM   1143  CA   GLN A 149     -22.449   0.309  -6.663  1.00 33.37       A
ATOM   1144  CB   GLN A 149     -21.922   1.256  -5.575  1.00 35.74       A
ATOM   1145  CG   GLN A 149     -20.875   0.614  -4.657  1.00 39.57       A
ATOM   1146  CD   GLN A 149     -20.358   1.564  -3.573  1.00 41.69       A
ATOM   1147  OE1  GLN A 149     -21.099   2.399  -3.059  1.00 42.95       A
ATOM   1148  NE2  GLN A 149     -19.084   1.420  -3.214  1.00 41.85       A
ATOM   1149  C    GLN A 149     -23.529   1.008  -7.486  1.00 32.00       A
ATOM   1150  O    GLN A 149     -24.177   1.957  -7.016  1.00 32.50       A
ATOM   1151  N    ASP A 150     -23.742   0.538  -8.704  1.00 29.36       A
ATOM   1152  CA   ASP A 150     -24.772   1.110  -9.560  1.00 27.85       A
ATOM   1153  CB   ASP A 150     -24.532   0.681 -11.006  1.00 26.70       A
ATOM   1154  CG   ASP A 150     -25.318   1.510 -12.007  1.00 27.39       A
ATOM   1155  OD1  ASP A 150     -24.695   2.262 -12.791  1.00 27.00       A
ATOM   1156  OD2  ASP A 150     -26.558   1.410 -12.017  1.00 26.08       A
ATOM   1157  C    ASP A 150     -26.143   0.601  -9.093  1.00 27.65       A
ATOM   1158  O    ASP A 150     -26.291  -0.565  -8.720  1.00 27.65       A
ATOM   1159  N    VAL A 151     -27.148   1.475  -9.100  1.00 28.95       A
ATOM   1160  CA   VAL A 151     -28.495   1.080  -8.702  1.00 30.15       A
ATOM   1161  CB   VAL A 151     -29.462   2.274  -8.840  1.00 30.10       A
ATOM   1162  CG1  VAL A 151     -30.898   1.825  -8.593  1.00 33.02       A
ATOM   1163  CG2  VAL A 151     -29.065   3.354  -7.856  1.00 32.71       A
ATOM   1164  C    VAL A 151     -28.985  -0.099  -9.552  1.00 29.78       A
ATOM   1165  O    VAL A 151     -29.860  -0.858  -9.137  1.00 29.45       A
```

Figure 1 (continued 12)

```
ATOM   1166  N    ARG A 152     -28.431   -0.251 -10.752  1.00 29.05           A
ATOM   1167  CA   ARG A 152     -28.804   -1.379 -11.596  1.00 27.89           A
ATOM   1168  CB   ARG A 152     -28.634   -1.019 -13.069  1.00 26.83           A
ATOM   1169  CG   ARG A 152     -29.512    0.180 -13.508  1.00 26.45           A
ATOM   1170  CD   ARG A 152     -29.040    0.760 -14.836  1.00 26.01           A
ATOM   1171  NE   ARG A 152     -27.778    1.484 -14.686  1.00 24.71           A
ATOM   1172  CZ   ARG A 152     -27.089    2.005 -15.701  1.00 21.61           A
ATOM   1173  NH1  ARG A 152     -27.529    1.890 -16.950  1.00 23.37           A
ATOM   1174  NH2  ARG A 152     -25.947    2.627 -15.469  1.00 22.47           A
ATOM   1175  C    ARG A 152     -27.813   -2.455 -11.176  1.00 27.21           A
ATOM   1176  O    ARG A 152     -26.719   -2.545 -11.722  1.00 24.79           A
ATOM   1177  N    TYR A 153     -28.197   -3.226 -10.163  1.00 27.89           A
ATOM   1178  CA   TYR A 153     -27.379   -4.284  -9.588  1.00 28.26           A
ATOM   1179  CB   TYR A 153     -28.198   -5.074  -8.566  1.00 32.74           A
ATOM   1180  CG   TYR A 153     -29.435   -5.685  -9.190  1.00 36.87           A
ATOM   1181  CD1  TYR A 153     -30.400   -4.879  -9.808  1.00 39.09           A
ATOM   1182  CE1  TYR A 153     -31.510   -5.434 -10.445  1.00 41.32           A
ATOM   1183  CD2  TYR A 153     -29.620   -7.069  -9.212  1.00 38.75           A
ATOM   1184  CE2  TYR A 153     -30.734   -7.637  -9.839  1.00 41.39           A
ATOM   1185  CZ   TYR A 153     -31.670   -6.814 -10.459  1.00 41.82           A
ATOM   1186  OH   TYR A 153     -32.744   -7.366 -11.122  1.00 43.97           A
ATOM   1187  C    TYR A 153     -26.802   -5.265 -10.594  1.00 25.95           A
ATOM   1188  O    TYR A 153     -25.720   -5.798 -10.355  1.00 25.41           A
ATOM   1189  N    TYR A 154     -27.521   -5.522 -11.683  1.00 24.27           A
ATOM   1190  CA   TYR A 154     -27.038   -6.478 -12.683  1.00 24.02           A
ATOM   1191  CB   TYR A 154     -28.138   -6.822 -13.697  1.00 24.80           A
ATOM   1192  CG   TYR A 154     -28.704   -5.632 -14.441  1.00 26.56           A
ATOM   1193  CD1  TYR A 154     -28.095   -5.150 -15.603  1.00 26.67           A
ATOM   1194  CE1  TYR A 154     -28.609   -4.046 -16.280  1.00 28.56           A
ATOM   1195  CD2  TYR A 154     -29.841   -4.982 -13.969  1.00 27.71           A
ATOM   1196  CE2  TYR A 154     -30.366   -3.868 -14.636  1.00 28.26           A
ATOM   1197  CZ   TYR A 154     -29.745   -3.411 -15.789  1.00 29.38           A
ATOM   1198  OH   TYR A 154     -30.269   -2.332 -16.463  1.00 31.98           A
ATOM   1199  C    TYR A 154     -25.786   -5.988 -13.410  1.00 23.05           A
ATOM   1200  O    TYR A 154     -25.156   -6.778 -14.135  1.00 24.65           A
ATOM   1201  N    LEU A 155     -25.433   -4.709 -13.249  1.00 19.62           A
ATOM   1202  CA   LEU A 155     -24.215   -4.190 -13.884  1.00 18.55           A
ATOM   1203  CB   LEU A 155     -24.397   -2.720 -14.330  1.00 18.29           A
ATOM   1204  CG   LEU A 155     -25.393   -2.508 -15.470  1.00 18.19           A
ATOM   1205  CD1  LEU A 155     -25.430   -1.025 -15.872  1.00 20.01           A
ATOM   1206  CD2  LEU A 155     -24.986   -3.351 -16.652  1.00 17.70           A
ATOM   1207  C    LEU A 155     -23.029   -4.270 -12.926  1.00 18.16           A
ATOM   1208  O    LEU A 155     -21.890   -4.047 -13.335  1.00 17.47           A
ATOM   1209  N    ASN A 156     -23.299   -4.538 -11.648  1.00 19.44           A
ATOM   1210  CA   ASN A 156     -22.258   -4.646 -10.622  1.00 19.29           A
ATOM   1211  CB   ASN A 156     -22.776   -4.318  -9.225  1.00 20.80           A
ATOM   1212  CG   ASN A 156     -23.318   -2.927  -9.107  1.00 21.25           A
ATOM   1213  OD1  ASN A 156     -24.221   -2.673  -8.287  1.00 24.83           A
ATOM   1214  ND2  ASN A 156     -22.777   -2.010  -9.887  1.00 16.70           A
ATOM   1215  C    ASN A 156     -21.821   -6.113 -10.587  1.00 19.89           A
ATOM   1216  O    ASN A 156     -21.828   -6.805  -9.535  1.00 23.37           A
ATOM   1217  N    GLY A 157     -21.518   -6.613 -11.753  1.00 17.85           A
ATOM   1218  CA   GLY A 157     -21.070   -7.981 -11.823  1.00 16.12           A
ATOM   1219  C    GLY A 157     -20.565   -8.215 -13.217  1.00 14.85           A
ATOM   1220  O    GLY A 157     -20.399   -7.275 -13.993  1.00 15.61           A
ATOM   1221  N    MET A 158     -20.343   -9.485 -13.544  1.00 13.48           A
ATOM   1222  CA   MET A 158     -19.800   -9.852 -14.842  1.00 13.97           A
ATOM   1223  CB   MET A 158     -18.349  -10.347 -14.646  1.00 13.51           A
ATOM   1224  CG   MET A 158     -17.648  -10.766 -15.928  1.00 12.71           A
ATOM   1225  SD   MET A 158     -15.937  -11.277 -15.551  1.00 12.75           A
ATOM   1226  CE   MET A 158     -15.144   -9.642 -15.273  1.00 14.07           A
ATOM   1227  C    MET A 158     -20.622  -10.936 -15.511  1.00 12.85           A
ATOM   1228  O    MET A 158     -20.950  -11.942 -14.890  1.00 12.99           A
ATOM   1229  N    LEU A 159     -20.941  -10.757 -16.787  1.00 11.15           A
ATOM   1230  CA   LEU A 159     -21.692  -11.772 -17.517  1.00 12.65           A
ATOM   1231  CB   LEU A 159     -22.302  -11.197 -18.799  1.00 14.78           A
ATOM   1232  CG   LEU A 159     -23.251  -12.145 -19.553  1.00 16.09           A
ATOM   1233  CD1  LEU A 159     -24.545  -12.193 -18.732  1.00 16.30           A
ATOM   1234  CD2  LEU A 159     -23.582  -11.680 -20.975  1.00 17.74           A
ATOM   1235  C    LEU A 159     -20.737  -12.884 -17.923  1.00 13.59           A
ATOM   1236  O    LEU A 159     -19.642  -12.598 -18.386  1.00 12.32           A
ATOM   1237  N    PHE A 160     -21.138  -14.119 -17.652  1.00 13.23           A
ATOM   1238  CA   PHE A 160     -20.369  -15.298 -18.110  1.00 13.78           A
ATOM   1239  CB   PHE A 160     -20.017  -16.243 -16.972  1.00 15.17           A
ATOM   1240  CG   PHE A 160     -18.810  -15.822 -16.206  1.00 15.50           A
ATOM   1241  CD1  PHE A 160     -18.845  -14.708 -15.386  1.00 16.70           A
ATOM   1242  CD2  PHE A 160     -17.619  -16.528 -16.340  1.00 20.57           A
ATOM   1243  CE1  PHE A 160     -17.690  -14.301 -14.696  1.00 15.09           A
ATOM   1244  CE2  PHE A 160     -16.473  -16.129 -15.664  1.00 21.51           A
ATOM   1245  CZ   PHE A 160     -16.516  -15.010 -14.837  1.00 19.20           A
ATOM   1246  C    PHE A 160     -21.324  -15.985 -19.078  1.00 14.91           A
ATOM   1247  O    PHE A 160     -22.457  -16.356 -18.712  1.00 14.88           A
ATOM   1248  N    GLU A 161     -20.883  -16.155 -20.326  1.00 14.48           A
ATOM   1249  CA   GLU A 161     -21.732  -16.732 -21.343  1.00 15.81           A
ATOM   1250  CB   GLU A 161     -22.136  -15.629 -22.347  1.00 17.40           A
ATOM   1251  CG   GLU A 161     -22.921  -16.096 -23.576  1.00 21.38           A
ATOM   1252  CD   GLU A 161     -23.306  -14.959 -24.539  1.00 25.94           A
ATOM   1253  OE1  GLU A 161     -22.630  -13.893 -24.551  1.00 23.68           A
ATOM   1254  OE2  GLU A 161     -24.296  -15.148 -25.306  1.00 27.60           A
ATOM   1255  C    GLU A 161     -21.042  -17.858 -22.070  1.00 16.27           A
ATOM   1256  O    GLU A 161     -19.852  -17.753 -22.420  1.00 16.32           A
ATOM   1257  N    THR A 162     -21.785  -18.939 -22.275  1.00 16.15           A
ATOM   1258  CA   THR A 162     -21.255  -20.072 -23.043  1.00 17.00           A
ATOM   1259  CB   THR A 162     -21.579  -21.418 -22.376  1.00 15.79           A
ATOM   1260  OG1  THR A 162     -22.976  -21.471 -22.079  1.00 17.17           A
ATOM   1261  CG2  THR A 162     -20.777  -21.587 -21.073  1.00 17.18           A
ATOM   1262  C    THR A 162     -21.943  -20.022 -24.408  1.00 16.86           A
ATOM   1263  O    THR A 162     -23.133  -19.814 -24.498  1.00 17.96           A
ATOM   1264  N    GLU A 163     -21.184  -20.213 -25.473  1.00 19.48           A
ATOM   1265  CA   GLU A 163     -21.770  -20.170 -26.807  1.00 20.26           A
```

Figure 1 (continued 13)

```
ATOM   1266  CB   GLU A 163     -21.892 -18.717 -27.287  1.00 21.73           A
ATOM   1267  CG   GLU A 163     -22.630 -18.615 -28.630  1.00 25.04           A
ATOM   1268  CD   GLU A 163     -22.892 -17.188 -29.043  1.00 28.71           A
ATOM   1269  OE1  GLU A 163     -22.046 -16.326 -28.755  1.00 29.00           A
ATOM   1270  OE2  GLU A 163     -23.937 -16.925 -29.672  1.00 33.20           A
ATOM   1271  C    GLU A 163     -20.857 -20.965 -27.717  1.00 20.58           A
ATOM   1272  O    GLU A 163     -19.670 -20.671 -27.849  1.00 19.51           A
ATOM   1273  N    GLY A 164     -21.427 -21.985 -28.336  1.00 21.25           A
ATOM   1274  CA   GLY A 164     -20.643 -22.834 -29.208  1.00 23.06           A
ATOM   1275  C    GLY A 164     -19.570 -23.516 -28.381  1.00 22.55           A
ATOM   1276  O    GLY A 164     -19.860 -24.269 -27.441  1.00 23.22           A
ATOM   1277  N    GLU A 165     -18.323 -23.232 -28.699  1.00 22.46           A
ATOM   1278  CA   GLU A 165     -17.233 -23.835 -27.965  1.00 21.86           A
ATOM   1279  CB   GLU A 165     -16.276 -24.498 -28.948  1.00 26.05           A
ATOM   1280  CG   GLU A 165     -15.133 -25.183 -28.299  1.00 31.89           A
ATOM   1281  CD   GLU A 165     -13.996 -25.386 -29.268  1.00 32.82           A
ATOM   1282  OE1  GLU A 165     -14.228 -26.054 -30.316  1.00 35.85           A
ATOM   1283  OE2  GLU A 165     -12.891 -24.872 -28.983  1.00 32.38           A
ATOM   1284  C    GLU A 165     -16.492 -22.792 -27.122  1.00 20.54           A
ATOM   1285  O    GLU A 165     -15.403 -23.031 -26.629  1.00 21.57           A
ATOM   1286  N    GLU A 166     -17.101 -21.632 -26.932  1.00 18.84           A
ATOM   1287  CA   GLU A 166     -16.419 -20.588 -26.183  1.00 18.69           A
ATOM   1288  CB   GLU A 166     -16.291 -19.332 -27.036  1.00 20.53           A
ATOM   1289  CG   GLU A 166     -15.371 -19.476 -28.244  1.00 25.65           A
ATOM   1290  CD   GLU A 166     -15.124 -18.128 -28.875  1.00 29.36           A
ATOM   1291  OE1  GLU A 166     -16.106 -17.495 -29.317  1.00 29.76           A
ATOM   1292  OE2  GLU A 166     -13.953 -17.697 -28.911  1.00 32.95           A
ATOM   1293  C    GLU A 166     -17.075 -20.149 -24.882  1.00 16.09           A
ATOM   1294  O    GLU A 166     -18.281 -20.299 -24.689  1.00 17.27           A
ATOM   1295  N    LEU A 167     -16.226 -19.667 -23.984  1.00 16.29           A
ATOM   1296  CA   LEU A 167     -16.685 -19.074 -22.722  1.00 14.08           A
ATOM   1297  CB   LEU A 167     -15.916 -19.586 -21.510  1.00 14.28           A
ATOM   1298  CG   LEU A 167     -16.345 -18.898 -20.199  1.00 14.34           A
ATOM   1299  CD1  LEU A 167     -17.852 -19.118 -19.991  1.00 15.20           A
ATOM   1300  CD2  LEU A 167     -15.572 -19.425 -18.995  1.00 15.60           A
ATOM   1301  C    LEU A 167     -16.356 -17.589 -22.956  1.00 14.38           A
ATOM   1302  O    LEU A 167     -15.249 -17.243 -23.413  1.00 14.90           A
ATOM   1303  N    ARG A 168     -17.314 -16.720 -22.632  1.00 13.15           A
ATOM   1304  CA   ARG A 168     -17.142 -15.283 -22.858  1.00 13.65           A
ATOM   1305  CB   ARG A 168     -18.109 -14.851 -23.974  1.00 14.89           A
ATOM   1306  CG   ARG A 168     -18.286 -13.333 -24.147  1.00 14.54           A
ATOM   1307  CD   ARG A 168     -19.316 -13.059 -25.217  1.00 16.30           A
ATOM   1308  NE   ARG A 168     -18.918 -13.676 -26.473  1.00 19.44           A
ATOM   1309  CZ   ARG A 168     -19.627 -14.584 -27.139  1.00 21.39           A
ATOM   1310  NH1  ARG A 168     -20.793 -15.006 -26.690  1.00 22.67           A
ATOM   1311  NH2  ARG A 168     -19.147 -15.073 -28.265  1.00 25.38           A
ATOM   1312  C    ARG A 168     -17.509 -14.523 -21.605  1.00 13.95           A
ATOM   1313  O    ARG A 168     -18.425 -14.932 -20.873  1.00 14.10           A
ATOM   1314  N    THR A 169     -16.794 -13.431 -21.351  1.00 12.43           A
ATOM   1315  CA   THR A 169     -17.153 -12.587 -20.230  1.00 10.45           A
ATOM   1316  CB   THR A 169     -16.053 -12.425 -19.186  1.00 12.78           A
ATOM   1317  OG1  THR A 169     -14.844 -11.981 -19.830  1.00 14.14           A
ATOM   1318  CG2  THR A 169     -15.808 -13.743 -18.422  1.00 11.68           A
ATOM   1319  C    THR A 169     -17.469 -11.219 -20.825  1.00 11.09           A
ATOM   1320  O    THR A 169     -16.932 -10.824 -21.853  1.00 10.97           A
ATOM   1321  N    VAL A 170     -18.421 -10.537 -20.198  1.00 10.12           A
ATOM   1322  CA   VAL A 170     -18.803  -9.205 -20.645  1.00 10.95           A
ATOM   1323  CB   VAL A 170     -20.166  -9.186 -21.364  1.00 10.17           A
ATOM   1324  CG1  VAL A 170     -20.344  -7.769 -22.015  1.00 11.54           A
ATOM   1325  CG2  VAL A 170     -20.197 -10.227 -22.491  1.00 13.32           A
ATOM   1326  C    VAL A 170     -18.967  -8.559 -19.376  1.00 10.18           A
ATOM   1327  O    VAL A 170     -19.500  -8.824 -18.361  1.00 13.17           A
ATOM   1328  N    ALA A 171     -18.471  -7.118 -19.426  1.00 11.08           A
ATOM   1329  CA   ALA A 171     -18.650  -6.212 -18.310  1.00 10.99           A
ATOM   1330  CB   ALA A 171     -17.451  -6.224 -17.401  1.00 12.41           A
ATOM   1331  C    ALA A 171     -18.898  -4.807 -18.854  1.00 12.83           A
ATOM   1332  O    ALA A 171     -18.353  -4.409 -19.875  1.00 13.33           A
ATOM   1333  N    THR A 172     -19.788  -4.091 -18.193  1.00 11.14           A
ATOM   1334  CA   THR A 172     -20.092  -2.723 -18.627  1.00 12.97           A
ATOM   1335  CB   THR A 172     -21.046  -2.669 -19.850  1.00 16.11           A
ATOM   1336  OG1  THR A 172     -21.222  -1.284 -20.236  1.00 15.65           A
ATOM   1337  CG2  THR A 172     -22.435  -3.271 -19.520  1.00 15.53           A
ATOM   1338  C    THR A 172     -20.697  -1.934 -17.486  1.00 13.38           A
ATOM   1339  O    THR A 172     -21.347  -2.484 -16.592  1.00 13.88           A
ATOM   1340  N    ASP A 173     -20.455  -0.624 -17.525  1.00 13.39           A
ATOM   1341  CA   ASP A 173     -20.994   0.264 -16.494  1.00 15.62           A
ATOM   1342  CB   ASP A 173     -19.864   0.956 -15.731  1.00 16.03           A
ATOM   1343  CG   ASP A 173     -18.990   1.833 -16.625  1.00 16.32           A
ATOM   1344  OD1  ASP A 173     -19.273   1.986 -17.831  1.00 15.70           A
ATOM   1345  OD2  ASP A 173     -18.005   2.370 -16.079  1.00 18.84           A
ATOM   1346  C    ASP A 173     -21.867   1.310 -17.164  1.00 16.64           A
ATOM   1347  O    ASP A 173     -22.214   2.322 -16.530  1.00 19.53           A
ATOM   1348  N    GLY A 174     -22.187   1.083 -18.436  1.00 16.21           A
ATOM   1349  CA   GLY A 174     -23.039   2.014 -19.178  1.00 18.97           A
ATOM   1350  C    GLY A 174     -22.302   3.071 -19.977  1.00 19.77           A
ATOM   1351  O    GLY A 174     -22.884   3.728 -20.860  1.00 21.66           A
ATOM   1352  N    HIS A 175     -21.023   3.258 -19.655  1.00 18.37           A
ATOM   1353  CA   HIS A 175     -20.182   4.210 -20.370  1.00 19.07           A
ATOM   1354  CB   HIS A 175     -19.434   5.082 -19.384  1.00 21.34           A
ATOM   1355  CG   HIS A 175     -20.339   5.944 -18.578  1.00 28.96           A
ATOM   1356  CD2  HIS A 175     -20.783   5.827 -17.305  1.00 31.83           A
ATOM   1357  ND1  HIS A 175     -21.007   7.017 -19.135  1.00 31.01           A
ATOM   1358  CE1  HIS A 175     -21.828   7.524 -18.235  1.00 30.50           A
ATOM   1359  NE2  HIS A 175     -21.713   6.820 -17.111  1.00 34.27           A
ATOM   1360  C    HIS A 175     -19.189   3.501 -21.254  1.00 17.40           A
ATOM   1361  O    HIS A 175     -18.861   3.970 -22.340  1.00 18.83           A
ATOM   1362  N    ARG A 176     -18.663   2.385 -20.755  1.00 15.38           A
ATOM   1363  CA   ARG A 176     -17.713   1.611 -21.529  1.00 14.12           A
ATOM   1364  CB   ARG A 176     -16.248   1.567 -21.167  1.00 14.64           A
ATOM   1365  CG   ARG A 176     -15.987   2.385 -19.734  1.00 15.67           A
```

| | | | | | | | | | |
|---|---|---|---|---|---|---|---|---|---|
|ATOM|1366|CD|ARG|A|176|-15.877|1.156|-18.816|1.00 15.21|A|
|ATOM|1367|NE|ARG|A|176|-15.566|1.544|-17.439|1.00 14.17|A|
|ATOM|1368|CZ|ARG|A|176|-14.353|1.799|-16.937|1.00 16.17|A|
|ATOM|1369|NH1|ARG|A|176|-13.264|1.720|-17.703|1.00 14.70|A|
|ATOM|1370|NH2|ARG|A|176|-14.223|2.102|-15.644|1.00 16.59|A|
|ATOM|1371|C|ARG|A|176|-18.026|0.146|-21.304|1.00 12.49|A|
|ATOM|1372|O|ARG|A|176|-18.629|-0.217|-20.380|1.00 13.08|A|
|ATOM|1373|N|LEU|A|177|-17.628|-0.684|-22.262|1.00 11.81|A|
|ATOM|1374|CA|LEU|A|177|-17.922|-2.105|-22.203|1.00 10.41|A|
|ATOM|1375|CB|LEU|A|177|-19.100|-2.440|-23.151|1.00 11.88|A|
|ATOM|1376|CG|LEU|A|177|-19.466|-3.935|-23.318|1.00 10.26|A|
|ATOM|1377|CD1|LEU|A|177|-20.967|-4.089|-23.579|1.00 13.42|A|
|ATOM|1378|CD2|LEU|A|177|-18.693|-4.547|-24.453|1.00 12.11|A|
|ATOM|1379|C|LEU|A|177|-16.685|-2.882|-22.630|1.00 11.58|A|
|ATOM|1380|O|LEU|A|177|-15.896|-2.415|-23.455|1.00 12.23|A|
|ATOM|1381|N|ALA|A|178|-16.524|-4.055|-22.029|1.00 10.67|A|
|ATOM|1382|CA|ALA|A|178|-15.417|-4.939|-22.349|1.00 11.62|A|
|ATOM|1383|CB|ALA|A|178|-14.417|-5.005|-21.178|1.00 11.64|A|
|ATOM|1384|C|ALA|A|178|-15.972|-6.330|-22.617|1.00 12.71|A|
|ATOM|1385|O|ALA|A|178|-16.842|-6.774|-21.876|1.00 12.95|A|
|ATOM|1386|N|VAL|A|179|-15.510|-7.003|-23.678|1.00 12.86|A|
|ATOM|1387|CA|VAL|A|179|-15.960|-8.374|-23.931|1.00 11.78|A|
|ATOM|1388|CB|VAL|A|179|-17.058|-8.434|-25.021|1.00 13.43|A|
|ATOM|1389|CG1|VAL|A|179|-16.623|-7.680|-26.291|1.00 13.32|A|
|ATOM|1390|CG2|VAL|A|179|-17.401|-9.905|-25.341|1.00 13.70|A|
|ATOM|1391|C|VAL|A|179|-14.771|-9.221|-24.330|1.00 12.02|A|
|ATOM|1392|O|VAL|A|179|-13.897|-8.750|-25.047|1.00 13.44|A|
|ATOM|1393|N|CYS|A|180|-14.736|-10.463|-23.853|1.00 11.67|A|
|ATOM|1394|CA|CYS|A|180|-13.611|-11.330|-24.205|1.00 12.63|A|
|ATOM|1395|CB|CYS|A|180|-12.567|-11.260|-23.107|1.00 12.65|A|
|ATOM|1396|SG|CYS|A|180|-11.064|-12.239|-23.457|1.00 16.29|A|
|ATOM|1397|C|CYS|A|180|-14.123|-12.752|-24.329|1.00 14.48|A|
|ATOM|1398|O|CYS|A|180|-14.900|-13.187|-23.487|1.00 14.59|A|
|ATOM|1399|N|SER|A|181|-13.722|-13.467|-25.379|1.00 14.95|A|
|ATOM|1400|CA|SER|A|181|-14.178|-14.859|-25.516|1.00 17.59|A|
|ATOM|1401|CB|SER|A|181|-15.229|-15.019|-26.640|1.00 20.93|A|
|ATOM|1402|OG|SER|A|181|-14.687|-14.808|-27.912|1.00 26.78|A|
|ATOM|1403|C|SER|A|181|-12.970|-15.726|-25.794|1.00 17.42|A|
|ATOM|1404|O|SER|A|181|-12.009|-15.274|-16.428|1.00 18.86|A|
|ATOM|1405|N|MET|A|182|-13.020|-16.953|-25.305|1.00 16.52|A|
|ATOM|1406|CA|MET|A|182|-11.929|-17.925|-25.453|1.00 17.26|A|
|ATOM|1407|CB|MET|A|182|-11.075|-17.953|-24.177|1.00 20.28|A|
|ATOM|1408|CG|MET|A|182|-10.358|-16.670|-23.853|1.00 22.98|A|
|ATOM|1409|SD|MET|A|182|-8.999|-16.391|-24.945|1.00 26.97|A|
|ATOM|1410|CE|MET|A|182|-7.746|-17.563|-24.206|1.00 26.51|A|
|ATOM|1411|C|MET|A|182|-12.489|-19.310|-25.681|1.00 18.28|A|
|ATOM|1412|O|MET|A|182|-13.421|-19.734|-25.022|1.00 17.56|A|
|ATOM|1413|N|PRO|A|183|-11.906|-20.056|-26.629|1.00 19.27|A|
|ATOM|1414|CD|PRO|A|183|-10.796|-19.620|-27.496|1.00 19.63|A|
|ATOM|1415|CA|PRO|A|183|-12.345|-21.411|-26.955|1.00 20.53|A|
|ATOM|1416|CB|PRO|A|183|-11.645|-21.677|-28.300|1.00 21.37|A|
|ATOM|1417|CG|PRO|A|183|-10.352|-20.944|-28.145|1.00 21.39|A|
|ATOM|1418|C|PRO|A|183|-11.899|-22.371|-25.856|1.00 21.32|A|
|ATOM|1419|O|PRO|A|183|-10.802|-22.220|-25.296|1.00 22.60|A|
|ATOM|1420|N|ILE|A|184|-12.748|-23.327|-25.517|1.00 21.08|A|
|ATOM|1421|CA|ILE|A|184|-12.345|-24.269|-24.494|1.00 23.29|A|
|ATOM|1422|CB|ILE|A|184|-13.118|-24.019|-23.185|1.00 22.91|A|
|ATOM|1423|CG2|ILE|A|184|-12.720|-22.669|-22.621|1.00 23.87|A|
|ATOM|1424|CG1|ILE|A|184|-14.624|-24.034|-23.439|1.00 22.45|A|
|ATOM|1425|CD1|ILE|A|184|-15.454|-23.874|-22.154|1.00 28.40|A|
|ATOM|1426|C|ILE|A|184|-12.427|-25.733|-24.928|1.00 23.80|A|
|ATOM|1427|O|ILE|A|184|-12.332|-26.637|-24.103|1.00 24.50|A|
|ATOM|1428|N|GLY|A|185|-12.597|-25.964|-26.225|1.00 26.05|A|
|ATOM|1429|CA|GLY|A|185|-12.600|-27.329|-26.740|1.00 25.71|A|
|ATOM|1430|C|GLY|A|185|-13.698|-28.288|-26.348|1.00 27.58|A|
|ATOM|1431|O|GLY|A|185|-13.512|-29.516|-26.410|1.00 27.68|A|
|ATOM|1432|N|GLN|A|186|-14.844|-27.738|-25.968|1.00 26.74|A|
|ATOM|1433|CA|GLN|A|186|-16.006|-28.518|-25.573|1.00 27.53|A|
|ATOM|1434|CB|GLN|A|186|-16.150|-28.518|-24.048|1.00 28.12|A|
|ATOM|1435|CG|GLN|A|186|-14.938|-29.039|-23.330|1.00 28.26|A|
|ATOM|1436|CD|GLN|A|186|-14.790|-28.436|-21.949|1.00 29.33|A|
|ATOM|1437|OE1|GLN|A|186|-15.532|-28.775|-21.025|1.00 28.19|A|
|ATOM|1438|NE2|GLN|A|186|-13.834|-27.525|-21.808|1.00 29.64|A|
|ATOM|1439|C|GLN|A|186|-17.217|-27.837|-26.192|1.00 27.94|A|
|ATOM|1440|O|GLN|A|186|-17.297|-26.613|-26.227|1.00 27.59|A|
|ATOM|1441|N|SER|A|187|-18.156|-28.632|-26.687|1.00 29.04|A|
|ATOM|1442|CA|SER|A|187|-19.368|-28.105|-27.290|1.00 28.26|A|
|ATOM|1443|CB|SER|A|187|-19.987|-29.173|-28.202|1.00 30.89|A|
|ATOM|1444|OG|SER|A|187|-21.163|-28.684|-28.826|1.00 35.18|A|
|ATOM|1445|C|SER|A|187|-20.294|-27.770|-26.120|1.00 27.81|A|
|ATOM|1446|O|SER|A|187|-20.650|-28.652|-25.339|1.00 28.41|A|
|ATOM|1447|N|LEU|A|188|-20.681|-26.502|-26.000|1.00 25.54|A|
|ATOM|1448|CA|LEU|A|188|-21.504|-26.055|-24.875|1.00 23.98|A|
|ATOM|1449|CB|LEU|A|188|-20.785|-24.911|-24.136|1.00 23.58|A|
|ATOM|1450|CG|LEU|A|188|-19.296|-25.012|-23.823|1.00 23.00|A|
|ATOM|1451|CD1|LEU|A|188|-18.653|-23.602|-23.655|1.00 22.33|A|
|ATOM|1452|CD2|LEU|A|188|-19.138|-25.849|-22.567|1.00 23.44|A|
|ATOM|1453|C|LEU|A|188|-22.883|-25.548|-25.235|1.00 24.43|A|
|ATOM|1454|O|LEU|A|188|-23.105|-25.040|-26.341|1.00 23.24|A|
|ATOM|1455|N|PRO|A|189|-23.843|-25.694|-24.308|1.00 24.44|A|
|ATOM|1456|CD|PRO|A|189|-23.775|-26.479|-23.057|1.00 26.09|A|
|ATOM|1457|CA|PRO|A|189|-25.204|-25.207|-24.547|1.00 24.88|A|
|ATOM|1458|CB|PRO|A|189|-26.014|-25.858|-23.420|1.00 26.37|A|
|ATOM|1459|CG|PRO|A|189|-25.007|-25.986|-22.303|1.00 25.65|A|
|ATOM|1460|C|PRO|A|189|-25.111|-23.687|-24.375|1.00 25.47|A|
|ATOM|1461|O|PRO|A|189|-24.212|-23.195|-23.668|1.00 24.66|A|
|ATOM|1462|N|SER|A|190|-26.019|-22.948|-25.005|1.00 25.63|A|
|ATOM|1463|CA|SER|A|190|-26.009|-21.492|-24.887|1.00 25.88|A|
|ATOM|1464|CB|SER|A|190|-26.878|-20.866|-25.960|1.00 26.21|A|
|ATOM|1465|OG|SER|A|190|-26.413|-21.232|-27.230|1.00 31.10|A|

```
ATOM   1466  C    SER A 190     -26.546 -21.121 -23.537  1.00 25.83           A
ATOM   1467  O    SER A 190     -27.690 -21.444 -23.194  1.00 26.64           A
ATOM   1468  N    HIS A 191     -25.741 -20.414 -22.757  1.00 24.59           A
ATOM   1469  CA   HIS A 191     -26.179 -20.046 -21.424  1.00 23.84           A
ATOM   1470  CB   HIS A 191     -25.761 -21.123 -20.433  1.00 28.01           A
ATOM   1471  CG   HIS A 191     -26.680 -21.250 -19.267  1.00 33.05           A
ATOM   1472  CD2  HIS A 191     -26.528 -20.901 -17.966  1.00 33.83           A
ATOM   1473  ND1  HIS A 191     -27.956 -21.759 -19.383  1.00 34.03           A
ATOM   1474  CE1  HIS A 191     -28.552 -21.716 -18.202  1.00 34.58           A
ATOM   1475  NE2  HIS A 191     -27.708 -21.200 -17.326  1.00 35.13           A
ATOM   1476  C    HIS A 191     -25.529 -18.727 -21.035  1.00 21.91           A
ATOM   1477  O    HIS A 191     -24.404 -18.450 -21.444  1.00 19.14           A
ATOM   1478  N    SER A 192     -26.236 -17.937 -20.238  1.00 18.95           A
ATOM   1479  CA   SER A 192     -25.741 -16.633 -19.821  1.00 19.59           A
ATOM   1480  CB   SER A 192     -26.394 -15.574 -20.743  1.00 22.50           A
ATOM   1481  OG   SER A 192     -26.222 -14.238 -20.342  1.00 27.62           A
ATOM   1482  C    SER A 192     -26.135 -16.407 -18.360  1.00 19.05           A
ATOM   1483  O    SER A 192     -27.304 -16.593 -18.004  1.00 21.16           A
ATOM   1484  N    VAL A 193     -25.165 -16.043 -17.524  1.00 16.50           A
ATOM   1485  CA   VAL A 193     -25.407 -15.734 -16.095  1.00 14.76           A
ATOM   1486  CB   VAL A 193     -25.093 -16.937 -15.138  1.00 13.63           A
ATOM   1487  CG1  VAL A 193     -25.999 -18.109 -15.494  1.00 17.20           A
ATOM   1488  CG2  VAL A 193     -23.620 -17.348 -15.216  1.00 15.41           A
ATOM   1489  C    VAL A 193     -24.538 -14.560 -15.664  1.00 14.41           A
ATOM   1490  O    VAL A 193     -23.516 -14.254 -16.291  1.00 12.96           A
ATOM   1491  N    ILE A 194     -24.958 -13.886 -14.607  1.00 12.61           A
ATOM   1492  CA   ILE A 194     -24.252 -12.716 -14.085  1.00 11.47           A
ATOM   1493  CB   ILE A 194     -25.213 -11.508 -13.867  1.00 12.39           A
ATOM   1494  CG2  ILE A 194     -24.396 -10.299 -13.430  1.00 12.88           A
ATOM   1495  CG1  ILE A 194     -25.983 -11.198 -15.146  1.00 14.24           A
ATOM   1496  CD1  ILE A 194     -27.031 -10.095 -14.967  1.00 17.17           A
ATOM   1497  C    ILE A 194     -23.660 -13.080 -12.736  1.00 13.07           A
ATOM   1498  O    ILE A 194     -24.376 -13.466 -11.803  1.00 13.64           A
ATOM   1499  N    VAL A 195     -22.336 -13.004 -12.632  1.00 12.90           A
ATOM   1500  CA   VAL A 195     -21.654 -13.314 -11.385  1.00 14.01           A
ATOM   1501  CB   VAL A 195     -20.301 -14.008 -11.696  1.00 15.92           A
ATOM   1502  CG1  VAL A 195     -19.560 -14.344 -10.413  1.00 14.56           A
ATOM   1503  CG2  VAL A 195     -20.545 -15.287 -12.497  1.00 13.57           A
ATOM   1504  C    VAL A 195     -21.424 -11.989 -10.641  1.00 13.97           A
ATOM   1505  O    VAL A 195     -20.949 -11.041 -11.214  1.00 14.63           A
ATOM   1506  N    PRO A 196     -21.783 -11.915  -9.351  1.00 15.51           A
ATOM   1507  CD   PRO A 196     -22.324 -12.986  -8.492  1.00 16.27           A
ATOM   1508  CA   PRO A 196     -21.573 -10.657  -8.622  1.00 16.07           A
ATOM   1509  CB   PRO A 196     -22.178 -10.929  -7.241  1.00 17.85           A
ATOM   1510  CG   PRO A 196     -22.132 -12.418  -7.098  1.00 18.14           A
ATOM   1511  C    PRO A 196     -20.114 -10.220  -8.553  1.00 16.89           A
ATOM   1512  O    PRO A 196     -19.202 -11.051  -8.543  1.00 15.71           A
ATOM   1513  N    ARG A 197     -19.868  -8.916  -8.473  1.00 17.07           A
ATOM   1514  CA   ARG A 197     -18.470  -8.494  -8.456  1.00 19.18           A
ATOM   1515  CB   ARG A 197     -18.351  -6.965  -8.477  1.00 23.00           A
ATOM   1516  CG   ARG A 197     -19.035  -6.236  -7.375  1.00 26.04           A
ATOM   1517  CD   ARG A 197     -18.680  -4.725  -7.481  1.00 28.79           A
ATOM   1518  NE   ARG A 197     -17.228  -4.495  -7.441  1.00 32.92           A
ATOM   1519  CZ   ARG A 197     -16.496  -4.048  -8.463  1.00 34.73           A
ATOM   1520  NH1  ARG A 197     -17.059  -3.761  -9.628  1.00 36.57           A
ATOM   1521  NH2  ARG A 197     -15.185  -3.905  -8.329  1.00 37.08           A
ATOM   1522  C    ARG A 197     -17.590  -9.107  -7.376  1.00 18.61           A
ATOM   1523  O    ARG A 197     -16.447  -9.437  -7.645  1.00 19.10           A
ATOM   1524  N    LYS A 198     -18.106  -9.310  -6.165  1.00 19.11           A
ATOM   1525  CA   LYS A 198     -17.295  -9.924  -5.130  1.00 21.70           A
ATOM   1526  CB   LYS A 198     -18.032  -9.861  -3.790  1.00 24.75           A
ATOM   1527  CG   LYS A 198     -17.243 -10.408  -2.616  1.00 30.79           A
ATOM   1528  CD   LYS A 198     -17.904  -9.948  -1.300  1.00 32.84           A
ATOM   1529  CE   LYS A 198     -17.265 -10.606  -0.086  1.00 35.71           A
ATOM   1530  NZ   LYS A 198     -17.913 -10.169   1.206  1.00 35.61           A
ATOM   1531  C    LYS A 198     -16.943 -11.377  -5.492  1.00 20.89           A
ATOM   1532  O    LYS A 198     -15.864 -11.885  -5.152  1.00 21.60           A
ATOM   1533  N    GLY A 199     -17.844 -12.052  -6.205  1.00 19.66           A
ATOM   1534  CA   GLY A 199     -17.583 -13.421  -6.613  1.00 18.99           A
ATOM   1535  C    GLY A 199     -16.488 -13.483  -7.678  1.00 17.60           A
ATOM   1536  O    GLY A 199     -15.678 -14.406  -7.751  1.00 18.00           A
ATOM   1537  N    VAL A 200     -16.492 -12.486  -8.553  1.00 18.22           A
ATOM   1538  CA   VAL A 200     -15.498 -12.422  -9.610  1.00 16.49           A
ATOM   1539  CB   VAL A 200     -15.780 -11.199 -10.534  1.00 15.63           A
ATOM   1540  CG1  VAL A 200     -14.604 -11.013 -11.522  1.00 16.76           A
ATOM   1541  CG2  VAL A 200     -17.104 -11.417 -11.287  1.00 17.52           A
ATOM   1542  C    VAL A 200     -14.097 -12.289  -8.978  1.00 18.83           A
ATOM   1543  O    VAL A 200     -13.138 -12.928  -9.425  1.00 19.59           A
ATOM   1544  N    ILE A 201     -14.002 -11.465  -7.937  1.00 21.69           A
ATOM   1545  CA   ILE A 201     -12.735 -11.240  -7.220  1.00 24.32           A
ATOM   1546  CB   ILE A 201     -12.897 -10.278  -6.026  1.00 26.86           A
ATOM   1547  CG2  ILE A 201     -11.547 -10.101  -5.327  1.00 28.23           A
ATOM   1548  CG1  ILE A 201     -13.504  -8.954  -6.471  1.00 28.44           A
ATOM   1549  CD1  ILE A 201     -13.047  -8.463  -7.799  1.00 29.79           A
ATOM   1550  C    ILE A 201     -12.227 -12.531  -6.619  1.00 24.50           A
ATOM   1551  O    ILE A 201     -11.042 -12.872  -6.721  1.00 24.04           A
ATOM   1552  N    GLU A 202     -13.141 -13.234  -5.971  1.00 26.55           A
ATOM   1553  CA   GLU A 202     -12.854 -14.491  -5.319  1.00 29.06           A
ATOM   1554  CB   GLU A 202     -14.113 -14.972  -4.574  1.00 32.98           A
ATOM   1555  CG   GLU A 202     -13.831 -15.705  -3.291  1.00 36.13           A
ATOM   1556  CD   GLU A 202     -12.688 -15.076  -2.521  1.00 38.29           A
ATOM   1557  OE1  GLU A 202     -12.804 -13.893  -2.097  1.00 38.50           A
ATOM   1558  OE2  GLU A 202     -11.665 -15.777  -2.356  1.00 39.57           A
ATOM   1559  C    GLU A 202     -12.405 -15.522  -6.346  1.00 29.53           A
ATOM   1560  O    GLU A 202     -11.447 -16.263  -6.117  1.00 29.66           A
ATOM   1561  N    LEU A 203     -13.080 -15.573  -7.490  1.00 28.27           A
ATOM   1562  CA   LEU A 203     -12.706 -16.519  -8.529  1.00 28.89           A
ATOM   1563  CB   LEU A 203     -13.595 -16.352  -9.761  1.00 31.21           A
ATOM   1564  CG   LEU A 203     -14.700 -17.368 -10.014  1.00 31.78           A
ATOM   1565  CD1  LEU A 203     -15.388 -17.044 -11.313  1.00 30.83           A
```

Figure 1 (continued 16)

| | | | | | | | | | |
|---|---|---|---|---|---|---|---|---|---|
| ATOM | 1566 | CD2 | LEU | A | 203 | -14.090 | -18.768 | -10.061 | 1.00 32.03 | A |
| ATOM | 1567 | C | LEU | A | 203 | -11.260 | -16.256 | -8.929 | 1.00 29.61 | A |
| ATOM | 1568 | O | LEU | A | 203 | -10.459 | -17.171 | -9.072 | 1.00 27.41 | A |
| ATOM | 1569 | N | MET | A | 204 | -10.951 | -14.984 | -9.134 | 1.00 28.89 | A |
| ATOM | 1570 | CA | MET | A | 204 | -9.615 | -14.578 | -9.514 | 1.00 31.07 | A |
| ATOM | 1571 | CB | MET | A | 204 | -9.589 | -13.048 | -9.635 | 1.00 32.20 | A |
| ATOM | 1572 | CG | MET | A | 204 | -8.538 | -12.491 | -10.565 | 1.00 36.14 | A |
| ATOM | 1573 | SD | MET | A | 204 | -8.637 | -13.238 | -12.199 | 1.00 37.25 | A |
| ATOM | 1574 | CE | MET | A | 204 | -7.159 | -14.209 | -12.153 | 1.00 38.24 | A |
| ATOM | 1575 | C | MET | A | 204 | -8.599 | -15.060 | -8.463 | 1.00 32.05 | A |
| ATOM | 1576 | O | MET | A | 204 | -7.545 | -15.592 | -8.813 | 1.00 31.41 | A |
| ATOM | 1577 | N | ARG | A | 205 | -8.936 | -14.905 | -7.182 | 1.00 33.59 | A |
| ATOM | 1578 | CA | ARG | A | 205 | -8.040 | -15.287 | -6.071 | 1.00 36.58 | A |
| ATOM | 1579 | CB | ARG | A | 205 | -8.659 | -14.940 | -4.707 | 1.00 38.43 | A |
| ATOM | 1580 | CG | ARG | A | 205 | -9.093 | -13.505 | -4.521 | 1.00 42.16 | A |
| ATOM | 1581 | CD | ARG | A | 205 | -7.928 | -12.549 | -4.307 | 1.00 45.61 | A |
| ATOM | 1582 | NE | ARG | A | 205 | -8.409 | -11.165 | -4.316 | 1.00 47.97 | A |
| ATOM | 1583 | CZ | ARG | A | 205 | -7.674 | -10.093 | -4.029 | 1.00 48.71 | A |
| ATOM | 1584 | NH1 | ARG | A | 205 | -6.392 | -10.219 | -3.694 | 1.00 49.29 | A |
| ATOM | 1585 | NH2 | ARG | A | 205 | -8.227 | -8.886 | -4.092 | 1.00 49.19 | A |
| ATOM | 1586 | C | ARG | A | 205 | -7.643 | -16.752 | -6.002 | 1.00 37.14 | A |
| ATOM | 1587 | O | ARG | A | 205 | -6.571 | -17.088 | -5.492 | 1.00 37.07 | A |
| ATOM | 1588 | N | MET | A | 206 | -8.496 | -17.641 | -6.482 | 1.00 37.50 | A |
| ATOM | 1589 | CA | MET | A | 206 | -8.162 | -19.049 | -6.380 | 1.00 39.03 | A |
| ATOM | 1590 | CB | MET | A | 206 | -9.435 | -19.869 | -6.144 | 1.00 39.34 | A |
| ATOM | 1591 | CG | MET | A | 206 | -10.340 | -19.984 | -7.341 | 1.00 39.33 | A |
| ATOM | 1592 | SD | MET | A | 206 | -11.995 | -20.514 | -6.838 | 1.00 39.83 | A |
| ATOM | 1593 | CE | MET | A | 206 | -11.592 | -22.096 | -5.995 | 1.00 37.83 | A |
| ATOM | 1594 | C | MET | A | 206 | -7.403 | -19.572 | -7.587 | 1.00 40.42 | A |
| ATOM | 1595 | O | MET | A | 206 | -7.071 | -20.759 | -7.657 | 1.00 39.42 | A |
| ATOM | 1596 | N | LEU | A | 207 | -7.117 | -18.686 | -8.534 | 1.00 41.79 | A |
| ATOM | 1597 | CA | LEU | A | 207 | -6.403 | -19.081 | -9.744 | 1.00 45.36 | A |
| ATOM | 1598 | CB | LEU | A | 207 | -6.972 | -18.329 | -10.955 | 1.00 45.10 | A |
| ATOM | 1599 | CG | LEU | A | 207 | -8.187 | -18.866 | -11.721 | 1.00 46.04 | A |
| ATOM | 1600 | CD1 | LEU | A | 207 | -9.219 | -19.475 | -10.799 | 1.00 45.64 | A |
| ATOM | 1601 | CD2 | LEU | A | 207 | -8.791 | -17.719 | -12.517 | 1.00 46.42 | A |
| ATOM | 1602 | C | LEU | A | 207 | -4.903 | -18.814 | -9.629 | 1.00 47.44 | A |
| ATOM | 1603 | O | LEU | A | 207 | -4.487 | -17.670 | -9.432 | 1.00 48.80 | A |
| ATOM | 1604 | N | ASP | A | 208 | -4.103 | -19.869 | -9.761 | 1.00 49.36 | A |
| ATOM | 1605 | CA | ASP | A | 208 | -2.648 | -19.759 | -9.681 | 1.00 51.16 | A |
| ATOM | 1606 | CB | ASP | A | 208 | -2.126 | -20.579 | -8.504 | 1.00 52.20 | A |
| ATOM | 1607 | CG | ASP | A | 208 | -2.697 | -20.119 | -7.180 | 1.00 54.01 | A |
| ATOM | 1608 | OD1 | ASP | A | 208 | -2.638 | -18.896 | -6.906 | 1.00 54.78 | A |
| ATOM | 1609 | OD2 | ASP | A | 208 | -3.198 | -20.978 | -6.412 | 1.00 53.95 | A |
| ATOM | 1610 | C | ASP | A | 208 | -1.954 | -20.215 | -10.967 | 1.00 51.89 | A |
| ATOM | 1611 | O | ASP | A | 208 | -0.786 | -20.611 | -10.950 | 1.00 52.13 | A |
| ATOM | 1612 | N | GLY | A | 209 | -2.689 | -20.168 | -12.076 | 1.00 52.31 | A |
| ATOM | 1613 | CA | GLY | A | 209 | -2.144 | -20.552 | -13.366 | 1.00 52.06 | A |
| ATOM | 1614 | C | GLY | A | 209 | -1.567 | -21.948 | -13.502 | 1.00 52.17 | A |
| ATOM | 1615 | O | GLY | A | 209 | -0.961 | -22.254 | -14.533 | 1.00 52.89 | A |
| ATOM | 1616 | N | GLY | A | 210 | -1.737 | -22.795 | -12.488 | 1.00 51.34 | A |
| ATOM | 1617 | CA | GLY | A | 210 | -1.215 | -24.152 | -12.566 | 1.00 50.65 | A |
| ATOM | 1618 | C | GLY | A | 210 | -1.779 | -24.891 | -13.769 | 1.00 49.99 | A |
| ATOM | 1619 | O | GLY | A | 210 | -2.751 | -24.435 | -14.367 | 1.00 49.83 | A |
| ATOM | 1620 | N | ASP | A | 211 | -1.180 | -26.023 | -14.135 | 1.00 49.29 | A |
| ATOM | 1621 | CA | ASP | A | 211 | -1.656 | -26.803 | -15.283 | 1.00 48.42 | A |
| ATOM | 1622 | CB | ASP | A | 211 | -0.602 | -27.833 | -15.701 | 1.00 49.93 | A |
| ATOM | 1623 | CG | ASP | A | 211 | 0.655 | -27.184 | -16.261 | 1.00 51.04 | A |
| ATOM | 1624 | OD1 | ASP | A | 211 | 0.568 | -26.549 | -17.334 | 1.00 52.21 | A |
| ATOM | 1625 | OD2 | ASP | A | 211 | 1.725 | -27.303 | -15.627 | 1.00 52.08 | A |
| ATOM | 1626 | C | ASP | A | 211 | -2.953 | -27.508 | -14.910 | 1.00 47.33 | A |
| ATOM | 1627 | O | ASP | A | 211 | -3.642 | -28.077 | -15.759 | 1.00 47.11 | A |
| ATOM | 1628 | N | ASN | A | 212 | -3.247 | -27.442 | -13.616 | 1.00 45.10 | A |
| ATOM | 1629 | CA | ASN | A | 212 | -4.425 | -28.013 | -12.974 | 1.00 43.75 | A |
| ATOM | 1630 | CB | ASN | A | 212 | -4.245 | -27.801 | -11.463 | 1.00 44.05 | A |
| ATOM | 1631 | CG | ASN | A | 212 | -5.009 | -28.795 | -10.619 | 1.00 45.06 | A |
| ATOM | 1632 | OD1 | ASN | A | 212 | -4.957 | -28.731 | -9.387 | 1.00 44.49 | A |
| ATOM | 1633 | ND2 | ASN | A | 212 | -5.715 | -29.722 | -11.263 | 1.00 45.44 | A |
| ATOM | 1634 | C | ASN | A | 212 | -5.653 | -27.237 | -13.497 | 1.00 41.13 | A |
| ATOM | 1635 | O | ASN | A | 212 | -5.779 | -26.045 | -13.252 | 1.00 42.29 | A |
| ATOM | 1636 | N | PRO | A | 213 | -6.573 | -27.899 | -14.221 | 1.00 38.67 | A |
| ATOM | 1637 | CD | PRO | A | 213 | -6.625 | -29.292 | -14.698 | 1.00 38.16 | A |
| ATOM | 1638 | CA | PRO | A | 213 | -7.731 | -27.143 | -14.716 | 1.00 35.46 | A |
| ATOM | 1639 | CB | PRO | A | 213 | -8.264 | -28.026 | -15.829 | 1.00 36.69 | A |
| ATOM | 1640 | CG | PRO | A | 213 | -8.037 | -29.389 | -15.267 | 1.00 38.80 | A |
| ATOM | 1641 | C | PRO | A | 213 | -8.806 | -26.834 | -13.686 | 1.00 32.37 | A |
| ATOM | 1642 | O | PRO | A | 213 | -8.897 | -27.468 | -12.635 | 1.00 32.62 | A |
| ATOM | 1643 | N | LEU | A | 214 | -9.622 | -25.840 | -14.013 | 1.00 29.01 | A |
| ATOM | 1644 | CA | LEU | A | 214 | -10.734 | -25.415 | -13.172 | 1.00 26.42 | A |
| ATOM | 1645 | CB | LEU | A | 214 | -10.934 | -23.896 | -13.338 | 1.00 27.73 | A |
| ATOM | 1646 | CG | LEU | A | 214 | -12.055 | -23.149 | -12.622 | 1.00 29.04 | A |
| ATOM | 1647 | CD1 | LEU | A | 214 | -11.718 | -23.086 | -11.170 | 1.00 31.24 | A |
| ATOM | 1648 | CD2 | LEU | A | 214 | -12.194 | -21.719 | -13.164 | 1.00 29.62 | A |
| ATOM | 1649 | C | LEU | A | 214 | -11.979 | -26.163 | -13.663 | 1.00 24.15 | A |
| ATOM | 1650 | O | LEU | A | 214 | -12.179 | -26.296 | -14.867 | 1.00 23.32 | A |
| ATOM | 1651 | N | ARG | A | 215 | -12.803 | -26.670 | -12.751 | 1.00 20.02 | A |
| ATOM | 1652 | CA | ARG | A | 215 | -14.025 | -27.355 | -13.139 | 1.00 20.46 | A |
| ATOM | 1653 | CB | ARG | A | 215 | -14.132 | -28.715 | -12.415 | 1.00 25.18 | A |
| ATOM | 1654 | CG | ARG | A | 215 | -12.876 | -29.577 | -12.626 | 1.00 31.55 | A |
| ATOM | 1655 | CD | ARG | A | 215 | -13.031 | -31.025 | -12.142 | 1.00 37.20 | A |
| ATOM | 1656 | NE | ARG | A | 215 | -13.414 | -31.946 | -13.221 | 1.00 42.35 | A |
| ATOM | 1657 | CZ | ARG | A | 215 | -14.626 | -32.003 | -13.779 | 1.00 44.98 | A |
| ATOM | 1658 | NH1 | ARG | A | 215 | -15.597 | -31.192 | -13.360 | 1.00 46.39 | A |
| ATOM | 1659 | NH2 | ARG | A | 215 | -14.871 | -32.862 | -14.771 | 1.00 44.99 | A |
| ATOM | 1660 | C | ARG | A | 215 | -15.158 | -26.422 | -12.724 | 1.00 18.21 | A |
| ATOM | 1661 | O | ARG | A | 215 | -15.280 | -26.064 | -11.564 | 1.00 18.66 | A |
| ATOM | 1662 | N | VAL | A | 216 | -15.978 | -26.026 | -13.682 | 1.00 15.42 | A |
| ATOM | 1663 | CA | VAL | A | 216 | -17.061 | -25.082 | -13.410 | 1.00 15.50 | A |
| ATOM | 1664 | CB | VAL | A | 216 | -16.988 | -23.890 | -14.404 | 1.00 14.33 | A |
| ATOM | 1665 | CG1 | VAL | A | 216 | -18.154 | -22.945 | -14.149 | 1.00 16.88 | A |

Figure 1 (continued 17)

| | | | | | | | | | |
|---|---|---|---|---|---|---|---|---|---|
|ATOM|1666|CG2|VAL|A|216|-15.661|-23.199|-14.269|1.00 16.10 A|
|ATOM|1667|C|VAL|A|216|-18.420|-25.727|-13.568|1.00 15.31 A|
|ATOM|1668|O|VAL|A|216|-18.641|-26.525|-14.488|1.00 18.21 A|
|ATOM|1669|N|GLN|A|217|-19.347|-25.373|-12.680|1.00 15.12 A|
|ATOM|1670|CA|GLN|A|217|-20.696|-25.879|-12.745|1.00 16.55 A|
|ATOM|1671|CB|GLN|A|217|-21.001|-26.859|-11.607|1.00 17.03 A|
|ATOM|1672|CG|GLN|A|217|-20.322|-28.182|-11.686|1.00 17.24 A|
|ATOM|1673|CD|GLN|A|217|-20.607|-29.052|-10.445|1.00 19.83 A|
|ATOM|1674|OE1|GLN|A|217|-20.179|-28.723|-9.334|1.00 24.23 A|
|ATOM|1675|NE2|GLN|A|217|-21.341|-30.150|-10.636|1.00 22.05 A|
|ATOM|1676|C|GLN|A|217|-21.590|-24.655|-12.596|1.00 16.13 A|
|ATOM|1677|O|GLN|A|217|-21.412|-23.872|-11.675|1.00 16.81 A|
|ATOM|1678|N|ILE|A|218|-22.543|-24.485|-13.510|1.00 16.16 A|
|ATOM|1679|CA|ILE|A|218|-23.457|-23.338|-13.436|1.00 14.93 A|
|ATOM|1680|CB|ILE|A|218|-23.312|-22.443|-14.721|1.00 17.67 A|
|ATOM|1681|CG2|ILE|A|218|-24.342|-21.285|-14.709|1.00 19.90 A|
|ATOM|1682|CG1|ILE|A|218|-21.885|-21.891|-14.797|1.00 18.86 A|
|ATOM|1683|CD1|ILE|A|218|-21.559|-21.069|-16.069|1.00 20.21 A|
|ATOM|1684|C|ILE|A|218|-24.895|-23.824|-13.317|1.00 15.21 A|
|ATOM|1685|O|ILE|A|218|-25.327|-24.690|-14.080|1.00 17.78 A|
|ATOM|1686|N|GLY|A|219|-25.622|-23.261|-12.357|1.00 16.39 A|
|ATOM|1687|CA|GLY|A|219|-27.028|-23.573|-12.144|1.00 17.69 A|
|ATOM|1688|C|GLY|A|219|-27.886|-22.361|-12.487|1.00 19.32 A|
|ATOM|1689|O|GLY|A|219|-27.381|-21.370|-12.982|1.00 20.27 A|
|ATOM|1690|N|SER|A|220|-29.188|-22.425|-12.243|1.00 20.22 A|
|ATOM|1691|CA|SER|A|220|-30.033|-21.285|-12.570|1.00 21.44 A|
|ATOM|1692|CB|SER|A|220|-31.498|-21.655|-12.409|1.00 22.40 A|
|ATOM|1693|OG|SER|A|220|-31.780|-22.064|-11.071|1.00 25.42 A|
|ATOM|1694|C|SER|A|220|-29.741|-20.079|-11.690|1.00 21.28 A|
|ATOM|1695|O|SER|A|220|-29.925|-18.935|-12.113|1.00 20.79 A|
|ATOM|1696|N|ASN|A|221|-29.283|-20.337|-10.470|1.00 19.85 A|
|ATOM|1697|CA|ASN|A|221|-29.033|-19.257|-9.523|1.00 20.14 A|
|ATOM|1698|CB|ASN|A|221|-30.174|-19.212|-8.498|1.00 23.10 A|
|ATOM|1699|CG|ASN|A|221|-31.536|-18.962|-9.162|1.00 26.82 A|
|ATOM|1700|OD1|ASN|A|221|-32.207|-19.897|-9.622|1.00 31.73 A|
|ATOM|1701|ND2|ASN|A|221|-31.927|-17.700|-9.245|1.00 27.82 A|
|ATOM|1702|C|ASN|A|221|-27.704|-19.312|-8.798|1.00 17.29 A|
|ATOM|1703|O|ASN|A|221|-27.487|-18.567|-7.845|1.00 16.83 A|
|ATOM|1704|N|ASN|A|222|-26.814|-20.188|-9.249|1.00 16.78 A|
|ATOM|1705|CA|ASN|A|222|-25.523|-20.398|-8.582|1.00 15.72 A|
|ATOM|1706|CB|ASN|A|222|-25.543|-21.424|-7.526|1.00 18.61 A|
|ATOM|1707|CG|ASN|A|222|-26.571|-21.310|-6.432|1.00 20.68 A|
|ATOM|1708|OD1|ASN|A|222|-27.756|-21.491|-6.615|1.00 22.08 A|
|ATOM|1709|ND2|ASN|A|222|-26.125|-20.705|-5.297|1.00 23.78 A|
|ATOM|1710|C|ASN|A|222|-24.439|-20.686|-9.564|1.00 13.83 A|
|ATOM|1711|O|ASN|A|222|-24.736|-21.188|-10.637|1.00 14.52 A|
|ATOM|1712|N|ILE|A|223|-23.170|-20.449|-9.191|1.00 12.97 A|
|ATOM|1713|CA|ILE|A|223|-22.034|-20.910|-10.008|1.00 13.44 A|
|ATOM|1714|CB|ILE|A|223|-21.357|-19.742|-10.831|1.00 12.76 A|
|ATOM|1715|CG2|ILE|A|223|-20.893|-18.636|-9.884|1.00 13.49 A|
|ATOM|1716|CG1|ILE|A|223|-20.166|-20.277|-11.648|1.00 13.07 A|
|ATOM|1717|CD1|ILE|A|223|-19.880|-19.360|-12.824|1.00 15.33 A|
|ATOM|1718|C|ILE|A|223|-21.027|-21.498|-8.989|1.00 13.40 A|
|ATOM|1719|O|ILE|A|223|-20.880|-20.994|-7.866|1.00 13.37 A|
|ATOM|1720|N|ARG|A|224|-20.373|-22.578|-9.388|1.00 12.68 A|
|ATOM|1721|CA|ARG|A|224|-19.398|-23.229|-8.544|1.00 13.73 A|
|ATOM|1722|CB|ARG|A|224|-19.948|-24.578|-8.058|1.00 16.50 A|
|ATOM|1723|CG|ARG|A|224|-18.928|-25.397|-7.280|1.00 18.24 A|
|ATOM|1724|CD|ARG|A|224|-19.612|-26.522|-6.521|1.00 21.35 A|
|ATOM|1725|NE|ARG|A|224|-20.401|-25.965|-5.432|1.00 23.07 A|
|ATOM|1726|CZ|ARG|A|224|-21.253|-26.655|-4.680|1.00 25.49 A|
|ATOM|1727|NH1|ARG|A|224|-21.440|-27.954|-4.897|1.00 27.26 A|
|ATOM|1728|NH2|ARG|A|224|-21.935|-26.039|-3.721|1.00 27.55 A|
|ATOM|1729|C|ARG|A|224|-18.152|-23.471|-9.370|1.00 13.92 A|
|ATOM|1730|O|ARG|A|224|-18.217|-23.780|-10.567|1.00 13.44 A|
|ATOM|1731|N|ALA|A|225|-17.014|-23.302|-8.723|1.00 13.45 A|
|ATOM|1732|CA|ALA|A|225|-15.738|-23.582|-9.362|1.00 15.31 A|
|ATOM|1733|CB|ALA|A|225|-15.027|-22.310|-9.670|1.00 16.60 A|
|ATOM|1734|C|ALA|A|225|-14.892|-24.435|-8.419|1.00 16.41 A|
|ATOM|1735|O|ALA|A|225|-14.763|-24.128|-7.236|1.00 15.00 A|
|ATOM|1736|N|HIS|A|226|-14.310|-25.501|-8.961|1.00 17.50 A|
|ATOM|1737|CA|HIS|A|226|-13.467|-26.417|-8.187|1.00 19.53 A|
|ATOM|1738|CB|HIS|A|226|-13.896|-27.882|-8.433|1.00 23.40 A|
|ATOM|1739|CG|HIS|A|226|-15.351|-28.163|-8.216|1.00 24.26 A|
|ATOM|1740|CD2|HIS|A|226|-16.444|-27.890|-8.972|1.00 26.04 A|
|ATOM|1741|ND1|HIS|A|226|-15.813|-28.853|-7.111|1.00 26.55 A|
|ATOM|1742|CE1|HIS|A|226|-17.123|-28.994|-7.194|1.00 26.31 A|
|ATOM|1743|NE2|HIS|A|226|-17.532|-28.420|-8.314|1.00 27.11 A|
|ATOM|1744|C|HIS|A|226|-12.027|-26.291|-8.703|1.00 22.32 A|
|ATOM|1745|O|HIS|A|226|-11.794|-26.492|-9.899|1.00 21.45 A|
|ATOM|1746|N|VAL|A|227|-11.077|-25.951|-7.832|1.00 22.02 A|
|ATOM|1747|CA|VAL|A|227|-9.660|-25.869|-8.218|1.00 26.25 A|
|ATOM|1748|CB|VAL|A|227|-9.119|-24.414|-8.243|1.00 28.90 A|
|ATOM|1749|CG1|VAL|A|227|-7.857|-24.334|-9.076|1.00 30.53 A|
|ATOM|1750|CG2|VAL|A|227|-10.153|-23.489|-8.788|1.00 31.33 A|
|ATOM|1751|C|VAL|A|227|-8.813|-26.600|-7.121|1.00 26.06 A|
|ATOM|1752|O|VAL|A|227|-8.965|-26.192|-5.963|1.00 25.67 A|
|ATOM|1753|N|GLY|A|228|-8.197|-27.651|-7.480|1.00 25.91 A|
|ATOM|1754|CA|GLY|A|228|-7.468|-28.410|-6.478|1.00 24.98 A|
|ATOM|1755|C|GLY|A|228|-8.417|-28.855|-5.381|1.00 24.00 A|
|ATOM|1756|O|GLY|A|228|-9.469|-29.398|-5.671|1.00 24.36 A|
|ATOM|1757|N|ASP|A|229|-8.079|-28.595|-4.126|1.00 22.64 A|
|ATOM|1758|CA|ASP|A|229|-8.973|-29.011|-3.059|1.00 22.40 A|
|ATOM|1759|CB|ASP|A|229|-8.214|-28.766|-1.989|1.00 24.16 A|
|ATOM|1760|CG|ASP|A|229|-7.531|-31.019|-2.540|1.00 26.13 A|
|ATOM|1761|OD1|ASP|A|229|-8.128|-31.718|-3.399|1.00 27.09 A|
|ATOM|1762|OD2|ASP|A|229|-6.395|-31.293|-2.106|1.00 28.22 A|
|ATOM|1763|C|ASP|A|229|-9.760|-27.837|-2.470|1.00 21.77 A|
|ATOM|1764|O|ASP|A|229|-10.066|-27.791|-1.262|1.00 23.00 A|
|ATOM|1765|N|PHE|A|230|-10.049|-26.873|-3.334|1.00 20.12 A|

Figure 1 (continued 18)

```
ATOM   1766  CA   PHE A 230     -10.841 -25.701  -2.949  1.00 20.28      A
ATOM   1767  CB   PHE A 230     -10.082 -24.407  -3.238  1.00 20.97      A
ATOM   1768  CG   PHE A 230      -8.878 -24.208  -2.391  1.00 25.22      A
ATOM   1769  CD1  PHE A 230      -8.991 -23.676  -1.118  1.00 26.34      A
ATOM   1770  CD2  PHE A 230      -7.621 -24.553  -2.865  1.00 27.57      A
ATOM   1771  CE1  PHE A 230      -7.854 -23.486  -0.322  1.00 26.07      A
ATOM   1772  CE2  PHE A 230      -6.474 -24.365  -2.071  1.00 28.73      A
ATOM   1773  CZ   PHE A 230      -6.607 -23.828  -0.800  1.00 25.38      A
ATOM   1774  C    PHE A 230     -12.113 -25.691  -3.786  1.00 19.64      A
ATOM   1775  O    PHE A 230     -12.101 -26.056  -4.975  1.00 18.35      A
ATOM   1776  N    ILE A 231     -13.221 -25.307  -3.156  1.00 16.55      A
ATOM   1777  CA   ILE A 231     -14.492 -25.232  -3.873  1.00 16.98      A
ATOM   1778  CB   ILE A 231     -15.467 -26.329  -3.471  1.00 16.59      A
ATOM   1779  CG2  ILE A 231     -16.784 -26.149  -4.274  1.00 16.05      A
ATOM   1780  CG1  ILE A 231     -14.856 -27.717  -3.733  1.00 18.23      A
ATOM   1781  CD1  ILE A 231     -15.848 -28.868  -3.521  1.00 21.86      A
ATOM   1782  C    ILE A 231     -15.136 -23.900  -3.555  1.00 17.85      A
ATOM   1783  O    ILE A 231     -15.429 -23.581  -2.379  1.00 18.50      A
ATOM   1784  N    PHE A 232     -15.326 -23.109  -4.609  1.00 15.87      A
ATOM   1785  CA   PHE A 232     -15.943 -21.804  -4.487  1.00 15.49      A
ATOM   1786  CB   PHE A 232     -15.150 -20.771  -5.281  1.00 15.94      A
ATOM   1787  CG   PHE A 232     -15.792 -19.429  -5.269  1.00 18.31      A
ATOM   1788  CD1  PHE A 232     -15.921 -18.748  -4.066  1.00 20.92      A
ATOM   1789  CD2  PHE A 232     -16.283 -18.871  -6.431  1.00 20.41      A
ATOM   1790  CE1  PHE A 232     -16.539 -17.502  -4.018  1.00 21.57      A
ATOM   1791  CE2  PHE A 232     -16.915 -17.599  -6.399  1.00 19.94      A
ATOM   1792  CZ   PHE A 232     -17.032 -16.929  -5.200  1.00 21.00      A
ATOM   1793  C    PHE A 232     -17.349 -21.836  -5.060  1.00 14.79      A
ATOM   1794  O    PHE A 232     -17.556 -22.351  -6.142  1.00 14.73      A
ATOM   1795  N    THR A 233     -18.317 -21.261  -4.337  1.00 13.80      A
ATOM   1796  CA   THR A 233     -19.683 -21.214  -4.858  1.00 14.57      A
ATOM   1797  CB   THR A 233     -20.616 -22.226  -4.151  1.00 16.94      A
ATOM   1798  OG1  THR A 233     -20.009 -23.517  -4.157  1.00 17.68      A
ATOM   1799  CG2  THR A 233     -21.972 -22.310  -4.883  1.00 17.95      A
ATOM   1800  C    THR A 233     -20.236 -19.822  -4.603  1.00 14.93      A
ATOM   1801  O    THR A 233     -20.018 -19.237  -3.544  1.00 16.82      A
ATOM   1802  N    SER A 234     -20.927 -19.274  -5.590  1.00 14.49      A
ATOM   1803  CA   SER A 234     -21.543 -17.968  -5.406  1.00 13.46      A
ATOM   1804  CB   SER A 234     -20.743 -16.883  -5.136  1.00 13.74      A
ATOM   1805  OG   SER A 234     -21.424 -15.612  -6.057  1.00 15.56      A
ATOM   1806  C    SER A 234     -22.952 -17.945  -5.976  1.00 13.72      A
ATOM   1807  O    SER A 234     -23.272 -18.673  -6.914  1.00 14.31      A
ATOM   1808  N    LYS A 235     -23.796 -17.096  -5.384  1.00 14.72      A
ATOM   1809  CA   LYS A 235     -25.140 -16.882  -5.941  1.00 15.52      A
ATOM   1810  CB   LYS A 235     -26.017 -16.089  -4.965  1.00 18.32      A
ATOM   1811  CG   LYS A 235     -26.346 -16.843  -3.692  1.00 22.03      A
ATOM   1812  CD   LYS A 235     -27.446 -16.147  -2.881  1.00 26.96      A
ATOM   1813  CE   LYS A 235     -28.805 -16.273  -3.561  1.00 31.30      A
ATOM   1814  NZ   LYS A 235     -29.279 -17.699  -3.762  1.00 34.33      A
ATOM   1815  C    LYS A 235     -24.904 -16.023  -7.181  1.00 13.85      A
ATOM   1816  O    LYS A 235     -23.843 -15.357  -7.310  1.00 14.11      A
ATOM   1817  N    LEU A 236     -25.865 -16.060  -8.109  1.00 14.19      A
ATOM   1818  CA   LEU A 236     -25.790 -15.236  -9.322  1.00 14.29      A
ATOM   1819  CB   LEU A 236     -26.307 -16.007 -10.538  1.00 14.06      A
ATOM   1820  CG   LEU A 236     -25.517 -17.278 -10.914  1.00 13.43      A
ATOM   1821  CD1  LEU A 236     -26.211 -18.059 -12.011  1.00 15.03      A
ATOM   1822  CD2  LEU A 236     -24.085 -16.907 -11.375  1.00 13.57      A
ATOM   1823  C    LEU A 236     -26.561 -14.004  -9.095  1.00 15.56      A
ATOM   1824  O    LEU A 236     -27.429 -13.931  -8.119  1.00 18.35      A
ATOM   1825  N    VAL A 237     -26.555 -13.052  -9.998  1.00 14.01      A
ATOM   1826  CA   VAL A 237     -27.324 -11.803  -9.903  1.00 17.40      A
ATOM   1827  CB   VAL A 237     -26.462 -10.592 -10.324  1.00 16.42      A
ATOM   1828  CG1  VAL A 237     -27.275  -9.292 -10.179  1.00 18.55      A
ATOM   1829  CG2  VAL A 237     -25.205 -10.504  -9.471  1.00 17.94      A
ATOM   1830  C    VAL A 237     -28.516 -11.863 -10.844  1.00 19.10      A
ATOM   1831  O    VAL A 237     -28.394 -12.262 -12.003  1.00 19.48      A
ATOM   1832  N    ASP A 238     -29.683 -11.441 -10.368  1.00 23.53      A
ATOM   1833  CA   ASP A 238     -30.842 -11.424 -11.253  1.00 27.58      A
ATOM   1834  CB   ASP A 238     -32.129 -11.384 -10.441  1.00 31.74      A
ATOM   1835  CG   ASP A 238     -33.093 -12.485 -10.849  1.00 36.33      A
ATOM   1836  OD1  ASP A 238     -33.506 -12.522 -12.038  1.00 38.03      A
ATOM   1837  OD2  ASP A 238     -33.429 -13.318  -9.979  1.00 39.43      A
ATOM   1838  C    ASP A 238     -30.788 -10.205 -12.193  1.00 27.85      A
ATOM   1839  O    ASP A 238     -30.073  -9.224 -11.951  1.00 27.68      A
ATOM   1840  N    GLY A 239     -31.516 -10.272 -13.288  1.00 27.65      A
ATOM   1841  CA   GLY A 239     -31.524  -9.143 -14.185  1.00 27.62      A
ATOM   1842  C    GLY A 239     -31.152  -9.550 -15.580  1.00 28.08      A
ATOM   1843  O    GLY A 239     -30.584 -10.616 -15.790  1.00 28.81      A
ATOM   1844  N    ARG A 240     -31.491  -8.683 -16.521  1.00 29.63      A
ATOM   1845  CA   ARG A 240     -31.208  -8.878 -17.932  1.00 30.14      A
ATOM   1846  CB   ARG A 240     -32.392  -8.389 -18.771  1.00 33.69      A
ATOM   1847  CG   ARG A 240     -32.239  -8.574 -20.279  1.00 38.96      A
ATOM   1848  CD   ARG A 240     -32.122 -10.052 -20.651  1.00 43.41      A
ATOM   1849  NE   ARG A 240     -32.302 -10.267 -22.087  1.00 46.82      A
ATOM   1850  CZ   ARG A 240     -32.389 -11.460 -22.569  1.00 48.33      A
ATOM   1851  NH1  ARG A 240     -32.313 -12.570 -21.944  1.00 49.90      A
ATOM   1852  NH2  ARG A 240     -32.553 -11.543 -23.985  1.00 49.72      A
ATOM   1853  C    ARG A 240     -29.980  -8.040 -18.242  1.00 28.28      A
ATOM   1854  O    ARG A 240     -30.031  -6.814 -18.260  1.00 26.65      A
ATOM   1855  N    PHE A 241     -28.872  -8.718 -18.502  1.00 25.31      A
ATOM   1856  CA   PHE A 241     -27.633  -8.025 -18.822  1.00 23.21      A
ATOM   1857  CB   PHE A 241     -26.463  -9.006 -18.705  1.00 20.31      A
ATOM   1858  CG   PHE A 241     -25.146  -8.345 -18.481  1.00 17.38      A
ATOM   1859  CD1  PHE A 241     -24.780  -7.948 -17.206  1.00 15.49      A
ATOM   1860  CD2  PHE A 241     -24.297  -8.068 -19.549  1.00 17.91      A
ATOM   1861  CE1  PHE A 241     -23.586  -7.276 -16.980  1.00 15.90      A
ATOM   1862  CE2  PHE A 241     -23.102  -7.391 -19.330  1.00 14.47      A
ATOM   1863  CZ   PHE A 241     -22.747  -6.997 -18.051  1.00 15.32      A
ATOM   1864  C    PHE A 241     -27.711  -7.517 -20.271  1.00 22.81      A
ATOM   1865  O    PHE A 241     -28.322  -8.155 -21.137  1.00 24.71      A
```

Figure 1 (continued 19)

| | | | | | | | | | |
|---|---|---|---|---|---|---|---|---|---|
| ATOM | 1866 | N | PRO | A | 242 | -27.092 | -6.365 | -20.556 | 1.00 21.66 A |
| ATOM | 1867 | CD | PRO | A | 242 | -26.466 | -5.383 | -19.664 | 1.00 20.82 A |
| ATOM | 1868 | CA | PRO | A | 242 | -27.147 | -5.870 | -21.936 | 1.00 22.07 A |
| ATOM | 1869 | CB | PRO | A | 242 | -26.503 | -4.489 | -21.849 | 1.00 23.09 A |
| ATOM | 1870 | CG | PRO | A | 242 | -25.687 | -4.543 | -20.635 | 1.00 23.90 A |
| ATOM | 1871 | C | PRO | A | 242 | -26.435 | -6.788 | -22.919 | 1.00 21.43 A |
| ATOM | 1872 | O | PRO | A | 242 | -25.517 | -7.513 | -22.559 | 1.00 21.56 A |
| ATOM | 1873 | N | ASP | A | 243 | -26.862 | -6.730 | -24.168 | 1.00 22.31 A |
| ATOM | 1874 | CA | ASP | A | 243 | -26.325 | -7.544 | -25.235 | 1.00 22.61 A |
| ATOM | 1875 | CB | ASP | A | 243 | -27.447 | -7.789 | -26.241 | 1.00 24.30 A |
| ATOM | 1876 | CG | ASP | A | 243 | -27.032 | -8.665 | -27.392 | 1.00 23.99 A |
| ATOM | 1877 | OD1 | ASP | A | 243 | -25.841 | -9.016 | -27.513 | 1.00 23.11 A |
| ATOM | 1878 | OD2 | ASP | A | 243 | -27.923 | -9.009 | -28.204 | 1.00 25.61 A |
| ATOM | 1879 | C | ASP | A | 243 | -25.164 | -6.810 | -25.884 | 1.00 22.10 A |
| ATOM | 1880 | O | ASP | A | 243 | -25.369 | -5.814 | -26.583 | 1.00 20.96 A |
| ATOM | 1881 | N | TYR | A | 244 | -23.946 | -7.307 | -25.690 | 1.00 20.24 A |
| ATOM | 1882 | CA | TYR | A | 244 | -22.770 | -6.623 | -26.253 | 1.00 19.79 A |
| ATOM | 1883 | CB | TYR | A | 244 | -21.471 | -7.367 | -25.865 | 1.00 18.34 A |
| ATOM | 1884 | CG | TYR | A | 244 | -21.137 | -8.593 | -26.702 | 1.00 19.53 A |
| ATOM | 1885 | CD1 | TYR | A | 244 | -20.406 | -8.482 | -27.886 | 1.00 17.48 A |
| ATOM | 1886 | CE1 | TYR | A | 244 | -20.127 | -9.596 | -28.685 | 1.00 19.93 A |
| ATOM | 1887 | CD2 | TYR | A | 244 | -21.593 | -9.867 | -26.332 | 1.00 19.90 A |
| ATOM | 1888 | CE2 | TYR | A | 244 | -21.327 | -10.988 | -27.129 | 1.00 19.80 A |
| ATOM | 1889 | CZ | TYR | A | 244 | -20.596 | -10.862 | -28.296 | 1.00 20.77 A |
| ATOM | 1890 | OH | TYR | A | 244 | -20.321 | -11.983 | -29.074 | 1.00 23.28 A |
| ATOM | 1891 | C | TYR | A | 244 | -22.837 | -6.509 | -27.775 | 1.00 20.37 A |
| ATOM | 1892 | O | TYR | A | 244 | -22.257 | -5.614 | -28.389 | 1.00 19.31 A |
| ATOM | 1893 | N | ARG | A | 245 | -23.534 | -7.435 | -28.413 | 1.00 19.69 A |
| ATOM | 1894 | CA | ARG | A | 245 | -23.627 | -7.419 | -29.862 | 1.00 22.13 A |
| ATOM | 1895 | CB | ARG | A | 245 | -24.410 | -8.644 | -30.335 | 1.00 22.26 A |
| ATOM | 1896 | CG | ARG | A | 245 | -23.819 | -9.936 | -29.832 | 1.00 24.54 A |
| ATOM | 1897 | CD | ARG | A | 245 | -24.691 | -11.115 | -30.214 | 1.00 27.20 A |
| ATOM | 1898 | NE | ARG | A | 245 | -24.296 | -12.348 | -29.532 | 1.00 28.66 A |
| ATOM | 1899 | CZ | ARG | A | 245 | -24.432 | -12.577 | -28.226 | 1.00 27.22 A |
| ATOM | 1900 | NH1 | ARG | A | 245 | -24.931 | -11.658 | -27.413 | 1.00 26.49 A |
| ATOM | 1901 | NH2 | ARG | A | 245 | -24.061 | -13.756 | -27.734 | 1.00 27.45 A |
| ATOM | 1902 | C | ARG | A | 245 | -24.284 | -6.151 | -30.393 | 1.00 22.87 A |
| ATOM | 1903 | O | ARG | A | 245 | -23.999 | -5.734 | -31.526 | 1.00 23.81 A |
| ATOM | 1904 | N | ARG | A | 246 | -25.168 | -5.559 | -29.592 | 1.00 22.53 A |
| ATOM | 1905 | CA | ARG | A | 246 | -25.866 | -4.326 | -29.978 | 1.00 23.83 A |
| ATOM | 1906 | CB | ARG | A | 246 | -27.271 | -4.311 | -29.361 | 1.00 23.77 A |
| ATOM | 1907 | CG | ARG | A | 246 | -28.060 | -5.575 | -29.729 | 1.00 27.25 A |
| ATOM | 1908 | CD | ARG | A | 246 | -29.543 | -5.486 | -29.396 | 1.00 29.82 A |
| ATOM | 1909 | NE | ARG | A | 246 | -30.202 | -4.515 | -30.263 | 1.00 32.86 A |
| ATOM | 1910 | CZ | ARG | A | 246 | -31.509 | -4.274 | -30.246 | 1.00 34.97 A |
| ATOM | 1911 | NH1 | ARG | A | 246 | -32.296 | -4.935 | -29.410 | 1.00 35.99 A |
| ATOM | 1912 | NH2 | ARG | A | 246 | -32.030 | -3.375 | -31.071 | 1.00 36.57 A |
| ATOM | 1913 | C | ARG | A | 246 | -25.093 | -3.074 | -29.554 | 1.00 22.99 A |
| ATOM | 1914 | O | ARG | A | 246 | -25.477 | -1.950 | -29.900 | 1.00 23.88 A |
| ATOM | 1915 | N | VAL | A | 247 | -24.027 | -3.274 | -28.773 | 1.00 21.04 A |
| ATOM | 1916 | CA | VAL | A | 247 | -23.177 | -2.178 | -28.299 | 1.00 20.18 A |
| ATOM | 1917 | CB | VAL | A | 247 | -22.685 | -2.447 | -26.850 | 1.00 19.13 A |
| ATOM | 1918 | CG1 | VAL | A | 247 | -21.570 | -1.393 | -26.413 | 1.00 20.39 A |
| ATOM | 1919 | CG2 | VAL | A | 247 | -23.885 | -2.440 | -25.907 | 1.00 21.24 A |
| ATOM | 1920 | C | VAL | A | 247 | -21.979 | -1.976 | -29.241 | 1.00 19.85 A |
| ATOM | 1921 | O | VAL | A | 247 | -21.472 | -0.844 | -29.390 | 1.00 20.50 A |
| ATOM | 1922 | N | LEU | A | 248 | -21.516 | -3.048 | -29.877 | 1.00 19.31 A |
| ATOM | 1923 | CA | LEU | A | 248 | -20.397 | -2.896 | -30.804 | 1.00 21.46 A |
| ATOM | 1924 | CB | LEU | A | 248 | -20.015 | -4.239 | -31.435 | 1.00 23.15 A |
| ATOM | 1925 | CG | LEU | A | 248 | -19.568 | -5.316 | -30.439 | 1.00 23.14 A |
| ATOM | 1926 | CD1 | LEU | A | 248 | -19.300 | -6.602 | -31.217 | 1.00 26.15 A |
| ATOM | 1927 | CD2 | LEU | A | 248 | -18.337 | -4.856 | -29.663 | 1.00 24.04 A |
| ATOM | 1928 | C | LEU | A | 248 | -20.810 | -1.939 | -31.923 | 1.00 22.45 A |
| ATOM | 1929 | O | LEU | A | 248 | -21.902 | -2.054 | -32.474 | 1.00 22.72 A |
| ATOM | 1930 | N | PRO | A | 249 | -19.946 | -0.977 | -32.273 | 1.00 21.88 A |
| ATOM | 1931 | CD | PRO | A | 249 | -18.668 | -0.598 | -31.642 | 1.00 20.48 A |
| ATOM | 1932 | CA | PRO | A | 249 | -20.321 | -0.052 | -33.353 | 1.00 23.12 A |
| ATOM | 1933 | CB | PRO | A | 249 | -19.090 | 0.843 | -33.496 | 1.00 23.55 A |
| ATOM | 1934 | CG | PRO | A | 249 | -18.466 | 0.807 | -32.149 | 1.00 22.18 A |
| ATOM | 1935 | C | PRO | A | 249 | -20.613 | -0.821 | -34.643 | 1.00 25.18 A |
| ATOM | 1936 | O | PRO | A | 249 | -19.874 | -1.745 | -35.018 | 1.00 25.69 A |
| ATOM | 1937 | N | LYS | A | 250 | -21.675 | -0.416 | -35.333 | 1.00 26.79 A |
| ATOM | 1938 | CA | LYS | A | 250 | -22.112 | -1.071 | -36.567 | 1.00 30.40 A |
| ATOM | 1939 | CB | LYS | A | 250 | -23.408 | -0.429 | -37.065 | 1.00 31.64 A |
| ATOM | 1940 | CG | LYS | A | 250 | -24.527 | -0.363 | -36.043 | 1.00 36.92 A |
| ATOM | 1941 | CD | LYS | A | 250 | -25.774 | 0.328 | -36.638 | 1.00 40.37 A |
| ATOM | 1942 | CE | LYS | A | 250 | -25.511 | 1.793 | -37.053 | 1.00 41.65 A |
| ATOM | 1943 | NZ | LYS | A | 250 | -26.750 | 2.478 | -37.569 | 1.00 42.08 A |
| ATOM | 1944 | C | LYS | A | 250 | -21.121 | -1.074 | -37.714 | 1.00 30.98 A |
| ATOM | 1945 | O | LYS | A | 250 | -20.828 | -2.113 | -38.296 | 1.00 32.45 A |
| ATOM | 1946 | N | ASN | A | 251 | -20.612 | 0.098 | -38.055 | 1.00 31.28 A |
| ATOM | 1947 | CA | ASN | A | 251 | -19.680 | 0.188 | -39.161 | 1.00 32.02 A |
| ATOM | 1948 | CB | ASN | A | 251 | -20.420 | 0.641 | -40.431 | 1.00 34.75 A |
| ATOM | 1949 | CG | ASN | A | 251 | -21.586 | -0.287 | -40.805 | 1.00 37.52 A |
| ATOM | 1950 | OD1 | ASN | A | 251 | -22.755 | 0.120 | -40.783 | 1.00 39.85 A |
| ATOM | 1951 | ND2 | ASN | A | 251 | -21.268 | -1.535 | -41.154 | 1.00 38.31 A |
| ATOM | 1952 | C | ASN | A | 251 | -18.563 | 1.164 | -38.809 | 1.00 30.42 A |
| ATOM | 1953 | O | ASN | A | 251 | -18.527 | 2.299 | -39.297 | 1.00 31.94 A |
| ATOM | 1954 | N | PRO | A | 252 | -17.649 | 0.734 | -37.928 | 1.00 28.72 A |
| ATOM | 1955 | CD | PRO | A | 252 | -17.660 | -0.563 | -37.218 | 1.00 27.35 A |
| ATOM | 1956 | CA | PRO | A | 252 | -16.517 | 1.563 | -37.492 | 1.00 27.89 A |
| ATOM | 1957 | CB | PRO | A | 252 | -16.132 | 0.917 | -36.167 | 1.00 26.42 A |
| ATOM | 1958 | CG | PRO | A | 252 | -16.328 | -0.561 | -36.468 | 1.00 27.43 A |
| ATOM | 1959 | C | PRO | A | 252 | -15.410 | 1.473 | -38.539 | 1.00 29.12 A |
| ATOM | 1960 | O | PRO | A | 252 | -14.323 | 0.959 | -38.263 | 1.00 29.62 A |
| ATOM | 1961 | N | ASP | A | 253 | -15.716 | 2.003 | -39.723 | 1.00 30.27 A |
| ATOM | 1962 | CA | ASP | A | 253 | -14.869 | 1.991 | -40.920 | 1.00 31.73 A |
| ATOM | 1963 | CB | ASP | A | 253 | -15.625 | 2.669 | -42.079 | 1.00 35.33 A |
| ATOM | 1964 | CG | ASP | A | 253 | -15.798 | 4.184 | -41.878 | 1.00 39.92 A |
| ATOM | 1965 | OD1 | ASP | A | 253 | -16.335 | 4.607 | -40.819 | 1.00 42.78 A |

Figure 1 (continued 20)

```
ATOM   1966  OD2 ASP A 253    -15.400   4.962 -43.784  1.00 41.27      A
ATOM   1967  C   ASP A 253    -13.467   2.586 -40.870  1.00 30.28      A
ATOM   1968  O   ASP A 253    -12.578   2.126 -41.600  1.00 31.43      A
ATOM   1969  N   LYS A 254    -13.277   3.606 -40.039  1.00 27.06      A
ATOM   1970  CA  LYS A 254    -11.991   4.285 -39.932  1.00 14.93      A
ATOM   1971  CB  LYS A 254    -12.232   5.728 -39.494  1.00 24.91      A
ATOM   1972  CG  LYS A 254    -13.148   6.522 -40.421  1.00 27.11      A
ATOM   1973  CD  LYS A 254    -13.379   7.918 -39.844  1.00 29.21      A
ATOM   1974  CE  LYS A 254    -14.184   8.777 -40.825  1.00 32.00      A
ATOM   1975  NZ  LYS A 254    -15.470   8.129 -41.185  1.00 34.43      A
ATOM   1976  C   LYS A 254    -11.094   3.553 -38.930  1.00 22.15      A
ATOM   1977  O   LYS A 254    -11.328   3.610 -37.730  1.00 22.88      A
ATOM   1978  N   HIS A 255    -10.067   2.884 -39.434  1.00 21.10      A
ATOM   1979  CA  HIS A 255     -9.165   2.101 -38.598  1.00 21.30      A
ATOM   1980  CB  HIS A 255     -8.939   0.721 -39.214  1.00 24.75      A
ATOM   1981  CG  HIS A 255    -10.171  -0.127 -39.294  1.00 26.36      A
ATOM   1982  CD2 HIS A 255    -10.391  -1.313 -39.905  1.00 28.26      A
ATOM   1983  ND1 HIS A 255    -11.359   0.219 -38.684  1.00 29.22      A
ATOM   1984  CE1 HIS A 255    -12.261  -0.718 -38.922  1.00 29.44      A
ATOM   1985  NE2 HIS A 255    -11.699  -1.658 -39.660  1.00 31.29      A
ATOM   1986  C   HIS A 255     -7.798   2.727 -38.381  1.00 20.47      A
ATOM   1987  O   HIS A 255     -7.045   2.966 -39.331  1.00 19.05      A
ATOM   1988  N   LEU A 256     -7.449   2.930 -37.120  1.00 18.43      A
ATOM   1989  CA  LEU A 256     -6.148   3.491 -36.778  1.00 18.02      A
ATOM   1990  CB  LEU A 256     -6.251   4.753 -35.927  1.00 19.89      A
ATOM   1991  CG  LEU A 256     -5.142   5.472 -35.324  1.00 22.32      A
ATOM   1992  CD1 LEU A 256     -5.493   6.944 -35.096  1.00 24.54      A
ATOM   1993  CD2 LEU A 256     -4.737   4.798 -34.007  1.00 25.40      A
ATOM   1994  C   LEU A 256     -5.368   2.452 -35.962  1.00 18.20      A
ATOM   1995  O   LEU A 256     -5.921   1.857 -35.042  1.00 17.77      A
ATOM   1996  N   GLU A 257     -4.099   2.224 -36.298  1.00 16.89      A
ATOM   1997  CA  GLU A 257     -3.295   1.292 -35.505  1.00 17.61      A
ATOM   1998  CB  GLU A 257     -2.702   0.186 -36.378  1.00 19.65      A
ATOM   1999  CG  GLU A 257     -1.850  -0.790 -35.585  1.00 25.47      A
ATOM   2000  CD  GLU A 257     -1.391  -1.990 -36.398  1.00 28.58      A
ATOM   2001  OE1 GLU A 257     -0.339  -2.592 -36.024  1.00 30.83      A
ATOM   2002  OE2 GLU A 257     -2.089  -2.333 -37.394  1.00 26.86      A
ATOM   2003  C   GLU A 257     -2.182   2.113 -34.861  1.00 17.45      A
ATOM   2004  O   GLU A 257     -1.570   2.963 -35.515  1.00 16.51      A
ATOM   2005  N   ALA A 258     -1.932   1.863 -33.579  1.00 17.17      A
ATOM   2006  CA  ALA A 258     -0.906   2.593 -32.830  1.00 17.02      A
ATOM   2007  CB  ALA A 258     -1.584   3.719 -32.020  1.00 18.18      A
ATOM   2008  C   ALA A 258     -0.172   1.666 -31.864  1.00 18.03      A
ATOM   2009  O   ALA A 258     -0.738   0.663 -31.398  1.00 17.35      A
ATOM   2010  N   GLY A 259      1.085   2.001 -31.571  1.00 16.83      A
ATOM   2011  CA  GLY A 259      1.860   1.248 -30.598  1.00 16.02      A
ATOM   2012  C   GLY A 259      1.145   1.382 -29.257  1.00 16.37      A
ATOM   2013  O   GLY A 259      0.829   2.476 -28.834  1.00 15.32      A
ATOM   2014  N   CYS A 260      0.894   0.270 -28.576  1.00 14.83      A
ATOM   2015  CA  CYS A 260      0.143   0.338 -27.323  1.00 14.73      A
ATOM   2016  CB  CYS A 260     -0.107  -1.069 -26.807  1.00 13.90      A
ATOM   2017  SG  CYS A 260     -1.234  -1.099 -25.368  1.00 18.12      A
ATOM   2018  C   CYS A 260      0.806   1.179 -26.253  1.00 14.83      A
ATOM   2019  O   CYS A 260      0.159   2.047 -25.640  1.00 15.46      A
ATOM   2020  N   ASP A 261      2.096   0.921 -26.017  1.00 15.27      A
ATOM   2021  CA  ASP A 261      2.834   1.655 -24.977  1.00 17.33      A
ATOM   2022  CB  ASP A 261      4.276   1.123 -24.801  1.00 18.87      A
ATOM   2023  CG  ASP A 261      5.188   2.109 -24.002  1.00 25.56      A
ATOM   2024  OD1 ASP A 261      5.948   2.946 -24.607  1.00 27.19      A
ATOM   2025  OD2 ASP A 261      5.128   2.056 -22.758  1.00 23.92      A
ATOM   2026  C   ASP A 261      2.924   3.126 -25.321  1.00 15.30      A
ATOM   2027  O   ASP A 261      2.689   3.977 -24.457  1.00 16.28      A
ATOM   2028  N   LEU A 262      3.263   3.435 -26.566  1.00 15.05      A
ATOM   2029  CA  LEU A 262      3.379   4.835 -26.940  1.00 14.87      A
ATOM   2030  CB  LEU A 262      3.900   4.980 -28.365  1.00 16.84      A
ATOM   2031  CG  LEU A 262      5.392   4.695 -28.564  1.00 19.33      A
ATOM   2032  CD1 LEU A 262      5.705   4.835 -30.069  1.00 20.64      A
ATOM   2033  CD2 LEU A 262      6.233   5.673 -27.721  1.00 19.45      A
ATOM   2034  C   LEU A 262      2.041   5.563 -26.782  1.00 15.27      A
ATOM   2035  O   LEU A 262      2.003   6.712 -26.332  1.00 15.81      A
ATOM   2036  N   LEU A 263      0.949   4.912 -27.161  1.00 13.33      A
ATOM   2037  CA  LEU A 263     -0.352   5.560 -26.991  1.00 13.53      A
ATOM   2038  CB  LEU A 263     -1.447   4.721 -27.673  1.00 13.61      A
ATOM   2039  CG  LEU A 263     -2.885   5.243 -27.627  1.00 16.53      A
ATOM   2040  CD1 LEU A 263     -2.965   6.612 -28.293  1.00 17.32      A
ATOM   2041  CD2 LEU A 263     -3.785   4.257 -28.319  1.00 15.91      A
ATOM   2042  C   LEU A 263     -0.658   5.735 -25.491  1.00 14.38      A
ATOM   2043  O   LEU A 263     -1.177   6.774 -25.064  1.00 13.47      A
ATOM   2044  N   LYS A 264     -0.372   4.719 -24.680  1.00 13.04      A
ATOM   2045  CA  LYS A 264     -0.655   4.778 -23.255  1.00 14.11      A
ATOM   2046  CB  LYS A 264     -0.299   3.420 -22.644  1.00 15.66      A
ATOM   2047  CG  LYS A 264     -0.539   3.304 -21.166  1.00 22.39      A
ATOM   2048  CD  LYS A 264     -0.002   1.952 -20.693  1.00 25.24      A
ATOM   2049  CE  LYS A 264     -0.624   0.789 -21.454  1.00 28.82      A
ATOM   2050  NZ  LYS A 264     -0.186  -0.554 -20.920  1.00 32.53      A
ATOM   2051  C   LYS A 264      0.110   5.920 -22.559  1.00 13.53      A
ATOM   2052  O   LYS A 264     -0.474   6.700 -21.798  1.00 13.19      A
ATOM   2053  N   GLN A 265      1.397   6.058 -22.861  1.00 12.97      A
ATOM   2054  CA  GLN A 265      2.167   7.097 -22.192  1.00 13.73      A
ATOM   2055  CB  GLN A 265      3.668   6.889 -22.418  1.00 14.32      A
ATOM   2056  CG  GLN A 265      4.187   5.506 -21.997  1.00 15.83      A
ATOM   2057  CD  GLN A 265      3.603   5.004 -20.674  1.00 16.85      A
ATOM   2058  OE1 GLN A 265      3.288   5.773 -19.777  1.00 18.55      A
ATOM   2059  NE2 GLN A 265      3.473   3.687 -20.551  1.00 19.72      A
ATOM   2060  C   GLN A 265      1.789   8.491 -22.685  1.00 13.91      A
ATOM   2061  O   GLN A 265      1.882   9.454 -21.921  1.00 14.00      A
ATOM   2062  N   ALA A 266      1.367   8.598 -23.947  1.00 12.99      A
ATOM   2063  CA  ALA A 266      0.949   9.897 -24.477  1.00 12.33      A
ATOM   2064  CB  ALA A 266      0.735   9.820 -25.983  1.00 13.59      A
ATOM   2065  C   ALA A 266     -0.356  10.311 -23.760  1.00 14.35      A
```

Figure 1 (continued 21)

| | | | | | | | | | |
|---|---|---|---|---|---|---|---|---|---|
|ATOM|2066|O|ALA|A|266|-0.533|11.459|-23.384|1.00 12.81 A|
|ATOM|2067|N|PHE|A|267|-1.264|9.349|-23.570|1.00 12.67 A|
|ATOM|2068|CA|PHE|A|267|-2.497|9.629|-22.832|1.00 14.64 A|
|ATOM|2069|CB|PHE|A|267|-3.412|8.384|-22.796|1.00 14.10 A|
|ATOM|2070|CG|PHE|A|267|-4.587|8.456|-23.724|1.00 17.70 A|
|ATOM|2071|CD1|PHE|A|267|-5.889|8.659|-23.221|1.00 16.72 A|
|ATOM|2072|CD2|PHE|A|267|-4.418|8.320|-25.085|1.00 16.56 A|
|ATOM|2073|CE1|PHE|A|267|-6.996|8.726|-24.090|1.00 18.75 A|
|ATOM|2074|CE2|PHE|A|267|-5.546|8.387|-25.986|1.00 17.43 A|
|ATOM|2075|CZ|PHE|A|267|-6.830|8.592|-25.468|1.00 18.69 A|
|ATOM|2076|C|PHE|A|267|-2.183|10.001|-21.400|1.00 13.98 A|
|ATOM|2077|O|PHE|A|267|-2.749|10.943|-20.853|1.00 13.44 A|
|ATOM|2078|N|ALA|A|268|-1.294|9.225|-20.777|1.00 13.32 A|
|ATOM|2079|CA|ALA|A|268|-0.945|9.470|-19.386|1.00 13.98 A|
|ATOM|2080|CB|ALA|A|268|-0.017|8.371|-18.892|1.00 13.57 A|
|ATOM|2081|C|ALA|A|268|-0.312|10.844|-19.175|1.00 11.09 A|
|ATOM|2082|O|ALA|A|268|-0.648|11.560|-18.212|1.00 12.76 A|
|ATOM|2083|N|ARG|A|269|0.568|11.264|-20.087|1.00 10.81 A|
|ATOM|2084|CA|ARG|A|269|1.206|12.564|-19.928|1.00 9.72 A|
|ATOM|2085|CB|ARG|A|269|2.418|12.695|-20.883|1.00 10.65 A|
|ATOM|2086|CG|ARG|A|269|3.640|11.953|-20.390|1.00 10.06 A|
|ATOM|2087|CD|ARG|A|269|4.892|12.362|-21.249|1.00 10.44 A|
|ATOM|2088|NE|ARG|A|269|4.685|12.077|-22.658|1.00 9.73 A|
|ATOM|2089|CZ|ARG|A|269|4.963|10.922|-23.254|1.00 9.84 A|
|ATOM|2090|NH1|ARG|A|269|5.499|9.908|-22.580|1.00 11.65 A|
|ATOM|2091|NH2|ARG|A|269|4.653|10.760|-24.520|1.00 10.88 A|
|ATOM|2092|C|ARG|A|269|0.217|13.699|-20.230|1.00 10.56 A|
|ATOM|2093|O|ARG|A|269|0.169|14.656|-19.489|1.00 11.75 A|
|ATOM|2094|N|ALA|A|270|-0.558|13.569|-21.309|1.00 9.54 A|
|ATOM|2095|CA|ALA|A|270|-1.515|14.637|-21.642|1.00 10.89 A|
|ATOM|2096|CB|ALA|A|270|-2.260|14.289|-22.911|1.00 13.90 A|
|ATOM|2097|C|ALA|A|270|-2.506|14.807|-20.483|1.00 11.27 A|
|ATOM|2098|O|ALA|A|270|-2.874|15.950|-20.153|1.00 12.70 A|
|ATOM|2099|N|ALA|A|271|-2.903|13.697|-19.871|1.00 13.03 A|
|ATOM|2100|CA|ALA|A|271|-3.876|13.755|-18.758|1.00 13.13 A|
|ATOM|2101|CB|ALA|A|271|-4.215|12.366|-18.293|1.00 12.98 A|
|ATOM|2102|C|ALA|A|271|-3.481|14.622|-17.569|1.00 12.80 A|
|ATOM|2103|O|ALA|A|271|-4.354|15.128|-16.831|1.00 12.02 A|
|ATOM|2104|N|ILE|A|272|-2.177|14.869|-17.385|1.00 11.81 A|
|ATOM|2105|CA|ILE|A|272|-1.711|15.689|-16.290|1.00 10.77 A|
|ATOM|2106|CB|ILE|A|272|-0.166|15.743|-16.339|1.00 10.82 A|
|ATOM|2107|CG2|ILE|A|272|0.362|16.726|-15.319|1.00 12.90 A|
|ATOM|2108|CG1|ILE|A|272|0.353|14.310|-16.155|1.00 10.24 A|
|ATOM|2109|CD1|ILE|A|272|1.872|14.133|-16.554|1.00 12.64 A|
|ATOM|2110|C|ILE|A|272|-2.287|17.132|-16.343|1.00 11.14 A|
|ATOM|2111|O|ILE|A|272|-2.512|17.770|-15.302|1.00 13.87 A|
|ATOM|2112|N|LEU|A|273|-2.507|17.638|-17.560|1.00 11.27 A|
|ATOM|2113|CA|LEU|A|273|-3.035|18.998|-17.702|1.00 11.91 A|
|ATOM|2114|CB|LEU|A|273|-2.145|19.857|-18.640|1.00 11.25 A|
|ATOM|2115|CG|LEU|A|273|-0.698|19.888|-18.117|1.00 12.82 A|
|ATOM|2116|CD1|LEU|A|273|0.147|20.788|-19.043|1.00 14.39 A|
|ATOM|2117|CD2|LEU|A|273|-0.605|20.368|-16.660|1.00 13.33 A|
|ATOM|2118|C|LEU|A|273|-4.479|19.034|-18.155|1.00 13.42 A|
|ATOM|2119|O|LEU|A|273|-4.918|20.032|-18.737|1.00 13.16 A|
|ATOM|2120|N|SER|A|274|-5.185|17.936|-17.879|1.00 13.18 A|
|ATOM|2121|CA|SER|A|274|-6.625|17.884|-18.193|1.00 16.03 A|
|ATOM|2122|CB|SER|A|274|-7.040|16.461|-18.570|1.00 15.17 A|
|ATOM|2123|OG|SER|A|274|-6.960|15.560|-17.484|1.00 16.66 A|
|ATOM|2124|C|SER|A|274|-7.363|18.365|-16.933|1.00 15.64 A|
|ATOM|2125|O|SER|A|274|-6.734|18.582|-15.911|1.00 17.51 A|
|ATOM|2126|N|ASN|A|275|-8.696|18.484|-16.988|1.00 14.62 A|
|ATOM|2127|CA|ASN|A|275|-9.397|18.935|-15.774|1.00 17.24 A|
|ATOM|2128|CB|ASN|A|275|-10.872|19.209|-16.082|1.00 16.46 A|
|ATOM|2129|CG|ASN|A|275|-11.590|19.909|-14.923|1.00 18.43 A|
|ATOM|2130|OD1|ASN|A|275|-11.704|19.358|-13.827|1.00 22.10 A|
|ATOM|2131|ND2|ASN|A|275|-12.067|21.138|-15.170|1.00 18.70 A|
|ATOM|2132|C|ASN|A|275|-9.307|17.879|-14.662|1.00 18.08 A|
|ATOM|2133|O|ASN|A|275|-9.747|16.752|-14.843|1.00 17.91 A|
|ATOM|2134|N|GLU|A|276|-8.718|18.235|-13.523|1.00 21.67 A|
|ATOM|2135|CA|GLU|A|276|-8.539|17.290|-12.401|1.00 25.21 A|
|ATOM|2136|CB|GLU|A|276|-7.902|17.993|-11.189|1.00 30.38 A|
|ATOM|2137|CG|GLU|A|276|-6.672|18.817|-11.475|1.00 37.32 A|
|ATOM|2138|CD|GLU|A|276|-5.401|17.997|-11.551|1.00 42.05 A|
|ATOM|2139|OE1|GLU|A|276|-5.122|17.211|-10.603|1.00 44.93 A|
|ATOM|2140|OE2|GLU|A|276|-4.667|18.154|-12.553|1.00 45.14 A|
|ATOM|2141|C|GLU|A|276|-9.796|16.578|-11.907|1.00 26.06 A|
|ATOM|2142|O|GLU|A|276|-9.724|15.425|-11.457|1.00 24.42 A|
|ATOM|2143|N|LYS|A|277|-10.946|17.254|-11.984|1.00 25.49 A|
|ATOM|2144|CA|LYS|A|277|-12.218|16.681|-11.525|1.00 27.23 A|
|ATOM|2145|CB|LYS|A|277|-13.203|17.806|-11.157|1.00 29.01 A|
|ATOM|2146|CG|LYS|A|277|-12.699|18.790|-10.106|1.00 33.53 A|
|ATOM|2147|CD|LYS|A|277|-12.724|18.215|-8.698|1.00 36.20 A|
|ATOM|2148|CE|LYS|A|277|-12.225|19.257|-7.698|1.00 37.26 A|
|ATOM|2149|NZ|LYS|A|277|-12.511|18.878|-6.273|1.00 39.68 A|
|ATOM|2150|C|LYS|A|277|-12.884|15.775|-12.562|1.00 25.59 A|
|ATOM|2151|O|LYS|A|277|-13.731|14.943|-12.220|1.00 25.69 A|
|ATOM|2152|N|PHE|A|278|-12.498|15.921|-13.825|1.00 24.84 A|
|ATOM|2153|CA|PHE|A|278|-13.092|15.122|-14.896|1.00 23.67 A|
|ATOM|2154|CB|PHE|A|278|-14.380|15.816|-15.313|1.00 25.91 A|
|ATOM|2155|CG|PHE|A|278|-15.369|14.929|-15.984|1.00 29.29 A|
|ATOM|2156|CD1|PHE|A|278|-15.276|13.538|-15.875|1.00 30.58 A|
|ATOM|2157|CD2|PHE|A|278|-16.425|15.485|-16.705|1.00 30.56 A|
|ATOM|2158|CE1|PHE|A|278|-16.220|12.710|-16.471|1.00 32.00 A|
|ATOM|2159|CE2|PHE|A|278|-17.383|14.658|-17.310|1.00 31.23 A|
|ATOM|2160|CZ|PHE|A|278|-17.278|13.270|-17.191|1.00 33.81 A|
|ATOM|2161|C|PHE|A|278|-12.076|15.063|-16.050|1.00 21.94 A|
|ATOM|2162|O|PHE|A|278|-12.137|15.874|-16.975|1.00 21.84 A|
|ATOM|2163|N|ARG|A|279|-11.154|14.096|-15.989|1.00 19.13 A|
|ATOM|2164|CA|ARG|A|279|-10.063|14.036|-16.962|1.00 18.33 A|
|ATOM|2165|CB|ARG|A|279|-8.844|13.272|-16.376|1.00 18.78 A|

Figure 1 (continued 22)

| | | | | | | | | | |
|---|---|---|---|---|---|---|---|---|---|
| ATOM | 2166 | CG | ARG | A | 279 | -8.186 | 13.898 | -15.146 | 1.00 23.64 | A |
| ATOM | 2167 | CD | ARG | A | 279 | -6.825 | 13.215 | -14.864 | 1.00 26.45 | A |
| ATOM | 2168 | NE | ARG | A | 279 | -6.393 | 13.464 | -13.493 | 1.00 31.51 | A |
| ATOM | 2169 | CZ | ARG | A | 279 | -5.871 | 14.612 | -13.074 | 1.00 33.69 | A |
| ATOM | 2170 | NH1 | ARG | A | 279 | -5.708 | 15.616 | -13.934 | 1.00 35.31 | A |
| ATOM | 2171 | NH2 | ARG | A | 279 | -5.529 | 14.763 | -11.792 | 1.00 33.02 | A |
| ATOM | 2172 | C | ARG | A | 279 | -10.359 | 13.458 | -18.314 | 1.00 14.43 | A |
| ATOM | 2173 | O | ARG | A | 279 | -10.674 | 12.294 | -18.433 | 1.00 16.83 | A |
| ATOM | 2174 | N | GLY | A | 280 | -10.222 | 14.291 | -19.333 | 1.00 14.30 | A |
| ATOM | 2175 | CA | GLY | A | 280 | -10.420 | 13.855 | -20.696 | 1.00 13.40 | A |
| ATOM | 2176 | C | GLY | A | 280 | -9.408 | 14.511 | -21.632 | 1.00 12.18 | A |
| ATOM | 2177 | O | GLY | A | 280 | -8.837 | 15.565 | -21.311 | 1.00 13.28 | A |
| ATOM | 2178 | N | VAL | A | 281 | -9.193 | 13.896 | -22.795 | 1.00 13.04 | A |
| ATOM | 2179 | CA | VAL | A | 281 | -8.254 | 14.440 | -23.796 | 1.00 12.38 | A |
| ATOM | 2180 | CB | VAL | A | 281 | -6.960 | 13.531 | -23.909 | 1.00 13.51 | A |
| ATOM | 2181 | CG1 | VAL | A | 281 | -6.103 | 13.679 | -22.671 | 1.00 12.12 | A |
| ATOM | 2182 | CG2 | VAL | A | 281 | -7.362 | 12.090 | -24.098 | 1.00 15.36 | A |
| ATOM | 2183 | C | VAL | A | 281 | -8.927 | 14.482 | -25.165 | 1.00 12.53 | A |
| ATOM | 2184 | O | VAL | A | 281 | -9.866 | 13.716 | -25.457 | 1.00 13.70 | A |
| ATOM | 2185 | N | ARG | A | 282 | -8.453 | 15.380 | -26.026 | 1.00 11.74 | A |
| ATOM | 2186 | CA | ARG | A | 282 | -8.987 | 15.486 | -27.364 | 1.00 13.08 | A |
| ATOM | 2187 | CB | ARG | A | 282 | -9.165 | 16.947 | -27.763 | 1.00 16.93 | A |
| ATOM | 2188 | CG | ARG | A | 282 | -9.831 | 17.086 | -29.125 | 1.00 25.93 | A |
| ATOM | 2189 | CD | ARG | A | 282 | -11.067 | 18.017 | -29.069 | 1.00 33.09 | A |
| ATOM | 2190 | NE | ARG | A | 282 | -11.959 | 17.715 | -27.949 | 1.00 37.55 | A |
| ATOM | 2191 | CZ | ARG | A | 282 | -13.099 | 17.025 | -28.033 | 1.00 38.42 | A |
| ATOM | 2192 | NH1 | ARG | A | 282 | -13.519 | 16.552 | -29.209 | 1.00 38.59 | A |
| ATOM | 2193 | NH2 | ARG | A | 282 | -13.923 | 16.805 | -26.943 | 1.00 38.91 | A |
| ATOM | 2194 | C | ARG | A | 282 | -8.025 | 14.816 | -28.330 | 1.00 14.43 | A |
| ATOM | 2195 | O | ARG | A | 282 | -6.815 | 15.031 | -28.216 | 1.00 16.20 | A |
| ATOM | 2196 | N | LEU | A | 283 | -8.566 | 14.022 | -29.267 | 1.00 12.40 | A |
| ATOM | 2197 | CA | LEU | A | 283 | -7.754 | 13.341 | -30.279 | 1.00 13.04 | A |
| ATOM | 2198 | CB | LEU | A | 283 | -8.052 | 11.840 | -30.387 | 1.00 14.68 | A |
| ATOM | 2199 | CG | LEU | A | 283 | -7.290 | 10.870 | -29.488 | 1.00 17.14 | A |
| ATOM | 2200 | CD1 | LEU | A | 283 | -7.408 | 11.334 | -28.017 | 1.00 18.12 | A |
| ATOM | 2201 | CD2 | LEU | A | 283 | -7.795 | 9.422 | -29.716 | 1.00 17.55 | A |
| ATOM | 2202 | C | LEU | A | 283 | -8.039 | 13.920 | -31.638 | 1.00 15.68 | A |
| ATOM | 2203 | O | LEU | A | 283 | -9.192 | 14.041 | -32.036 | 1.00 15.80 | A |
| ATOM | 2204 | N | TYR | A | 284 | -6.988 | 14.308 | -32.338 | 1.00 13.31 | A |
| ATOM | 2205 | CA | TYR | A | 284 | -7.186 | 14.776 | -33.696 | 1.00 14.87 | A |
| ATOM | 2206 | CB | TYR | A | 284 | -6.561 | 16.144 | -33.942 | 1.00 14.87 | A |
| ATOM | 2207 | CG | TYR | A | 284 | -7.063 | 16.684 | -35.265 | 1.00 16.70 | A |
| ATOM | 2208 | CD1 | TYR | A | 284 | -8.155 | 17.562 | -35.312 | 1.00 18.02 | A |
| ATOM | 2209 | CE1 | TYR | A | 284 | -8.709 | 17.978 | -36.542 | 1.00 19.42 | A |
| ATOM | 2210 | CD2 | TYR | A | 284 | -6.532 | 16.232 | -36.466 | 1.00 16.24 | A |
| ATOM | 2211 | CE2 | TYR | A | 284 | -7.077 | 16.638 | -37.685 | 1.00 18.82 | A |
| ATOM | 2212 | CZ | TYR | A | 284 | -8.165 | 17.514 | -37.713 | 1.00 19.97 | A |
| ATOM | 2213 | OH | TYR | A | 284 | -8.692 | 17.919 | -38.933 | 1.00 20.44 | A |
| ATOM | 2214 | C | TYR | A | 284 | -6.517 | 13.731 | -34.561 | 1.00 14.90 | A |
| ATOM | 2215 | O | TYR | A | 284 | -5.293 | 13.519 | -34.503 | 1.00 15.97 | A |
| ATOM | 2216 | N | VAL | A | 285 | -7.320 | 13.050 | -35.369 | 1.00 14.02 | A |
| ATOM | 2217 | CA | VAL | A | 285 | -6.768 | 12.007 | -36.209 | 1.00 14.58 | A |
| ATOM | 2218 | CB | VAL | A | 285 | -7.728 | 10.797 | -36.264 | 1.00 16.41 | A |
| ATOM | 2219 | CG1 | VAL | A | 285 | -7.087 | 9.678 | -37.030 | 1.00 19.28 | A |
| ATOM | 2220 | CG2 | VAL | A | 285 | -8.053 | 10.335 | -34.836 | 1.00 17.87 | A |
| ATOM | 2221 | C | VAL | A | 285 | -6.566 | 12.520 | -37.615 | 1.00 13.95 | A |
| ATOM | 2222 | O | VAL | A | 285 | -7.463 | 13.109 | -38.191 | 1.00 16.55 | A |
| ATOM | 2223 | N | SER | A | 286 | -5.376 | 12.297 | -38.163 | 1.00 13.98 | A |
| ATOM | 2224 | CA | SER | A | 286 | -5.094 | 12.724 | -39.555 | 1.00 13.75 | A |
| ATOM | 2225 | CB | SER | A | 286 | -4.453 | 14.129 | -39.576 | 1.00 15.23 | A |
| ATOM | 2226 | OG | SER | A | 286 | -3.165 | 14.108 | -38.984 | 1.00 15.02 | A |
| ATOM | 2227 | C | SER | A | 286 | -4.198 | 11.659 | -40.201 | 1.00 15.02 | A |
| ATOM | 2228 | O | SER | A | 286 | -3.859 | 10.670 | -39.558 | 1.00 15.90 | A |
| ATOM | 2229 | N | GLU | A | 287 | -3.806 | 11.824 | -41.465 | 1.00 16.50 | A |
| ATOM | 2230 | CA | GLU | A | 287 | -3.006 | 10.788 | -42.132 | 1.00 17.09 | A |
| ATOM | 2231 | CB | GLU | A | 287 | -2.655 | 11.245 | -43.568 | 1.00 20.13 | A |
| ATOM | 2232 | CG | GLU | A | 287 | -2.338 | 10.108 | -44.526 | 1.00 25.94 | A |
| ATOM | 2233 | CD | GLU | A | 287 | -3.594 | 9.464 | -45.178 | 1.00 31.11 | A |
| ATOM | 2234 | OE1 | GLU | A | 287 | -4.753 | 9.927 | -44.995 | 1.00 33.30 | A |
| ATOM | 2235 | OE2 | GLU | A | 287 | -3.410 | 8.466 | -45.909 | 1.00 36.38 | A |
| ATOM | 2236 | C | GLU | A | 287 | -1.752 | 10.371 | -41.363 | 1.00 17.84 | A |
| ATOM | 2237 | O | GLU | A | 287 | -0.845 | 11.172 | -41.104 | 1.00 16.79 | A |
| ATOM | 2238 | N | ASN | A | 288 | -1.734 | 9.100 | -40.955 | 1.00 15.55 | A |
| ATOM | 2239 | CA | ASN | A | 288 | -0.648 | 8.524 | -40.188 | 1.00 15.15 | A |
| ATOM | 2240 | CB | ASN | A | 288 | 0.548 | 8.265 | -41.097 | 1.00 18.14 | A |
| ATOM | 2241 | CG | ASN | A | 288 | 0.272 | 7.178 | -42.139 | 1.00 19.57 | A |
| ATOM | 2242 | OD1 | ASN | A | 288 | 0.911 | 7.151 | -43.202 | 1.00 24.08 | A |
| ATOM | 2243 | ND2 | ASN | A | 288 | -0.643 | 6.263 | -41.837 | 1.00 15.66 | A |
| ATOM | 2244 | C | ASN | A | 288 | -0.221 | 9.333 | -38.969 | 1.00 14.72 | A |
| ATOM | 2245 | O | ASN | A | 288 | 0.933 | 9.275 | -38.548 | 1.00 15.32 | A |
| ATOM | 2246 | N | GLN | A | 289 | -1.149 | 10.083 | -38.380 | 1.00 12.97 | A |
| ATOM | 2247 | CA | GLN | A | 289 | -0.790 | 10.867 | -37.209 | 1.00 13.76 | A |
| ATOM | 2248 | CB | GLN | A | 289 | -0.352 | 12.282 | -37.632 | 1.00 14.58 | A |
| ATOM | 2249 | CG | GLN | A | 289 | 0.205 | 13.125 | -36.486 | 1.00 15.69 | A |
| ATOM | 2250 | CD | GLN | A | 289 | 0.526 | 14.534 | -36.923 | 1.00 19.41 | A |
| ATOM | 2251 | OE1 | GLN | A | 289 | -0.299 | 15.468 | -36.764 | 1.00 21.72 | A |
| ATOM | 2252 | NE2 | GLN | A | 289 | 1.714 | 14.705 | -37.504 | 1.00 20.35 | A |
| ATOM | 2253 | C | GLN | A | 289 | -1.906 | 11.022 | -36.223 | 1.00 15.19 | A |
| ATOM | 2254 | O | GLN | A | 289 | -3.074 | 11.137 | -36.603 | 1.00 15.32 | A |
| ATOM | 2255 | N | LEU | A | 290 | -1.554 | 11.041 | -34.941 | 1.00 14.85 | A |
| ATOM | 2256 | CA | LEU | A | 290 | -2.559 | 11.258 | -33.903 | 1.00 13.50 | A |
| ATOM | 2257 | CB | LEU | A | 290 | -2.739 | 10.022 | -33.017 | 1.00 13.73 | A |
| ATOM | 2258 | CG | LEU | A | 290 | -3.773 | 10.099 | -31.894 | 1.00 15.95 | A |
| ATOM | 2259 | CD1 | LEU | A | 290 | -5.182 | 10.294 | -32.481 | 1.00 15.63 | A |
| ATOM | 2260 | CD2 | LEU | A | 290 | -3.706 | 8.818 | -31.090 | 1.00 17.47 | A |
| ATOM | 2261 | C | LEU | A | 290 | -2.022 | 12.403 | -33.039 | 1.00 13.83 | A |
| ATOM | 2262 | O | LEU | A | 290 | -0.872 | 12.377 | -32.625 | 1.00 14.65 | A |
| ATOM | 2263 | N | LYS | A | 291 | -2.864 | 13.395 | -32.755 | 1.00 12.16 | A |
| ATOM | 2264 | CA | LYS | A | 291 | -2.478 | 14.486 | -31.879 | 1.00 13.66 | A |
| ATOM | 2265 | CB | LYS | A | 291 | -2.713 | 15.847 | -32.532 | 1.00 16.40 | A |

Figure 1 (continued 23)

```
ATOM   2266  CG   LYS A 291      -2.319  17.009 -31.620  1.00 19.58      A
ATOM   2267  CD   LYS A 291      -2.331  18.365 -32.360  1.00 23.93      A
ATOM   2268  CE   LYS A 291      -1.322  18.403 -33.488  1.00 28.14      A
ATOM   2269  NZ   LYS A 291      -1.660  19.396 -34.584  1.00 31.96      A
ATOM   2270  C    LYS A 291      -3.376  14.347 -30.667  1.00 14.91      A
ATOM   2271  O    LYS A 291      -4.586  14.165 -30.812  1.00 16.66      A
ATOM   2272  N    ILE A 292      -2.798  14.395 -29.480  1.00 12.63      A
ATOM   2273  CA   ILE A 292      -3.606  14.274 -28.272  1.00 12.23      A
ATOM   2274  CB   ILE A 292      -3.133  13.080 -27.435  1.00 10.96      A
ATOM   2275  CG2  ILE A 292      -3.842  13.062 -26.067  1.00 11.48      A
ATOM   2276  CG1  ILE A 292      -3.343  11.776 -28.240  1.00 13.80      A
ATOM   2277  CD1  ILE A 292      -2.721  10.538 -27.591  1.00 15.45      A
ATOM   2278  C    ILE A 292      -3.413  15.562 -27.478  1.00 14.22      A
ATOM   2279  O    ILE A 292      -2.275  15.928 -27.152  1.00 14.71      A
ATOM   2280  N    THR A 293      -4.514  16.240 -27.130  1.00 12.06      A
ATOM   2281  CA   THR A 293      -4.395  17.489 -26.392  1.00 12.49      A
ATOM   2282  CB   THR A 293      -4.757  18.694 -27.302  1.00 14.10      A
ATOM   2283  OG1  THR A 293      -6.127  18.615 -27.691  1.00 20.69      A
ATOM   2284  CG2  THR A 293      -3.957  18.676 -28.566  1.00 13.47      A
ATOM   2285  C    THR A 293      -5.284  17.512 -25.142  1.00 13.28      A
ATOM   2286  O    THR A 293      -6.324  16.840 -25.073  1.00 13.69      A
ATOM   2287  N    ALA A 294      -4.817  18.231 -24.147  1.00 11.90      A
ATOM   2288  CA   ALA A 294      -5.546  18.421 -22.880  1.00 11.99      A
ATOM   2289  CB   ALA A 294      -4.986  17.521 -21.790  1.00 14.59      A
ATOM   2290  C    ALA A 294      -5.443  19.858 -22.433  1.00 11.96      A
ATOM   2291  O    ALA A 294      -4.440  20.536 -22.685  1.00 13.42      A
ATOM   2292  N    ASN A 295      -6.472  20.330 -21.721  1.00 13.29      A
ATOM   2293  CA   ASN A 295      -6.503  21.690 -21.209  1.00 15.53      A
ATOM   2294  CB   ASN A 295      -7.326  22.622 -22.129  1.00 20.85      A
ATOM   2295  CG   ASN A 295      -6.805  22.666 -23.539  1.00 23.25      A
ATOM   2296  OD1  ASN A 295      -6.030  23.558 -23.901  1.00 29.01      A
ATOM   2297  ND2  ASN A 295      -7.217  21.704 -24.350  1.00 25.32      A
ATOM   2298  C    ASN A 295      -7.244  21.643 -19.881  1.00 13.79      A
ATOM   2299  O    ASN A 295      -8.046  20.725 -19.625  1.00 14.51      A
ATOM   2300  N    ASN A 296      -6.970  22.631 -19.048  1.00 14.40      A
ATOM   2301  CA   ASN A 296      -7.627  22.709 -17.746  1.00 15.59      A
ATOM   2302  CB   ASN A 296      -6.711  22.122 -16.646  1.00 15.58      A
ATOM   2303  CG   ASN A 296      -5.444  22.935 -16.427  1.00 15.76      A
ATOM   2304  OD1  ASN A 296      -5.394  24.114 -16.766  1.00 15.10      A
ATOM   2305  ND2  ASN A 296      -4.415  22.304 -15.829  1.00 18.05      A
ATOM   2306  C    ASN A 296      -8.068  24.163 -17.462  1.00 16.76      A
ATOM   2307  O    ASN A 296      -7.770  25.094 -18.230  1.00 15.08      A
ATOM   2308  N    PRO A 297      -8.769  24.383 -16.344  1.00 20.01      A
ATOM   2309  CD   PRO A 297      -9.315  23.409 -15.393  1.00 21.18      A
ATOM   2310  CA   PRO A 297      -9.225  25.747 -16.039  1.00 22.92      A
ATOM   2311  CB   PRO A 297     -10.099  25.553 -14.792  1.00 23.25      A
ATOM   2312  CG   PRO A 297     -10.607  24.125 -14.971  1.00 22.77      A
ATOM   2313  C    PRO A 297      -8.127  26.786 -15.819  1.00 24.45      A
ATOM   2314  O    PRO A 297      -8.382  28.000 -15.915  1.00 27.11      A
ATOM   2315  N    GLU A 298      -6.919  26.306 -15.521  1.00 24.38      A
ATOM   2316  CA   GLU A 298      -5.767  27.174 -15.283  1.00 24.08      A
ATOM   2317  CB   GLU A 298      -4.690  26.433 -14.480  1.00 26.78      A
ATOM   2318  CG   GLU A 298      -5.007  26.166 -12.995  1.00 33.37      A
ATOM   2319  CD   GLU A 298      -5.908  24.952 -12.723  1.00 35.97      A
ATOM   2320  OE1  GLU A 298      -6.051  24.608 -11.528  1.00 39.62      A
ATOM   2321  OE2  GLU A 298      -6.473  24.342 -13.664  1.00 36.85      A
ATOM   2322  C    GLU A 298      -5.177  27.605 -16.627  1.00 23.08      A
ATOM   2323  O    GLU A 298      -4.175  28.329 -16.679  1.00 21.84      A
ATOM   2324  N    GLN A 299      -5.801  27.151 -17.707  1.00 19.62      A
ATOM   2325  CA   GLN A 299      -5.382  27.475 -19.060  1.00 20.73      A
ATOM   2326  CB   GLN A 299      -5.146  28.983 -19.244  1.00 25.04      A
ATOM   2327  CG   GLN A 299      -6.153  29.921 -18.590  1.00 31.94      A
ATOM   2328  CD   GLN A 299      -5.734  31.391 -18.727  1.00 35.89      A
ATOM   2329  OE1  GLN A 299      -5.505  31.880 -19.840  1.00 38.44      A
ATOM   2330  NE2  GLN A 299      -5.626  32.098 -17.592  1.00 37.47      A
ATOM   2331  C    GLN A 299      -4.089  26.767 -19.419  1.00 18.90      A
ATOM   2332  O    GLN A 299      -3.418  27.164 -20.383  1.00 18.74      A
ATOM   2333  N    GLU A 300      -3.720  25.771 -18.624  1.00 14.58      A
ATOM   2334  CA   GLU A 300      -2.511  24.997 -18.951  1.00 13.30      A
ATOM   2335  CB   GLU A 300      -2.035  24.255 -17.708  1.00 14.18      A
ATOM   2336  CG   GLU A 300      -1.593  25.228 -16.642  1.00 12.48      A
ATOM   2337  CD   GLU A 300      -1.279  24.555 -15.320  1.00 14.90      A
ATOM   2338  OE1  GLU A 300      -1.927  23.543 -14.997  1.00 15.04      A
ATOM   2339  OE2  GLU A 300      -0.394  25.073 -14.583  1.00 17.40      A
ATOM   2340  C    GLU A 300      -2.889  24.054 -20.079  1.00 13.11      A
ATOM   2341  O    GLU A 300      -4.065  23.715 -20.262  1.00 14.26      A
ATOM   2342  N    GLU A 301      -1.899  23.602 -20.856  1.00 12.23      A
ATOM   2343  CA   GLU A 301      -2.215  22.772 -22.001  1.00 13.64      A
ATOM   2344  CB   GLU A 301      -2.406  23.648 -23.246  1.00 17.30      A
ATOM   2345  CG   GLU A 301      -2.865  22.871 -24.488  1.00 22.48      A
ATOM   2346  CD   GLU A 301      -3.254  23.787 -25.635  1.00 27.65      A
ATOM   2347  OE1  GLU A 301      -2.342  24.430 -26.200  1.00 31.10      A
ATOM   2348  OE2  GLU A 301      -4.462  23.877 -25.961  1.00 30.41      A
ATOM   2349  C    GLU A 301      -1.105  21.789 -22.298  1.00 12.28      A
ATOM   2350  O    GLU A 301       0.074  22.112 -22.107  1.00 12.26      A
ATOM   2351  N    ALA A 302      -1.515  20.604 -22.734  1.00 11.02      A
ATOM   2352  CA   ALA A 302      -0.562  19.544 -23.111  1.00 11.63      A
ATOM   2353  CB   ALA A 302      -0.699  18.342 -22.188  1.00 12.84      A
ATOM   2354  C    ALA A 302      -0.834  19.101 -24.550  1.00 13.62      A
ATOM   2355  O    ALA A 302      -1.992  19.077 -25.003  1.00 15.53      A
ATOM   2356  N    GLU A 303       0.223  18.780 -25.301  1.00 10.01      A
ATOM   2357  CA   GLU A 303       0.036  18.255 -26.635  1.00 11.02      A
ATOM   2358  CB   GLU A 303       0.253  19.320 -27.697  1.00 13.49      A
ATOM   2359  CG   GLU A 303       0.127  18.797 -29.115  1.00 16.09      A
ATOM   2360  CD   GLU A 303       0.446  19.851 -30.167  1.00 19.61      A
ATOM   2361  OE1  GLU A 303      -0.479  20.607 -30.584  1.00 20.94      A
ATOM   2362  OE2  GLU A 303       1.628  19.928 -30.579  1.00 18.80      A
ATOM   2363  C    GLU A 303       1.009  17.109 -26.887  1.00 11.44      A
ATOM   2364  O    GLU A 303       2.169  17.226 -26.550  1.00 13.57      A
ATOM   2365  N    GLU A 304       0.513  16.006 -27.427  1.00 10.72      A
```

Figure 1 (continued 24)

```
ATOM   2366  CA   GLU A 304       1.385  14.866 -27.767  1.00 10.97           A
ATOM   2367  CB   GLU A 304       0.994  13.647 -26.932  1.00 12.53           A
ATOM   2368  CG   GLU A 304       1.248  13.808 -25.483  1.00 12.60           A
ATOM   2369  CD   GLU A 304       2.714  13.563 -25.117  1.00 12.60           A
ATOM   2370  OE1  GLU A 304       3.469  13.052 -25.981  1.00 12.80           A
ATOM   2371  OE2  GLU A 304       3.069  13.857 -23.965  1.00 12.17           A
ATOM   2372  C    GLU A 304       1.147  14.532 -29.244  1.00 12.99           A
ATOM   2373  O    GLU A 304      -0.007  14.450 -29.672  1.00 14.50           A
ATOM   2374  N    ILE A 305       2.205  14.349 -30.033  1.00 11.72           A
ATOM   2375  CA   ILE A 305       1.999  13.953 -31.414  1.00 13.62           A
ATOM   2376  CB   ILE A 305       2.631  14.950 -32.417  1.00 15.28           A
ATOM   2377  CG2  ILE A 305       2.424  14.412 -33.857  1.00 16.72           A
ATOM   2378  CG1  ILE A 305       1.904  16.312 -32.316  1.00 14.51           A
ATOM   2379  CD1  ILE A 305       2.546  17.468 -33.066  1.00 19.83           A
ATOM   2380  C    ILE A 305       2.611  12.557 -31.532  1.00 14.02           A
ATOM   2381  O    ILE A 305       3.727  12.288 -31.012  1.00 13.98           A
ATOM   2382  N    LEU A 306       1.859  11.651 -32.154  1.00 12.94           A
ATOM   2383  CA   LEU A 306       2.313  10.259 -32.344  1.00 14.07           A
ATOM   2384  CB   LEU A 306       1.444   9.265 -31.558  1.00 17.83           A
ATOM   2385  CG   LEU A 306       1.426   9.316 -30.037  1.00 19.01           A
ATOM   2386  CD1  LEU A 306       0.496   8.218 -29.532  1.00 21.97           A
ATOM   2387  CD2  LEU A 306       2.844   9.079 -29.473  1.00 23.23           A
ATOM   2388  C    LEU A 306       2.203   9.831 -33.795  1.00 14.91           A
ATOM   2389  O    LEU A 306       1.284  10.228 -34.487  1.00 14.55           A
ATOM   2390  N    ASP A 307       3.165   9.032 -34.271  1.00 14.49           A
ATOM   2391  CA   ASP A 307       3.013   8.483 -35.615  1.00 16.69           A
ATOM   2392  CB   ASP A 307       4.337   7.966 -36.168  1.00 19.50           A
ATOM   2393  CG   ASP A 307       5.282   9.065 -36.529  1.00 22.90           A
ATOM   2394  OD1  ASP A 307       4.830  10.194 -36.789  1.00 22.13           A
ATOM   2395  OD2  ASP A 307       6.491   8.777 -36.579  1.00 29.27           A
ATOM   2396  C    ASP A 307       2.109   7.266 -35.421  1.00 16.05           A
ATOM   2397  O    ASP A 307       2.294   6.492 -34.470  1.00 16.80           A
ATOM   2398  N    VAL A 308       1.148   7.074 -36.308  1.00 14.24           A
ATOM   2399  CA   VAL A 308       0.244   5.918 -36.228  1.00 14.78           A
ATOM   2400  CB   VAL A 308      -1.128   6.256 -35.539  1.00 14.59           A
ATOM   2401  CG1  VAL A 308      -0.889   6.738 -34.086  1.00 14.50           A
ATOM   2402  CG2  VAL A 308      -1.906   7.299 -36.330  1.00 16.78           A
ATOM   2403  C    VAL A 308      -0.028   5.511 -37.664  1.00 15.25           A
ATOM   2404  O    VAL A 308       0.473   6.156 -38.597  1.00 14.77           A
ATOM   2405  N    THR A 309      -0.820   4.458 -37.649  1.00 15.22           A
ATOM   2406  CA   THR A 309      -1.192   4.055 -39.199  1.00 16.94           A
ATOM   2407  CB   THR A 309      -0.982   2.562 -39.446  1.00 18.38           A
ATOM   2408  OG1  THR A 309       0.392   2.246 -39.265  1.00 20.45           A
ATOM   2409  CG2  THR A 309      -1.399   2.210 -40.906  1.00 21.07           A
ATOM   2410  C    THR A 309      -2.653   4.383 -39.373  1.00 16.41           A
ATOM   2411  O    THR A 309      -3.508   3.790 -38.723  1.00 18.35           A
ATOM   2412  N    TYR A 310      -2.936   5.346 -40.240  1.00 14.86           A
ATOM   2413  CA   TYR A 310      -4.291   5.797 -40.505  1.00 15.78           A
ATOM   2414  CB   TYR A 310      -4.743   6.802 -39.441  1.00 17.41           A
ATOM   2415  CG   TYR A 310      -6.152   7.240 -39.641  1.00 18.61           A
ATOM   2416  CD1  TYR A 310      -7.202   6.359 -39.418  1.00 20.45           A
ATOM   2417  CE1  TYR A 310      -8.519   6.753 -39.640  1.00 22.76           A
ATOM   2418  CD2  TYR A 310      -6.453   8.526 -40.087  1.00 20.08           A
ATOM   2419  CE2  TYR A 310      -7.758   8.926 -40.308  1.00 20.45           A
ATOM   2420  CZ   TYR A 310      -8.787   8.036 -40.087  1.00 22.23           A
ATOM   2421  OH   TYR A 310     -10.077   8.431 -40.323  1.00 23.32           A
ATOM   2422  C    TYR A 310      -4.412   6.478 -41.843  1.00 19.52           A
ATOM   2423  O    TYR A 310      -3.625   7.372 -42.149  1.00 18.32           A
ATOM   2424  N    SER A 311      -5.406   6.070 -42.633  1.00 20.36           A
ATOM   2425  CA   SER A 311      -5.620   6.668 -43.951  1.00 24.14           A
ATOM   2426  CB   SER A 311      -5.341   5.642 -45.027  1.00 24.45           A
ATOM   2427  OG   SER A 311      -6.267   4.577 -44.882  1.00 29.21           A
ATOM   2428  C    SER A 311      -7.028   7.222 -44.203  1.00 26.37           A
ATOM   2429  O    SER A 311      -7.348   7.596 -45.336  1.00 30.35           A
ATOM   2430  N    GLY A 312      -7.880   7.275 -43.196  1.00 28.49           A
ATOM   2431  CA   GLY A 312      -9.217   7.803 -43.441  1.00 28.97           A
ATOM   2432  C    GLY A 312      -9.365   9.320 -43.383  1.00 28.05           A
ATOM   2433  O    GLY A 312      -8.380  10.057 -43.420  1.00 29.05           A
ATOM   2434  N    ALA A 313     -10.607   9.794 -43.303  1.00 27.21           A
ATOM   2435  CA   ALA A 313     -10.876  11.232 -43.199  1.00 24.74           A
ATOM   2436  CB   ALA A 313     -12.346  11.499 -43.370  1.00 26.37           A
ATOM   2437  C    ALA A 313     -10.436  11.749 -41.826  1.00 22.97           A
ATOM   2438  O    ALA A 313     -10.352  10.984 -40.871  1.00 21.96           A
ATOM   2439  N    GLU A 314     -10.168  13.043 -41.720  1.00 20.72           A
ATOM   2440  CA   GLU A 314      -9.756  13.591 -40.439  1.00 18.80           A
ATOM   2441  CB   GLU A 314      -9.055  14.960 -40.587  1.00 17.54           A
ATOM   2442  CG   GLU A 314      -7.815  14.898 -41.505  1.00 16.92           A
ATOM   2443  CD   GLU A 314      -6.990  16.211 -41.564  1.00 13.92           A
ATOM   2444  OE1  GLU A 314      -7.488  17.275 -41.169  1.00 16.98           A
ATOM   2445  OE2  GLU A 314      -5.833  16.145 -42.040  1.00 16.78           A
ATOM   2446  C    GLU A 314     -10.962  13.753 -39.540  1.00 16.78           A
ATOM   2447  O    GLU A 314     -12.103  13.914 -39.997  1.00 19.37           A
ATOM   2448  N    MET A 315     -10.712  13.695 -38.244  1.00 19.24           A
ATOM   2449  CA   MET A 315     -11.773  13.901 -37.273  1.00 17.56           A
ATOM   2450  CB   MET A 315     -12.687  12.671 -37.207  1.00 18.80           A
ATOM   2451  CG   MET A 315     -11.969  11.387 -36.964  1.00 20.81           A
ATOM   2452  SD   MET A 315     -13.164  10.037 -36.647  1.00 21.30           A
ATOM   2453  CE   MET A 315     -13.747  10.557 -35.201  1.00 27.18           A
ATOM   2454  C    MET A 315     -11.181  14.209 -35.907  1.00 21.45           A
ATOM   2455  O    MET A 315     -10.018  13.895 -35.531  1.00 18.44           A
ATOM   2456  N    GLU A 316     -11.973  14.872 -35.075  1.00 17.20           A
ATOM   2457  CA   GLU A 316     -11.563  15.231 -33.736  1.00 16.93           A
ATOM   2458  CB   GLU A 316     -11.582  16.742 -33.551  1.00 18.29           A
ATOM   2459  CG   GLU A 316     -11.083  17.217 -32.220  1.00 21.52           A
ATOM   2460  CD   GLU A 316     -10.835  18.712 -32.236  1.00 27.35           A
ATOM   2461  OE1  GLU A 316     -11.793  19.470 -32.520  1.00 32.67           A
ATOM   2462  OE2  GLU A 316      -9.685  19.135 -31.984  1.00 33.72           A
ATOM   2463  C    GLU A 316     -12.582  14.584 -32.819  1.00 35.34           A
ATOM   2464  O    GLU A 316     -13.801  14.685 -33.042  1.00 20.54           A
ATOM   2465  N    ILE A 317     -12.087  13.908 -31.801  1.00 14.19           A
```

Figure 1 (continued 25)

```
ATOM   2466  CA   ILE A 317     -12.975  13.213 -30.866  1.00 13.52           A
ATOM   2467  CB   ILE A 317     -13.258  11.774 -31.384  1.00 14.49           A
ATOM   2468  CG2  ILE A 317     -11.953  10.954 -31.387  1.00 12.63           A
ATOM   2469  CG1  ILE A 317     -14.247  11.046 -30.452  1.00 14.36           A
ATOM   2470  CD1  ILE A 317     -14.811   9.786 -31.076  1.00 14.83           A
ATOM   2471  C    ILE A 317     -12.334  13.179 -29.487  1.00 14.51           A
ATOM   2472  O    ILE A 317     -11.106  13.015 -29.353  1.00 13.70           A
ATOM   2473  N    GLY A 318     -13.151  13.355 -28.452  1.00 11.91           A
ATOM   2474  CA   GLY A 318     -12.635  13.353 -27.095  1.00 12.78           A
ATOM   2475  C    GLY A 318     -12.935  12.063 -26.344  1.00 11.89           A
ATOM   2476  O    GLY A 318     -13.880  11.343 -26.682  1.00 13.28           A
ATOM   2477  N    PHE A 319     -12.125  11.754 -25.347  1.00 11.46           A
ATOM   2478  CA   PHE A 319     -12.299  10.573 -24.517  1.00 13.15           A
ATOM   2479  CB   PHE A 319     -11.423   9.386 -25.007  1.00 12.94           A
ATOM   2480  CG   PHE A 319     -11.886   8.803 -26.316  1.00 15.51           A
ATOM   2481  CD1  PHE A 319     -11.104   8.922 -27.448  1.00 17.96           A
ATOM   2482  CD2  PHE A 319     -13.145   8.191 -26.426  1.00 16.52           A
ATOM   2483  CE1  PHE A 319     -11.557   8.453 -28.684  1.00 16.81           A
ATOM   2484  CE2  PHE A 319     -13.594   7.718 -27.660  1.00 17.65           A
ATOM   2485  CZ   PHE A 319     -12.784   7.858 -28.794  1.00 20.90           A
ATOM   2486  C    PHE A 319     -11.891  10.818 -23.103  1.00 12.47           A
ATOM   2487  O    PHE A 319     -10.995  11.607 -22.820  1.00 12.56           A
ATOM   2488  N    ASN A 320     -12.540  10.070 -22.217  1.00 12.28           A
ATOM   2489  CA   ASN A 320     -12.241  10.066 -20.818  1.00 12.72           A
ATOM   2490  CB   ASN A 320     -13.337   9.290 -20.074  1.00 15.27           A
ATOM   2491  CG   ASN A 320     -13.046   9.141 -18.604  1.00 15.22           A
ATOM   2492  OD1  ASN A 320     -12.276   8.268 -18.171  1.00 17.44           A
ATOM   2493  ND2  ASN A 320     -13.668   9.997 -17.806  1.00 18.20           A
ATOM   2494  C    ASN A 320     -10.919   9.318 -20.736  1.00 13.50           A
ATOM   2495  O    ASN A 320     -10.775   8.232 -21.314  1.00 14.56           A
ATOM   2496  N    VAL A 321      -9.948   9.923 -20.051  1.00 13.54           A
ATOM   2497  CA   VAL A 321      -8.627   9.283 -19.905  1.00 15.24           A
ATOM   2498  CB   VAL A 321      -7.661  10.211 -19.117  1.00 14.76           A
ATOM   2499  CG1  VAL A 321      -6.363   9.465 -18.756  1.00 15.84           A
ATOM   2500  CG2  VAL A 321      -7.370  11.417 -19.929  1.00 15.30           A
ATOM   2501  C    VAL A 321      -8.620   7.936 -19.231  1.00 14.40           A
ATOM   2502  O    VAL A 321      -8.011   6.999 -19.749  1.00 16.49           A
ATOM   2503  N    SER A 322      -9.279   7.825 -18.093  1.00 14.64           A
ATOM   2504  CA   SER A 322      -9.247   6.562 -17.370  1.00 16.47           A
ATOM   2505  CB   SER A 322      -9.934   6.699 -15.995  1.00 18.37           A
ATOM   2506  OG   SER A 322     -11.351   6.726 -16.106  1.00 22.86           A
ATOM   2507  C    SER A 322      -9.852   5.443 -18.196  1.00 15.99           A
ATOM   2508  O    SER A 322      -9.372   4.306 -18.142  1.00 14.69           A
ATOM   2509  N    TYR A 323     -10.887   5.743 -18.986  1.00 15.32           A
ATOM   2510  CA   TYR A 323     -11.497   4.659 -19.767  1.00 14.14           A
ATOM   2511  CB   TYR A 323     -12.762   5.104 -20.509  1.00 13.38           A
ATOM   2512  CG   TYR A 323     -13.911   5.510 -19.615  1.00 13.92           A
ATOM   2513  CD1  TYR A 323     -13.925   5.195 -18.261  1.00 15.72           A
ATOM   2514  CE1  TYR A 323     -15.014   5.562 -17.426  1.00 18.29           A
ATOM   2515  CD2  TYR A 323     -14.992   6.184 -20.154  1.00 16.28           A
ATOM   2516  CE2  TYR A 323     -16.080   6.546 -19.337  1.00 16.03           A
ATOM   2517  CZ   TYR A 323     -16.074   6.238 -17.996  1.00 18.77           A
ATOM   2518  OH   TYR A 323     -17.159   6.615 -17.192  1.00 19.53           A
ATOM   2519  C    TYR A 323     -10.522   4.097 -20.798  1.00 13.72           A
ATOM   2520  O    TYR A 323     -10.472   2.871 -20.988  1.00 14.43           A
ATOM   2521  N    VAL A 324      -9.766   4.979 -21.458  1.00 14.57           A
ATOM   2522  CA   VAL A 324      -8.827   4.508 -22.469  1.00 13.06           A
ATOM   2523  CB   VAL A 324      -8.372   5.662 -23.389  1.00 13.33           A
ATOM   2524  CG1  VAL A 324      -7.307   5.165 -24.365  1.00 13.38           A
ATOM   2525  CG2  VAL A 324      -9.556   6.227 -24.142  1.00 13.06           A
ATOM   2526  C    VAL A 324      -7.625   3.863 -21.805  1.00 13.51           A
ATOM   2527  O    VAL A 324      -7.180   2.778 -22.239  1.00 13.91           A
ATOM   2528  N    LEU A 325      -7.103   4.485 -20.749  1.00 13.19           A
ATOM   2529  CA   LEU A 325      -5.958   3.856 -20.062  1.00 12.30           A
ATOM   2530  CB   LEU A 325      -5.421   4.740 -18.922  1.00 14.09           A
ATOM   2531  CG   LEU A 325      -4.756   6.018 -19.451  1.00 15.74           A
ATOM   2532  CD1  LEU A 325      -4.309   6.898 -18.293  1.00 16.69           A
ATOM   2533  CD2  LEU A 325      -3.511   5.670 -20.297  1.00 16.07           A
ATOM   2534  C    LEU A 325      -6.340   2.486 -19.523  1.00 12.94           A
ATOM   2535  O    LEU A 325      -5.530   1.561 -19.557  1.00 13.40           A
ATOM   2536  N    ASP A 326      -7.558   2.333 -18.993  1.00 12.70           A
ATOM   2537  CA   ASP A 326      -7.979   1.036 -18.483  1.00 13.88           A
ATOM   2538  CB   ASP A 326      -9.424   1.066 -17.982  1.00 15.00           A
ATOM   2539  CG   ASP A 326      -9.580   1.726 -16.613  1.00 18.64           A
ATOM   2540  OD1  ASP A 326      -8.568   1.979 -15.900  1.00 17.79           A
ATOM   2541  OD2  ASP A 326     -10.754   2.016 -16.228  1.00 17.43           A
ATOM   2542  C    ASP A 326      -7.882  -0.010 -19.589  1.00 11.78           A
ATOM   2543  O    ASP A 326      -7.433  -1.134 -19.355  1.00 14.48           A
ATOM   2544  N    VAL A 327      -8.349   0.350 -20.785  1.00 12.78           A
ATOM   2545  CA   VAL A 327      -8.317  -0.577 -21.919  1.00 12.19           A
ATOM   2546  CB   VAL A 327      -9.036   0.029 -23.136  1.00 13.17           A
ATOM   2547  CG1  VAL A 327      -8.820  -0.794 -24.388  1.00 13.91           A
ATOM   2548  CG2  VAL A 327     -10.544   0.097 -22.800  1.00 11.68           A
ATOM   2549  C    VAL A 327      -6.889  -0.925 -22.325  1.00 12.85           A
ATOM   2550  O    VAL A 327      -6.582  -2.089 -22.542  1.00 13.03           A
ATOM   2551  N    LEU A 328      -6.037   0.086 -22.418  1.00 13.64           A
ATOM   2552  CA   LEU A 328      -4.646  -0.142 -22.856  1.00 13.56           A
ATOM   2553  CB   LEU A 328      -3.949   1.201 -23.100  1.00 12.03           A
ATOM   2554  CG   LEU A 328      -4.626   2.058 -24.192  1.00 13.75           A
ATOM   2555  CD1  LEU A 328      -3.799   3.306 -24.432  1.00 14.51           A
ATOM   2556  CD2  LEU A 328      -4.758   1.253 -25.503  1.00 15.65           A
ATOM   2557  C    LEU A 328      -3.888  -0.972 -21.825  1.00 16.00           A
ATOM   2558  O    LEU A 328      -2.982  -1.748 -22.174  1.00 17.28           A
ATOM   2559  N    ASN A 329      -4.252  -0.830 -20.557  1.00 14.82           A
ATOM   2560  CA   ASN A 329      -3.639  -1.609 -19.486  1.00 16.78           A
ATOM   2561  CB   ASN A 329      -3.965  -0.957 -18.143  1.00 18.81           A
ATOM   2562  CG   ASN A 329      -3.039   0.182 -17.815  1.00 22.88           A
ATOM   2563  OD1  ASN A 329      -3.410   1.088 -17.067  1.00 27.05           A
ATOM   2564  ND2  ASN A 329      -1.810   0.139 -18.340  1.00 24.22           A
ATOM   2565  C    ASN A 329      -4.112  -3.059 -19.522  1.00 19.68           A
```

Figure 1 (continued 26)

```
ATOM   2566  O    ASN A 329      -3.353   -3.984 -19.177  1.00 20.96           A
ATOM   2567  N    ALA A 330      -5.347   -3.282 -19.966  1.00 18.19           A
ATOM   2568  CA   ALA A 330      -5.893   -4.635 -20.059  1.00 20.30           A
ATOM   2569  CB   ALA A 330      -7.444   -4.597 -20.070  1.00 20.07           A
ATOM   2570  C    ALA A 330      -5.385   -5.363 -21.304  1.00 20.84           A
ATOM   2571  O    ALA A 330      -5.261   -6.601 -21.312  1.00 21.96           A
ATOM   2572  N    LEU A 331      -5.092   -4.614 -22.365  1.00 20.51           A
ATOM   2573  CA   LEU A 331      -4.607   -5.238 -23.606  1.00 22.56           A
ATOM   2574  CB   LEU A 331      -4.857   -4.311 -24.807  1.00 19.58           A
ATOM   2575  CG   LEU A 331      -6.319   -4.242 -25.284  1.00 20.93           A
ATOM   2576  CD1  LEU A 331      -6.493   -3.076 -26.290  1.00 20.46           A
ATOM   2577  CD2  LEU A 331      -6.749   -5.570 -25.905  1.00 19.08           A
ATOM   2578  C    LEU A 331      -3.127   -5.621 -23.508  1.00 25.46           A
ATOM   2579  O    LEU A 331      -2.742   -6.688 -23.998  1.00 27.06           A
ATOM   2580  N    LYS A 332      -2.313   -4.753 -22.903  1.00 26.68           A
ATOM   2581  CA   LYS A 332      -0.877   -5.002 -22.724  1.00 28.23           A
ATOM   2582  CB   LYS A 332      -0.651   -5.661 -21.356  1.00 29.27           A
ATOM   2583  CG   LYS A 332      -1.401   -6.966 -21.184  1.00 29.90           A
ATOM   2584  CD   LYS A 332      -1.468   -7.412 -19.728  1.00 32.09           A
ATOM   2585  CE   LYS A 332      -2.173   -8.745 -19.658  1.00 32.35           A
ATOM   2586  NZ   LYS A 332      -2.345   -9.225 -18.268  1.00 35.40           A
ATOM   2587  C    LYS A 332      -0.266   -5.853 -23.855  1.00 27.53           A
ATOM   2588  O    LYS A 332       0.361   -6.884 -23.618  1.00 31.18           A
ATOM   2589  N    CYS A 333      -0.484   -5.404 -25.087  1.00 25.22           A
ATOM   2590  CA   CYS A 333       0.010   -6.074 -26.301  1.00 21.25           A
ATOM   2591  CB   CYS A 333      -1.158   -6.522 -27.166  1.00 19.35           A
ATOM   2592  SG   CYS A 333      -2.257   -5.131 -27.559  1.00 20.24           A
ATOM   2593  C    CYS A 333       0.878   -5.087 -27.069  1.00 20.62           A
ATOM   2594  O    CYS A 333       1.047   -3.966 -26.640  1.00 20.60           A
ATOM   2595  N    GLU A 334       1.422   -5.490 -28.218  1.00 19.42           A
ATOM   2596  CA   GLU A 334       2.317   -4.604 -28.956  1.00 19.82           A
ATOM   2597  CB   GLU A 334       3.102   -5.421 -29.998  1.00 21.89           A
ATOM   2598  CG   GLU A 334       4.169   -4.663 -30.765  1.00 27.12           A
ATOM   2599  CD   GLU A 334       5.320   -4.181 -29.882  1.00 29.45           A
ATOM   2600  OE1  GLU A 334       5.657   -4.863 -28.890  1.00 32.60           A
ATOM   2601  OE2  GLU A 334       5.902   -3.121 -30.198  1.00 32.88           A
ATOM   2602  C    GLU A 334       1.625   -3.429 -29.636  1.00 16.58           A
ATOM   2603  O    GLU A 334       2.060   -2.292 -29.474  1.00 16.78           A
ATOM   2604  N    ASN A 335       0.576   -3.704 -30.402  1.00 16.51           A
ATOM   2605  CA   ASN A 335      -0.146   -2.651 -31.136  1.00 15.36           A
ATOM   2606  CB   ASN A 335       0.089   -2.780 -32.646  1.00 18.00           A
ATOM   2607  CG   ASN A 335       1.546   -2.690 -33.022  1.00 20.47           A
ATOM   2608  OD1  ASN A 335       2.162   -3.672 -33.464  1.00 25.38           A
ATOM   2609  ND2  ASN A 335       2.103   -1.518 -32.867  1.00 18.14           A
ATOM   2610  C    ASN A 335      -1.646   -2.792 -30.914  1.00 16.50           A
ATOM   2611  O    ASN A 335      -2.167   -3.914 -30.726  1.00 16.59           A
ATOM   2612  N    VAL A 336      -2.327   -1.661 -30.918  1.00 16.20           A
ATOM   2613  CA   VAL A 336      -3.764   -1.655 -30.767  1.00 14.76           A
ATOM   2614  CB   VAL A 336      -4.247   -0.853 -29.501  1.00 16.01           A
ATOM   2615  CG1  VAL A 336      -3.681   -1.469 -28.239  1.00 19.32           A
ATOM   2616  CG2  VAL A 336      -3.854    0.619 -29.614  1.00 18.64           A
ATOM   2617  C    VAL A 336      -4.390   -1.040 -31.993  1.00 16.20           A
ATOM   2618  O    VAL A 336      -3.766   -0.257 -32.719  1.00 15.92           A
ATOM   2619  N    ARG A 337      -5.631   -1.422 -32.238  1.00 16.08           A
ATOM   2620  CA   ARG A 337      -6.391   -0.860 -33.330  1.00 17.59           A
ATOM   2621  CB   ARG A 337      -6.879   -1.961 -34.281  1.00 20.37           A
ATOM   2622  CG   ARG A 337      -7.779   -1.445 -35.423  1.00 24.09           A
ATOM   2623  CD   ARG A 337      -8.161   -2.499 -36.481  1.00 26.96           A
ATOM   2624  NE   ARG A 337      -6.983   -3.165 -37.020  1.00 29.58           A
ATOM   2625  CZ   ARG A 337      -6.568   -4.369 -36.628  1.00 30.93           A
ATOM   2626  NH1  ARG A 337      -7.254   -5.040 -35.706  1.00 33.27           A
ATOM   2627  NH2  ARG A 337      -5.446   -4.880 -37.124  1.00 31.58           A
ATOM   2628  C    ARG A 337      -7.602   -0.160 -32.741  1.00 17.83           A
ATOM   2629  O    ARG A 337      -8.342   -0.739 -31.919  1.00 17.99           A
ATOM   2630  N    MET A 338      -7.803    1.092 -33.154  1.00 16.35           A
ATOM   2631  CA   MET A 338      -8.976    1.881 -32.731  1.00 17.54           A
ATOM   2632  CB   MET A 338      -8.561    3.298 -32.322  1.00 19.03           A
ATOM   2633  CG   MET A 338      -7.696    3.343 -31.067  1.00 22.98           A
ATOM   2634  SD   MET A 338      -7.251    5.013 -30.485  1.00 28.14           A
ATOM   2635  CE   MET A 338      -8.672    5.347 -29.411  1.00 24.78           A
ATOM   2636  C    MET A 338      -9.867    1.943 -33.963  1.00 17.28           A
ATOM   2637  O    MET A 338      -9.398    2.321 -35.033  1.00 18.78           A
ATOM   2638  N    MET A 339     -11.144    1.591 -33.825  1.00 17.39           A
ATOM   2639  CA   MET A 339     -12.064    1.582 -34.955  1.00 17.39           A
ATOM   2640  CB   MET A 339     -12.686    0.180 -35.053  1.00 20.98           A
ATOM   2641  CG   MET A 339     -11.628   -0.888 -34.852  1.00 25.07           A
ATOM   2642  SD   MET A 339     -12.307   -2.536 -34.442  1.00 30.90           A
ATOM   2643  CE   MET A 339     -12.758   -2.891 -36.141  1.00 27.62           A
ATOM   2644  C    MET A 339     -13.075    2.576 -34.673  1.00 18.45           A
ATOM   2645  O    MET A 339     -13.868    2.596 -33.729  1.00 17.17           A
ATOM   2646  N    LEU A 340     -13.009    3.728 -35.490  1.00 17.41           A
ATOM   2647  CA   LEU A 340     -13.853    4.898 -35.313  1.00 19.07           A
ATOM   2648  CB   LEU A 340     -12.974    6.150 -35.330  1.00 21.15           A
ATOM   2649  CG   LEU A 340     -11.856    6.140 -34.291  1.00 22.56           A
ATOM   2650  CD1  LEU A 340     -10.597    6.765 -34.885  1.00 27.71           A
ATOM   2651  CD2  LEU A 340     -12.321    6.986 -33.043  1.00 24.99           A
ATOM   2652  C    LEU A 340     -14.892    5.036 -36.396  1.00 20.06           A
ATOM   2653  O    LEU A 340     -14.739    4.483 -37.481  1.00 20.26           A
ATOM   2654  N    THR A 341     -15.941    5.783 -36.086  1.00 22.17           A
ATOM   2655  CA   THR A 341     -17.029    6.020 -37.026  1.00 25.08           A
ATOM   2656  CB   THR A 341     -18.350    5.576 -36.433  1.00 26.10           A
ATOM   2657  OG1  THR A 341     -18.287    4.178 -36.133  1.00 25.61           A
ATOM   2658  CG2  THR A 341     -19.487    5.811 -37.438  1.00 26.42           A
ATOM   2659  C    THR A 341     -17.084    7.509 -37.328  1.00 25.45           A
ATOM   2660  O    THR A 341     -16.921    7.922 -38.481  1.00 27.99           A
ATOM   2661  N    ASP A 342     -17.320    8.298 -36.284  1.00 25.19           A
ATOM   2662  CA   ASP A 342     -17.367    9.757 -36.381  1.00 24.72           A
ATOM   2663  CB   ASP A 342     -18.690   10.235 -37.008  1.00 25.68           A
ATOM   2664  CG   ASP A 342     -19.905    9.816 -36.214  1.00 27.08           A
ATOM   2665  OD1  ASP A 342     -19.828    9.819 -34.967  1.00 25.99           A
```

Figure 1 (continued 27)

| ATOM | 2666 | OD2 | ASP | A | 342 | -20.947 | 9.513 | -36.855 | 1.00 | 30.26 | A |
|---|---|---|---|---|---|---|---|---|---|---|---|
| ATOM | 2667 | C | ASP | A | 342 | -17.137 | 10.406 | -35.019 | 1.00 | 23.68 | A |
| ATOM | 2668 | O | ASP | A | 342 | -16.889 | 9.725 | -34.014 | 1.00 | 21.46 | A |
| ATOM | 2669 | N | SER | A | 343 | -17.216 | 11.729 | -34.969 | 1.00 | 23.14 | A |
| ATOM | 2670 | CA | SER | A | 343 | -16.929 | 12.436 | -33.744 | 1.00 | 24.43 | A |
| ATOM | 2671 | CB | SER | A | 343 | -16.755 | 13.936 | -34.034 | 1.00 | 26.47 | A |
| ATOM | 2672 | OG | SER | A | 343 | -17.994 | 14.549 | -34.368 | 1.00 | 29.79 | A |
| ATOM | 2673 | C | SER | A | 343 | -17.905 | 12.249 | -32.602 | 1.00 | 24.03 | A |
| ATOM | 2674 | O | SER | A | 343 | -17.567 | 12.520 | -31.457 | 1.00 | 24.30 | A |
| ATOM | 2675 | N | VAL | A | 344 | -19.109 | 11.758 | -32.884 | 1.00 | 23.83 | A |
| ATOM | 2676 | CA | VAL | A | 344 | -20.078 | 11.630 | -31.809 | 1.00 | 23.12 | A |
| ATOM | 2677 | CB | VAL | A | 344 | -21.357 | 12.448 | -32.132 | 1.00 | 24.91 | A |
| ATOM | 2678 | CG1 | VAL | A | 344 | -21.003 | 13.909 | -32.356 | 1.00 | 25.01 | A |
| ATOM | 2679 | CG2 | VAL | A | 344 | -22.011 | 11.888 | -33.359 | 1.00 | 23.59 | A |
| ATOM | 2680 | C | VAL | A | 344 | -20.487 | 10.192 | -31.504 | 1.00 | 23.42 | A |
| ATOM | 2681 | O | VAL | A | 344 | -21.458 | 9.951 | -30.788 | 1.00 | 25.49 | A |
| ATOM | 2682 | N | SER | A | 345 | -19.731 | 9.244 | -32.026 | 1.00 | 21.89 | A |
| ATOM | 2683 | CA | SER | A | 345 | -20.013 | 7.829 | -31.834 | 1.00 | 21.04 | A |
| ATOM | 2684 | CB | SER | A | 345 | -20.163 | 7.177 | -33.197 | 1.00 | 22.41 | A |
| ATOM | 2685 | OG | SER | A | 345 | -21.229 | 7.826 | -33.898 | 1.00 | 25.59 | A |
| ATOM | 2686 | C | SER | A | 345 | -18.903 | 7.139 | -31.038 | 1.00 | 20.75 | A |
| ATOM | 2687 | O | SER | A | 345 | -17.768 | 7.582 | -31.036 | 1.00 | 20.76 | A |
| ATOM | 2688 | N | SER | A | 346 | -19.241 | 6.045 | -30.367 | 1.00 | 18.72 | A |
| ATOM | 2689 | CA | SER | A | 346 | -18.246 | 5.325 | -29.580 | 1.00 | 17.41 | A |
| ATOM | 2690 | CB | SER | A | 346 | -18.942 | 4.243 | -28.754 | 1.00 | 18.74 | A |
| ATOM | 2691 | OG | SER | A | 346 | -19.913 | 4.838 | -27.930 | 1.00 | 22.66 | A |
| ATOM | 2692 | C | SER | A | 346 | -17.184 | 4.697 | -30.466 | 1.00 | 17.40 | A |
| ATOM | 2693 | O | SER | A | 346 | -17.398 | 4.490 | -31.656 | 1.00 | 21.59 | A |
| ATOM | 2694 | N | VAL | A | 347 | -16.045 | 4.390 | -29.869 | 1.00 | 16.03 | A |
| ATOM | 2695 | CA | VAL | A | 347 | -14.916 | 3.754 | -30.558 | 1.00 | 15.59 | A |
| ATOM | 2696 | CB | VAL | A | 347 | -13.561 | 4.492 | -30.225 | 1.00 | 16.49 | A |
| ATOM | 2697 | CG1 | VAL | A | 347 | -13.206 | 4.415 | -28.731 | 1.00 | 17.48 | A |
| ATOM | 2698 | CG2 | VAL | A | 347 | -12.426 | 3.924 | -31.045 | 1.00 | 19.46 | A |
| ATOM | 2699 | C | VAL | A | 347 | -14.809 | 2.305 | -30.088 | 1.00 | 14.00 | A |
| ATOM | 2700 | O | VAL | A | 347 | -15.213 | 2.005 | -28.974 | 1.00 | 15.79 | A |
| ATOM | 2701 | N | GLN | A | 348 | -14.340 | 1.420 | -30.957 | 1.00 | 13.62 | A |
| ATOM | 2702 | CA | GLN | A | 348 | -14.081 | 0.025 | -30.547 | 1.00 | 12.23 | A |
| ATOM | 2703 | CB | GLN | A | 348 | -14.702 | -0.983 | -31.533 | 1.00 | 13.64 | A |
| ATOM | 2704 | CG | GLN | A | 348 | -14.416 | -2.454 | -31.162 | 1.00 | 15.65 | A |
| ATOM | 2705 | CD | GLN | A | 348 | -15.268 | -3.431 | -31.957 | 1.00 | 16.97 | A |
| ATOM | 2706 | OE1 | GLN | A | 348 | -14.825 | -4.545 | -32.272 | 1.00 | 22.42 | A |
| ATOM | 2707 | NE2 | GLN | A | 348 | -16.499 | -3.035 | -32.262 | 1.00 | 16.85 | A |
| ATOM | 2708 | C | GLN | A | 348 | -12.548 | -0.121 | -30.580 | 1.00 | 13.90 | A |
| ATOM | 2709 | O | GLN | A | 348 | -11.909 | 0.275 | -31.563 | 1.00 | 13.82 | A |
| ATOM | 2710 | N | ILE | A | 349 | -11.971 | -0.681 | -29.513 | 1.00 | 12.76 | A |
| ATOM | 2711 | CA | ILE | A | 349 | -10.516 | -0.865 | -29.425 | 1.00 | 12.30 | A |
| ATOM | 2712 | CB | ILE | A | 349 | -9.967 | -0.071 | -28.210 | 1.00 | 14.15 | A |
| ATOM | 2713 | CG2 | ILE | A | 349 | -8.434 | -0.148 | -28.138 | 1.00 | 14.43 | A |
| ATOM | 2714 | CG1 | ILE | A | 349 | -10.359 | 1.398 | -28.357 | 1.00 | 13.90 | A |
| ATOM | 2715 | CD1 | ILE | A | 349 | -9.959 | 2.196 | -27.088 | 1.00 | 14.25 | A |
| ATOM | 2716 | C | ILE | A | 349 | -10.232 | -2.339 | -29.247 | 1.00 | 14.06 | A |
| ATOM | 2717 | O | ILE | A | 349 | -10.933 | -3.012 | -28.480 | 1.00 | 14.91 | A |
| ATOM | 2718 | N | GLU | A | 350 | -9.195 | -2.824 | -29.938 | 1.00 | 14.83 | A |
| ATOM | 2719 | CA | GLU | A | 350 | -8.765 | -4.231 | -29.850 | 1.00 | 15.53 | A |
| ATOM | 2720 | CB | GLU | A | 350 | -9.357 | -5.077 | -30.975 | 1.00 | 17.90 | A |
| ATOM | 2721 | CG | GLU | A | 350 | -10.870 | -5.018 | -31.138 | 1.00 | 19.30 | A |
| ATOM | 2722 | CD | GLU | A | 350 | -11.361 | -5.919 | -32.260 | 1.00 | 24.15 | A |
| ATOM | 2723 | OE1 | GLU | A | 350 | -10.523 | -6.447 | -33.034 | 1.00 | 25.09 | A |
| ATOM | 2724 | OE2 | GLU | A | 350 | -12.589 | -6.095 | -32.374 | 1.00 | 23.78 | A |
| ATOM | 2725 | C | GLU | A | 350 | -7.247 | -4.312 | -30.037 | 1.00 | 15.60 | A |
| ATOM | 2726 | O | GLU | A | 350 | -6.600 | -3.359 | -30.479 | 1.00 | 15.29 | A |
| ATOM | 2727 | N | ASP | A | 351 | -6.693 | -5.471 | -29.693 | 1.00 | 16.12 | A |
| ATOM | 2728 | CA | ASP | A | 351 | -5.276 | -5.765 | -29.898 | 1.00 | 15.76 | A |
| ATOM | 2729 | CB | ASP | A | 351 | -4.976 | -7.144 | -29.283 | 1.00 | 15.10 | A |
| ATOM | 2730 | CG | ASP | A | 351 | -3.542 | -7.604 | -29.489 | 1.00 | 17.20 | A |
| ATOM | 2731 | OD1 | ASP | A | 351 | -2.865 | -7.057 | -30.377 | 1.00 | 17.43 | A |
| ATOM | 2732 | OD2 | ASP | A | 351 | -3.085 | -8.526 | -28.744 | 1.00 | 18.87 | A |
| ATOM | 2733 | C | ASP | A | 351 | -5.253 | -5.849 | -31.438 | 1.00 | 15.75 | A |
| ATOM | 2734 | O | ASP | A | 351 | -6.140 | -6.458 | -32.049 | 1.00 | 16.51 | A |
| ATOM | 2735 | N | ALA | A | 352 | -4.278 | -5.224 | -32.096 | 1.00 | 16.21 | A |
| ATOM | 2736 | CA | ALA | A | 352 | -4.269 | -5.276 | -33.558 | 1.00 | 18.09 | A |
| ATOM | 2737 | CB | ALA | A | 352 | -3.158 | -4.347 | -34.121 | 1.00 | 18.36 | A |
| ATOM | 2738 | C | ALA | A | 352 | -4.046 | -6.711 | -34.030 | 1.00 | 18.81 | A |
| ATOM | 2739 | O | ALA | A | 352 | -4.396 | -7.044 | -35.158 | 1.00 | 21.06 | A |
| ATOM | 2740 | N | ALA | A | 353 | -3.496 | -7.552 | -33.157 | 1.00 | 19.56 | A |
| ATOM | 2741 | CA | ALA | A | 353 | -3.194 | -8.946 | -33.502 | 1.00 | 20.21 | A |
| ATOM | 2742 | CB | ALA | A | 353 | -1.792 | -9.285 | -33.026 | 1.00 | 20.26 | A |
| ATOM | 2743 | C | ALA | A | 353 | -4.167 | -10.006 | -32.977 | 1.00 | 21.68 | A |
| ATOM | 2744 | O | ALA | A | 353 | -3.901 | -11.201 | -33.108 | 1.00 | 23.17 | A |
| ATOM | 2745 | N | SER | A | 354 | -5.281 | -9.598 | -32.382 | 1.00 | 20.83 | A |
| ATOM | 2746 | CA | SER | A | 354 | -6.225 | -10.577 | -31.843 | 1.00 | 19.77 | A |
| ATOM | 2747 | CB | SER | A | 354 | -5.780 | -11.029 | -30.468 | 1.00 | 20.42 | A |
| ATOM | 2748 | OG | SER | A | 354 | -6.738 | -11.943 | -29.917 | 1.00 | 22.32 | A |
| ATOM | 2749 | C | SER | A | 354 | -7.597 | -9.986 | -31.687 | 1.00 | 20.59 | A |
| ATOM | 2750 | O | SER | A | 354 | -7.720 | -8.890 | -31.151 | 1.00 | 19.79 | A |
| ATOM | 2751 | N | GLN | A | 355 | -8.618 | -10.720 | -32.129 | 1.00 | 20.97 | A |
| ATOM | 2752 | CA | GLN | A | 355 | -9.990 | -10.266 | -32.014 | 1.00 | 22.47 | A |
| ATOM | 2753 | CB | GLN | A | 355 | -10.786 | -10.602 | -33.278 | 1.00 | 26.42 | A |
| ATOM | 2754 | CG | GLN | A | 355 | -10.487 | -9.680 | -34.457 | 1.00 | 29.56 | A |
| ATOM | 2755 | CD | GLN | A | 355 | -11.532 | -9.777 | -35.552 | 1.00 | 32.83 | A |
| ATOM | 2756 | OE1 | GLN | A | 355 | -12.725 | -9.567 | -35.307 | 1.00 | 34.38 | A |
| ATOM | 2757 | NE2 | GLN | A | 355 | -11.088 | -10.083 | -36.773 | 1.00 | 33.96 | A |
| ATOM | 2758 | C | GLN | A | 355 | -10.664 | -10.924 | -30.809 | 1.00 | 20.74 | A |
| ATOM | 2759 | O | GLN | A | 355 | -11.869 | -10.815 | -30.648 | 1.00 | 23.27 | A |
| ATOM | 2760 | N | SER | A | 356 | -9.887 | -11.573 | -29.956 | 1.00 | 18.84 | A |
| ATOM | 2761 | CA | SER | A | 356 | -10.456 | -12.239 | -28.769 | 1.00 | 19.15 | A |
| ATOM | 2762 | CB | SER | A | 356 | -9.386 | -13.050 | -28.027 | 1.00 | 19.93 | A |
| ATOM | 2763 | OG | SER | A | 356 | -8.338 | -12.230 | -27.573 | 1.00 | 26.23 | A |
| ATOM | 2764 | C | SER | A | 356 | -11.136 | -11.293 | -27.793 | 1.00 | 17.16 | A |
| ATOM | 2765 | O | SER | A | 356 | -12.118 | -11.664 | -27.158 | 1.00 | 17.71 | A |

Figure 1 (continued 28)

| | | | | | | | | | |
|---|---|---|---|---|---|---|---|---|---|
| ATOM | 2766 | N | ALA | A | 357 | -10.623 | -10.084 | -27.649 | 1.00 16.33 | A |
| ATOM | 2767 | CA | ALA | A | 357 | -11.258 | -9.113 | -26.750 | 1.00 16.01 | A |
| ATOM | 2768 | CB | ALA | A | 357 | -10.362 | -8.779 | -25.603 | 1.00 17.39 | A |
| ATOM | 2769 | C | ALA | A | 357 | -11.590 | -7.841 | -27.524 | 1.00 15.77 | A |
| ATOM | 2770 | O | ALA | A | 357 | -10.883 | -7.481 | -28.477 | 1.00 18.23 | A |
| ATOM | 2771 | N | ALA | A | 358 | -12.673 | -7.180 | -27.129 | 1.00 15.41 | A |
| ATOM | 2772 | CA | ALA | A | 358 | -13.047 | -5.907 | -27.761 | 1.00 12.42 | A |
| ATOM | 2773 | CB | ALA | A | 358 | -14.140 | -6.118 | -28.811 | 1.00 14.36 | A |
| ATOM | 2774 | C | ALA | A | 358 | -13.535 | -4.944 | -26.677 | 1.00 13.39 | A |
| ATOM | 2775 | O | ALA | A | 358 | -14.168 | -5.354 | -25.689 | 1.00 13.08 | A |
| ATOM | 2776 | N | TYR | A | 359 | -13.250 | -3.662 | -26.853 | 1.00 11.92 | A |
| ATOM | 2777 | CA | TYR | A | 359 | -13.638 | -2.664 | -25.873 | 1.00 12.31 | A |
| ATOM | 2778 | CB | TYR | A | 359 | -12.385 | -2.123 | -25.143 | 1.00 12.39 | A |
| ATOM | 2779 | CG | TYR | A | 359 | -11.605 | -3.220 | -24.463 | 1.00 12.04 | A |
| ATOM | 2780 | CD1 | TYR | A | 359 | -11.895 | -3.596 | -23.151 | 1.00 11.11 | A |
| ATOM | 2781 | CE1 | TYR | A | 359 | -11.257 | -4.683 | -22.558 | 1.00 12.06 | A |
| ATOM | 2782 | CD2 | TYR | A | 359 | -10.643 | -3.958 | -25.175 | 1.00 12.43 | A |
| ATOM | 2783 | CE2 | TYR | A | 359 | -10.014 | -5.054 | -24.588 | 1.00 12.80 | A |
| ATOM | 2784 | CZ | TYR | A | 359 | -10.328 | -5.396 | -23.286 | 1.00 13.52 | A |
| ATOM | 2785 | OH | TYR | A | 359 | -9.685 | -6.468 | -22.703 | 1.00 14.61 | A |
| ATOM | 2786 | C | TYR | A | 359 | -14.380 | -1.543 | -26.564 | 1.00 12.62 | A |
| ATOM | 2787 | O | TYR | A | 359 | -14.014 | -1.160 | -27.671 | 1.00 13.90 | A |
| ATOM | 2788 | N | VAL | A | 360 | -15.470 | -1.072 | -25.961 | 1.00 12.93 | A |
| ATOM | 2789 | CA | VAL | A | 360 | -16.245 | 0.015 | -26.567 | 1.00 14.00 | A |
| ATOM | 2790 | CB | VAL | A | 360 | -17.670 | -0.433 | -26.861 | 1.00 12.46 | A |
| ATOM | 2791 | CG1 | VAL | A | 360 | -18.476 | 0.737 | -27.477 | 1.00 15.11 | A |
| ATOM | 2792 | CG2 | VAL | A | 360 | -17.624 | -1.638 | -27.791 | 1.00 14.89 | A |
| ATOM | 2793 | C | VAL | A | 360 | -16.255 | 1.158 | -25.586 | 1.00 13.57 | A |
| ATOM | 2794 | O | VAL | A | 360 | -16.573 | 0.967 | -24.419 | 1.00 12.80 | A |
| ATOM | 2795 | N | VAL | A | 361 | -15.883 | 2.359 | -26.044 | 1.00 13.11 | A |
| ATOM | 2796 | CA | VAL | A | 361 | -15.821 | 3.496 | -25.157 | 1.00 14.02 | A |
| ATOM | 2797 | CB | VAL | A | 361 | -14.346 | 3.931 | -24.924 | 1.00 13.31 | A |
| ATOM | 2798 | CG1 | VAL | A | 361 | -14.272 | 5.047 | -23.911 | 1.00 14.14 | A |
| ATOM | 2799 | CG2 | VAL | A | 361 | -13.542 | 2.718 | -24.402 | 1.00 14.27 | A |
| ATOM | 2800 | C | VAL | A | 361 | -16.566 | 4.648 | -25.785 | 1.00 13.41 | A |
| ATOM | 2801 | O | VAL | A | 361 | -16.339 | 4.947 | -26.948 | 1.00 13.82 | A |
| ATOM | 2802 | N | MET | A | 362 | -17.494 | 5.247 | -25.043 | 1.00 14.34 | A |
| ATOM | 2803 | CA | MET | A | 362 | -18.208 | 6.383 | -25.612 | 1.00 15.43 | A |
| ATOM | 2804 | CB | MET | A | 362 | -19.406 | 6.802 | -24.729 | 1.00 17.04 | A |
| ATOM | 2805 | CG | MET | A | 362 | -20.532 | 5.811 | -24.542 | 1.00 24.10 | A |
| ATOM | 2806 | SD | MET | A | 362 | -21.744 | 6.650 | -23.450 | 1.00 30.22 | A |
| ATOM | 2807 | CE | MET | A | 362 | -20.595 | 7.445 | -22.182 | 1.00 27.70 | A |
| ATOM | 2808 | C | MET | A | 362 | -17.290 | 7.592 | -25.674 | 1.00 16.05 | A |
| ATOM | 2809 | O | MET | A | 362 | -16.327 | 7.689 | -24.949 | 1.00 16.00 | A |
| ATOM | 2810 | N | PRO | A | 363 | -17.602 | 8.535 | -26.550 | 1.00 16.34 | A |
| ATOM | 2811 | CD | PRO | A | 363 | -18.565 | 8.438 | -27.661 | 1.00 19.07 | A |
| ATOM | 2812 | CA | PRO | A | 363 | -16.771 | 9.736 | -26.643 | 1.00 17.39 | A |
| ATOM | 2813 | CB | PRO | A | 363 | -17.127 | 10.292 | -28.017 | 1.00 20.19 | A |
| ATOM | 2814 | CG | PRO | A | 363 | -18.547 | 9.841 | -28.237 | 1.00 20.14 | A |
| ATOM | 2815 | C | PRO | A | 363 | -17.113 | 10.686 | -25.490 | 1.00 18.96 | A |
| ATOM | 2816 | O | PRO | A | 363 | -18.201 | 10.583 | -24.888 | 1.00 19.41 | A |
| ATOM | 2817 | N | MET | A | 364 | -16.172 | 11.557 | -25.138 | 1.00 17.22 | A |
| ATOM | 2818 | CA | MET | A | 364 | -16.369 | 12.584 | -24.095 | 1.00 16.88 | A |
| ATOM | 2819 | CB | MET | A | 364 | -15.308 | 12.451 | -22.998 | 1.00 18.63 | A |
| ATOM | 2820 | CG | MET | A | 364 | -15.448 | 13.444 | -21.856 | 1.00 19.86 | A |
| ATOM | 2821 | SD | MET | A | 364 | -14.143 | 13.161 | -20.684 | 1.00 20.18 | A |
| ATOM | 2822 | CE | MET | A | 364 | -14.902 | 12.079 | -19.580 | 1.00 21.47 | A |
| ATOM | 2823 | C | MET | A | 364 | -16.309 | 13.976 | -24.722 | 1.00 19.03 | A |
| ATOM | 2824 | O | MET | A | 364 | -15.394 | 14.297 | -25.489 | 1.00 19.45 | A |
| ATOM | 2825 | N | ARG | A | 365 | -17.297 | 14.828 | -24.430 | 1.00 18.40 | A |
| ATOM | 2826 | CA | ARG | A | 365 | -17.304 | 16.180 | -24.984 | 1.00 21.57 | A |
| ATOM | 2827 | CB | ARG | A | 365 | -18.723 | 16.759 | -24.976 | 1.00 23.93 | A |
| ATOM | 2828 | CG | ARG | A | 365 | -19.660 | 16.122 | -25.961 | 1.00 30.14 | A |
| ATOM | 2829 | CD | ARG | A | 365 | -19.240 | 16.437 | -27.376 | 1.00 35.93 | A |
| ATOM | 2830 | NE | ARG | A | 365 | -20.353 | 16.314 | -28.317 | 1.00 41.53 | A |
| ATOM | 2831 | CZ | ARG | A | 365 | -20.214 | 16.365 | -29.639 | 1.00 43.21 | A |
| ATOM | 2832 | NH1 | ARG | A | 365 | -19.009 | 16.526 | -30.174 | 1.00 43.54 | A |
| ATOM | 2833 | NH2 | ARG | A | 365 | -21.281 | 16.282 | -30.426 | 1.00 44.53 | A |
| ATOM | 2834 | C | ARG | A | 365 | -16.402 | 17.079 | -24.164 | 1.00 20.31 | A |
| ATOM | 2835 | O | ARG | A | 365 | -16.487 | 17.099 | -22.932 | 1.00 19.99 | A |
| ATOM | 2836 | N | LEU | A | 366 | -15.549 | 17.842 | -24.850 | 1.00 19.74 | A |
| ATOM | 2837 | CA | LEU | A | 366 | -14.637 | 18.744 | -24.152 | 1.00 21.42 | A |
| ATOM | 2838 | CB | LEU | A | 366 | -13.205 | 18.186 | -24.236 | 1.00 21.30 | A |
| ATOM | 2839 | CG | LEU | A | 366 | -12.987 | 16.831 | -23.568 | 1.00 22.44 | A |
| ATOM | 2840 | CD1 | LEU | A | 366 | -11.670 | 16.240 | -24.049 | 1.00 22.25 | A |
| ATOM | 2841 | CD2 | LEU | A | 366 | -12.952 | 16.997 | -22.073 | 1.00 21.14 | A |
| ATOM | 2842 | C | LEU | A | 366 | -14.675 | 20.182 | -24.703 | 1.00 23.50 | A |
| ATOM | 2843 | O | LEU | A | 366 | -13.631 | 20.879 | -24.600 | 1.00 24.15 | A |
| ATOM | 2844 | OXT | LEU | A | 366 | -15.757 | 20.610 | -25.202 | 1.00 25.87 | A |
| ATOM | 2845 | CB | MET | B | 1 | 14.354 | 31.226 | -16.722 | 1.00 14.72 | B |
| ATOM | 2846 | CG | MET | B | 1 | 14.917 | 30.008 | -15.980 | 1.00 13.54 | B |
| ATOM | 2847 | SD | MET | B | 1 | 13.753 | 29.266 | -14.804 | 1.00 17.51 | B |
| ATOM | 2848 | CE | MET | B | 1 | 12.697 | 28.387 | -15.952 | 1.00 16.34 | B |
| ATOM | 2849 | C | MET | B | 1 | 14.966 | 30.414 | -18.998 | 1.00 14.66 | B |
| ATOM | 2850 | O | MET | B | 1 | 13.867 | 30.217 | -19.542 | 1.00 16.39 | B |
| ATOM | 2851 | N | MET | B | 1 | 14.668 | 32.827 | -18.638 | 1.00 16.03 | B |
| ATOM | 2852 | CA | MET | B | 1 | 15.135 | 31.538 | -18.017 | 1.00 13.94 | B |
| ATOM | 2853 | N | LYS | B | 2 | 16.047 | 29.666 | -19.238 | 1.00 14.97 | B |
| ATOM | 2854 | CA | LYS | B | 2 | 16.015 | 28.554 | -20.195 | 1.00 15.37 | B |
| ATOM | 2855 | CB | LYS | B | 2 | 16.413 | 29.068 | -21.575 | 1.00 17.84 | B |
| ATOM | 2856 | CG | LYS | B | 2 | 16.273 | 28.083 | -22.709 | 1.00 23.16 | B |
| ATOM | 2857 | CD | LYS | B | 2 | 16.371 | 28.841 | -24.054 | 1.00 27.33 | B |
| ATOM | 2858 | CE | LYS | B | 2 | 15.972 | 27.950 | -25.222 | 1.00 30.66 | B |
| ATOM | 2859 | NZ | LYS | B | 2 | 16.920 | 26.805 | -25.375 | 1.00 31.91 | B |
| ATOM | 2860 | C | LYS | B | 2 | 17.004 | 27.477 | -19.805 | 1.00 16.00 | B |
| ATOM | 2861 | O | LYS | B | 2 | 18.106 | 27.776 | -19.356 | 1.00 14.43 | B |
| ATOM | 2862 | N | PHE | B | 3 | 16.592 | 26.224 | -19.918 | 1.00 12.71 | B |
| ATOM | 2863 | CA | PHE | B | 3 | 17.524 | 25.132 | -19.669 | 1.00 13.78 | B |
| ATOM | 2864 | CB | PHE | B | 3 | 17.744 | 24.912 | -18.154 | 1.00 12.36 | B |
| ATOM | 2865 | CG | PHE | B | 3 | 16.521 | 24.464 | -17.403 | 1.00 11.46 | B |

Figure 1 (continued 29)

```
ATOM  2866 CD1 PHE B   3      15.726  25.391 -16.719  1.00 12.95        B
ATOM  2867 CD2 PHE B   3      16.192  23.108 -17.354  1.00 11.17        B
ATOM  2868 CE1 PHE B   3      14.607  24.944 -15.988  1.00 13.10        B
ATOM  2869 CE2 PHE B   3      15.088  22.664 -16.639  1.00 13.73        B
ATOM  2870 CZ  PHE B   3      14.300  23.598 -15.956  1.00 11.90        B
ATOM  2871 C   PHE B   3      17.047  23.863 -20.358  1.00 12.91        B
ATOM  2872 O   PHE B   3      15.870  23.705 -20.657  1.00 14.61        B
ATOM  2873 N   THR B   4      17.981  22.983 -20.677  1.00 12.44        B
ATOM  2874 CA  THR B   4      17.647  21.694 -21.264  1.00 12.80        B
ATOM  2875 CB  THR B   4      18.054  21.570 -22.727  1.00 14.32        B
ATOM  2876 OG1 THR B   4      17.465  22.636 -23.492  1.00 17.57        B
ATOM  2877 CG2 THR B   4      17.564  20.235 -23.258  1.00 15.46        B
ATOM  2878 C   THR B   4      18.437  20.668 -20.440  1.00 14.04        B
ATOM  2879 O   THR B   4      19.658  20.774 -20.291  1.00 14.28        B
ATOM  2880 N   VAL B   5      17.740  19.692 -19.870  1.00 14.07        B
ATOM  2881 CA  VAL B   5      18.377  18.702 -19.003  1.00 14.50        B
ATOM  2882 CB  VAL B   5      18.137  19.055 -17.497  1.00 14.63        B
ATOM  2883 CG1 VAL B   5      18.774  17.995 -16.572  1.00 19.00        B
ATOM  2884 CG2 VAL B   5      18.711  20.379 -17.153  1.00 19.65        B
ATOM  2885 C   VAL B   5      17.841  17.296 -19.293  1.00 16.13        B
ATOM  2886 O   VAL B   5      16.685  17.117 -19.675  1.00 16.46        B
ATOM  2887 N   GLU B   6      18.694  16.294 -19.151  1.00 15.26        B
ATOM  2888 CA  GLU B   6      18.295  14.932 -19.348  1.00 14.93        B
ATOM  2889 CB  GLU B   6      19.563  14.057 -19.314  1.00 17.40        B
ATOM  2890 CG  GLU B   6      19.320  12.568 -19.294  1.00 24.92        B
ATOM  2891 CD  GLU B   6      20.397  11.849 -18.509  1.00 30.16        B
ATOM  2892 OE1 GLU B   6      21.409  11.429 -19.117  1.00 31.47        B
ATOM  2893 OE2 GLU B   6      20.235  11.721 -17.269  1.00 30.79        B
ATOM  2894 C   GLU B   6      17.304  14.577 -18.204  1.00 14.96        B
ATOM  2895 O   GLU B   6      17.478  14.983 -17.044  1.00 13.59        B
ATOM  2896 N   ARG B   7      16.268  13.831 -18.547  1.00 13.17        B
ATOM  2897 CA  ARG B   7      15.235  13.435 -17.595  1.00 13.08        B
ATOM  2898 CB  ARG B   7      14.341  12.368 -18.216  1.00 12.64        B
ATOM  2899 CG  ARG B   7      13.332  11.764 -17.240  1.00 11.85        B
ATOM  2900 CD  ARG B   7      12.547  10.721 -17.988  1.00 14.66        B
ATOM  2901 NE  ARG B   7      11.561  10.026 -17.142  1.00 13.57        B
ATOM  2902 CZ  ARG B   7      11.809   8.942 -16.404  1.00 17.64        B
ATOM  2903 NH1 ARG B   7      13.015   8.381 -16.365  1.00 17.50        B
ATOM  2904 NH2 ARG B   7      10.839   8.391 -15.706  1.00 15.79        B
ATOM  2905 C   ARG B   7      15.748  12.932 -16.243  1.00 14.94        B
ATOM  2906 O   ARG B   7      15.326  13.421 -15.202  1.00 13.48        B
ATOM  2907 N   GLU B   8      16.679  11.981 -16.256  1.00 15.15        B
ATOM  2908 CA  GLU B   8      17.145  11.434 -14.973  1.00 18.15        B
ATOM  2909 CB  GLU B   8      17.861  10.104 -15.238  1.00 18.04        B
ATOM  2910 CG  GLU B   8      16.929   9.035 -15.849  1.00 19.35        B
ATOM  2911 CD  GLU B   8      16.576   9.297 -17.297  1.00 17.91        B
ATOM  2912 OE1 GLU B   8      17.433   9.801 -18.024  1.00 19.66        B
ATOM  2913 OE2 GLU B   8      15.460   8.978 -17.745  1.00 18.19        B
ATOM  2914 C   GLU B   8      17.988  12.368 -14.103  1.00 20.48        B
ATOM  2915 O   GLU B   8      18.056  12.219 -12.878  1.00 19.63        B
ATOM  2916 N   HIS B   9      18.613  13.364 -14.728  1.00 21.28        B
ATOM  2917 CA  HIS B   9      19.426  14.333 -14.008  1.00 23.49        B
ATOM  2918 CB  HIS B   9      20.297  15.041 -15.071  1.00 25.02        B
ATOM  2919 CG  HIS B   9      21.522  15.711 -14.538  1.00 25.42        B
ATOM  2920 CD2 HIS B   9      21.915  17.007 -14.589  1.00 28.09        B
ATOM  2921 ND1 HIS B   9      22.466  15.056 -13.780  1.00 26.71        B
ATOM  2922 CE1 HIS B   9      23.377  15.920 -13.367  1.00 27.14        B
ATOM  2923 NE2 HIS B   9      23.064  17.114 -13.843  1.00 29.19        B
ATOM  2924 C   HIS B   9      18.460  15.284 -13.250  1.00 22.99        B
ATOM  2925 O   HIS B   9      18.789  15.913 -12.229  1.00 23.60        B
ATOM  2926 N   LEU B  10      17.222  15.347 -13.737  1.00 21.72        B
ATOM  2927 CA  LEU B  10      16.202  16.182 -13.157  1.00 21.01        B
ATOM  2928 CB  LEU B  10      15.454  16.876 -14.310  1.00 21.10        B
ATOM  2929 CG  LEU B  10      14.381  17.868 -13.903  1.00 19.07        B
ATOM  2930 CD1 LEU B  10      15.051  19.052 -13.212  1.00 20.85        B
ATOM  2931 CD2 LEU B  10      13.613  18.369 -15.152  1.00 18.56        B
ATOM  2932 C   LEU B  10      15.181  15.513 -12.200  1.00 22.03        B
ATOM  2933 O   LEU B  10      14.732  16.119 -11.216  1.00 23.32        B
ATOM  2934 N   LEU B  11      14.860  14.247 -12.460  1.00 19.50        B
ATOM  2935 CA  LEU B  11      13.848  13.520 -11.718  1.00 21.06        B
ATOM  2936 CB  LEU B  11      13.667  12.159 -12.376  1.00 21.78        B
ATOM  2937 CG  LEU B  11      12.270  11.573 -12.315  1.00 23.01        B
ATOM  2938 CD1 LEU B  11      11.245  12.601 -12.812  1.00 26.14        B
ATOM  2939 CD2 LEU B  11      12.219  10.366 -13.214  1.00 26.14        B
ATOM  2940 C   LEU B  11      13.979  13.363 -10.192  1.00 21.79        B
ATOM  2941 O   LEU B  11      13.053  13.717  -9.453  1.00 21.56        B
ATOM  2942 N   LYS B  12      15.095  12.826  -9.717  1.00 23.82        B
ATOM  2943 CA  LYS B  12      15.250  12.672  -8.267  1.00 24.71        B
ATOM  2944 CB  LYS B  12      16.543  11.923  -7.915  1.00 28.61        B
ATOM  2945 CG  LYS B  12      16.608  11.564  -6.431  1.00 31.97        B
ATOM  2946 CD  LYS B  12      17.856  10.741  -6.085  1.00 36.79        B
ATOM  2947 CE  LYS B  12      17.795  10.213  -4.650  1.00 37.65        B
ATOM  2948 NZ  LYS B  12      17.449  11.262  -3.640  1.00 39.04        B
ATOM  2949 C   LYS B  12      15.224  14.040  -7.576  1.00 22.39        B
ATOM  2950 O   LYS B  12      14.586  14.193  -6.542  1.00 22.26        B
ATOM  2951 N   PRO B  13      15.932  15.052  -8.123  1.00 20.35        B
ATOM  2952 CD  PRO B  13      17.026  15.053  -9.103  1.00 19.55        B
ATOM  2953 CA  PRO B  13      15.855  16.346  -7.434  1.00 19.49        B
ATOM  2954 CB  PRO B  13      16.669  17.272  -8.333  1.00 19.36        B
ATOM  2955 CG  PRO B  13      17.750  16.376  -8.827  1.00 19.86        B
ATOM  2956 C   PRO B  13      14.420  16.838  -7.294  1.00 19.87        B
ATOM  2957 O   PRO B  13      14.041  17.346  -6.250  1.00 17.95        B
ATOM  2958 N   LEU B  14      13.620  16.710  -8.363  1.00 18.71        B
ATOM  2959 CA  LEU B  14      12.231  17.130  -8.294  1.00 22.23        B
ATOM  2960 CB  LEU B  14      11.532  16.907  -9.641  1.00 21.65        B
ATOM  2961 CG  LEU B  14      11.656  17.995 -10.680  1.00 20.62        B
ATOM  2962 CD1 LEU B  14      10.975  17.528 -11.993  1.00 18.11        B
ATOM  2963 CD2 LEU B  14      11.024  19.287 -10.152  1.00 20.79        B
ATOM  2964 C   LEU B  14      11.464  16.390  -7.215  1.00 22.60        B
ATOM  2965 O   LEU B  14      10.644  16.963  -6.504  1.00 23.92        B
```

Figure 1 (continued 30)

| | | | | | | | | | | |
|---|---|---|---|---|---|---|---|---|---|---|
| ATOM | 2966 | N | GLN | B | 15 | 11.720 | 15.091 | -7.121 | 1.00 24.48 | B |
| ATOM | 2967 | CA | GLN | B | 15 | 11.053 | 14.254 | -6.149 | 1.00 25.57 | B |
| ATOM | 2968 | CB | GLN | B | 15 | 11.481 | 12.808 | -6.340 | 1.00 28.51 | B |
| ATOM | 2969 | CG | GLN | B | 15 | 10.827 | 11.860 | -5.383 | 1.00 32.34 | B |
| ATOM | 2970 | CD | GLN | B | 15 | 11.261 | 10.436 | -5.657 | 1.00 35.26 | B |
| ATOM | 2971 | OE1 | GLN | B | 15 | 11.086 | 9.924 | -6.769 | 1.00 36.87 | B |
| ATOM | 2972 | NE2 | GLN | B | 15 | 11.841 | 9.789 | -4.651 | 1.00 37.81 | B |
| ATOM | 2973 | C | GLN | B | 15 | 11.402 | 14.692 | -4.746 | 1.00 25.12 | B |
| ATOM | 2974 | O | GLN | B | 15 | 10.546 | 14.800 | -3.872 | 1.00 24.87 | B |
| ATOM | 2975 | N | GLN | B | 16 | 12.685 | 14.941 | -4.533 | 1.00 23.65 | B |
| ATOM | 2976 | CA | GLN | B | 16 | 13.133 | 15.374 | -3.224 | 1.00 23.01 | B |
| ATOM | 2977 | CB | GLN | B | 16 | 14.649 | 15.351 | -3.161 | 1.00 26.68 | B |
| ATOM | 2978 | CG | GLN | B | 16 | 15.220 | 13.938 | -3.057 | 1.00 33.06 | B |
| ATOM | 2979 | CD | GLN | B | 16 | 15.149 | 13.363 | -1.639 | 1.00 34.57 | B |
| ATOM | 2980 | OE1 | GLN | B | 16 | 15.499 | 12.208 | -1.417 | 1.00 37.92 | B |
| ATOM | 2981 | NE2 | GLN | B | 16 | 14.709 | 14.170 | -0.683 | 1.00 36.18 | B |
| ATOM | 2982 | C | GLN | B | 16 | 12.640 | 16.761 | -2.798 | 1.00 22.25 | B |
| ATOM | 2983 | O | GLN | B | 16 | 12.218 | 16.966 | -1.657 | 1.00 21.67 | B |
| ATOM | 2984 | N | VAL | B | 17 | 12.665 | 17.731 | -3.697 | 1.00 19.74 | B |
| ATOM | 2985 | CA | VAL | B | 17 | 12.234 | 19.045 | -3.234 | 1.00 21.71 | B |
| ATOM | 2986 | CB | VAL | B | 17 | 12.701 | 20.165 | -4.175 | 1.00 21.43 | B |
| ATOM | 2987 | CG1 | VAL | B | 17 | 14.229 | 20.161 | -4.234 | 1.00 21.95 | B |
| ATOM | 2988 | CG2 | VAL | B | 17 | 12.098 | 20.000 | -5.563 | 1.00 17.76 | B |
| ATOM | 2989 | C | VAL | B | 17 | 10.738 | 19.160 | -3.002 | 1.00 21.93 | B |
| ATOM | 2990 | O | VAL | B | 17 | 10.278 | 20.075 | -2.330 | 1.00 23.73 | B |
| ATOM | 2991 | N | SER | B | 18 | 9.993 | 18.221 | -3.545 | 1.00 23.91 | B |
| ATOM | 2992 | CA | SER | B | 18 | 8.548 | 18.205 | -3.374 | 1.00 25.13 | B |
| ATOM | 2993 | CB | SER | B | 18 | 7.923 | 17.397 | -4.502 | 1.00 25.03 | B |
| ATOM | 2994 | OG | SER | B | 18 | 8.075 | 18.078 | -5.727 | 1.00 24.69 | B |
| ATOM | 2995 | C | SER | B | 18 | 8.092 | 17.636 | -2.024 | 1.00 26.98 | B |
| ATOM | 2996 | O | SER | B | 18 | 6.926 | 17.771 | -1.660 | 1.00 27.31 | B |
| ATOM | 2997 | N | GLY | B | 19 | 9.017 | 17.010 | -1.300 | 1.00 26.53 | B |
| ATOM | 2998 | CA | GLY | B | 19 | 8.706 | 16.413 | -0.012 | 1.00 27.63 | B |
| ATOM | 2999 | C | GLY | B | 19 | 7.842 | 17.206 | 0.951 | 1.00 27.65 | B |
| ATOM | 3000 | O | GLY | B | 19 | 6.788 | 16.717 | 1.364 | 1.00 27.01 | B |
| ATOM | 3001 | N | PRO | B | 20 | 8.265 | 18.416 | 1.351 | 1.00 28.69 | B |
| ATOM | 3002 | CD | PRO | B | 20 | 9.611 | 18.974 | 1.119 | 1.00 30.14 | B |
| ATOM | 3003 | CA | PRO | B | 20 | 7.499 | 19.255 | 2.288 | 1.00 29.93 | B |
| ATOM | 3004 | CB | PRO | B | 20 | 8.462 | 20.415 | 2.594 | 1.00 30.20 | B |
| ATOM | 3005 | CG | PRO | B | 20 | 9.415 | 20.424 | 1.436 | 1.00 30.31 | B |
| ATOM | 3006 | C | PRO | B | 20 | 6.111 | 19.744 | 1.848 | 1.00 31.66 | B |
| ATOM | 3007 | O | PRO | B | 20 | 5.360 | 20.297 | 2.650 | 1.00 32.04 | B |
| ATOM | 3008 | N | LEU | B | 21 | 5.759 | 19.532 | 0.585 | 1.00 33.35 | B |
| ATOM | 3009 | CA | LEU | B | 21 | 4.456 | 19.982 | 0.089 | 1.00 34.98 | B |
| ATOM | 3010 | CB | LEU | B | 21 | 4.506 | 20.208 | -1.429 | 1.00 33.56 | B |
| ATOM | 3011 | CG | LEU | B | 21 | 5.187 | 21.476 | -1.954 | 1.00 33.69 | B |
| ATOM | 3012 | CD1 | LEU | B | 21 | 6.657 | 21.499 | -1.573 | 1.00 32.31 | B |
| ATOM | 3013 | CD2 | LEU | B | 21 | 5.034 | 21.520 | -3.473 | 1.00 33.19 | B |
| ATOM | 3014 | C | LEU | B | 21 | 3.331 | 19.003 | 0.412 | 1.00 36.25 | B |
| ATOM | 3015 | O | LEU | B | 21 | 3.543 | 17.799 | 0.452 | 1.00 37.14 | B |
| ATOM | 3016 | N | GLY | B | 22 | 2.132 | 19.540 | 0.636 | 1.00 38.77 | B |
| ATOM | 3017 | CA | GLY | B | 22 | 0.982 | 18.707 | 0.941 | 1.00 40.45 | B |
| ATOM | 3018 | C | GLY | B | 22 | 0.122 | 18.423 | -0.278 | 1.00 41.52 | B |
| ATOM | 3019 | O | GLY | B | 22 | 0.323 | 19.015 | -1.348 | 1.00 42.14 | B |
| ATOM | 3020 | N | GLY | B | 23 | -0.840 | 17.516 | -0.117 | 1.00 42.36 | B |
| ATOM | 3021 | CA | GLY | B | 23 | -1.731 | 17.170 | -1.214 | 1.00 42.80 | B |
| ATOM | 3022 | C | GLY | B | 23 | -2.597 | 18.349 | -1.621 | 1.00 42.52 | B |
| ATOM | 3023 | O | GLY | B | 23 | -3.306 | 18.470 | -2.775 | 1.00 42.78 | B |
| ATOM | 3024 | N | ARG | B | 24 | -2.886 | 19.223 | -0.664 | 1.00 42.28 | B |
| ATOM | 3025 | CA | ARG | B | 24 | -3.691 | 20.400 | -0.951 | 1.00 41.15 | B |
| ATOM | 3026 | CB | ARG | B | 24 | -5.114 | 20.243 | -0.415 | 1.00 44.69 | B |
| ATOM | 3027 | CG | ARG | B | 24 | -6.032 | 21.311 | -0.973 | 1.00 48.56 | B |
| ATOM | 3028 | CD | ARG | B | 24 | -7.337 | 21.431 | -0.212 | 1.00 52.31 | B |
| ATOM | 3029 | NE | ARG | B | 24 | -8.207 | 22.431 | -0.831 | 1.00 55.67 | B |
| ATOM | 3030 | CZ | ARG | B | 24 | -7.851 | 23.690 | -1.079 | 1.00 57.36 | B |
| ATOM | 3031 | NH1 | ARG | B | 24 | -6.634 | 24.122 | -0.760 | 1.00 58.66 | B |
| ATOM | 3032 | NH2 | ARG | B | 24 | -8.711 | 24.521 | -1.656 | 1.00 58.21 | B |
| ATOM | 3033 | C | ARG | B | 24 | -3.067 | 21.645 | -0.332 | 1.00 38.07 | B |
| ATOM | 3034 | O | ARG | B | 24 | -3.273 | 21.934 | 0.845 | 1.00 38.01 | B |
| ATOM | 3035 | N | PRO | B | 25 | -2.295 | 22.401 | -1.124 | 1.00 35.11 | B |
| ATOM | 3036 | CD | PRO | B | 25 | -2.021 | 22.244 | -2.565 | 1.00 34.80 | B |
| ATOM | 3037 | CA | PRO | B | 25 | -1.663 | 23.611 | -0.601 | 1.00 32.06 | B |
| ATOM | 3038 | CB | PRO | B | 25 | -0.820 | 24.099 | -1.779 | 1.00 31.38 | B |
| ATOM | 3039 | CG | PRO | B | 25 | -1.619 | 23.646 | -2.967 | 1.00 33.86 | B |
| ATOM | 3040 | C | PRO | B | 25 | -2.692 | 24.634 | -0.147 | 1.00 29.51 | B |
| ATOM | 3041 | O | PRO | B | 25 | -3.711 | 24.864 | -0.803 | 1.00 28.23 | B |
| ATOM | 3042 | N | THR | B | 26 | -2.412 | 25.236 | 0.996 | 1.00 28.41 | B |
| ATOM | 3043 | CA | THR | B | 26 | -3.285 | 26.240 | 1.565 | 1.00 27.34 | B |
| ATOM | 3044 | CB | THR | B | 26 | -2.673 | 26.752 | 2.861 | 1.00 28.45 | B |
| ATOM | 3045 | OG1 | THR | B | 26 | -2.397 | 25.643 | 3.717 | 1.00 31.15 | B |
| ATOM | 3046 | CG2 | THR | B | 26 | -3.626 | 27.732 | 3.546 | 1.00 28.57 | B |
| ATOM | 3047 | C | THR | B | 26 | -3.504 | 27.389 | 0.587 | 1.00 25.70 | B |
| ATOM | 3048 | O | THR | B | 26 | -4.624 | 27.893 | 0.428 | 1.00 27.11 | B |
| ATOM | 3049 | N | LEU | B | 27 | -2.426 | 27.829 | -0.044 | 1.00 23.09 | B |
| ATOM | 3050 | CA | LEU | B | 27 | -2.507 | 28.881 | -1.043 | 1.00 21.25 | B |
| ATOM | 3051 | CB | LEU | B | 27 | -1.953 | 30.195 | -0.511 | 1.00 21.63 | B |
| ATOM | 3052 | CG | LEU | B | 27 | -3.900 | 30.896 | 0.483 | 1.00 23.04 | B |
| ATOM | 3053 | CD1 | LEU | B | 27 | -2.264 | 32.203 | 0.895 | 1.00 24.85 | B |
| ATOM | 3054 | CD2 | LEU | B | 27 | -4.270 | 31.144 | -0.160 | 1.00 24.74 | B |
| ATOM | 3055 | C | LEU | B | 27 | -1.718 | 28.392 | -2.247 | 1.00 20.75 | B |
| ATOM | 3056 | O | LEU | B | 27 | -0.775 | 27.601 | -2.105 | 1.00 17.68 | B |
| ATOM | 3057 | N | PRO | B | 28 | -2.084 | 28.863 | -3.443 | 1.00 18.82 | B |
| ATOM | 3058 | CD | PRO | B | 28 | -3.134 | 29.903 | -3.700 | 1.00 18.71 | B |
| ATOM | 3059 | CA | PRO | B | 28 | -1.413 | 28.443 | -4.682 | 1.00 18.57 | B |
| ATOM | 3060 | CB | PRO | B | 28 | -1.917 | 29.446 | -5.722 | 1.00 20.77 | B |
| ATOM | 3061 | CG | PRO | B | 28 | -3.292 | 29.834 | -5.195 | 1.00 20.10 | B |
| ATOM | 3062 | C | PRO | B | 28 | 0.110 | 28.355 | -4.684 | 1.00 18.35 | B |
| ATOM | 3063 | O | PRO | B | 28 | 0.666 | 27.322 | -5.114 | 1.00 18.61 | B |
| ATOM | 3064 | N | ILE | B | 29 | 0.781 | 29.409 | -4.230 | 1.00 16.22 | B |
| ATOM | 3065 | CA | ILE | B | 29 | 2.257 | 29.431 | -4.241 | 1.00 17.45 | B |

```
ATOM   3066  CB   ILE B  29       2.810  30.770  -3.637  1.00 19.27      B
ATOM   3067  CG2  ILE B  29       2.555  30.812  -2.154  1.00 20.68      B
ATOM   3068  CG1  ILE B  29       4.304  30.917  -3.901  1.00 23.27      B
ATOM   3069  CD1  ILE B  29       4.653  31.204  -5.338  1.00 22.71      B
ATOM   3070  C    ILE B  29       2.880  28.264  -3.502  1.00 15.97      B
ATOM   3071  O    ILE B  29       3.957  27.778  -3.907  1.00 14.64      B
ATOM   3072  N    LEU B  30       2.218  27.775  -2.452  1.00 16.95      B
ATOM   3073  CA   LEU B  30       2.782  26.670  -1.664  1.00 16.78      B
ATOM   3074  CB   LEU B  30       2.094  26.575  -0.300  1.00 18.79      B
ATOM   3075  CG   LEU B  30       2.283  27.856   0.524  1.00 19.43      B
ATOM   3076  CD1  LEU B  30       1.556  27.675   1.859  1.00 19.92      B
ATOM   3077  CD2  LEU B  30       3.728  28.159   0.783  1.00 18.87      B
ATOM   3078  C    LEU B  30       2.752  25.322  -2.374  1.00 17.78      B
ATOM   3079  O    LEU B  30       3.343  24.340  -1.901  1.00 18.71      B
ATOM   3080  N    GLY B  31       2.066  25.280  -3.505  1.00 14.09      B
ATOM   3081  CA   GLY B  31       1.999  24.068  -4.318  1.00 15.57      B
ATOM   3082  C    GLY B  31       2.992  24.160  -5.466  1.00 13.53      B
ATOM   3083  O    GLY B  31       3.038  23.269  -6.317  1.00 15.55      B
ATOM   3084  N    ASN B  32       3.796  25.200  -5.476  1.00 12.64      B
ATOM   3085  CA   ASN B  32       4.767  25.400  -6.551  1.00 12.56      B
ATOM   3086  CB   ASN B  32       4.690  26.838  -7.107  1.00 12.94      B
ATOM   3087  CG   ASN B  32       3.502  27.045  -8.024  1.00 10.96      B
ATOM   3088  OD1  ASN B  32       2.599  26.224  -8.085  1.00 12.20      B
ATOM   3089  ND2  ASN B  32       3.523  28.158  -8.771  1.00 13.16      B
ATOM   3090  C    ASN B  32       6.178  25.175  -6.075  1.00 14.19      B
ATOM   3091  O    ASN B  32       6.481  25.195  -4.868  1.00 14.24      B
ATOM   3092  N    LEU B  33       7.050  24.957  -7.052  1.00 13.85      B
ATOM   3093  CA   LEU B  33       8.459  24.861  -6.774  1.00 13.97      B
ATOM   3094  CB   LEU B  33       9.097  23.641  -7.433  1.00 15.40      B
ATOM   3095  CG   LEU B  33       8.586  22.254  -7.072  1.00 17.90      B
ATOM   3096  CD1  LEU B  33       9.410  21.236  -7.867  1.00 18.49      B
ATOM   3097  CD2  LEU B  33       8.782  22.024  -5.568  1.00 19.70      B
ATOM   3098  C    LEU B  33       9.115  26.086  -7.395  1.00 13.05      B
ATOM   3099  O    LEU B  33       8.725  26.540  -8.465  1.00 13.07      B
ATOM   3100  N    LEU B  34      10.126  26.610  -6.722  1.00 12.75      B
ATOM   3101  CA   LEU B  34      10.895  27.732  -7.225  1.00 12.14      B
ATOM   3102  CB   LEU B  34      11.510  28.520  -6.056  1.00 13.47      B
ATOM   3103  CG   LEU B  34      12.562  29.560  -6.427  1.00 12.92      B
ATOM   3104  CD1  LEU B  34      11.973  30.697  -7.293  1.00 14.04      B
ATOM   3105  CD2  LEU B  34      13.130  30.156  -5.123  1.00 14.82      B
ATOM   3106  C    LEU B  34      12.029  27.176  -8.099  1.00 13.14      B
ATOM   3107  O    LEU B  34      12.760  26.275  -7.652  1.00 12.90      B
ATOM   3108  N    LEU B  35      12.125  27.651  -9.351  1.00 11.64      B
ATOM   3109  CA   LEU B  35      13.187  27.245 -10.291  1.00 11.91      B
ATOM   3110  CB   LEU B  35      12.615  26.811 -11.669  1.00 11.42      B
ATOM   3111  CG   LEU B  35      12.046  25.413 -11.738  1.00 14.74      B
ATOM   3112  CD1  LEU B  35      11.127  25.120 -10.596  1.00 18.38      B
ATOM   3113  CD2  LEU B  35      11.288  25.299 -13.074  1.00 15.91      B
ATOM   3114  C    LEU B  35      14.071  28.445 -10.542  1.00 13.47      B
ATOM   3115  O    LEU B  35      13.573  29.535 -10.900  1.00 14.51      B
ATOM   3116  N    GLN B  36      15.376  28.285 -10.350  1.00 13.11      B
ATOM   3117  CA   GLN B  36      16.300  29.400 -10.578  1.00 13.83      B
ATOM   3118  CB   GLN B  36      16.806  29.935  -9.223  1.00 16.19      B
ATOM   3119  CG   GLN B  36      15.726  30.383  -8.281  1.00 16.86      B
ATOM   3120  CD   GLN B  36      16.264  30.626  -6.866  1.00 21.22      B
ATOM   3121  OE1  GLN B  36      16.232  31.760  -6.363  1.00 25.16      B
ATOM   3122  NE2  GLN B  36      16.770  29.570  -6.229  1.00 16.45      B
ATOM   3123  C    GLN B  36      17.495  28.935 -11.376  1.00 13.60      B
ATOM   3124  O    GLN B  36      18.135  27.952 -10.993  1.00 14.49      B
ATOM   3125  N    VAL B  37      17.810  29.640 -12.474  1.00 11.55      B
ATOM   3126  CA   VAL B  37      18.997  29.285 -13.248  1.00 13.61      B
ATOM   3127  CB   VAL B  37      18.731  29.191 -14.777  1.00 12.84      B
ATOM   3128  CG1  VAL B  37      20.074  29.020 -15.553  1.00 14.43      B
ATOM   3129  CG2  VAL B  37      17.804  27.985 -15.051  1.00 14.23      B
ATOM   3130  C    VAL B  37      19.965  30.435 -13.005  1.00 15.18      B
ATOM   3131  O    VAL B  37      19.611  31.603 -13.228  1.00 15.34      B
ATOM   3132  N    ALA B  38      21.139  30.117 -12.472  1.00 15.02      B
ATOM   3133  CA   ALA B  38      22.161  31.146 -12.227  1.00 15.51      B
ATOM   3134  CB   ALA B  38      21.954  31.783 -10.878  1.00 15.09      B
ATOM   3135  C    ALA B  38      23.493  30.446 -12.291  1.00 19.33      B
ATOM   3136  O    ALA B  38      23.644  29.366 -11.747  1.00 18.26      B
ATOM   3137  N    ASP B  39      24.473  31.060 -12.953  1.00 22.66      B
ATOM   3138  CA   ASP B  39      25.765  30.393 -13.153  1.00 26.58      B
ATOM   3139  CB   ASP B  39      26.389  29.982 -11.829  1.00 32.37      B
ATOM   3140  CG   ASP B  39      27.184  31.097 -11.201  1.00 36.57      B
ATOM   3141  OD1  ASP B  39      28.336  31.328 -11.655  1.00 39.34      B
ATOM   3142  OD2  ASP B  39      26.658  31.756 -10.270  1.00 38.78      B
ATOM   3143  C    ASP B  39      25.429  29.150 -13.986  1.00 26.82      B
ATOM   3144  O    ASP B  39      24.550  29.189 -14.844  1.00 29.26      B
ATOM   3145  N    GLY B  40      26.080  28.031 -13.733  1.00 26.59      B
ATOM   3146  CA   GLY B  40      25.759  26.871 -14.539  1.00 23.64      B
ATOM   3147  C    GLY B  40      24.910  25.927 -13.730  1.00 19.76      B
ATOM   3148  O    GLY B  40      25.044  24.723 -13.871  1.00 20.20      B
ATOM   3149  N    THR B  41      24.046  26.498 -12.863  1.00 18.09      B
ATOM   3150  CA   THR B  41      23.215  25.701 -11.983  1.00 15.70      B
ATOM   3151  CB   THR B  41      23.684  25.916 -10.551  1.00 16.47      B
ATOM   3152  OG1  THR B  41      25.090  25.633 -10.486  1.00 19.61      B
ATOM   3153  CG2  THR B  41      22.918  25.016  -9.549  1.00 17.43      B
ATOM   3154  C    THR B  41      21.721  25.988 -11.974  1.00 13.03      B
ATOM   3155  O    THR B  41      21.308  27.129 -11.944  1.00 14.12      B
ATOM   3156  N    LEU B  42      20.924  24.933 -12.005  1.00 13.26      B
ATOM   3157  CA   LEU B  42      19.483  25.093 -11.850  1.00 11.94      B
ATOM   3158  CB   LEU B  42      18.743  24.661 -12.723  1.00 11.35      B
ATOM   3159  CG   LEU B  42      17.292  23.803 -12.339  1.00 10.89      B
ATOM   3160  CD1  LEU B  42      16.422  25.083 -12.504  1.00 13.06      B
ATOM   3161  CD2  LEU B  42      16.760  22.694 -13.241  1.00 12.39      B
ATOM   3162  C    LEU B  42      19.222  24.731 -10.385  1.00 12.70      B
ATOM   3163  O    LEU B  42      19.633  23.642  -9.935  1.00 13.40      B
ATOM   3164  N    SER B  43      18.551  25.613  -9.641  1.00 10.83      B
ATOM   3165  CA   SER B  43      18.212  25.317  -8.240  1.00 13.03      B
```

Figure 1 (continued 32)

```
ATOM   3166  CB  SER B  43      18.605  26.457  -7.298  1.00 15.48      B
ATOM   3167  OG  SER B  43      20.017  26.635  -7.258  1.00 16.36      B
ATOM   3168  C   SER B  43      16.699  25.141  -8.194  1.00 12.37      B
ATOM   3169  O   SER B  43      15.953  25.873  -8.875  1.00 13.81      B
ATOM   3170  N   LEU B  44      16.259  24.133  -7.427  1.00 12.48      B
ATOM   3171  CA  LEU B  44      14.832  23.840  -7.249  1.00 11.34      B
ATOM   3172  CB  LEU B  44      14.504  22.413  -7.724  1.00 12.56      B
ATOM   3173  CG  LEU B  44      14.993  22.028  -9.122  1.00 14.70      B
ATOM   3174  CD1 LEU B  44      14.964  20.500  -9.306  1.00 18.40      B
ATOM   3175  CD2 LEU B  44      14.105  22.717 -10.133  1.00 19.25      B
ATOM   3176  C   LEU B  44      14.581  23.918  -5.746  1.00 13.84      B
ATOM   3177  O   LEU B  44      15.344  23.356  -4.936  1.00 12.96      B
ATOM   3178  N   THR B  45      13.499  24.583  -5.359  1.00 11.87      B
ATOM   3179  CA  THR B  45      13.179  24.726  -3.928  1.00 13.31      B
ATOM   3180  CB  THR B  45      13.481  26.166  -3.421  1.00 13.75      B
ATOM   3181  OG1 THR B  45      14.869  26.485  -3.627  1.00 15.13      B
ATOM   3182  CG2 THR B  45      13.157  26.269  -1.922  1.00 14.06      B
ATOM   3183  C   THR B  45      11.698  24.477  -3.666  1.00 14.00      B
ATOM   3184  O   THR B  45      10.867  24.948  -4.423  1.00 13.55      B
ATOM   3185  N   GLY B  46      11.396  23.696  -2.631  1.00 13.36      B
ATOM   3186  CA  GLY B  46      10.029  23.408  -2.203  1.00 13.22      B
ATOM   3187  C   GLY B  46       9.898  23.843  -0.738  1.00 14.39      B
ATOM   3188  O   GLY B  46      10.856  23.711   0.017  1.00 15.56      B
ATOM   3189  N   THR B  47       8.736  24.387  -0.333  1.00 14.57      B
ATOM   3190  CA  THR B  47       8.592  24.822   1.061  1.00 15.34      B
ATOM   3191  CB  THR B  47       8.985  26.317   1.236  1.00 16.19      B
ATOM   3192  OG1 THR B  47       9.049  26.655   2.632  1.00 15.79      B
ATOM   3193  CG2 THR B  47       7.967  27.253   0.564  1.00 17.31      B
ATOM   3194  C   THR B  47       7.162  24.668   1.564  1.00 15.59      B
ATOM   3195  O   THR B  47       6.226  24.562   0.758  1.00 15.42      B
ATOM   3196  N   ASP B  48       7.009  24.615   2.887  1.00 17.13      B
ATOM   3197  CA  ASP B  48       5.658  24.598   3.487  1.00 16.11      B
ATOM   3198  CB  ASP B  48       5.344  23.244   4.132  1.00 15.80      B
ATOM   3199  CG  ASP B  48       6.136  22.986   5.398  1.00 16.28      B
ATOM   3200  OD1 ASP B  48       7.041  23.773   5.722  1.00 16.79      B
ATOM   3201  OD2 ASP B  48       5.825  21.976   6.074  1.00 20.58      B
ATOM   3202  C   ASP B  48       5.559  25.736   4.521  1.00 18.07      B
ATOM   3203  O   ASP B  48       4.612  25.768   5.321  1.00 18.39      B
ATOM   3204  N   LEU B  49       6.545  26.641   4.479  1.00 15.86      B
ATOM   3205  CA  LEU B  49       6.712  27.827   5.343  1.00 17.77      B
ATOM   3206  CB  LEU B  49       5.383  28.520   5.666  1.00 17.51      B
ATOM   3207  CG  LEU B  49       4.676  29.110   4.453  1.00 17.64      B
ATOM   3208  CD1 LEU B  49       3.373  29.816   4.956  1.00 21.50      B
ATOM   3209  CD2 LEU B  49       5.594  30.102   3.756  1.00 19.20      B
ATOM   3210  C   LEU B  49       7.406  27.475   6.656  1.00 16.84      B
ATOM   3211  O   LEU B  49       7.860  28.372   7.370  1.00 20.06      B
ATOM   3212  N   GLU B  50       7.467  26.189   6.991  1.00 17.57      B
ATOM   3213  CA  GLU B  50       8.164  25.802   8.228  1.00 16.55      B
ATOM   3214  CB  GLU B  50       7.359  24.747   9.000  1.00 20.80      B
ATOM   3215  CG  GLU B  50       7.969  24.377  10.373  1.00 25.34      B
ATOM   3216  CD  GLU B  50       7.109  23.396  11.186  1.00 29.02      B
ATOM   3217  OE1 GLU B  50       7.079  23.504  12.435  1.00 30.09      B
ATOM   3218  OE2 GLU B  50       6.487  22.496  10.592  1.00 31.29      B
ATOM   3219  C   GLU B  50       9.540  25.238   7.842  1.00 16.32      B
ATOM   3220  O   GLU B  50      10.511  25.373   8.580  1.00 16.99      B
ATOM   3221  N   MET B  51       9.611  24.630   6.672  1.00 15.47      B
ATOM   3222  CA  MET B  51      10.882  24.074   6.215  1.00 14.90      B
ATOM   3223  CB  MET B  51      10.987  22.609   6.653  1.00 15.67      B
ATOM   3224  CG  MET B  51       9.910  21.720   6.114  1.00 17.25      B
ATOM   3225  SD  MET B  51       9.719  20.228   7.113  1.00 21.05      B
ATOM   3226  CE  MET B  51       8.965  20.945   8.604  1.00 23.10      B
ATOM   3227  C   MET B  51      10.988  24.187   4.721  1.00 14.86      B
ATOM   3228  O   MET B  51       9.978  24.437   4.029  1.00 15.26      B
ATOM   3229  N   GLU B  52      12.210  24.027   4.202  1.00 14.83      B
ATOM   3230  CA  GLU B  52      12.367  24.087   2.755  1.00 13.34      B
ATOM   3231  CB  GLU B  52      12.761  25.477   2.295  1.00 18.93      B
ATOM   3232  CG  GLU B  52      13.998  26.005   2.925  1.00 25.39      B
ATOM   3233  CD  GLU B  52      14.361  27.374   2.411  1.00 31.84      B
ATOM   3234  OE1 GLU B  52      13.504  28.295   2.473  1.00 32.96      B
ATOM   3235  OE2 GLU B  52      15.520  27.508   1.960  1.00 35.26      B
ATOM   3236  C   GLU B  52      13.420  23.100   2.339  1.00 14.63      B
ATOM   3237  O   GLU B  52      14.317  22.798   3.108  1.00 14.47      B
ATOM   3238  N   MET B  53      13.314  22.604   1.117  1.00 13.33      B
ATOM   3239  CA  MET B  53      14.280  21.636   0.610  1.00 14.02      B
ATOM   3240  CB  MET B  53      13.575  20.289   0.379  1.00 16.35      B
ATOM   3241  CG  MET B  53      14.496  19.209  -0.220  1.00 19.16      B
ATOM   3242  SD  MET B  53      15.833  18.696   0.914  1.00 23.65      B
ATOM   3243  CE  MET B  53      14.878  17.649   1.951  1.00 20.87      B
ATOM   3244  C   MET B  53      14.777  22.225  -0.701  1.00 14.06      B
ATOM   3245  O   MET B  53      13.977  22.607  -1.546  1.00 13.90      B
ATOM   3246  N   VAL B  54      16.091  22.294  -0.872  1.00 13.10      B
ATOM   3247  CA  VAL B  54      16.687  22.882  -2.089  1.00 13.22      B
ATOM   3248  CB  VAL B  54      17.539  24.079  -1.725  1.00 14.45      B
ATOM   3249  CG1 VAL B  54      18.117  24.704  -2.984  1.00 14.52      B
ATOM   3250  CG2 VAL B  54      16.699  25.088  -0.938  1.00 13.15      B
ATOM   3251  C   VAL B  54      17.590  21.867  -2.768  1.00 13.82      B
ATOM   3252  O   VAL B  54      18.330  21.169  -2.093  1.00 16.01      B
ATOM   3253  N   ALA B  55      17.513  21.765  -4.096  1.00 11.25      B
ATOM   3254  CA  ALA B  55      18.380  20.865  -4.850  1.00 13.21      B
ATOM   3255  CB  ALA B  55      17.548  19.820  -5.605  1.00 12.81      B
ATOM   3256  C   ALA B  55      19.144  21.706  -5.863  1.00 15.53      B
ATOM   3257  O   ALA B  55      18.564  22.606  -6.461  1.00 15.73      B
ATOM   3258  N   ARG B  56      20.433  21.410  -6.059  1.00 14.23      B
ATOM   3259  CA  ARG B  56      21.258  22.119  -7.044  1.00 15.31      B
ATOM   3260  CB  ARG B  56      22.601  22.523  -6.432  1.00 16.38      B
ATOM   3261  CG  ARG B  56      22.482  23.229  -5.112  1.00 22.20      B
ATOM   3262  CD  ARG B  56      22.101  24.643  -5.283  1.00 24.40      B
ATOM   3263  NE  ARG B  56      22.131  25.327  -3.990  1.00 26.52      B
ATOM   3264  CZ  ARG B  56      21.494  26.463  -3.729  1.00 27.62      B
ATOM   3265  NH1 ARG B  56      20.779  27.069  -4.676  1.00 23.46      B
```

| ATOM | 3266 | NH2 | ARG | B | 56 | 21.523 | 26.966 | -2.496 | 1.00 | 28.24 | B |
|------|------|-----|-----|---|----|--------|--------|--------|------|-------|---|
| ATOM | 3267 | C | ARG | B | 56 | 21.525 | 21.120 | -8.158 | 1.00 | 14.84 | B |
| ATOM | 3268 | O | ARG | B | 56 | 21.995 | 19.996 | -7.905 | 1.00 | 16.83 | B |
| ATOM | 3269 | N | VAL | B | 57 | 21.203 | 21.504 | -9.387 | 1.00 | 13.57 | B |
| ATOM | 3270 | CA | VAL | B | 57 | 21.402 | 20.616 | -10.511 | 1.00 | 15.14 | B |
| ATOM | 3271 | CB | VAL | B | 57 | 20.049 | 20.326 | -11.197 | 1.00 | 17.22 | B |
| ATOM | 3272 | CG1 | VAL | B | 57 | 20.238 | 19.426 | -13.403 | 1.00 | 17.28 | B |
| ATOM | 3273 | CG2 | VAL | B | 57 | 19.076 | 19.642 | -10.185 | 1.00 | 16.94 | B |
| ATOM | 3274 | C | VAL | B | 57 | 22.378 | 21.261 | -11.510 | 1.00 | 14.02 | B |
| ATOM | 3275 | O | VAL | B | 57 | 22.090 | 22.326 | -12.063 | 1.00 | 15.02 | B |
| ATOM | 3276 | N | ALA | B | 58 | 23.495 | 20.589 | -11.786 | 1.00 | 15.91 | B |
| ATOM | 3277 | CA | ALA | B | 58 | 24.457 | 21.141 | -12.749 | 1.00 | 15.97 | B |
| ATOM | 3278 | CB | ALA | B | 58 | 25.763 | 20.328 | -12.705 | 1.00 | 16.60 | B |
| ATOM | 3279 | C | ALA | B | 58 | 23.883 | 21.096 | -14.178 | 1.00 | 15.88 | B |
| ATOM | 3280 | O | ALA | B | 58 | 23.266 | 20.118 | -14.569 | 1.00 | 16.91 | B |
| ATOM | 3281 | N | LEU | B | 59 | 24.106 | 22.157 | -14.947 | 1.00 | 13.80 | B |
| ATOM | 3282 | CA | LEU | B | 59 | 23.618 | 22.249 | -16.321 | 1.00 | 13.84 | B |
| ATOM | 3283 | CB | LEU | B | 59 | 22.888 | 23.587 | -16.527 | 1.00 | 14.79 | B |
| ATOM | 3284 | CG | LEU | B | 59 | 21.708 | 23.860 | -15.578 | 1.00 | 13.18 | B |
| ATOM | 3285 | CD1 | LEU | B | 59 | 21.112 | 25.257 | -15.826 | 1.00 | 16.02 | B |
| ATOM | 3286 | CD2 | LEU | B | 59 | 20.641 | 22.815 | -15.803 | 1.00 | 13.77 | B |
| ATOM | 3287 | C | LEU | B | 59 | 24.820 | 22.178 | -17.264 | 1.00 | 16.59 | B |
| ATOM | 3288 | O | LEU | B | 59 | 25.670 | 23.089 | -17.254 | 1.00 | 18.41 | B |
| ATOM | 3289 | N | VAL | B | 60 | 24.906 | 21.089 | -18.037 | 1.00 | 16.00 | B |
| ATOM | 3290 | CA | VAL | B | 60 | 25.987 | 20.866 | -19.030 | 1.00 | 16.12 | B |
| ATOM | 3291 | CB | VAL | B | 60 | 26.497 | 19.402 | -19.011 | 1.00 | 17.87 | B |
| ATOM | 3292 | CG1 | VAL | B | 60 | 27.080 | 19.074 | -17.627 | 1.00 | 17.15 | B |
| ATOM | 3293 | CG2 | VAL | B | 60 | 25.361 | 18.434 | -19.397 | 1.00 | 15.97 | B |
| ATOM | 3294 | C | VAL | B | 60 | 25.541 | 21.219 | -20.443 | 1.00 | 18.35 | B |
| ATOM | 3295 | O | VAL | B | 60 | 26.366 | 21.214 | -21.382 | 1.00 | 18.50 | B |
| ATOM | 3296 | N | GLN | B | 61 | 24.259 | 21.561 | -20.617 | 1.00 | 17.91 | B |
| ATOM | 3297 | CA | GLN | B | 61 | 23.731 | 21.970 | -21.926 | 1.00 | 18.15 | B |
| ATOM | 3298 | CB | GLN | B | 61 | 22.400 | 21.256 | -22.242 | 1.00 | 17.50 | B |
| ATOM | 3299 | CG | GLN | B | 61 | 22.541 | 19.751 | -22.248 | 1.00 | 17.69 | B |
| ATOM | 3300 | CD | GLN | B | 61 | 21.298 | 19.043 | -22.798 | 1.00 | 14.84 | B |
| ATOM | 3301 | OE1 | GLN | B | 61 | 20.828 | 19.336 | -23.922 | 1.00 | 16.87 | B |
| ATOM | 3302 | NE2 | GLN | B | 61 | 20.776 | 18.097 | -22.026 | 1.00 | 16.99 | B |
| ATOM | 3303 | C | GLN | B | 61 | 23.478 | 23.468 | -21.873 | 1.00 | 19.28 | B |
| ATOM | 3304 | O | GLN | B | 61 | 23.366 | 24.036 | -20.778 | 1.00 | 17.31 | B |
| ATOM | 3305 | N | PRO | B | 62 | 23.351 | 24.125 | -23.046 | 1.00 | 18.68 | B |
| ATOM | 3306 | CD | PRO | B | 62 | 23.472 | 23.548 | -24.401 | 1.00 | 20.65 | B |
| ATOM | 3307 | CA | PRO | B | 62 | 23.098 | 25.577 | -23.114 | 1.00 | 19.82 | B |
| ATOM | 3308 | CB | PRO | B | 62 | 22.828 | 25.809 | -24.591 | 1.00 | 22.37 | B |
| ATOM | 3309 | CG | PRO | B | 62 | 23.740 | 24.781 | -25.242 | 1.00 | 21.05 | B |
| ATOM | 3310 | C | PRO | B | 62 | 21.934 | 26.045 | -22.220 | 1.00 | 19.61 | B |
| ATOM | 3311 | O | PRO | B | 62 | 20.901 | 25.388 | -22.159 | 1.00 | 19.83 | B |
| ATOM | 3312 | N | HIS | B | 63 | 22.121 | 27.174 | -21.533 | 1.00 | 16.71 | B |
| ATOM | 3313 | CA | HIS | B | 63 | 21.102 | 27.720 | -20.624 | 1.00 | 15.04 | B |
| ATOM | 3314 | CB | HIS | B | 63 | 21.307 | 27.117 | -19.223 | 1.00 | 16.87 | B |
| ATOM | 3315 | CG | HIS | B | 63 | 22.718 | 27.225 | -18.743 | 1.00 | 16.35 | B |
| ATOM | 3316 | CD2 | HIS | B | 63 | 23.352 | 28.194 | -18.045 | 1.00 | 19.97 | B |
| ATOM | 3317 | ND1 | HIS | B | 63 | 23.674 | 26.284 | -19.052 | 1.00 | 19.14 | B |
| ATOM | 3318 | CE1 | HIS | B | 63 | 24.844 | 26.671 | -18.566 | 1.00 | 18.64 | B |
| ATOM | 3319 | NE2 | HIS | B | 63 | 24.676 | 27.828 | -17.954 | 1.00 | 21.06 | B |
| ATOM | 3320 | C | HIS | B | 63 | 21.120 | 29.242 | -20.524 | 1.00 | 16.64 | B |
| ATOM | 3321 | O | HIS | B | 63 | 22.102 | 29.903 | -20.917 | 1.00 | 18.95 | B |
| ATOM | 3322 | N | GLU | B | 64 | 20.043 | 29.811 | -19.988 | 1.00 | 14.93 | B |
| ATOM | 3323 | CA | GLU | B | 64 | 19.904 | 31.269 | -19.792 | 1.00 | 16.90 | B |
| ATOM | 3324 | CB | GLU | B | 64 | 18.948 | 31.878 | -20.827 | 1.00 | 20.34 | B |
| ATOM | 3325 | CG | GLU | B | 64 | 19.523 | 31.891 | -22.209 | 1.00 | 23.46 | B |
| ATOM | 3326 | CD | GLU | B | 64 | 18.491 | 32.235 | -23.268 | 1.00 | 28.27 | B |
| ATOM | 3327 | OE1 | GLU | B | 64 | 17.465 | 32.858 | -22.936 | 1.00 | 28.18 | B |
| ATOM | 3328 | OE2 | GLU | B | 64 | 18.725 | 31.878 | -24.441 | 1.00 | 30.88 | B |
| ATOM | 3329 | C | GLU | B | 64 | 19.369 | 31.526 | -18.386 | 1.00 | 16.81 | B |
| ATOM | 3330 | O | GLU | B | 64 | 18.451 | 30.834 | -17.941 | 1.00 | 16.15 | B |
| ATOM | 3331 | N | PRO | B | 65 | 19.945 | 32.500 | -17.653 | 1.00 | 15.86 | B |
| ATOM | 3332 | CD | PRO | B | 65 | 21.078 | 33.356 | -18.046 | 1.00 | 17.72 | B |
| ATOM | 3333 | CA | PRO | B | 65 | 19.502 | 32.808 | -16.292 | 1.00 | 15.04 | B |
| ATOM | 3334 | CB | PRO | B | 65 | 20.587 | 33.780 | -15.774 | 1.00 | 17.31 | B |
| ATOM | 3335 | CG | PRO | B | 65 | 21.018 | 34.457 | -16.991 | 1.00 | 18.09 | B |
| ATOM | 3336 | C | PRO | B | 65 | 18.088 | 33.355 | -16.113 | 1.00 | 15.66 | B |
| ATOM | 3337 | O | PRO | B | 65 | 17.508 | 33.964 | -17.024 | 1.00 | 16.81 | B |
| ATOM | 3338 | N | GLY | B | 66 | 17.530 | 33.112 | -14.930 | 1.00 | 14.69 | B |
| ATOM | 3339 | CA | GLY | B | 66 | 16.200 | 33.578 | -14.601 | 1.00 | 14.85 | B |
| ATOM | 3340 | C | GLY | B | 66 | 15.477 | 32.710 | -13.600 | 1.00 | 15.33 | B |
| ATOM | 3341 | O | GLY | B | 66 | 16.001 | 31.653 | -13.195 | 1.00 | 14.73 | B |
| ATOM | 3342 | N | ALA | B | 67 | 14.286 | 33.140 | -13.187 | 1.00 | 13.47 | B |
| ATOM | 3343 | CA | ALA | B | 67 | 13.542 | 32.384 | -12.182 | 1.00 | 14.65 | B |
| ATOM | 3344 | CB | ALA | B | 67 | 13.917 | 32.882 | -10.767 | 1.00 | 14.42 | B |
| ATOM | 3345 | C | ALA | B | 67 | 12.054 | 32.455 | -12.334 | 1.00 | 14.70 | B |
| ATOM | 3346 | O | ALA | B | 67 | 11.505 | 33.439 | -12.854 | 1.00 | 15.40 | B |
| ATOM | 3347 | N | THR | B | 68 | 11.386 | 31.417 | -11.857 | 1.00 | 13.62 | B |
| ATOM | 3348 | CA | THR | B | 68 | 9.929 | 31.390 | -11.878 | 1.00 | 13.91 | B |
| ATOM | 3349 | CB | THR | B | 68 | 9.391 | 31.110 | -13.317 | 1.00 | 14.48 | B |
| ATOM | 3350 | OG1 | THR | B | 68 | 7.963 | 31.295 | -13.339 | 1.00 | 15.83 | B |
| ATOM | 3351 | CG2 | THR | B | 68 | 9.694 | 29.668 | -13.731 | 1.00 | 16.00 | B |
| ATOM | 3352 | C | THR | B | 68 | 9.472 | 30.302 | -10.924 | 1.00 | 14.71 | B |
| ATOM | 3353 | O | THR | B | 68 | 10.311 | 29.641 | -10.323 | 1.00 | 15.32 | B |
| ATOM | 3354 | N | THR | B | 69 | 8.157 | 30.162 | -10.724 | 1.00 | 13.55 | B |
| ATOM | 3355 | CA | THR | B | 69 | 7.636 | 29.056 | -9.894 | 1.00 | 12.29 | B |
| ATOM | 3356 | CB | THR | B | 69 | 7.048 | 29.522 | -8.520 | 1.00 | 14.79 | B |
| ATOM | 3357 | OG1 | THR | B | 69 | 5.754 | 30.105 | -8.695 | 1.00 | 15.03 | B |
| ATOM | 3358 | CG2 | THR | B | 69 | 7.983 | 30.537 | -7.876 | 1.00 | 14.41 | B |
| ATOM | 3359 | C | THR | B | 69 | 6.555 | 28.385 | -10.714 | 1.00 | 14.44 | B |
| ATOM | 3360 | O | THR | B | 69 | 5.847 | 29.055 | -11.465 | 1.00 | 14.38 | B |
| ATOM | 3361 | N | VAL | B | 70 | 6.458 | 27.063 | -10.629 | 1.00 | 13.03 | B |
| ATOM | 3362 | CA | VAL | B | 70 | 5.464 | 26.297 | -11.370 | 1.00 | 12.62 | B |
| ATOM | 3363 | CB | VAL | B | 70 | 6.044 | 25.655 | -12.631 | 1.00 | 14.60 | B |
| ATOM | 3364 | CG1 | VAL | B | 70 | 6.340 | 26.733 | -13.667 | 1.00 | 17.68 | B |
| ATOM | 3365 | CG2 | VAL | B | 70 | 7.284 | 24.840 | -12.267 | 1.00 | 16.64 | B |

Figure 1 (continued 34)

```
ATOM   3366  C    VAL B  70       4.913  25.183 -10.490  1.00 12.72           B
ATOM   3367  O    VAL B  70       5.550  24.803  -9.489  1.00 12.07           B
ATOM   3368  N    PRO B  71       3.734  24.651 -10.825  1.00 12.89           B
ATOM   3369  CD   PRO B  71       2.872  25.050 -11.964  1.00 14.31           B
ATOM   3370  CA   PRO B  71       3.129  23.572 -10.016  1.00 12.87           B
ATOM   3371  CB   PRO B  71       1.845  23.239 -10.756  1.00 14.80           B
ATOM   3372  CG   PRO B  71       1.522  24.614 -11.481  1.00 19.52           B
ATOM   3373  C    PRO B  71       4.044  22.363  -9.848  1.00 12.82           B
ATOM   3374  O    PRO B  71       4.480  21.743 -10.813  1.00 13.40           B
ATOM   3375  N    ALA B  72       4.340  22.035  -8.599  1.00 11.96           B
ATOM   3376  CA   ALA B  72       5.293  20.944  -8.344  1.00 11.56           B
ATOM   3377  CB   ALA B  72       5.611  20.907  -6.847  1.00 12.77           B
ATOM   3378  C    ALA B  72       4.857  19.587  -8.805  1.00 13.14           B
ATOM   3379  O    ALA B  72       5.618  18.899  -9.515  1.00 11.71           B
ATOM   3380  N    ARG B  73       3.654  19.178  -8.426  1.00 12.89           B
ATOM   3381  CA   ARG B  73       3.155  17.856  -8.777  1.00 15.37           B
ATOM   3382  CB   ARG B  73       1.769  17.634  -8.137  1.00 19.29           B
ATOM   3383  CG   ARG B  73       1.189  16.241  -8.362  1.00 28.52           B
ATOM   3384  CD   ARG B  73       2.091  15.198  -7.713  1.00 33.56           B
ATOM   3385  NE   ARG B  73       1.915  13.802  -8.310  1.00 39.25           B
ATOM   3386  CZ   ARG B  73       2.786  12.882  -8.182  1.00 39.95           B
ATOM   3387  NH1  ARG B  73       3.894  13.052  -7.476  1.00 40.90           B
ATOM   3388  NH2  ARG B  73       2.549  11.711  -8.772  1.00 41.65           B
ATOM   3389  C    ARG B  73       3.074  17.695 -10.292  1.00 12.85           B
ATOM   3390  O    ARG B  73       3.480  16.668 -10.851  1.00 12.28           B
ATOM   3391  N    LYS B  74       2.530  18.708 -10.956  1.00 12.56           B
ATOM   3392  CA   LYS B  74       2.387  18.655 -12.419  1.00 12.58           B
ATOM   3393  CB   LYS B  74       1.647  19.886 -12.933  1.00 11.93           B
ATOM   3394  CG   LYS B  74       0.149  19.815 -12.596  1.00 13.85           B
ATOM   3395  CD   LYS B  74      -0.493  21.183 -12.811  1.00 15.33           B
ATOM   3396  CE   LYS B  74      -1.982  21.112 -12.597  1.00 16.90           B
ATOM   3397  NZ   LYS B  74      -2.482  22.535 -12.538  1.00 17.31           B
ATOM   3398  C    LYS B  74       3.729  18.561 -13.101  1.00 11.10           B
ATOM   3399  O    LYS B  74       3.882  17.738 -14.009  1.00 11.83           B
ATOM   3400  N    PHE B  75       4.687  19.379 -12.673  1.00 11.16           B
ATOM   3401  CA   PHE B  75       6.015  19.357 -13.326  1.00  8.77           B
ATOM   3402  CB   PHE B  75       6.851  20.553 -12.866  1.00  9.59           B
ATOM   3403  CG   PHE B  75       8.199  20.686 -13.568  1.00 11.61           B
ATOM   3404  CD1  PHE B  75       8.300  20.587 -14.956  1.00 12.29           B
ATOM   3405  CD2  PHE B  75       9.320  20.975 -12.835  1.00 12.93           B
ATOM   3406  CE1  PHE B  75       9.567  20.782 -15.596  1.00 14.18           B
ATOM   3407  CE2  PHE B  75      10.561  21.172 -13.448  1.00 16.28           B
ATOM   3408  CZ   PHE B  75      10.677  21.069 -14.836  1.00 13.85           B
ATOM   3409  C    PHE B  75       6.699  18.029 -13.066  1.00 10.84           B
ATOM   3410  O    PHE B  75       7.225  17.420 -14.009  1.00  9.16           B
ATOM   3411  N    PHE B  76       6.663  17.552 -11.819  1.00 10.39           B
ATOM   3412  CA   PHE B  76       7.252  16.230 -11.555  1.00 11.16           B
ATOM   3413  CB   PHE B  76       7.138  15.862 -10.092  1.00 12.22           B
ATOM   3414  CG   PHE B  76       7.546  14.459  -9.823  1.00 14.40           B
ATOM   3415  CD1  PHE B  76       8.888  14.117  -9.730  1.00 16.66           B
ATOM   3416  CD2  PHE B  76       6.583  13.475  -9.667  1.00 16.99           B
ATOM   3417  CE1  PHE B  76       9.252  12.795  -9.461  1.00 17.02           B
ATOM   3418  CE2  PHE B  76       6.946  12.143  -9.407  1.00 17.99           B
ATOM   3419  CZ   PHE B  76       8.275  11.821  -9.302  1.00 18.48           B
ATOM   3420  C    PHE B  76       6.579  15.133 -12.373  1.00 12.82           B
ATOM   3421  O    PHE B  76       7.255  14.307 -12.999  1.00 10.50           B
ATOM   3422  N    ASP B  77       5.247  15.103 -12.399  1.00 10.55           B
ATOM   3423  CA   ASP B  77       4.563  14.074 -13.173  1.00  9.78           B
ATOM   3424  CB   ASP B  77       3.053  14.178 -12.970  1.00 11.78           B
ATOM   3425  CG   ASP B  77       2.626  13.732 -11.596  1.00 17.39           B
ATOM   3426  OD1  ASP B  77       3.429  13.121 -10.843  1.00 17.35           B
ATOM   3427  OD2  ASP B  77       1.441  13.973 -11.260  1.00 18.13           B
ATOM   3428  C    ASP B  77       4.893  14.113 -14.663  1.00  8.50           B
ATOM   3429  O    ASP B  77       5.004  13.055 -15.288  1.00 10.06           B
ATOM   3430  N    ILE B  78       5.065  15.316 -15.218  1.00  9.33           B
ATOM   3431  CA   ILE B  78       5.427  15.449 -16.628  1.00  9.86           B
ATOM   3432  CB   ILE B  78       5.451  16.940 -17.049  1.00 11.48           B
ATOM   3433  CG2  ILE B  78       6.191  17.139 -18.424  1.00 13.90           B
ATOM   3434  CG1  ILE B  78       3.976  17.389 -17.151  1.00 13.19           B
ATOM   3435  CD1  ILE B  78       3.776  18.939 -17.260  1.00 16.24           B
ATOM   3436  C    ILE B  78       6.817  14.832 -16.839  1.00  9.23           B
ATOM   3437  O    ILE B  78       6.993  13.993 -17.726  1.00 10.91           B
ATOM   3438  N    CYS B  79       7.762  15.226 -16.013  1.00 10.15           B
ATOM   3439  CA   CYS B  79       9.131  14.699 -16.223  1.00 10.57           B
ATOM   3440  CB   CYS B  79      10.081  15.403 -15.269  1.00 10.45           B
ATOM   3441  SG   CYS B  79      10.273  17.176 -15.649  1.00 15.50           B
ATOM   3442  C    CYS B  79       9.176  13.190 -16.024  1.00 12.39           B
ATOM   3443  O    CYS B  79       9.819  12.455 -16.788  1.00 13.55           B
ATOM   3444  N    ARG B  80       8.500  12.725 -14.986  1.00 10.64           B
ATOM   3445  CA   ARG B  80       8.491  11.273 -14.719  1.00 12.98           B
ATOM   3446  CB   ARG B  80       7.744  11.007 -13.399  1.00 15.52           B
ATOM   3447  CG   ARG B  80       7.791   9.534 -12.911  1.00 20.13           B
ATOM   3448  CD   ARG B  80       6.843   9.325 -11.713  1.00 25.38           B
ATOM   3449  NE   ARG B  80       5.482   9.714 -12.093  1.00 31.58           B
ATOM   3450  CZ   ARG B  80       4.456   9.888 -11.254  1.00 33.35           B
ATOM   3451  NH1  ARG B  80       4.598   9.704  -9.939  1.00 35.49           B
ATOM   3452  NH2  ARG B  80       3.280  10.257 -11.732  1.00 34.33           B
ATOM   3453  C    ARG B  80       7.819  10.507 -15.846  1.00 13.18           B
ATOM   3454  O    ARG B  80       8.159   9.360 -16.140  1.00 13.55           B
ATOM   3455  N    GLY B  81       6.836  11.128 -16.484  1.00 11.84           B
ATOM   3456  CA   GLY B  81       6.116  10.437 -17.522  1.00 11.90           B
ATOM   3457  C    GLY B  81       6.781  10.356 -18.869  1.00 11.01           B
ATOM   3458  O    GLY B  81       6.335   9.605 -19.734  1.00 11.50           B
ATOM   3459  N    LEU B  82       7.806  11.186 -19.071  1.00 11.31           B
ATOM   3460  CA   LEU B  82       8.514  11.169 -20.328  1.00  9.84           B
ATOM   3461  CB   LEU B  82       9.370  12.430 -20.446  1.00  8.66           B
ATOM   3462  CG   LEU B  82       8.522  13.680 -20.801  1.00  9.38           B
ATOM   3463  CD1  LEU B  82       9.372  14.967 -20.574  1.00  9.37           B
ATOM   3464  CD2  LEU B  82       8.050  13.551 -22.262  1.00 11.14           B
ATOM   3465  C    LEU B  82       9.376   9.916 -20.380  1.00 11.17           B
```

Figure 1 (continued 35)

| | | | | | | | | | | |
|---|---|---|---|---|---|---|---|---|---|---|
| ATOM | 3466 | O | LEU | B | 82 | 9.726 | 9.344 | -19.347 | 1.00 | 12.58 | B |
| ATOM | 3467 | N | PRO | B | 83 | 9.758 | 9.523 | -21.590 | 1.00 | 11.69 | B |
| ATOM | 3468 | CD | PRO | B | 83 | 9.531 | 10.208 | -22.863 | 1.00 | 13.36 | B |
| ATOM | 3469 | CA | PRO | B | 83 | 10.575 | 8.309 | -21.770 | 1.00 | 12.94 | B |
| ATOM | 3470 | CB | PRO | B | 83 | 10.597 | 8.140 | -23.290 | 1.00 | 15.08 | B |
| ATOM | 3471 | CG | PRO | B | 83 | 10.505 | 9.493 | -23.806 | 1.00 | 14.86 | B |
| ATOM | 3472 | C | PRO | B | 83 | 11.964 | 8.393 | -21.150 | 1.00 | 15.17 | B |
| ATOM | 3473 | O | PRO | B | 83 | 12.542 | 9.473 | -21.023 | 1.00 | 14.86 | B |
| ATOM | 3474 | N | GLU | B | 84 | 12.495 | 7.237 | -20.759 | 1.00 | 15.45 | B |
| ATOM | 3475 | CA | GLU | B | 84 | 13.817 | 7.220 | -20.152 | 1.00 | 15.30 | B |
| ATOM | 3476 | CB | GLU | B | 84 | 14.193 | 5.761 | -19.825 | 1.00 | 17.19 | B |
| ATOM | 3477 | CG | GLU | B | 84 | 15.507 | 5.588 | -19.128 | 1.00 | 20.25 | B |
| ATOM | 3478 | CD | GLU | B | 84 | 15.564 | 4.266 | -18.419 | 1.00 | 22.78 | B |
| ATOM | 3479 | OE1 | GLU | B | 84 | 14.981 | 3.297 | -18.955 | 1.00 | 27.86 | B |
| ATOM | 3480 | OE2 | GLU | B | 84 | 16.180 | 4.197 | -17.344 | 1.00 | 25.77 | B |
| ATOM | 3481 | C | GLU | B | 84 | 14.831 | 7.848 | -21.116 | 1.00 | 13.55 | B |
| ATOM | 3482 | O | GLU | B | 84 | 14.815 | 7.576 | -22.325 | 1.00 | 16.08 | B |
| ATOM | 3483 | N | GLY | B | 85 | 15.682 | 8.719 | -20.573 | 1.00 | 15.12 | B |
| ATOM | 3484 | CA | GLY | B | 85 | 16.714 | 9.359 | -21.386 | 1.00 | 15.70 | B |
| ATOM | 3485 | C | GLY | B | 85 | 16.279 | 10.612 | -22.136 | 1.00 | 16.21 | B |
| ATOM | 3486 | O | GLY | B | 85 | 17.088 | 11.268 | -22.797 | 1.00 | 17.94 | B |
| ATOM | 3487 | N | ALA | B | 86 | 14.995 | 10.955 | -22.013 | 1.00 | 13.60 | B |
| ATOM | 3488 | CA | ALA | B | 86 | 14.450 | 12.128 | -22.688 | 1.00 | 13.37 | B |
| ATOM | 3489 | CB | ALA | B | 86 | 12.944 | 12.293 | -22.330 | 1.00 | 15.70 | B |
| ATOM | 3490 | C | ALA | B | 86 | 15.161 | 13.415 | -22.324 | 1.00 | 12.98 | B |
| ATOM | 3491 | O | ALA | B | 86 | 15.551 | 13.631 | -21.183 | 1.00 | 13.52 | B |
| ATOM | 3492 | N | GLU | B | 87 | 15.341 | 14.285 | -23.316 | 1.00 | 12.60 | B |
| ATOM | 3493 | CA | GLU | B | 87 | 15.926 | 15.594 | -23.086 | 1.00 | 12.20 | B |
| ATOM | 3494 | CB | GLU | B | 87 | 16.650 | 16.050 | -24.339 | 1.00 | 16.46 | B |
| ATOM | 3495 | CG | GLU | B | 87 | 17.818 | 15.137 | -24.688 | 1.00 | 20.50 | B |
| ATOM | 3496 | CD | GLU | B | 87 | 18.945 | 15.208 | -23.669 | 1.00 | 24.25 | B |
| ATOM | 3497 | OE1 | GLU | B | 87 | 18.958 | 16.145 | -22.844 | 1.00 | 21.60 | B |
| ATOM | 3498 | OE2 | GLU | B | 87 | 19.827 | 14.308 | -23.719 | 1.00 | 25.73 | B |
| ATOM | 3499 | C | GLU | B | 87 | 14.734 | 16.512 | -22.814 | 1.00 | 12.64 | B |
| ATOM | 3500 | O | GLU | B | 87 | 13.810 | 16.527 | -23.623 | 1.00 | 15.78 | B |
| ATOM | 3501 | N | ILE | B | 88 | 14.770 | 17.241 | -21.707 | 1.00 | 12.08 | B |
| ATOM | 3502 | CA | ILE | B | 88 | 13.645 | 18.127 | -21.325 | 1.00 | 11.17 | B |
| ATOM | 3503 | CB | ILE | B | 88 | 13.218 | 17.788 | -19.878 | 1.00 | 11.48 | B |
| ATOM | 3504 | CG2 | ILE | B | 88 | 11.990 | 18.637 | -19.452 | 1.00 | 12.56 | B |
| ATOM | 3505 | CG1 | ILE | B | 88 | 12.887 | 16.294 | -19.815 | 1.00 | 12.51 | B |
| ATOM | 3506 | CD1 | ILE | B | 88 | 12.482 | 15.794 | -18.471 | 1.00 | 11.91 | B |
| ATOM | 3507 | C | ILE | B | 88 | 14.067 | 19.573 | -21.468 | 1.00 | 10.83 | B |
| ATOM | 3508 | O | ILE | B | 88 | 14.909 | 20.066 | -20.691 | 1.00 | 12.26 | B |
| ATOM | 3509 | N | ALA | B | 89 | 13.477 | 20.261 | -22.448 | 1.00 | 10.23 | B |
| ATOM | 3510 | CA | ALA | B | 89 | 13.802 | 21.659 | -22.723 | 1.00 | 10.42 | B |
| ATOM | 3511 | CB | ALA | B | 89 | 13.784 | 21.911 | -24.227 | 1.00 | 11.36 | B |
| ATOM | 3512 | C | ALA | B | 89 | 12.738 | 22.517 | -22.046 | 1.00 | 11.07 | B |
| ATOM | 3513 | O | ALA | B | 89 | 11.542 | 22.297 | -22.226 | 1.00 | 12.01 | B |
| ATOM | 3514 | N | VAL | B | 90 | 13.196 | 23.508 | -21.307 | 1.00 | 10.02 | B |
| ATOM | 3515 | CA | VAL | B | 90 | 12.301 | 24.367 | -20.549 | 1.00 | 9.76 | B |
| ATOM | 3516 | CB | VAL | B | 90 | 12.499 | 24.064 | -19.045 | 1.00 | 10.85 | B |
| ATOM | 3517 | CG1 | VAL | B | 90 | 11.583 | 24.955 | -18.217 | 1.00 | 12.19 | B |
| ATOM | 3518 | CG2 | VAL | B | 90 | 12.171 | 22.613 | -18.750 | 1.00 | 11.27 | B |
| ATOM | 3519 | C | VAL | B | 90 | 12.577 | 25.830 | -20.791 | 1.00 | 11.53 | B |
| ATOM | 3520 | O | VAL | B | 90 | 13.731 | 26.256 | -20.768 | 1.00 | 13.48 | B |
| ATOM | 3521 | N | GLN | B | 91 | 11.523 | 26.617 | -21.015 | 1.00 | 11.55 | B |
| ATOM | 3522 | CA | GLN | B | 91 | 11.705 | 28.051 | -21.210 | 1.00 | 14.62 | B |
| ATOM | 3523 | CB | GLN | B | 91 | 11.889 | 28.401 | -22.692 | 1.00 | 18.48 | B |
| ATOM | 3524 | CG | GLN | B | 91 | 12.135 | 29.913 | -22.891 | 1.00 | 26.33 | B |
| ATOM | 3525 | CD | GLN | B | 91 | 12.980 | 30.211 | -24.112 | 1.00 | 29.12 | B |
| ATOM | 3526 | OE1 | GLN | B | 91 | 13.538 | 31.308 | -24.238 | 1.00 | 34.56 | B |
| ATOM | 3527 | NE2 | GLN | B | 91 | 13.073 | 29.248 | -25.024 | 1.00 | 31.87 | B |
| ATOM | 3528 | C | GLN | B | 91 | 10.550 | 28.838 | -20.631 | 1.00 | 14.08 | B |
| ATOM | 3529 | O | GLN | B | 91 | 9.367 | 28.487 | -20.811 | 1.00 | 13.76 | B |
| ATOM | 3530 | N | LEU | B | 92 | 10.908 | 29.885 | -39.884 | 1.00 | 14.73 | B |
| ATOM | 3531 | CA | LEU | B | 92 | 9.928 | 30.771 | -19.267 | 1.00 | 15.30 | B |
| ATOM | 3532 | CB | LEU | B | 92 | 10.575 | 31.606 | -18.144 | 1.00 | 16.00 | B |
| ATOM | 3533 | CG | LEU | B | 92 | 9.636 | 32.613 | -17.459 | 1.00 | 15.51 | B |
| ATOM | 3534 | CD1 | LEU | B | 92 | 8.460 | 31.882 | -16.765 | 1.00 | 18.05 | B |
| ATOM | 3535 | CD2 | LEU | B | 92 | 10.387 | 33.405 | -16.426 | 1.00 | 17.67 | B |
| ATOM | 3536 | C | LEU | B | 92 | 9.435 | 31.694 | -20.368 | 1.00 | 16.50 | B |
| ATOM | 3537 | O | LEU | B | 92 | 10.259 | 32.293 | -21.102 | 1.00 | 17.36 | B |
| ATOM | 3538 | N | GLU | B | 93 | 8.107 | 31.790 | -20.487 | 1.00 | 17.70 | B |
| ATOM | 3539 | CA | GLU | B | 93 | 7.456 | 32.645 | -21.469 | 1.00 | 20.10 | B |
| ATOM | 3540 | CB | GLU | B | 93 | 6.889 | 31.788 | -22.615 | 1.00 | 19.07 | B |
| ATOM | 3541 | CG | GLU | B | 93 | 8.021 | 30.998 | -23.341 | 1.00 | 20.16 | B |
| ATOM | 3542 | CD | GLU | B | 93 | 7.622 | 30.371 | -24.678 | 1.00 | 21.44 | B |
| ATOM | 3543 | OE1 | GLU | B | 93 | 6.413 | 30.147 | -24.893 | 1.00 | 22.08 | B |
| ATOM | 3544 | OE2 | GLU | B | 93 | 8.530 | 30.087 | -25.504 | 1.00 | 20.59 | B |
| ATOM | 3545 | C | GLU | B | 93 | 6.358 | 33.451 | -20.767 | 1.00 | 21.41 | B |
| ATOM | 3546 | O | GLU | B | 93 | 5.165 | 33.286 | -21.039 | 1.00 | 22.54 | B |
| ATOM | 3547 | N | GLY | B | 94 | 6.774 | 34.296 | -19.821 | 1.00 | 23.49 | B |
| ATOM | 3548 | CA | GLY | B | 94 | 5.826 | 35.136 | -19.099 | 1.00 | 23.13 | B |
| ATOM | 3549 | C | GLY | B | 94 | 4.835 | 34.435 | -18.182 | 1.00 | 23.80 | B |
| ATOM | 3550 | O | GLY | B | 94 | 5.205 | 33.923 | -17.126 | 1.00 | 23.56 | B |
| ATOM | 3551 | N | GLU | B | 95 | 3.569 | 34.428 | -18.574 | 1.00 | 21.90 | B |
| ATOM | 3552 | CA | GLU | B | 95 | 2.539 | 33.797 | -17.756 | 1.00 | 22.03 | B |
| ATOM | 3553 | CB | GLU | B | 95 | 1.135 | 34.201 | -18.269 | 1.00 | 25.70 | B |
| ATOM | 3554 | CG | GLU | B | 95 | 0.715 | 33.489 | -19.565 | 1.00 | 32.06 | B |
| ATOM | 3555 | CD | GLU | B | 95 | -0.577 | 34.015 | -20.188 | 1.00 | 34.90 | B |
| ATOM | 3556 | OE1 | GLU | B | 95 | -1.491 | 34.428 | -19.437 | 1.00 | 35.44 | B |
| ATOM | 3557 | OE2 | GLU | B | 95 | -0.679 | 33.994 | -21.442 | 1.00 | 37.09 | B |
| ATOM | 3558 | C | GLU | B | 95 | 2.680 | 32.262 | -17.760 | 1.00 | 20.12 | B |
| ATOM | 3559 | O | GLU | B | 95 | 2.076 | 31.573 | -16.932 | 1.00 | 19.55 | B |
| ATOM | 3560 | N | ARG | B | 96 | 3.465 | 31.726 | -18.694 | 1.00 | 17.37 | B |
| ATOM | 3561 | CA | ARG | B | 96 | 3.605 | 30.271 | -18.751 | 1.00 | 14.55 | B |
| ATOM | 3562 | CB | ARG | B | 96 | 2.777 | 29.683 | -19.912 | 1.00 | 16.86 | B |
| ATOM | 3563 | CG | ARG | B | 96 | 3.296 | 29.992 | -21.341 | 1.00 | 16.89 | B |
| ATOM | 3564 | CD | ARG | B | 96 | 4.258 | 28.903 | -21.876 | 1.00 | 20.34 | B |
| ATOM | 3565 | NE | ARG | B | 96 | 4.551 | 28.994 | -23.319 | 1.00 | 22.54 | B |

Figure 1 (continued 36)

```
ATOM   3566  CZ   ARG B  96    3.842  28.445 -24.308  1.00 25.11    B
ATOM   3567  NH1  ARG B  96    2.742  27.746 -24.054  1.00 24.38    B
ATOM   3568  NH2  ARG B  96    4.276  28.546 -25.577  1.00 20.68    B
ATOM   3569  C    ARG B  96    5.025  29.829 -18.904  1.00 13.94    B
ATOM   3570  O    ARG B  96    5.883  30.602 -19.331  1.00 14.85    B
ATOM   3571  N    MET B  97    5.266  28.578 -18.520  1.00 12.30    B
ATOM   3572  CA   MET B  97    6.582  27.961 -18.667  1.00 10.91    B
ATOM   3573  CB   MET B  97    7.093  27.392 -17.326  1.00 10.86    B
ATOM   3574  CG   MET B  97    8.503  26.885 -17.487  1.00 14.36    B
ATOM   3575  SD   MET B  97    9.268  26.288 -15.952  1.00 14.09    B
ATOM   3576  CE   MET B  97    8.674  24.617 -15.920  1.00 15.27    B
ATOM   3577  C    MET B  97    6.336  26.817 -19.641  1.00 11.29    B
ATOM   3578  O    MET B  97    5.493  25.956 -19.386  1.00 11.55    B
ATOM   3579  N    LEU B  98    7.099  26.798 -20.750  1.00 10.37    B
ATOM   3580  CA   LEU B  98    6.935  25.818 -21.793  1.00  9.09    B
ATOM   3581  CB   LEU B  98    7.140  26.502 -23.145  1.00 10.04    B
ATOM   3582  CG   LEU B  98    7.119  25.556 -24.343  1.00 13.03    B
ATOM   3583  CD1  LEU B  98    5.756  24.875 -24.484  1.00 14.58    B
ATOM   3584  CD2  LEU B  98    7.499  26.390 -25.593  1.00 15.51    B
ATOM   3585  C    LEU B  98    7.936  24.703 -21.615  1.00 10.17    B
ATOM   3586  O    LEU B  98    9.121  24.991 -21.439  1.00 12.00    B
ATOM   3587  N    VAL B  99    7.440  23.469 -21.569  1.00  8.14    B
ATOM   3588  CA   VAL B  99    8.303  22.284 -21.423  1.00  9.99    B
ATOM   3589  CB   VAL B  99    7.831  21.408 -20.182  1.00  8.49    B
ATOM   3590  CG1  VAL B  99    8.712  20.156 -20.085  1.00 12.22    B
ATOM   3591  CG2  VAL B  99    7.813  22.225 -18.916  1.00 10.21    B
ATOM   3592  C    VAL B  99    8.169  21.454 -22.700  1.00 11.04    B
ATOM   3593  O    VAL B  99    7.031  21.087 -23.108  1.00 10.88    B
ATOM   3594  N    ARG B 100    9.293  21.137 -23.366  1.00  8.40    B
ATOM   3595  CA   ARG B 100    9.218  20.368 -24.593  1.00  8.30    B
ATOM   3596  CB   ARG B 100    9.613  21.220 -25.829  1.00 10.50    B
ATOM   3597  CG   ARG B 100    8.754  22.464 -26.057  1.00 11.28    B
ATOM   3598  CD   ARG B 100    9.404  23.363 -27.152  1.00 15.41    B
ATOM   3599  NE   ARG B 100   10.676  23.920 -26.707  1.00 16.70    B
ATOM   3600  CZ   ARG B 100   11.829  23.803 -27.375  1.00 17.28    B
ATOM   3601  NH1  ARG B 100   11.889  23.144 -28.526  1.00 21.89    B
ATOM   3602  NH2  ARG B 100   12.927  24.341 -26.876  1.00 22.39    B
ATOM   3603  C    ARG B 100   10.176  19.198 -24.523  1.00  9.77    B
ATOM   3604  O    ARG B 100   11.283  19.325 -23.982  1.00  9.86    B
ATOM   3605  N    SER B 101    9.725  18.074 -25.051  1.00  7.91    B
ATOM   3606  CA   SER B 101   10.578  16.881 -25.125  1.00 10.45    B
ATOM   3607  CB   SER B 101   10.549  16.126 -23.787  1.00 10.43    B
ATOM   3608  OG   SER B 101   11.462  14.998 -23.840  1.00 13.17    B
ATOM   3609  C    SER B 101   10.043  16.057 -26.265  1.00 12.22    B
ATOM   3610  O    SER B 101    8.875  15.686 -26.263  1.00 11.21    B
ATOM   3611  N    GLY B 102   10.900  15.720 -27.235  1.00 11.77    B
ATOM   3612  CA   GLY B 102   10.396  14.967 -28.376  1.00 11.79    B
ATOM   3613  C    GLY B 102    9.269  15.772 -29.010  1.00 11.95    B
ATOM   3614  O    GLY B 102    9.440  16.944 -29.277  1.00 13.86    B
ATOM   3615  N    ARG B 103    8.113  15.137 -29.248  1.00 13.24    B
ATOM   3616  CA   ARG B 103    6.950  15.842 -29.786  1.00 13.56    B
ATOM   3617  CB   ARG B 103    6.404  15.140 -31.024  1.00 15.71    B
ATOM   3618  CG   ARG B 103    7.403  15.240 -32.172  1.00 18.07    B
ATOM   3619  CD   ARG B 103    6.753  14.857 -33.491  1.00 20.42    B
ATOM   3620  NE   ARG B 103    6.426  13.446 -33.518  1.00 21.82    B
ATOM   3621  CZ   ARG B 103    5.798  12.861 -34.539  1.00 24.65    B
ATOM   3622  NH1  ARG B 103    5.437  13.580 -35.598  1.00 24.54    B
ATOM   3623  NH2  ARG B 103    5.564  11.560 -34.517  1.00 25.63    B
ATOM   3624  C    ARG B 103    5.893  15.933 -28.597  1.00 13.10    B
ATOM   3625  O    ARG B 103    4.685  15.809 -28.966  1.00 14.85    B
ATOM   3626  N    SER B 104    6.372  16.100 -27.468  1.00 10.09    B
ATOM   3627  CA   SER B 104    5.503  16.309 -26.293  1.00 11.86    B
ATOM   3628  CB   SER B 104    5.888  15.378 -25.138  1.00 12.18    B
ATOM   3629  OG   SER B 104    5.938  14.020 -25.597  1.00 12.05    B
ATOM   3630  C    SER B 104    5.701  17.775 -25.877  1.00 12.30    B
ATOM   3631  O    SER B 104    6.849  18.298 -25.815  1.00 12.26    B
ATOM   3632  N    ARG B 105    4.587  18.470 -25.625  1.00 10.81    B
ATOM   3633  CA   ARG B 105    4.659  19.867 -25.234  1.00 10.24    B
ATOM   3634  CB   ARG B 105    4.158  20.772 -26.370  1.00 12.01    B
ATOM   3635  CG   ARG B 105    5.004  20.788 -27.618  1.00 12.34    B
ATOM   3636  CD   ARG B 105    4.285  21.560 -28.760  1.00 13.57    B
ATOM   3637  NE   ARG B 105    3.799  22.896 -28.364  1.00 13.32    B
ATOM   3638  CZ   ARG B 105    4.552  23.991 -28.366  1.00 14.90    B
ATOM   3639  NH1  ARG B 105    5.822  23.903 -28.740  1.00 13.50    B
ATOM   3640  NH2  ARG B 105    4.037  25.165 -28.014  1.00 14.92    B
ATOM   3641  C    ARG B 105    3.757  20.122 -24.052  1.00  9.77    B
ATOM   3642  O    ARG B 105    2.639  19.588 -24.006  1.00 11.33    B
ATOM   3643  N    PHE B 106    4.221  20.929 -23.108  1.00 10.77    B
ATOM   3644  CA   PHE B 106    3.380  21.252 -21.939  1.00  9.20    B
ATOM   3645  CB   PHE B 106    3.795  20.410 -20.719  1.00 10.28    B
ATOM   3646  CG   PHE B 106    3.876  18.955 -21.000  1.00  9.68    B
ATOM   3647  CD1  PHE B 106    5.019  18.433 -21.591  1.00 12.41    B
ATOM   3648  CD2  PHE B 106    2.775  18.115 -20.793  1.00 12.06    B
ATOM   3649  CE1  PHE B 106    5.072  17.120 -21.982  1.00 12.35    B
ATOM   3650  CE2  PHE B 106    2.812  16.797 -21.182  1.00 13.89    B
ATOM   3651  CZ   PHE B 106    3.953  16.280 -21.783  1.00 14.71    B
ATOM   3652  C    PHE B 106    3.525  22.714 -21.579  1.00 12.00    B
ATOM   3653  O    PHE B 106    4.649  23.241 -21.528  1.00 11.63    B
ATOM   3654  N    SER B 107    2.389  23.375 -21.291  1.00 10.03    B
ATOM   3655  CA   SER B 107    2.415  24.766 -20.896  1.00 13.00    B
ATOM   3656  CB   SER B 107    1.559  25.595 -21.848  1.00 13.92    B
ATOM   3657  OG   SER B 107    1.547  26.962 -21.475  1.00 17.21    B
ATOM   3658  C    SER B 107    1.897  24.858 -19.471  1.00 13.30    B
ATOM   3659  O    SER B 107    0.741  24.512 -19.219  1.00 13.25    B
ATOM   3660  N    LEU B 108    2.774  25.213 -18.543  1.00 11.97    B
ATOM   3661  CA   LEU B 108    2.399  25.335 -17.130  1.00 12.30    B
ATOM   3662  CB   LEU B 108    3.497  24.741 -16.221  1.00 13.26    B
ATOM   3663  CG   LEU B 108    3.715  23.249 -16.427  1.00 15.24    B
ATOM   3664  CD1  LEU B 108    4.883  22.751 -15.567  1.00 14.96    B
ATOM   3665  CD2  LEU B 108    2.441  22.561 -16.079  1.00 15.65    B
```

Figure 1 (continued 37)

```
ATOM   3666  C   LEU B 108       2.210  26.768 -16.703  1.00 12.13           B
ATOM   3667  O   LEU B 108       2.935  27.647 -17.149  1.00 12.73           B
ATOM   3668  N   SER B 109       1.249  27.021 -15.807  1.00 13.50           B
ATOM   3669  CA  SER B 109       1.036  28.382 -15.313  1.00 15.61           B
ATOM   3670  CB  SER B 109      -0.345  28.466 -14.642  1.00 17.76           B
ATOM   3671  OG  SER B 109      -0.427  27.508 -13.599  1.00 25.01           B
ATOM   3672  C   SER B 109       2.118  28.695 -14.290  1.00 15.55           B
ATOM   3673  O   SER B 109       2.547  27.799 -13.536  1.00 18.85           B
ATOM   3674  N   THR B 110       2.550  29.935 -14.259  1.00 13.95           B
ATOM   3675  CA  THR B 110       3.587  30.367 -13.332  1.00 14.07           B
ATOM   3676  CB  THR B 110       4.749  31.074 -14.088  1.00 15.61           B
ATOM   3677  OG1 THR B 110       4.262  32.260 -14.719  1.00 16.22           B
ATOM   3678  CG2 THR B 110       5.333  30.173 -15.168  1.00 13.87           B
ATOM   3679  C   THR B 110       3.081  31.376 -12.323  1.00 14.62           B
ATOM   3680  O   THR B 110       2.028  32.023 -12.521  1.00 16.48           B
ATOM   3681  N   LEU B 111       3.835  31.498 -11.234  1.00 14.53           B
ATOM   3682  CA  LEU B 111       3.626  32.540 -10.236  1.00 14.82           B
ATOM   3683  CB  LEU B 111       3.048  31.999  -8.916  1.00 15.27           B
ATOM   3684  CG  LEU B 111       1.577  31.535  -8.991  1.00 16.13           B
ATOM   3685  CD1 LEU B 111       1.177  30.854  -7.706  1.00 15.76           B
ATOM   3686  CD2 LEU B 111       0.650  32.769  -9.243  1.00 15.24           B
ATOM   3687  C   LEU B 111       5.047  33.114 -10.070  1.00 16.26           B
ATOM   3688  O   LEU B 111       6.064  32.403 -10.174  1.00 16.00           B
ATOM   3689  N   PRO B 112       5.158  34.428  -9.873  1.00 15.54           B
ATOM   3690  CD  PRO B 112       4.031  35.374  -9.725  1.00 18.98           B
ATOM   3691  CA  PRO B 112       6.430  35.129  -9.711  1.00 16.92           B
ATOM   3692  CB  PRO B 112       5.984  36.546  -9.325  1.00 17.38           B
ATOM   3693  CG  PRO B 112       4.697  36.676 -10.033  1.00 19.99           B
ATOM   3694  C   PRO B 112       7.388  34.571  -8.674  1.00 15.89           B
ATOM   3695  O   PRO B 112       6.978  34.259  -7.552  1.00 17.87           B
ATOM   3696  N   ALA B 113       8.654  34.451  -9.066  1.00 17.65           B
ATOM   3697  CA  ALA B 113       9.702  33.993  -8.159  1.00 17.75           B
ATOM   3698  CB  ALA B 113      11.050  33.908  -8.901  1.00 18.59           B
ATOM   3699  C   ALA B 113       9.794  35.003  -6.997  1.00 19.95           B
ATOM   3700  O   ALA B 113      10.098  34.604  -5.873  1.00 18.56           B
ATOM   3701  N   ALA B 114       9.494  36.285  -7.254  1.00 19.88           B
ATOM   3702  CA  ALA B 114       9.546  37.297  -6.190  1.00 22.97           B
ATOM   3703  CB  ALA B 114       9.274  38.686  -6.762  1.00 24.68           B
ATOM   3704  C   ALA B 114       8.551  37.025  -5.073  1.00 24.13           B
ATOM   3705  O   ALA B 114       8.735  37.506  -3.948  1.00 25.27           B
ATOM   3706  N   ASP B 115       7.499  36.270  -5.374  1.00 22.97           B
ATOM   3707  CA  ASP B 115       6.458  35.936  -4.398  1.00 21.92           B
ATOM   3708  CB  ASP B 115       5.095  35.838  -5.085  1.00 25.25           B
ATOM   3709  CG  ASP B 115       4.653  37.144  -5.702  1.00 27.35           B
ATOM   3710  OD1 ASP B 115       5.197  38.200  -5.325  1.00 32.10           B
ATOM   3711  OD2 ASP B 115       3.756  37.115  -6.562  1.00 30.15           B
ATOM   3712  C   ASP B 115       6.686  34.620  -3.639  1.00 20.39           B
ATOM   3713  O   ASP B 115       5.892  34.256  -2.770  1.00 19.74           B
ATOM   3714  N   PHE B 116       7.743  33.883  -3.987  1.00 17.71           B
ATOM   3715  CA  PHE B 116       7.987  32.602  -3.323  1.00 18.38           B
ATOM   3716  CB  PHE B 116       9.004  31.796  -4.157  1.00 17.21           B
ATOM   3717  CG  PHE B 116       9.043  30.332  -3.810  1.00 18.03           B
ATOM   3718  CD1 PHE B 116       8.071  29.452  -4.300  1.00 16.40           B
ATOM   3719  CD2 PHE B 116      10.026  29.837  -2.955  1.00 17.20           B
ATOM   3720  CE1 PHE B 116       8.072  28.104  -3.949  1.00 18.94           B
ATOM   3721  CE2 PHE B 116      10.029  28.479  -2.596  1.00 15.80           B
ATOM   3722  CZ  PHE B 116       9.057  27.613  -3.091  1.00 18.24           B
ATOM   3723  C   PHE B 116       8.510  32.836  -1.896  1.00 18.89           B
ATOM   3724  O   PHE B 116       9.449  33.594  -1.716  1.00 19.05           B
ATOM   3725  N   PRO B 117       7.914  32.172  -0.888  1.00 20.37           B
ATOM   3726  CD  PRO B 117       6.913  31.117  -1.080  1.00 20.82           B
ATOM   3727  CA  PRO B 117       8.284  32.285   0.535  1.00 22.94           B
ATOM   3728  CB  PRO B 117       7.397  31.244   1.226  1.00 24.98           B
ATOM   3729  CG  PRO B 117       6.285  30.991   0.290  1.00 22.83           B
ATOM   3730  C   PRO B 117       9.736  31.922   0.684  1.00 25.37           B
ATOM   3731  O   PRO B 117      10.204  31.012   0.018  1.00 26.02           B
ATOM   3732  N   ASN B 118      10.441  32.630   1.556  1.00 27.41           B
ATOM   3733  CA  ASN B 118      11.857  32.398   1.767  1.00 30.63           B
ATOM   3734  CB  ASN B 118      12.638  33.537   1.081  1.00 34.20           B
ATOM   3735  CG  ASN B 118      14.111  33.525   1.411  1.00 36.43           B
ATOM   3736  OD1 ASN B 118      14.518  33.929   2.500  1.00 39.71           B
ATOM   3737  ND2 ASN B 118      14.922  33.052   0.472  1.00 40.26           B
ATOM   3738  C   ASN B 118      12.103  32.399   3.275  1.00 31.98           B
ATOM   3739  O   ASN B 118      11.683  33.332   3.959  1.00 32.47           B
ATOM   3740  N   LEU B 119      12.746  31.365   3.810  1.00 31.29           B
ATOM   3741  CA  LEU B 119      13.013  31.372   5.242  1.00 32.34           B
ATOM   3742  CB  LEU B 119      13.616  30.042   5.713  1.00 32.40           B
ATOM   3743  CG  LEU B 119      12.712  28.820   5.889  1.00 32.42           B
ATOM   3744  CD1 LEU B 119      13.507  27.710   6.551  1.00 34.29           B
ATOM   3745  CD2 LEU B 119      11.516  29.170   6.758  1.00 30.06           B
ATOM   3746  C   LEU B 119      13.996  32.502   5.540  1.00 32.87           B
ATOM   3747  O   LEU B 119      14.922  32.751   4.767  1.00 32.78           B
ATOM   3748  N   ASP B 120      13.785  33.170   6.668  1.00 33.27           B
ATOM   3749  CA  ASP B 120      14.634  34.264   7.106  1.00 35.53           B
ATOM   3750  CB  ASP B 120      14.100  34.820   8.442  1.00 38.51           B
ATOM   3751  CG  ASP B 120      14.813  36.102   8.896  1.00 41.15           B
ATOM   3752  OD1 ASP B 120      15.288  36.880   8.032  1.00 42.97           B
ATOM   3753  OD2 ASP B 120      14.878  36.341  10.128  1.00 41.78           B
ATOM   3754  C   ASP B 120      16.076  33.793   7.240  1.00 34.92           B
ATOM   3755  O   ASP B 120      16.366  32.615   7.430  1.00 33.81           B
ATOM   3756  N   ASP B 121      16.984  34.737   7.103  1.00 34.47           B
ATOM   3757  CA  ASP B 121      18.393  34.466   7.212  1.00 33.96           B
ATOM   3758  CB  ASP B 121      19.125  35.724   6.770  1.00 38.12           B
ATOM   3759  CG  ASP B 121      18.471  36.339   5.540  1.00 41.54           B
ATOM   3760  OD1 ASP B 121      18.665  35.786   4.433  1.00 42.91           B
ATOM   3761  OD2 ASP B 121      17.730  37.344   5.687  1.00 44.40           B
ATOM   3762  C   ASP B 121      18.648  34.144   8.672  1.00 31.06           B
ATOM   3763  O   ASP B 121      17.935  34.611   9.549  1.00 30.33           B
ATOM   3764  N   TRP B 122      19.642  33.314   8.927  1.00 29.45           B
ATOM   3765  CA  TRP B 122      19.953  32.969  10.301  1.00 26.54           B
```

Figure 1 (continued 38)

```
ATOM   3766  CB   TRP B 122      19.021  31.833  10.766  1.00 24.27           B
ATOM   3767  CG   TRP B 122      19.072  30.629   9.899  1.00 23.67           B
ATOM   3768  CD2  TRP B 122      19.832  29.445  10.127  1.00 23.03           B
ATOM   3769  CE2  TRP B 122      19.617  28.587   9.027  1.00 24.46           B
ATOM   3770  CE3  TRP B 122      20.680  29.020  11.157  1.00 21.61           B
ATOM   3771  CD1  TRP B 122      18.435  30.451   8.697  1.00 25.67           B
ATOM   3772  NE1  TRP B 122      18.760  29.225   8.167  1.00 25.03           B
ATOM   3773  CZ2  TRP B 122      20.224  27.337   8.929  1.00 24.86           B
ATOM   3774  CZ3  TRP B 122      21.276  27.769  11.061  1.00 21.60           B
ATOM   3775  CH2  TRP B 122      21.047  26.940   9.956  1.00 25.02           B
ATOM   3776  C    TRP B 122      21.416  32.581  10.381  1.00 25.76           B
ATOM   3777  O    TRP B 122      22.061  32.419   9.354  1.00 25.40           B
ATOM   3778  N    GLN B 123      21.932  32.437  11.600  1.00 22.86           B
ATOM   3779  CA   GLN B 123      23.330  32.106  11.786  1.00 25.29           B
ATOM   3780  CB   GLN B 123      23.960  33.225  12.614  1.00 23.33           B
ATOM   3781  CG   GLN B 123      23.736  34.611  12.017  1.00 28.45           B
ATOM   3782  CD   GLN B 123      24.576  34.837  10.772  1.00 28.70           B
ATOM   3783  OE1  GLN B 123      24.445  35.856  10.099  1.00 32.60           B
ATOM   3784  NE2  GLN B 123      25.447  33.889  10.469  1.00 32.57           B
ATOM   3785  C    GLN B 123      23.537  30.762  12.492  1.00 24.00           B
ATOM   3786  O    GLN B 123      22.879  30.502  13.494  1.00 25.77           B
ATOM   3787  N    SER B 124      24.440  29.917  11.994  1.00 23.58           B
ATOM   3788  CA   SER B 124      24.680  28.643  12.680  1.00 24.40           B
ATOM   3789  CB   SER B 124      25.295  27.574  11.778  1.00 26.13           B
ATOM   3790  OG   SER B 124      26.636  27.883  11.441  1.00 32.13           E
ATOM   3791  C    SER B 124      25.600  28.849  13.870  1.00 32.43           E
ATOM   3792  O    SER B 124      26.566  29.622  13.803  1.00 24.71           E
ATOM   3793  N    GLU B 125      25.274  28.155  14.953  1.00 23.06           B
ATOM   3794  CA   GLU B 125      26.035  28.205  16.203  1.00 24.57           B
ATOM   3795  CB   GLU B 125      25.093  28.516  17.360  1.00 25.73           B
ATOM   3796  CG   GLU B 125      24.399  29.857  17.254  1.00 32.47           B
ATOM   3797  CD   GLU B 125      23.353  30.051  18.344  1.00 35.90           B
ATOM   3798  OE1  GLU B 125      23.423  29.345  19.381  1.00 39.08           B
ATOM   3799  OE2  GLU B 125      22.464  30.912  18.168  1.00 39.18           B
ATOM   3800  C    GLU B 125      26.786  26.907  16.508  1.00 24.50           B
ATOM   3801  O    GLU B 125      27.665  26.879  17.382  1.00 24.43           B
ATOM   3802  N    VAL B 126      26.419  25.815  15.844  1.00 22.81           B
ATOM   3803  CA   VAL B 126      27.106  24.539  16.031  1.00 24.05           B
ATOM   3804  CB   VAL B 126      26.434  23.637  17.119  1.00 24.27           B
ATOM   3805  CG1  VAL B 126      25.027  23.339  16.751  1.00 25.14           B
ATOM   3806  CG2  VAL B 126      27.216  22.320  17.271  1.00 27.01           B
ATOM   3807  C    VAL B 126      27.078  23.835  14.690  1.00 23.78           B
ATOM   3808  O    VAL B 126      26.073  23.885  13.967  1.00 24.92           B
ATOM   3809  N    GLU B 127      28.182  23.193  14.344  1.00 22.15           B
ATOM   3810  CA   GLU B 127      28.281  22.509  13.081  1.00 21.91           B
ATOM   3811  CB   GLU B 127      29.002  23.394  12.051  1.00 23.10           B
ATOM   3812  CG   GLU B 127      28.426  24.768  11.966  1.00 26.12           B
ATOM   3813  CD   GLU B 127      29.056  25.636  10.884  1.00 27.63           B
ATOM   3814  OE1  GLU B 127      28.434  26.672  10.546  1.00 27.53           B
ATOM   3815  OE2  GLU B 127      30.157  25.298  10.403  1.00 28.31           B
ATOM   3816  C    GLU B 127      29.069  21.240  13.254  1.00 21.48           B
ATOM   3817  O    GLU B 127      30.034  21.189  14.027  1.00 22.56           B
ATOM   3818  N    PHE B 128      28.665  20.215  12.536  1.00 20.20           B
ATOM   3819  CA   PHE B 128      29.377  18.956  12.576  1.00 19.84           B
ATOM   3820  CB   PHE B 128      29.096  18.211  13.895  1.00 21.34           B
ATOM   3821  CG   PHE B 128      27.632  18.001  14.172  1.00 19.59           B
ATOM   3822  CD1  PHE B 128      26.892  18.969  14.829  1.00 20.54           B
ATOM   3823  CD2  PHE B 128      26.993  16.851  13.729  1.00 19.54           B
ATOM   3824  CE1  PHE B 128      25.516  18.802  15.043  1.00 18.79           B
ATOM   3825  CE2  PHE B 128      25.616  16.672  13.938  1.00 20.56           B
ATOM   3826  CZ   PHE B 128      24.886  17.646  14.591  1.00 20.20           B
ATOM   3827  C    PHE B 128      28.997  18.096  11.392  1.00 21.44           B
ATOM   3828  O    PHE B 128      27.986  18.338  10.707  1.00 19.41           B
ATOM   3829  N    THR B 129      29.836  17.110  11.111  1.00 19.99           B
ATOM   3830  CA   THR B 129      29.562  16.198  10.029  1.00 22.84           B
ATOM   3831  CB   THR B 129      30.712  16.238   8.982  1.00 25.69           B
ATOM   3832  OG1  THR B 129      31.949  15.897   9.626  1.00 32.56           B
ATOM   3833  CG2  THR B 129      30.846  17.633   8.404  1.00 25.73           B
ATOM   3834  C    THR B 129      29.415  14.792  10.608  1.00 24.49           B
ATOM   3835  O    THR B 129      30.021  14.476  11.630  1.00 26.37           B
ATOM   3836  N    LEU B 130      28.577  13.964  10.000  1.00 24.49           B
ATOM   3837  CA   LEU B 130      28.423  12.589  10.477  1.00 24.08           B
ATOM   3838  CB   LEU B 130      27.407  12.505  11.633  1.00 25.54           B
ATOM   3839  CG   LEU B 130      25.900  12.579  11.337  1.00 25.32           B
ATOM   3840  CD1  LEU B 130      25.149  12.111  12.598  1.00 24.84           B
ATOM   3841  CD2  LEU B 130      25.477  13.989  10.960  1.00 23.86           B
ATOM   3842  C    LEU B 130      27.965  11.707   9.327  1.00 23.70           B
ATOM   3843  O    LEU B 130      27.413  12.191   8.343  1.00 23.84           B
ATOM   3844  N    PRO B 131      28.197  10.389   9.425  1.00 23.64           B
ATOM   3845  CD   PRO B 131      28.932   9.700  10.501  1.00 22.59           B
ATOM   3846  CA   PRO B 131      27.790   9.465   8.371  1.00 22.27           B
ATOM   3847  CB   PRO B 131      28.311   8.105   8.871  1.00 23.69           B
ATOM   3848  CG   PRO B 131      29.456   8.479   9.793  1.00 23.88           B
ATOM   3849  C    PRO B 131      26.273   9.459   8.237  1.00 23.45           B
ATOM   3850  O    PRO B 131      25.555   9.578   9.239  1.00 21.35           B
ATOM   3851  N    GLN B 132      25.778   9.341   7.013  1.00 22.22           B
ATOM   3852  CA   GLN B 132      24.337   9.290   6.833  1.00 24.38           B
ATOM   3853  CB   GLN B 132      23.975   9.060   5.383  1.00 27.52           B
ATOM   3854  CG   GLN B 132      24.306  10.174   4.466  1.00 30.36           B
ATOM   3855  CD   GLN B 132      23.834   9.867   3.061  1.00 32.41           B
ATOM   3856  OE1  GLN B 132      22.667   9.539   2.845  1.00 34.45           B
ATOM   3857  NE2  GLN B 132      24.736   9.964   2.100  1.00 33.22           B
ATOM   3858  C    GLN B 132      23.737   8.134   7.642  1.00 24.58           B
ATOM   3859  O    GLN B 132      22.646   8.253   8.187  1.00 23.73           B
ATOM   3860  N    ALA B 133      24.446   7.005   7.692  1.00 24.46           B
ATOM   3861  CA   ALA B 133      23.940   5.844   8.416  1.00 23.74           B
ATOM   3862  CB   ALA B 133      24.911   4.650   8.241  1.00 25.48           B
ATOM   3863  C    ALA B 133      23.677   6.103   9.896  1.00 22.24           B
ATOM   3864  O    ALA B 133      22.768   5.493  10.482  1.00 23.23           B
ATOM   3865  N    THR B 134      24.470   6.976  10.498  1.00 21.71           B
```

Figure 1 (continued 39)

```
ATOM   3866  CA   THR B 134      24.329   7.337  11.906  1.00 21.35      B
ATOM   3867  CB   THR B 134      25.520   8.155  12.368  1.00 23.54      B
ATOM   3868  OG1  THR B 134      26.705   7.376  12.169  1.00 25.66      B
ATOM   3869  CG2  THR B 134      25.375   8.570  13.822  1.00 22.93      B
ATOM   3870  C    THR B 134      23.077   8.161  12.089  1.00 20.95      B
ATOM   3871  O    THR B 134      22.329   7.988  13.053  1.00 20.93      B
ATOM   3872  N    MET B 135      22.855   9.097  11.172  1.00 19.95      B
ATOM   3873  CA   MET B 135      21.654   9.897  11.284  1.00 20.19      B
ATOM   3874  CB   MET B 135      21.626  10.994  10.222  1.00 20.76      B
ATOM   3875  CG   MET B 135      20.385  11.886  10.326  1.00 22.47      B
ATOM   3876  SD   MET B 135      20.158  12.699  11.928  1.00 25.83      B
ATOM   3877  CE   MET B 135      21.360  14.018  11.870  1.00 26.97      B
ATOM   3878  C    MET B 135      20.442   8.986  11.114  1.00 18.60      B
ATOM   3879  O    MET B 135      19.453   9.134  11.831  1.00 18.63      B
ATOM   3880  N    LYS B 136      20.487   8.053  10.169  1.00 19.85      B
ATOM   3881  CA   LYS B 136      19.356   7.155   9.976  1.00 21.55      B
ATOM   3882  CB   LYS B 136      19.595   6.173   8.831  1.00 24.24      B
ATOM   3883  CG   LYS B 136      18.382   5.263   8.598  1.00 25.85      B
ATOM   3884  CD   LYS B 136      18.333   4.703   7.182  1.00 32.16      B
ATOM   3885  CE   LYS B 136      19.291   3.541   7.025  1.00 33.18      B
ATOM   3886  NZ   LYS B 136      18.863   2.381   7.861  1.00 36.66      B
ATOM   3887  C    LYS B 136      19.092   6.348  11.249  1.00 22.36      B
ATOM   3888  O    LYS B 136      17.957   6.211  11.685  1.00 21.54      B
ATOM   3889  N    ARG B 137      20.154   5.791  11.819  1.00 21.72      B
ATOM   3890  CA   ARG B 137      20.004   4.998  13.037  1.00 21.93      B
ATOM   3891  CB   ARG B 137      21.368   4.481  13.501  1.00 24.73      B
ATOM   3892  CG   ARG B 137      21.339   3.432  14.643  1.00 28.08      B
ATOM   3893  CD   ARG B 137      21.297   4.069  16.012  1.00 30.79      B
ATOM   3894  NE   ARG B 137      21.609   3.129  17.104  1.00 31.38      B
ATOM   3895  CZ   ARG B 137      20.802   2.161  17.547  1.00 31.74      B
ATOM   3896  NH1  ARG B 137      19.604   1.962  17.003  1.00 31.80      B
ATOM   3897  NH2  ARG B 137      21.184   1.411  18.578  1.00 29.88      B
ATOM   3898  C    ARG B 137      19.360   5.820  14.141  1.00 20.76      B
ATOM   3899  O    ARG B 137      18.389   5.386  14.770  1.00 21.28      B
ATOM   3900  N    LEU B 138      19.880   7.021  14.364  1.00 19.03      B
ATOM   3901  CA   LEU B 138      19.355   7.902  15.415  1.00 17.43      B
ATOM   3902  CB   LEU B 138      20.123   9.223  15.421  1.00 17.77      B
ATOM   3903  CG   LEU B 138      21.500   9.129  16.066  1.00 18.25      B
ATOM   3904  CD1  LEU B 138      22.325  10.379  15.773  1.00 18.28      B
ATOM   3905  CD2  LEU B 138      21.330   8.948  17.581  1.00 18.59      B
ATOM   3906  C    LEU B 138      17.875   8.209  15.283  1.00 19.04      B
ATOM   3907  O    LEU B 138      17.130   8.236  16.291  1.00 17.18      B
ATOM   3908  N    ILE B 139      17.436   8.467  14.055  1.00 16.38      B
ATOM   3909  CA   ILE B 139      16.027   8.783  13.843  1.00 16.79      B
ATOM   3910  CB   ILE B 139      15.811   9.516  12.479  1.00 16.68      B
ATOM   3911  CG2  ILE B 139      14.322   9.634  12.168  1.00 20.18      B
ATOM   3912  CG1  ILE B 139      16.478  10.883  12.561  1.00 18.34      B
ATOM   3913  CD1  ILE B 139      16.478  11.689  11.221  1.00 19.90      B
ATOM   3914  C    ILE B 139      15.143   7.553  13.916  1.00 16.56      B
ATOM   3915  O    ILE B 139      14.128   7.563  14.590  1.00 16.80      B
ATOM   3916  N    GLU B 140      15.526   6.482  13.238  1.00 15.43      B
ATOM   3917  CA   GLU B 140      14.720   5.276  13.263  1.00 16.12      B
ATOM   3918  CB   GLU B 140      15.316   4.232  12.322  1.00 17.99      B
ATOM   3919  CG   GLU B 140      15.176   4.640  10.858  1.00 22.86      B
ATOM   3920  CD   GLU B 140      15.372   3.489   9.890  1.00 27.30      B
ATOM   3921  OE1  GLU B 140      16.289   2.678  10.103  1.00 28.72      B
ATOM   3922  OE2  GLU B 140      14.609   3.402   8.905  1.00 31.19      B
ATOM   3923  C    GLU B 140      14.595   4.687  14.676 -1.00 15.11      B
ATOM   3924  O    GLU B 140      13.591   4.042  15.003  1.00 17.70      B
ATOM   3925  N    ALA B 141      15.609   4.903  15.503  1.00 15.65      B
ATOM   3926  CA   ALA B 141      15.577   4.336  16.849  1.00 15.07      B
ATOM   3927  CB   ALA B 141      16.963   4.469  17.487  1.00 18.37      B
ATOM   3928  C    ALA B 141      14.530   5.000  17.751  1.00 14.92      B
ATOM   3929  O    ALA B 141      14.080   4.409  18.734  1.00 14.81      B
ATOM   3930  N    THR B 142      14.097   6.209  17.401  1.00 13.57      B
ATOM   3931  CA   THR B 142      13.205   6.922  18.309  1.00 13.58      B
ATOM   3932  CB   THR B 142      13.994   8.081  18.978  1.00 17.09      B
ATOM   3933  OG1  THR B 142      14.329   9.057  17.963  1.00 17.94      B
ATOM   3934  CG2  THR B 142      15.336   7.553  19.627  1.00 15.55      B
ATOM   3935  C    THR B 142      11.943   7.507  17.706  1.00 14.63      B
ATOM   3936  O    THR B 142      11.004   7.820  18.438  1.00 13.14      B
ATOM   3937  N    GLN B 143      11.899   7.640  16.381  1.00 13.61      B
ATOM   3938  CA   GLN B 143      10.752   8.313  15.743  1.00 15.74      B
ATOM   3939  CB   GLN B 143      10.937   8.285  14.215  1.00 17.04      B
ATOM   3940  CG   GLN B 143       9.799   8.931  13.418  1.00 18.95      B
ATOM   3941  CD   GLN B 143      10.073   8.866  11.922  1.00 22.30      B
ATOM   3942  OE1  GLN B 143      10.552   7.873  11.411  1.00 23.43      B
ATOM   3943  NE2  GLN B 143       9.769   9.989  11.211  1.00 23.11      B
ATOM   3944  C    GLN B 143       9.380   7.797  16.137  1.00 15.74      B
ATOM   3945  O    GLN B 143       8.438   8.577  16.322  1.00 17.49      B
ATOM   3946  N    PHE B 144       9.254   6.489  16.319  1.00 15.47      B
ATOM   3947  CA   PHE B 144       7.951   5.942  16.640  1.00 15.79      B
ATOM   3948  CB   PHE B 144       8.009   4.408  16.623  1.00 16.45      B
ATOM   3949  CG   PHE B 144       8.745   3.818  17.785  1.00 15.61      B
ATOM   3950  CD1  PHE B 144      10.129   3.644  17.740  1.00 14.87      B
ATOM   3951  CD2  PHE B 144       8.052   3.490  18.952  1.00 15.49      B
ATOM   3952  CE1  PHE B 144      10.825   3.158  18.849  1.00 14.78      B
ATOM   3953  CE2  PHE B 144       8.730   3.002  20.072  1.00 14.34      B
ATOM   3954  CZ   PHE B 144      10.108   2.836  20.033  1.00 15.36      B
ATOM   3955  C    PHE B 144       7.390   6.402  17.979  1.00 16.39      B
ATOM   3956  O    PHE B 144       6.196   6.252  18.206  1.00 16.31      B
ATOM   3957  N    SER B 145       8.233   6.932  18.857  1.00 15.52      B
ATOM   3958  CA   SER B 145       7.765   7.357  20.178  1.00 15.49      B
ATOM   3959  CB   SER B 145       8.842   7.137  21.236  1.00 19.43      B
ATOM   3960  OG   SER B 145       9.051   5.743  21.459  1.00 19.03      B
ATOM   3961  C    SER B 145       7.321   8.812  20.231  1.00 17.97      B
ATOM   3962  O    SER B 145       6.983   9.307  21.325  1.00 17.36      B
ATOM   3963  N    MET B 146       7.362   9.507  19.093  1.00 17.94      B
ATOM   3964  CA   MET B 146       6.910  10.907  19.066  1.00 19.19      B
ATOM   3965  CB   MET B 146       7.260  11.560  17.711  1.00 21.36      B
```

Figure 1 (continued 40)

| | | | | | | | | | |
|---|---|---|---|---|---|---|---|---|---|
| ATOM | 3966 | CG | MET | B | 146 | 8.716 | 11.608 | 17.434 | 1.00 19.66 | B |
| ATOM | 3967 | SD | MET | B | 146 | 8.961 | 11.941 | 15.674 | 1.00 23.93 | B |
| ATOM | 3968 | CE | MET | B | 146 | 8.838 | 13.621 | 15.659 | 1.00 23.07 | B |
| ATOM | 3969 | C | MET | B | 146 | 5.393 | 10.948 | 19.237 | 1.00 19.89 | B |
| ATOM | 3970 | O | MET | B | 146 | 4.683 | 10.038 | 18.798 | 1.00 21.24 | B |
| ATOM | 3971 | N | ALA | B | 147 | 4.879 | 12.014 | 19.853 | 1.00 21.60 | B |
| ATOM | 3972 | CA | ALA | B | 147 | 3.438 | 12.137 | 20.009 | 1.00 24.00 | B |
| ATOM | 3973 | CB | ALA | B | 147 | 3.112 | 13.270 | 21.028 | 1.00 23.97 | B |
| ATOM | 3974 | C | ALA | B | 147 | 2.775 | 12.439 | 18.661 | 1.00 25.73 | B |
| ATOM | 3975 | O | ALA | B | 147 | 3.433 | 12.878 | 17.714 | 1.00 23.85 | B |
| ATOM | 3976 | N | HIS | B | 148 | 1.473 | 12.184 | 18.568 | 1.00 30.66 | B |
| ATOM | 3977 | CA | HIS | B | 148 | 0.719 | 12.469 | 17.348 | 1.00 34.48 | B |
| ATOM | 3978 | CB | HIS | B | 148 | 0.020 | 11.211 | 16.829 | 1.00 37.35 | B |
| ATOM | 3979 | CG | HIS | B | 148 | 0.944 | 10.060 | 16.595 | 1.00 40.57 | B |
| ATOM | 3980 | CD2 | HIS | B | 148 | 0.913 | 8.786 | 17.053 | 1.00 41.90 | B |
| ATOM | 3981 | ND1 | HIS | B | 148 | 2.056 | 10.150 | 15.783 | 1.00 42.40 | B |
| ATOM | 3982 | CE1 | HIS | B | 148 | 2.672 | 8.981 | 15.754 | 1.00 42.24 | B |
| ATOM | 3983 | NE2 | HIS | B | 148 | 1.998 | 8.136 | 16.515 | 1.00 43.11 | B |
| ATOM | 3984 | C | HIS | B | 148 | -0.344 | 13.519 | 17.668 | 1.00 36.54 | B |
| ATOM | 3985 | O | HIS | B | 148 | -1.386 | 13.201 | 18.262 | 1.00 36.38 | B |
| ATOM | 3986 | N | GLN | B | 149 | -0.078 | 14.761 | 17.281 | 1.00 37.77 | B |
| ATOM | 3987 | CA | GLN | B | 149 | -1.019 | 15.853 | 17.523 | 1.00 39.65 | B |
| ATOM | 3988 | CB | GLN | B | 149 | -2.290 | 15.638 | 16.680 | 1.00 41.57 | B |
| ATOM | 3989 | CG | GLN | B | 149 | -2.022 | 15.462 | 15.185 | 1.00 44.91 | B |
| ATOM | 3990 | CD | GLN | B | 149 | -3.278 | 15.215 | 14.355 | 1.00 46.65 | B |
| ATOM | 3991 | OE1 | GLN | B | 149 | -4.068 | 14.320 | 14.648 | 1.00 48.28 | B |
| ATOM | 3992 | NE2 | GLN | B | 149 | -3.453 | 16.003 | 13.300 | 1.00 48.05 | B |
| ATOM | 3993 | C | GLN | B | 149 | -1.376 | 15.995 | 19.005 | 1.00 39.02 | B |
| ATOM | 3994 | O | GLN | B | 149 | -2.558 | 16.067 | 19.370 | 1.00 40.48 | B |
| ATOM | 3995 | N | ASP | B | 150 | -0.354 | 16.029 | 19.857 | 1.00 38.46 | B |
| ATOM | 3996 | CA | ASP | B | 150 | -0.534 | 16.192 | 21.299 | 1.00 37.30 | B |
| ATOM | 3997 | CB | ASP | B | 150 | 0.679 | 15.640 | 22.059 | 1.00 37.60 | B |
| ATOM | 3998 | CG | ASP | B | 150 | 0.445 | 15.547 | 23.561 | 1.00 38.25 | B |
| ATOM | 3999 | OD1 | ASP | B | 150 | 0.093 | 16.575 | 24.172 | 1.00 38.49 | B |
| ATOM | 4000 | OD2 | ASP | B | 150 | 0.621 | 14.450 | 24.149 | 1.00 37.98 | B |
| ATOM | 4001 | C | ASP | B | 150 | -0.673 | 17.695 | 21.578 | 1.00 38.03 | B |
| ATOM | 4002 | O | ASP | B | 150 | -0.191 | 18.526 | 20.803 | 1.00 35.91 | B |
| ATOM | 4003 | N | VAL | B | 151 | -1.325 | 18.036 | 22.687 | 1.00 38.58 | B |
| ATOM | 4004 | CA | VAL | B | 151 | -1.527 | 19.432 | 23.055 | 1.00 38.83 | B |
| ATOM | 4005 | CB | VAL | B | 151 | -2.403 | 19.567 | 24.316 | 1.00 39.52 | B |
| ATOM | 4006 | CG1 | VAL | B | 151 | -2.705 | 21.028 | 24.579 | 1.00 39.97 | B |
| ATOM | 4007 | CG2 | VAL | B | 151 | -3.678 | 18.778 | 24.142 | 1.00 40.52 | B |
| ATOM | 4008 | C | VAL | B | 151 | -0.185 | 20.057 | 23.331 | 1.00 38.33 | B |
| ATOM | 4009 | O | VAL | B | 151 | 0.047 | 21.213 | 22.982 | 1.00 38.42 | B |
| ATOM | 4010 | N | ARG | B | 152 | 0.676 | 19.302 | 24.012 | 1.00 37.29 | B |
| ATOM | 4011 | CA | ARG | B | 152 | 2.022 | 19.761 | 24.291 | 1.00 36.95 | B |
| ATOM | 4012 | CB | ARG | B | 152 | 2.718 | 18.842 | 25.304 | 1.00 38.55 | B |
| ATOM | 4013 | CG | ARG | B | 152 | 2.144 | 18.896 | 26.717 | 1.00 40.64 | B |
| ATOM | 4014 | CD | ARG | B | 152 | 0.984 | 17.935 | 26.875 | 1.00 41.39 | B |
| ATOM | 4015 | NE | ARG | B | 152 | 1.454 | 16.561 | 27.041 | 1.00 43.21 | B |
| ATOM | 4016 | CZ | ARG | B | 152 | 0.674 | 15.492 | 26.935 | 1.00 44.44 | B |
| ATOM | 4017 | NH1 | ARG | B | 152 | -0.619 | 15.645 | 26.656 | 1.00 46.42 | B |
| ATOM | 4018 | NH2 | ARG | B | 152 | 1.176 | 14.274 | 27.116 | 1.00 43.86 | B |
| ATOM | 4019 | C | ARG | B | 152 | 2.683 | 19.626 | 22.921 | 1.00 36.41 | B |
| ATOM | 4020 | O | ARG | B | 152 | 3.410 | 18.659 | 22.678 | 1.00 34.83 | B |
| ATOM | 4021 | N | TYR | B | 153 | 2.403 | 20.580 | 22.031 | 1.00 34.80 | B |
| ATOM | 4022 | CA | TYR | B | 153 | 2.927 | 20.555 | 20.665 | 1.00 33.74 | B |
| ATOM | 4023 | CB | TYR | B | 153 | 2.686 | 21.906 | 19.963 | 1.00 35.98 | B |
| ATOM | 4024 | CG | TYR | B | 153 | 3.406 | 23.061 | 20.611 | 1.00 38.54 | B |
| ATOM | 4025 | CD1 | TYR | B | 153 | 2.975 | 23.581 | 21.835 | 1.00 39.34 | B |
| ATOM | 4026 | CE1 | TYR | B | 153 | 3.698 | 24.581 | 22.487 | 1.00 39.67 | B |
| ATOM | 4027 | CD2 | TYR | B | 153 | 4.574 | 23.582 | 20.049 | 1.00 39.01 | B |
| ATOM | 4028 | CE2 | TYR | B | 153 | 5.310 | 24.586 | 20.696 | 1.00 39.82 | B |
| ATOM | 4029 | CZ | TYR | B | 153 | 4.866 | 25.075 | 21.915 | 1.00 40.12 | B |
| ATOM | 4030 | OH | TYR | B | 153 | 5.607 | 26.030 | 22.574 | 1.00 39.51 | B |
| ATOM | 4031 | C | TYR | B | 153 | 4.403 | 20.171 | 20.568 | 1.00 32.24 | B |
| ATOM | 4032 | O | TYR | B | 153 | 4.833 | 19.616 | 19.554 | 1.00 30.69 | B |
| ATOM | 4033 | N | TYR | B | 154 | 5.175 | 20.445 | 21.612 | 1.00 30.25 | B |
| ATOM | 4034 | CA | TYR | B | 154 | 6.585 | 20.103 | 21.597 | 1.00 30.50 | B |
| ATOM | 4035 | CB | TYR | B | 154 | 7.324 | 20.751 | 22.779 | 1.00 32.66 | B |
| ATOM | 4036 | CG | TYR | B | 154 | 6.785 | 20.471 | 24.172 | 1.00 35.85 | B |
| ATOM | 4037 | CD1 | TYR | B | 154 | 7.325 | 19.450 | 24.953 | 1.00 36.54 | B |
| ATOM | 4038 | CE1 | TYR | B | 154 | 6.888 | 19.225 | 26.267 | 1.00 37.57 | B |
| ATOM | 4039 | CD2 | TYR | B | 154 | 5.779 | 21.270 | 24.734 | 1.00 37.28 | B |
| ATOM | 4040 | CE2 | TYR | B | 154 | 5.334 | 21.053 | 26.047 | 1.00 37.15 | B |
| ATOM | 4041 | CZ | TYR | B | 154 | 5.895 | 20.030 | 26.805 | 1.00 38.13 | B |
| ATOM | 4042 | OH | TYR | B | 154 | 5.477 | 19.804 | 28.098 | 1.00 38.78 | B |
| ATOM | 4043 | C | TYR | B | 154 | 6.813 | 18.585 | 21.571 | 1.00 29.59 | B |
| ATOM | 4044 | O | TYR | B | 154 | 7.817 | 18.113 | 21.040 | 1.00 28.98 | B |
| ATOM | 4045 | N | LEU | B | 155 | 5.874 | 17.816 | 22.109 | 1.00 27.11 | B |
| ATOM | 4046 | CA | LEU | B | 155 | 6.029 | 16.359 | 22.087 | 1.00 26.11 | B |
| ATOM | 4047 | CB | LEU | B | 155 | 5.055 | 15.686 | 23.064 | 1.00 25.90 | B |
| ATOM | 4048 | CG | LEU | B | 155 | 5.260 | 16.046 | 24.536 | 1.00 27.10 | B |
| ATOM | 4049 | CD1 | LEU | B | 155 | 4.256 | 15.237 | 25.360 | 1.00 29.20 | B |
| ATOM | 4050 | CD2 | LEU | B | 155 | 6.686 | 15.757 | 24.980 | 1.00 28.73 | B |
| ATOM | 4051 | C | LEU | B | 155 | 5.808 | 15.776 | 20.682 | 1.00 25.64 | B |
| ATOM | 4052 | O | LEU | B | 155 | 6.177 | 14.613 | 20.431 | 1.00 25.89 | B |
| ATOM | 4053 | N | ASN | B | 156 | 5.210 | 16.560 | 19.781 | 1.00 23.01 | B |
| ATOM | 4054 | CA | ASN | B | 156 | 4.962 | 16.121 | 18.405 | 1.00 23.44 | B |
| ATOM | 4055 | CB | ASN | B | 156 | 3.911 | 16.986 | 17.737 | 1.00 25.76 | B |
| ATOM | 4056 | CG | ASN | B | 156 | 2.570 | 16.900 | 18.436 | 1.00 29.20 | B |
| ATOM | 4057 | OD1 | ASN | B | 156 | 1.720 | 17.790 | 18.396 | 1.00 30.71 | B |
| ATOM | 4058 | ND2 | ASN | B | 156 | 2.373 | 15.830 | 19.194 | 1.00 24.28 | B |
| ATOM | 4059 | C | ASN | B | 156 | 6.235 | 16.141 | 17.547 | 1.00 23.66 | B |
| ATOM | 4060 | O | ASN | B | 156 | 6.203 | 15.696 | 16.400 | 1.00 23.66 | B |
| ATOM | 4061 | N | GLY | B | 157 | 7.332 | 16.630 | 18.122 | 1.00 23.58 | B |
| ATOM | 4062 | CA | GLY | B | 157 | 8.596 | 16.686 | 17.399 | 1.00 22.86 | B |
| ATOM | 4063 | C | GLY | B | 157 | 9.630 | 15.756 | 18.000 | 1.00 22.29 | B |
| ATOM | 4064 | O | GLY | B | 157 | 9.307 | 14.894 | 18.819 | 1.00 21.77 | B |
| ATOM | 4065 | N | MET | B | 158 | 10.890 | 15.911 | 17.604 | 1.00 19.12 | B |

Figure 1 (continued 41)

```
ATOM   4066  CA   MET B 158    11.963  15.074  18.121  1.00 18.96      B
ATOM   4067  CB   MET B 158    12.516  14.163  17.003  1.00 16.50      B
ATOM   4068  CG   MET B 158    13.688  13.297  17.395  1.00 15.32      B
ATOM   4069  SD   MET B 158    14.254  12.235  16.035  1.00 16.20      B
ATOM   4070  CE   MET B 158    12.919  10.970  15.928  1.00 15.94      B
ATOM   4071  C    MET B 158    13.095  15.928  18.658  1.00 19.64      B
ATOM   4072  O    MET B 158    13.530  16.880  18.006  1.00 18.73      B
ATOM   4073  N    LEU B 159    13.564  15.621  19.854  1.00 19.03      B
ATOM   4074  CA   LEU B 159    14.674  16.383  20.397  1.00 19.89      B
ATOM   4075  CB   LEU B 159    14.747  16.250  21.921  1.00 21.16      B
ATOM   4076  CG   LEU B 159    15.847  17.145  22.504  1.00 23.17      B
ATOM   4077  CD1  LEU B 159    15.239  18.525  22.690  1.00 24.44      B
ATOM   4078  CD2  LEU B 159    16.406  16.575  23.857  1.00 26.60      B
ATOM   4079  C    LEU B 159    15.999  15.897  19.816  1.00 18.80      B
ATOM   4080  O    LEU B 159    16.232  14.693  19.707  1.00 19.10      B
ATOM   4081  N    PHE B 160    16.854  16.844  19.397  1.00 18.54      B
ATOM   4082  CA   PHE B 160    18.194  16.522  18.906  1.00 18.56      B
ATOM   4083  CB   PHE B 160    18.414  17.041  17.481  1.00 17.32      B
ATOM   4084  CG   PHE B 160    17.833  16.158  16.414  1.00 16.68      B
ATOM   4085  CD1  PHE B 160    16.460  16.129  16.172  1.00 16.33      B
ATOM   4086  CD2  PHE B 160    18.668  15.338  15.644  1.00 18.29      B
ATOM   4087  CE1  PHE B 160    15.916  15.291  15.170  1.00 15.09      B
ATOM   4088  CE2  PHE B 160    18.145  14.498  14.641  1.00 18.37      B
ATOM   4089  CZ   PHE B 160    16.758  14.474  14.400  1.00 16.02      B
ATOM   4090  C    PHE B 160    19.169  17.220  19.862  1.00 20.39      B
ATOM   4091  O    PHE B 160    19.045  18.421  20.088  1.00 22.48      B
ATOM   4092  N    GLU B 161    20.123  16.472  20.409  1.00 22.11      B
ATOM   4093  CA   GLU B 161    21.062  17.021  21.371  1.00 23.08      B
ATOM   4094  CB   GLU B 161    20.595  16.616  22.795  1.00 25.07      B
ATOM   4095  CG   GLU B 161    21.687  16.649  23.845  1.00 29.45      B
ATOM   4096  CD   GLU B 161    21.216  16.219  25.237  1.00 32.67      B
ATOM   4097  OE1  GLU B 161    20.335  15.337  25.350  1.00 33.61      B
ATOM   4098  OE2  GLU B 161    21.762  16.750  26.232  1.00 35.08      B
ATOM   4099  C    GLU B 161    22.515  16.620  21.139  1.00 23.37      B
ATOM   4100  O    GLU B 161    22.817  15.483  20.812  1.00 22.03      B
ATOM   4101  N    THR B 162    23.422  17.589  21.282  1.00 24.63      B
ATOM   4102  CA   THR B 162    24.848  17.337  21.145  1.00 26.40      B
ATOM   4103  CB   THR B 162    25.546  18.444  20.281  1.00 25.08      B
ATOM   4104  OG1  THR B 162    25.086  19.747  20.676  1.00 24.91      B
ATOM   4105  CG2  THR B 162    25.223  18.231  18.803  1.00 27.18      B
ATOM   4106  C    THR B 162    25.438  17.336  22.565  1.00 27.15      B
ATOM   4107  O    THR B 162    25.127  18.222  23.359  1.00 28.33      B
ATOM   4108  N    GLU B 163    26.256  16.332  22.881  1.00 29.67      B
ATOM   4109  CA   GLU B 163    26.883  16.224  24.207  1.00 31.99      B
ATOM   4110  CB   GLU B 163    25.975  15.463  25.173  1.00 34.55      B
ATOM   4111  CG   GLU B 163    24.640  16.124  25.426  1.00 37.21      B
ATOM   4112  CD   GLU B 163    24.739  17.368  26.290  1.00 40.30      B
ATOM   4113  OE1  GLU B 163    25.272  17.271  27.421  1.00 42.28      B
ATOM   4114  OE2  GLU B 163    24.272  18.442  25.843  1.00 40.47      B
ATOM   4115  C    GLU B 163    28.208  15.514  24.119  1.00 31.89      B
ATOM   4116  O    GLU B 163    28.284  14.360  23.703  1.00 31.49      B
ATOM   4117  N    GLY B 164    29.263  16.208  24.524  1.00 33.08      B
ATOM   4118  CA   GLY B 164    30.578  15.612  24.458  1.00 34.03      B
ATOM   4119  C    GLY B 164    30.958  15.337  23.015  1.00 34.75      B
ATOM   4120  O    GLY B 164    31.279  16.249  22.251  1.00 35.89      B
ATOM   4121  N    GLU B 165    30.900  14.070  22.637  1.00 33.48      B
ATOM   4122  CA   GLU B 165    31.243  13.651  21.296  1.00 33.45      B
ATOM   4123  CB   GLU B 165    32.465  12.749  21.359 -1.00 36.52      B
ATOM   4124  CG   GLU B 165    32.859  12.136  20.032  1.00 40.64      B
ATOM   4125  CD   GLU B 165    33.569  10.807  20.209  1.00 41.89      B
ATOM   4126  OE1  GLU B 165    34.538  10.756  21.003  1.00 45.17      B
ATOM   4127  OE2  GLU B 165    33.163   9.825  19.552  1.00 42.89      B
ATOM   4128  C    GLU B 165    30.069  12.886  20.686  1.00 31.49      B
ATOM   4129  O    GLU B 165    30.216  12.207  19.680  1.00 30.99      B
ATOM   4130  N    GLU B 166    28.898  12.996  21.301  1.00 31.17      B
ATOM   4131  CA   GLU B 166    27.734  12.272  20.786  1.00 30.34      B
ATOM   4132  CB   GLU B 166    27.186  11.327  21.852  1.00 32.23      B
ATOM   4133  CG   GLU B 166    28.125  10.236  22.339  1.00 35.23      B
ATOM   4134  CD   GLU B 166    27.417   9.289  23.290  1.00 37.38      B
ATOM   4135  OE1  GLU B 166    27.041   9.723  24.405  1.00 38.59      B
ATOM   4136  OE2  GLU B 166    27.218   8.120  22.913  1.00 39.47      B
ATOM   4137  C    GLU B 166    26.570  13.156  20.329  1.00 27.86      B
ATOM   4138  O    GLU B 166    26.408  14.273  20.797  1.00 27.41      B
ATOM   4139  N    LEU B 167    25.776  12.628  19.397  1.00 25.92      B
ATOM   4140  CA   LEU B 167    24.560  13.291  18.930  1.00 23.86      B
ATOM   4141  CB   LEU B 167    24.455  13.313  17.402  1.00 23.73      B
ATOM   4142  CG   LEU B 167    23.631  14.415  16.685  1.00 24.90      B
ATOM   4143  CD1  LEU B 167    23.059  13.834  15.415  1.00 21.07      B
ATOM   4144  CD2  LEU B 167    22.555  15.041  17.534  1.00 23.85      B
ATOM   4145  C    LEU B 167    23.520  12.303  19.481  1.00 21.77      B
ATOM   4146  O    LEU B 167    23.705  11.083  19.405  1.00 22.33      B
ATOM   4147  N    ARG B 168    22.439  12.834  20.021  1.00 21.49      B
ATOM   4148  CA   ARG B 168    21.393  11.996  20.596  1.00 21.70      B
ATOM   4149  CB   ARG B 168    21.549  12.047  22.117  1.00 24.79      B
ATOM   4150  CG   ARG B 168    20.309  11.678  22.928  1.00 27.63      B
ATOM   4151  CD   ARG B 168    20.635  11.575  24.419  1.00 31.15      B
ATOM   4152  NE   ARG B 168    21.104  12.813  25.018  1.00 33.80      B
ATOM   4153  CZ   ARG B 168    22.333  13.005  25.502  1.00 33.14      B
ATOM   4154  NH1  ARG B 168    23.245  12.040  25.466  1.00 33.70      B
ATOM   4155  NH2  ARG B 168    22.646  14.169  26.022  1.00 34.73      B
ATOM   4156  C    ARG B 168    20.001  12.475  20.188  1.00 20.96      B
ATOM   4157  O    ARG B 168    19.782  13.564  19.977  1.00 20.05      B
ATOM   4158  N    THR B 169    19.059  11.549  20.026  1.00 18.53      B
ATOM   4159  CA   THR B 169    17.693  11.945  19.748  1.00 17.19      B
ATOM   4160  CB   THR B 169    17.141  11.377  18.420  1.00 17.29      B
ATOM   4161  OG1  THR B 169    17.290   9.961  18.415  1.00 17.62      B
ATOM   4162  CG2  THR B 169    17.936  11.920  17.241  1.00 17.89      B
ATOM   4163  C    THR B 169    16.846  11.382  20.870  1.00 18.82      B
ATOM   4164  O    THR B 169    17.200  10.356  21.474  1.00 18.41      B
ATOM   4165  N    VAL B 170    15.772  12.095  21.151  1.00 18.62      B
```

Figure 1 (continued 42)

```
ATOM   4166  CA   VAL B 170      14.796  11.705  22.176  1.00 18.28      B
ATOM   4167  CB   VAL B 170      15.031  12.497  23.489  1.00 17.76      B
ATOM   4168  CG1  VAL B 170      14.085  11.948  24.589  1.00 18.88      B
ATOM   4169  CG2  VAL B 170      16.520  12.397  23.913  1.00 18.42      B
ATOM   4170  C    VAL B 170      13.368  11.981  21.674  1.00 18.46      B
ATOM   4171  O    VAL B 170      13.087  13.010  21.060  1.00 18.89      B
ATOM   4172  N    ALA B 171      12.455  11.031  21.908  1.00 15.83      B
ATOM   4173  CA   ALA B 171      11.069  11.206  21.518  1.00 16.19      B
ATOM   4174  CB   ALA B 171      10.771  10.503  20.212  1.00 16.47      B
ATOM   4175  C    ALA B 171      10.234  10.606  22.617  1.00 17.41      B
ATOM   4176  O    ALA B 171      10.642   9.616  23.213  1.00 18.10      B
ATOM   4177  N    THR B 172       9.112  11.246  22.902  1.00 16.52      B
ATOM   4178  CA   THR B 172       8.212  10.730  23.917  1.00 17.52      B
ATOM   4179  CB   THR B 172       8.776  11.014  25.344  1.00 18.95      B
ATOM   4180  OG1  THR B 172       7.931  10.400  26.328  1.00 19.33      B
ATOM   4181  CG2  THR B 172       8.870  12.532  25.619  1.00 18.29      B
ATOM   4182  C    THR B 172       6.805  11.269  23.709  1.00 18.84      B
ATOM   4183  O    THR B 172       6.588  12.352  23.145  1.00 20.21      B
ATOM   4184  N    ASP B 173       5.820  10.481  24.134  1.00 18.12      B
ATOM   4185  CA   ASP B 173       4.447  10.902  23.972  1.00 19.17      B
ATOM   4186  CB   ASP B 173       3.709   9.980  22.996  1.00 19.41      B
ATOM   4187  CG   ASP B 173       3.663   8.531  23.461  1.00 19.37      B
ATOM   4188  OD1  ASP B 173       4.197   8.212  24.540  1.00 20.26      B
ATOM   4189  OD2  ASP B 173       3.087   7.712  22.710  1.00 18.53      B
ATOM   4190  C    ASP B 173       3.766  10.895  25.336  1.00 19.52      B
ATOM   4191  O    ASP B 173       2.546  11.011  25.408  1.00 22.02      B
ATOM   4192  N    GLY B 174       4.562  10.770  26.397  1.00 20.37      B
ATOM   4193  CA   GLY B 174       3.992  10.745  27.737  1.00 22.96      B
ATOM   4194  C    GLY B 174       3.762   9.337  28.266  1.00 24.51      B
ATOM   4195  O    GLY B 174       3.667   9.141  29.489  1.00 26.84      B
ATOM   4196  N    HIS B 175       3.650   8.349  27.375  1.00 23.92      B
ATOM   4197  CA   HIS B 175       3.440   6.953  27.796  1.00 22.95      B
ATOM   4198  CB   HIS B 175       2.313   6.309  26.977  1.00 25.89      B
ATOM   4199  CG   HIS B 175       0.992   6.997  27.119  1.00 28.87      B
ATOM   4200  CD2  HIS B 175       0.106   7.435  26.193  1.00 30.90      B
ATOM   4201  ND1  HIS B 175       0.420   7.255  28.345  1.00 30.54      B
ATOM   4202  CE1  HIS B 175      -0.763   7.817  28.170  1.00 28.94      B
ATOM   4203  NE2  HIS B 175      -0.977   7.938  26.875  1.00 31.49      B
ATOM   4204  C    HIS B 175       4.706   6.135  27.641  1.00 23.03      B
ATOM   4205  O    HIS B 175       4.990   5.212  28.403  1.00 22.08      B
ATOM   4206  N    ARG B 176       5.481   6.461  26.617  1.00 18.76      B
ATOM   4207  CA   ARG B 176       6.711   5.768  26.422  1.00 18.30      B
ATOM   4208  CB   ARG B 176       6.575   4.633  25.398  1.00 19.53      B
ATOM   4209  CG   ARG B 176       6.329   5.094  23.954  1.00 22.88      B
ATOM   4210  CD   ARG B 176       4.876   4.888  23.657  1.00 22.11      B
ATOM   4211  NE   ARG B 176       4.435   5.312  22.314  1.00 22.09      B
ATOM   4212  CZ   ARG B 176       4.555   4.591  21.202  1.00 20.17      B
ATOM   4213  NH1  ARG B 176       5.159   3.403  21.213  1.00 17.04      B
ATOM   4214  NH2  ARG B 176       3.914   4.977  20.120  1.00 20.02      B
ATOM   4215  C    ARG B 176       7.684   6.807  25.902  1.00 17.30      B
ATOM   4216  O    ARG B 176       7.255   7.860  25.374  1.00 18.10      B
ATOM   4217  N    LEU B 177       8.957   6.504  26.080  1.00 17.97      B
ATOM   4218  CA   LEU B 177      10.049   7.360  25.633  1.00 17.85      B
ATOM   4219  CB   LEU B 177      10.664   8.095  26.827  1.00 18.29      B
ATOM   4220  CG   LEU B 177      11.921   8.955  26.611  1.00 16.28      B
ATOM   4221  CD1  LEU B 177      11.819  10.163  27.559  1.00 19.52      B
ATOM   4222  CD2  LEU B 177      13.191   8.172  26.839  1.00 19.12      B
ATOM   4223  C    LEU B 177      11.110   6.517  24.964  1.00 18.45      B
ATOM   4224  O    LEU B 177      11.291   5.329  25.281  1.00 18.33      B
ATOM   4225  N    ALA B 178      11.801   7.131  24.006  1.00 15.84      B
ATOM   4226  CA   ALA B 178      12.899   6.489  23.308  1.00 15.12      B
ATOM   4227  CB   ALA B 178      12.495   6.133  21.883  1.00 13.82      B
ATOM   4228  C    ALA B 178      14.041   7.488  23.279  1.00 15.48      B
ATOM   4229  O    ALA B 178      13.797   8.670  23.053  1.00 17.09      B
ATOM   4230  N    VAL B 179      15.258   7.014  23.546  1.00 17.40      B
ATOM   4231  CA   VAL B 179      16.470   7.851  23.508  1.00 18.38      B
ATOM   4232  CB   VAL B 179      16.881   8.318  24.937  1.00 18.67      B
ATOM   4233  CG1  VAL B 179      17.294   7.120  25.770  1.00 19.18      B
ATOM   4234  CG2  VAL B 179      18.060   9.286  24.864  1.00 20.37      B
ATOM   4235  C    VAL B 179      17.590   7.037  22.849  1.00 19.44      B
ATOM   4236  O    VAL B 179      17.737   5.829  23.092  1.00 19.37      B
ATOM   4237  N    CYS B 180      18.370   7.676  21.968  1.00 17.08      B
ATOM   4238  CA   CYS B 180      19.434   6.979  21.293  1.00 18.58      B
ATOM   4239  CB   CYS B 180      18.961   6.489  19.918  1.00 17.06      B
ATOM   4240  SG   CYS B 180      20.198   5.643  18.973  1.00 22.31      B
ATOM   4241  C    CYS B 180      20.602   7.948  21.135  1.00 19.35      B
ATOM   4242  O    CYS B 180      20.405   9.093  20.736  1.00 19.68      B
ATOM   4243  N    SER B 181      21.798   7.464  21.442  1.00 21.74      B
ATOM   4244  CA   SER B 181      23.015   8.277  21.369  1.00 25.46      B
ATOM   4245  CB   SER B 181      23.615   8.457  22.774  1.00 28.11      B
ATOM   4246  OG   SER B 181      22.674   9.033  23.654  1.00 30.74      B
ATOM   4247  C    SER B 181      24.037   7.590  20.498  1.00 26.06      B
ATOM   4248  O    SER B 181      24.182   6.370  20.554  1.00 25.12      B
ATOM   4249  N    MET B 182      24.765   8.374  19.704  1.00 25.90      B
ATOM   4250  CA   MET B 182      25.779   7.846  18.813  1.00 29.20      B
ATOM   4251  CB   MET B 182      25.238   7.784  17.382  1.00 31.43      B
ATOM   4252  CG   MET B 182      24.114   6.789  17.181  1.00 33.69      B
ATOM   4253  SD   MET B 182      24.722   5.139  17.524  1.00 34.88      B
ATOM   4254  CE   MET B 182      25.373   4.651  15.929  1.00 34.59      B
ATOM   4255  C    MET B 182      27.001   8.758  18.834  1.00 30.52      B
ATOM   4256  O    MET B 182      26.857   9.983  18.819  1.00 30.18      B
ATOM   4257  N    PRO B 183      28.214   8.177  18.872  1.00 32.39      B
ATOM   4258  CD   PRO B 183      28.529   6.737  18.860  1.00 34.00      B
ATOM   4259  CA   PRO B 183      29.449   8.977  18.888  1.00 34.40      B
ATOM   4260  CB   PRO B 183      30.521   7.940  19.199  1.00 34.66      B
ATOM   4261  CG   PRO B 183      29.998   6.735  18.481  1.00 35.09      B
ATOM   4262  C    PRO B 183      29.663   9.624  17.517  1.00 35.33      B
ATOM   4263  O    PRO B 183      29.355   9.015  16.502  1.00 35.46      B
ATOM   4264  N    ILE B 184      30.199  10.843  17.506  1.00 36.88      B
ATOM   4265  CA   ILE B 184      30.445  11.589  16.271  1.00 38.38      B
```

Figure 1 (continued 43)

```
ATOM   4266  CB   ILE B 184      29.676  12.942  16.305  1.00 37.59      B
ATOM   4267  CG2  ILE B 184      30.131  13.872  15.192  1.00 39.18      B
ATOM   4268  CG1  ILE B 184      28.185  12.670  16.154  1.00 39.46      B
ATOM   4269  CD1  ILE B 184      27.857  11.818  14.939  1.00 38.79      B
ATOM   4270  C    ILE B 184      31.926  11.864  15.976  1.00 39.26      B
ATOM   4271  O    ILE B 184      32.266  12.371  14.913  1.00 39.33      B
ATOM   4272  N    GLY B 185      32.810  11.528  16.906  1.00 40.53      B
ATOM   4273  CA   GLY B 185      34.225  11.777  16.671  1.00 42.10      B
ATOM   4274  C    GLY B 185      34.630  13.227  16.897  1.00 43.16      B
ATOM   4275  O    GLY B 185      35.821  13.542  16.982  1.00 44.33      B
ATOM   4276  N    GLN B 186      33.646  14.117  16.988  1.00 43.84      B
ATOM   4277  CA   GLN B 186      33.898  15.541  17.208  1.00 44.08      B
ATOM   4278  CB   GLN B 186      33.069  16.406  16.254  1.00 43.89      B
ATOM   4279  CG   GLN B 186      33.456  16.388  14.800  1.00 44.39      B
ATOM   4280  CD   GLN B 186      32.677  17.426  14.006  1.00 43.95      B
ATOM   4281  OE1  GLN B 186      32.773  18.631  14.269  1.00 44.45      B
ATOM   4282  NE2  GLN B 186      31.893  16.963  13.039  1.00 42.44      B
ATOM   4283  C    GLN B 186      33.503  15.952  18.614  1.00 44.05      B
ATOM   4284  O    GLN B 186      32.650  15.325  19.228  1.00 44.15      B
ATOM   4285  N    SER B 187      34.115  17.019  19.115  1.00 43.83      B
ATOM   4286  CA   SER B 187      33.779  17.544  20.434  1.00 43.99      B
ATOM   4287  CB   SER B 187      35.025  18.105  21.138  1.00 44.53      B
ATOM   4288  OG   SER B 187      36.033  17.117  21.304  1.00 45.53      B
ATOM   4289  C    SER B 187      32.797  18.675  20.121  1.00 43.54      B
ATOM   4290  O    SER B 187      33.117  19.573  19.338  1.00 43.42      B
ATOM   4291  N    LEU B 188      31.603  18.635  20.705  1.00 42.54      B
ATOM   4292  CA   LEU B 188      30.616  19.669  20.425  1.00 41.93      B
ATOM   4293  CB   LEU B 188      29.425  19.083  19.652  1.00 42.36      B
ATOM   4294  CG   LEU B 188      29.558  18.823  18.148  1.00 42.40      B
ATOM   4295  CD1  LEU B 188      30.321  19.973  17.494  1.00 42.81      B
ATOM   4296  CD2  LEU B 188      30.269  17.515  17.910  1.00 42.43      B
ATOM   4297  C    LEU B 188      30.074  20.411  21.623  1.00 41.46      B
ATOM   4298  O    LEU B 188      30.097  19.910  22.742  1.00 42.28      B
ATOM   4299  N    PRO B 189      29.580  21.638  21.398  1.00 40.92      B
ATOM   4300  CD   PRO B 189      29.691  22.410  20.147  1.00 40.91      B
ATOM   4301  CA   PRO B 189      29.009  22.457  22.466  1.00 39.91      B
ATOM   4302  CB   PRO B 189      28.784  23.810  21.793  1.00 40.82      B
ATOM   4303  CG   PRO B 189      29.770  23.819  20.656  1.00 41.55      B
ATOM   4304  C    PRO B 189      27.683  21.801  22.853  1.00 39.55      B
ATOM   4305  O    PRO B 189      26.834  21.544  21.995  1.00 37.81      B
ATOM   4306  N    SER B 190      27.507  21.512  24.134  1.00 38.79      B
ATOM   4307  CA   SER B 190      26.266  20.889  24.577  1.00 38.03      B
ATOM   4308  CB   SER B 190      26.237  20.860  26.103  1.00 38.64      B
ATOM   4309  OG   SER B 190      27.459  20.337  26.593  1.00 41.63      B
ATOM   4310  C    SER B 190      25.126  21.733  24.005  1.00 36.48      B
ATOM   4311  O    SER B 190      25.072  22.937  24.221  1.00 37.47      B
ATOM   4312  N    HIS B 191      24.214  21.102  23.268  1.00 34.74      B
ATOM   4313  CA   HIS B 191      23.122  21.831  22.620  1.00 32.42      B
ATOM   4314  CB   HIS B 191      23.568  22.172  21.214  1.00 33.72      B
ATOM   4315  CG   HIS B 191      23.168  23.535  20.772  1.00 34.73      B
ATOM   4316  CD2  HIS B 191      22.084  23.968  20.094  1.00 35.24      B
ATOM   4317  ND1  HIS B 191      23.936  24.649  21.031  1.00 35.16      B
ATOM   4318  CE1  HIS B 191      23.339  25.714  20.527  1.00 36.06      B
ATOM   4319  NE2  HIS B 191      22.212  26.328  19.955  1.00 35.42      B
ATOM   4320  C    HIS B 191      21.803  21.029  22.537  1.00 31.03      B
ATOM   4321  O    HIS B 191      21.851  19.831  22.375  1.00 31.38      B
ATOM   4322  N    SER B 192      20.649  21.695  22.605  1.00 29.69      B
ATOM   4323  CA   SER B 192      19.354  20.993  22.547  1.00 28.86      B
ATOM   4324  CB   SER B 192      18.819  20.691  23.955  1.00 28.56      B
ATOM   4325  OG   SER B 192      19.649  19.762  24.617  1.00 32.04      B
ATOM   4326  C    SER B 192      18.239  21.687  21.801  1.00 28.26      B
ATOM   4327  O    SER B 192      17.764  22.768  22.223  1.00 29.68      B
ATOM   4328  N    VAL B 193      17.765  21.042  20.731  1.00 23.60      B
ATOM   4329  CA   VAL B 193      16.676  21.602  19.942  1.00 22.38      B
ATOM   4330  CB   VAL B 193      17.198  22.242  18.651  1.00 20.07      B
ATOM   4331  CG1  VAL B 193      18.139  23.408  18.996  1.00 22.51      B
ATOM   4332  CG2  VAL B 193      17.914  21.209  17.824  1.00 21.46      B
ATOM   4333  C    VAL B 193      15.618  20.598  19.542  1.00 21.51      B
ATOM   4334  O    VAL B 193      15.877  19.389  19.444  1.00 20.75      B
ATOM   4335  N    ILE B 194      14.431  21.113  19.297  1.00 19.19      B
ATOM   4336  CA   ILE B 194      13.300  20.279  18.885  1.00 18.69      B
ATOM   4337  CB   ILE B 194      12.047  20.662  19.661  1.00 20.65      B
ATOM   4338  CG2  ILE B 194      10.879  19.737  19.263  1.00 20.91      B
ATOM   4339  CG1  ILE B 194      12.351  20.584  21.156  1.00 22.06      B
ATOM   4340  CD1  ILE B 194      11.268  21.174  21.991  1.00 25.62      B
ATOM   4341  C    ILE B 194      13.025  20.452  17.392  1.00 17.66      B
ATOM   4342  O    ILE B 194      12.699  21.535  16.925  1.00 17.42      B
ATOM   4343  N    VAL B 195      13.147  19.361  16.641  1.00 17.07      B
ATOM   4344  CA   VAL B 195      12.878  19.360  15.212  1.00 15.23      B
ATOM   4345  CB   VAL B 195      13.834  18.401  14.473  1.00 17.30      B
ATOM   4346  CG1  VAL B 195      13.491  18.338  12.979  1.00 16.64      B
ATOM   4347  CG2  VAL B 195      15.268  18.857  14.695  1.00 16.68      B
ATOM   4348  C    VAL B 195      11.412  18.916  15.005  1.00 16.31      B
ATOM   4349  O    VAL B 195      10.978  17.903  15.567  1.00 16.90      B
ATOM   4350  N    PRO B 196      10.632  19.670  14.207  1.00 17.47      B
ATOM   4351  CD   PRO B 196      11.074  20.815  13.395  1.00 18.83      B
ATOM   4352  CA   PRO B 196       9.215  19.364  13.933  1.00 19.05      B
ATOM   4353  CB   PRO B 196       8.772  20.478  12.980  1.00 20.57      B
ATOM   4354  CG   PRO B 196       9.793  21.504  13.114  1.00 22.10      B
ATOM   4355  C    PRO B 196       9.046  18.009  13.265  1.00 19.72      B
ATOM   4356  O    PRO B 196       9.944  17.513  12.607  1.00 18.66      B
ATOM   4357  N    ARG B 197       7.862  17.440  13.430  1.00 20.21      B
ATOM   4358  CA   ARG B 197       7.519  16.149  12.846  1.00 21.19      B
ATOM   4359  CB   ARG B 197       6.012  15.904  13.000  1.00 25.71      B
ATOM   4360  CG   ARG B 197       5.519  14.646  12.322  1.00 30.00      B
ATOM   4361  CD   ARG B 197       3.984  14.652  12.252  1.00 32.19      B
ATOM   4362  NE   ARG B 197       3.458  15.525  11.200  1.00 35.51      B
ATOM   4363  CZ   ARG B 197       3.290  15.155   9.929  1.00 36.04      B
ATOM   4364  NH1  ARG B 197       3.606  13.925   9.536  1.00 36.85      B
ATOM   4365  NH2  ARG B 197       2.793  16.012   9.051  1.00 37.72      B
```

Figure 1 (continued 44)

```
ATOM   4366  C   ARG B 197       7.873  16.032  11.374  1.00 20.20           B
ATOM   4367  O   ARG B 197       8.529  15.075  10.978  1.00 18.75           B
ATOM   4368  N   LYS B 198       7.426  16.982  10.553  1.00 19.22           B
ATOM   4369  CA  LYS B 198       7.713  16.900   9.122  1.00 20.05           B
ATOM   4370  CB  LYS B 198       6.956  17.965   8.323  1.00 22.68           B
ATOM   4371  CG  LYS B 198       5.458  17.685   8.160  1.00 27.88           B
ATOM   4372  CD  LYS B 198       4.815  18.821   7.335  1.00 32.73           B
ATOM   4373  CE  LYS B 198       3.313  18.648   7.098  1.00 36.66           B
ATOM   4374  NZ  LYS B 198       2.468  18.767   8.340  1.00 38.58           B
ATOM   4375  C   LYS B 198       9.190  17.058   8.872  1.00 17.68           B
ATOM   4376  O   LYS B 198       9.709  16.583   7.873  1.00 19.10           B
ATOM   4377  N   GLY B 199       9.866  17.731   9.790  1.00 15.43           B
ATOM   4378  CA  GLY B 199      11.292  17.946   9.628  1.00 16.07           B
ATOM   4379  C   GLY B 199      12.045  16.641   9.766  1.00 15.66           B
ATOM   4380  O   GLY B 199      13.015  16.380   9.059  1.00 15.20           B
ATOM   4381  N   VAL B 200      11.624  15.841  10.737  1.00 14.98           B
ATOM   4382  CA  VAL B 200      12.245  14.548  10.958  1.00 15.69           B
ATOM   4383  CB  VAL B 200      11.617  13.864  12.175  1.00 16.41           B
ATOM   4384  CG1 VAL B 200      12.217  12.449  12.354  1.00 18.05           B
ATOM   4385  CG2 VAL B 200      11.899  14.718  13.380  1.00 17.11           B
ATOM   4386  C   VAL B 200      12.056  13.678   9.722  1.00 15.55           B
ATOM   4387  O   VAL B 200      12.977  12.967   9.284  1.00 17.07           B
ATOM   4388  N   ILE B 201      10.858  13.703   9.165  1.00 18.07           B
ATOM   4389  CA  ILE B 201      10.567  12.942   7.950  1.00 18.45           B
ATOM   4390  CB  ILE B 201       9.084  13.098   7.563  1.00 19.51           B
ATOM   4391  CG2 ILE B 201       8.814  12.494   6.175  1.00 21.46           B
ATOM   4392  CG1 ILE B 201       8.238  12.391   8.602  1.00 20.58           B
ATOM   4393  CD1 ILE B 201       6.738  12.554   8.392  1.00 24.22           B
ATOM   4394  C   ILE B 201      11.447  13.367   6.789  1.00 18.72           B
ATOM   4395  O   ILE B 201      11.960  12.519   6.065  1.00 20.22           B
ATOM   4396  N   GLU B 202      11.643  14.673   6.607  1.00 19.15           B
ATOM   4397  CA  GLU B 202      12.483  15.152   5.514  1.00 20.05           B
ATOM   4398  CB  GLU B 202      12.426  16.681   5.362  1.00 21.56           B
ATOM   4399  CG  GLU B 202      11.174  17.168   4.689  1.00 24.74           B
ATOM   4400  CD  GLU B 202      10.866  16.349   3.452  1.00 27.41           B
ATOM   4401  OE1 GLU B 202       9.725  15.850   3.346  1.00 27.85           B
ATOM   4402  OE2 GLU B 202      11.770  16.185   2.602  1.00 28.02           B
ATOM   4403  C   GLU B 202      13.923  14.751   5.734  1.00 20.02           B
ATOM   4404  O   GLU B 202      14.602  14.397   4.773  1.00 21.05           B
ATOM   4405  N   LEU B 203      14.405  14.838   6.979  1.00 18.48           B
ATOM   4406  CA  LEU B 203      15.780  14.445   7.272  1.00 19.51           B
ATOM   4407  CB  LEU B 203      16.102  14.570   8.764  1.00 20.96           B
ATOM   4408  CG  LEU B 203      16.378  15.983   9.271  1.00 22.79           B
ATOM   4409  CD1 LEU B 203      16.571  15.960  10.797  1.00 23.58           B
ATOM   4410  CD2 LEU B 203      17.644  16.526   8.556  1.00 24.88           B
ATOM   4411  C   LEU B 203      15.987  13.009   6.848  1.00 20.44           B
ATOM   4412  O   LEU B 203      17.008  12.674   6.231  1.00 18.72           B
ATOM   4413  N   MET B 204      15.027  12.142   7.171  1.00 18.16           B
ATOM   4414  CA  MET B 204      15.153  10.734   6.784  1.00 21.15           B
ATOM   4415  CB  MET B 204      14.008   9.914   7.399  1.00 23.53           B
ATOM   4416  CG  MET B 204      13.959   8.461   6.938  1.00 29.56           B
ATOM   4417  SD  MET B 204      15.384   7.475   7.480  1.00 38.65           B
ATOM   4418  CE  MET B 204      15.782   8.308   8.992  1.00 30.14           B
ATOM   4419  C   MET B 204      15.147  10.530   5.265  1.00 22.14           B
ATOM   4420  O   MET B 204      15.920   9.728   4.732  1.00 22.11           B
ATOM   4421  N   ARG B 205      14.278  11.264   4.579  1.00 22.90           B
ATOM   4422  CA  ARG B 205      14.147  11.174   3.132  1.00 25.90           B
ATOM   4423  CB  ARG B 205      13.008  12.052   2.631  1.00 28.24           B
ATOM   4424  CG  ARG B 205      11.659  11.451   2.747  1.00 31.40           B
ATOM   4425  CD  ARG B 205      10.612  12.462   2.312  1.00 33.52           B
ATOM   4426  NE  ARG B 205       9.282  11.913   2.527  1.00 34.98           B
ATOM   4427  CZ  ARG B 205       8.155  12.614   2.484  1.00 36.39           B
ATOM   4428  NH1 ARG B 205       8.186  13.912   2.228  1.00 36.54           B
ATOM   4429  NH2 ARG B 205       6.997  12.008   2.717  1.00 36.70           B
ATOM   4430  C   ARG B 205      15.360  11.583   2.355  1.00 26.12           B
ATOM   4431  O   ARG B 205      15.548  11.131   1.226  1.00 25.57           B
ATOM   4432  N   MET B 206      16.182  12.453   2.923  1.00 25.37           B
ATOM   4433  CA  MET B 206      17.332  12.907   2.167  1.00 26.52           B
ATOM   4434  CB  MET B 206      17.690  14.334   2.563  1.00 27.58           B
ATOM   4435  CG  MET B 206      18.358  14.497   3.881  1.00 25.49           B
ATOM   4436  SD  MET B 206      18.341  16.237   4.294  1.00 27.01           B
ATOM   4437  CE  MET B 206      18.905  16.967   2.700  1.00 25.57           B
ATOM   4438  C   MET B 206      18.541  12.008   2.269  1.00 27.45           B
ATOM   4439  O   MET B 206      19.584  12.282   1.669  1.00 26.91           B
ATOM   4440  N   LEU B 207      18.407  10.934   3.036  1.00 28.07           B
ATOM   4441  CA  LEU B 207      19.512  10.010   3.172  1.00 30.58           B
ATOM   4442  CB  LEU B 207      19.407   9.290   4.512  1.00 29.11           B
ATOM   4443  CG  LEU B 207      19.312  10.219   5.724  1.00 26.96           B
ATOM   4444  CD1 LEU B 207      19.271   9.343   6.995  1.00 27.09           B
ATOM   4445  CD2 LEU B 207      20.482  11.190   5.763  1.00 24.96           B
ATOM   4446  C   LEU B 207      19.442   9.029   2.000  1.00 33.44           B
ATOM   4447  O   LEU B 207      18.468   8.306   1.835  1.00 34.23           B
ATOM   4448  N   ASP B 208      20.476   9.020   1.170  1.00 37.29           B
ATOM   4449  CA  ASP B 208      20.490   8.136   0.016  1.00 40.97           B
ATOM   4450  CB  ASP B 208      21.349   8.726  -1.099  1.00 42.41           B
ATOM   4451  CG  ASP B 208      22.832   8.627  -0.799  1.00 43.64           B
ATOM   4452  OD1 ASP B 208      23.355   9.451  -0.024  1.00 45.03           B
ATOM   4453  OD2 ASP B 208      23.483   7.705  -1.330  1.00 46.54           B
ATOM   4454  C   ASP B 208      21.079   6.806   0.437  1.00 42.45           B
ATOM   4455  O   ASP B 208      20.948   5.805  -0.266  1.00 44.07           B
ATOM   4456  N   GLY B 209      21.728   6.795   1.593  1.00 43.63           B
ATOM   4457  CA  GLY B 209      22.347   5.573   2.055  1.00 45.09           B
ATOM   4458  C   GLY B 209      23.590   5.341   1.220  1.00 45.45           B
ATOM   4459  O   GLY B 209      23.921   4.207   0.865  1.00 46.37           B
ATOM   4460  N   GLY B 210      24.273   6.434   0.892  1.00 45.49           B
ATOM   4461  CA  GLY B 210      25.489   6.350   0.111  1.00 44.86           B
ATOM   4462  C   GLY B 210      26.648   6.835   0.952  1.00 44.61           B
ATOM   4463  O   GLY B 210      26.506   7.031   2.158  1.00 44.29           B
ATOM   4464  N   ASP B 211      27.793   7.036   0.311  1.00 44.84           B
ATOM   4465  CA  ASP B 211      28.998   7.499   0.985  1.00 44.68           B
```

Figure 1 (continued 45)

| | | | | | | | | | | |
|---|---|---|---|---|---|---|---|---|---|---|
| ATOM | 4466 | CB | ASP | B | 211 | 30.220 | 7.108 | 0.154 | 1.00 46.96 | B |
| ATOM | 4467 | CG | ASP | B | 211 | 30.015 | 7.377 | -1.327 | 1.00 49.59 | B |
| ATOM | 4468 | OD1 | ASP | B | 211 | 29.929 | 8.565 | -1.718 | 1.00 51.33 | B |
| ATOM | 4469 | OD2 | ASP | B | 211 | 29.924 | 6.398 | -2.100 | 1.00 51.23 | B |
| ATOM | 4470 | C | ASP | B | 211 | 29.023 | 9.008 | 1.253 | 1.00 43.00 | B |
| ATOM | 4471 | O | ASP | B | 211 | 29.901 | 9.493 | 1.970 | 1.00 42.86 | B |
| ATOM | 4472 | N | ASN | B | 212 | 28.082 | 9.758 | 0.679 | 1.00 40.95 | B |
| ATOM | 4473 | CA | ASN | B | 212 | 28.054 | 11.201 | 0.917 | 1.00 38.13 | B |
| ATOM | 4474 | CB | ASN | B | 212 | 26.875 | 11.872 | 0.200 | 1.00 40.65 | B |
| ATOM | 4475 | CG | ASN | B | 212 | 26.909 | 11.679 | -1.298 | 1.00 42.99 | B |
| ATOM | 4476 | OD1 | ASN | B | 212 | 26.795 | 10.553 | -1.799 | 1.00 46.74 | B |
| ATOM | 4477 | ND2 | ASN | B | 212 | 27.064 | 12.774 | -2.026 | 1.00 43.95 | B |
| ATOM | 4478 | C | ASN | B | 212 | 27.891 | 11.442 | 2.417 | 1.00 35.10 | B |
| ATOM | 4479 | O | ASN | B | 212 | 27.031 | 10.845 | 3.062 | 1.00 34.26 | B |
| ATOM | 4480 | N | PRO | B | 213 | 28.722 | 12.313 | 2.992 | 1.00 32.02 | B |
| ATOM | 4481 | CD | PRO | B | 213 | 29.862 | 13.029 | 2.379 | 1.00 33.01 | B |
| ATOM | 4482 | CA | PRO | B | 213 | 28.622 | 12.604 | 4.422 | 1.00 29.13 | B |
| ATOM | 4483 | CB | PRO | B | 213 | 29.993 | 13.183 | 4.742 | 1.00 31.02 | B |
| ATOM | 4484 | CG | PRO | B | 213 | 30.301 | 13.958 | 3.492 | 1.00 31.64 | B |
| ATOM | 4485 | C | PRO | B | 213 | 27.493 | 13.627 | 4.641 | 1.00 26.76 | B |
| ATOM | 4486 | O | PRO | B | 213 | 27.099 | 14.330 | 3.711 | 1.00 25.59 | B |
| ATOM | 4487 | N | LEU | B | 214 | 26.964 | 13.676 | 5.856 | 1.00 23.19 | B |
| ATOM | 4488 | CA | LEU | B | 214 | 25.892 | 14.608 | 6.189 | 1.00 22.69 | B |
| ATOM | 4489 | CB | LEU | B | 214 | 24.805 | 13.875 | 7.006 | 1.00 25.15 | B |
| ATOM | 4490 | CG | LEU | B | 214 | 23.706 | 14.726 | 7.524 | 1.00 27.21 | B |
| ATOM | 4491 | CD1 | LEU | B | 214 | 22.868 | 15.298 | 6.520 | 1.00 28.20 | B |
| ATOM | 4492 | CD2 | LEU | B | 214 | 22.840 | 13.877 | 8.557 | 1.00 27.67 | B |
| ATOM | 4493 | C | LEU | B | 214 | 26.465 | 15.766 | 6.993 | 1.00 21.63 | B |
| ATOM | 4494 | O | LEU | B | 214 | 27.109 | 15.551 | 8.008 | 1.00 22.98 | B |
| ATOM | 4495 | N | ARG | B | 215 | 26.255 | 17.004 | 6.540 | 1.00 20.26 | B |
| ATOM | 4496 | CA | ARG | B | 215 | 26.763 | 18.148 | 7.275 | 1.00 20.31 | B |
| ATOM | 4497 | CB | ARG | B | 215 | 27.529 | 19.121 | 6.367 | 1.00 24.44 | B |
| ATOM | 4498 | CG | ARG | B | 215 | 28.163 | 20.269 | 7.151 | 1.00 28.96 | B |
| ATOM | 4499 | CD | ARG | B | 215 | 29.021 | 21.199 | 6.288 | 1.00 34.52 | B |
| ATOM | 4500 | NE | ARG | B | 215 | 28.826 | 22.593 | 6.691 | 1.00 38.13 | B |
| ATOM | 4501 | CZ | ARG | B | 215 | 28.386 | 23.555 | 5.879 | 1.00 39.89 | B |
| ATOM | 4502 | NH1 | ARG | B | 215 | 28.100 | 23.297 | 4.605 | 1.00 41.19 | B |
| ATOM | 4503 | NH2 | ARG | B | 215 | 28.197 | 24.775 | 6.352 | 1.00 42.36 | B |
| ATOM | 4504 | C | ARG | B | 215 | 25.607 | 18.863 | 7.923 | 1.00 19.25 | B |
| ATOM | 4505 | O | ARG | B | 215 | 24.672 | 19.274 | 7.263 | 1.00 19.32 | B |
| ATOM | 4506 | N | VAL | B | 216 | 25.702 | 19.027 | 9.231 | 1.00 16.59 | B |
| ATOM | 4507 | CA | VAL | B | 216 | 24.645 | 19.655 | 10.002 | 1.00 16.36 | B |
| ATOM | 4508 | CB | VAL | B | 216 | 24.224 | 18.737 | 11.177 | 1.00 15.73 | B |
| ATOM | 4509 | CG1 | VAL | B | 216 | 23.045 | 19.383 | 11.949 | 1.00 16.54 | B |
| ATOM | 4510 | CG2 | VAL | B | 216 | 23.924 | 17.379 | 10.674 | 1.00 16.55 | B |
| ATOM | 4511 | C | VAL | B | 216 | 25.029 | 20.994 | 10.583 | 1.00 18.40 | B |
| ATOM | 4512 | O | VAL | B | 216 | 26.137 | 21.168 | 11.094 | 1.00 18.97 | B |
| ATOM | 4513 | N | GLN | B | 217 | 24.104 | 21.951 | 10.521 | 1.00 16.54 | B |
| ATOM | 4514 | CA | GLN | B | 217 | 24.331 | 23.265 | 11.096 | 1.00 18.52 | B |
| ATOM | 4515 | CB | GLN | B | 217 | 24.482 | 24.346 | 10.021 | 1.00 19.71 | B |
| ATOM | 4516 | CG | GLN | B | 217 | 25.754 | 24.294 | 9.206 | 1.00 21.74 | B |
| ATOM | 4517 | CD | GLN | B | 217 | 25.778 | 25.415 | 8.168 | 1.00 24.98 | B |
| ATOM | 4518 | OE1 | GLN | B | 217 | 26.529 | 26.403 | 8.299 | 1.00 28.72 | B |
| ATOM | 4519 | NE2 | GLN | B | 217 | 24.932 | 25.283 | 7.141 | 1.00 23.49 | B |
| ATOM | 4520 | C | GLN | B | 217 | 23.088 | 23.566 | 11.929 | 1.00 18.28 | B |
| ATOM | 4521 | O | GLN | B | 217 | 21.970 | 23.360 | 11.466 | 1.00 17.82 | B |
| ATOM | 4522 | N | ILE | B | 218 | 23.293 | 23.999 | 13.170 | 1.00 17.89 | B |
| ATOM | 4523 | CA | ILE | B | 218 | 22.184 | 24.327 | 14.049 | 1.00 18.52 | B |
| ATOM | 4524 | CB | ILE | B | 218 | 22.125 | 23.382 | 15.290 | 1.00 19.36 | B |
| ATOM | 4525 | CG2 | ILE | B | 218 | 20.877 | 23.687 | 16.133 | 1.00 21.63 | B |
| ATOM | 4526 | CG1 | ILE | B | 218 | 22.098 | 21.932 | 14.849 | 1.00 19.91 | B |
| ATOM | 4527 | CD1 | ILE | B | 218 | 22.008 | 20.959 | 16.021 | 1.00 19.55 | B |
| ATOM | 4528 | C | ILE | B | 218 | 22.333 | 25.745 | 14.567 | 1.00 19.93 | B |
| ATOM | 4529 | O | ILE | B | 218 | 23.418 | 26.145 | 15.038 | 1.00 18.55 | B |
| ATOM | 4530 | N | GLY | B | 219 | 21.231 | 26.488 | 14.485 | 1.00 18.45 | B |
| ATOM | 4531 | CA | GLY | B | 219 | 21.173 | 27.845 | 14.966 | 1.00 20.72 | B |
| ATOM | 4532 | C | GLY | B | 219 | 20.213 | 27.895 | 16.139 | 1.00 21.48 | B |
| ATOM | 4533 | O | GLY | B | 219 | 19.724 | 26.859 | 16.621 | 1.00 20.11 | B |
| ATOM | 4534 | N | SER | B | 220 | 19.917 | 29.104 | 16.597 | 1.00 23.01 | B |
| ATOM | 4535 | CA | SER | B | 220 | 19.014 | 29.266 | 17.724 | 1.00 23.61 | B |
| ATOM | 4536 | CB | SER | B | 220 | 19.009 | 30.718 | 18.198 | 1.00 26.05 | B |
| ATOM | 4537 | OG | SER | B | 220 | 18.517 | 31.556 | 17.166 | 1.00 29.78 | B |
| ATOM | 4538 | C | SER | B | 220 | 17.593 | 28.866 | 17.345 | 1.00 23.25 | B |
| ATOM | 4539 | O | SER | B | 220 | 16.825 | 28.449 | 18.203 | 1.00 21.92 | B |
| ATOM | 4540 | N | ASN | B | 221 | 17.240 | 28.989 | 16.068 | 1.00 21.87 | B |
| ATOM | 4541 | CA | ASN | B | 221 | 15.879 | 28.662 | 15.667 | 1.00 21.63 | B |
| ATOM | 4542 | CB | ASN | B | 221 | 15.065 | 29.948 | 15.549 | 1.00 25.88 | B |
| ATOM | 4543 | CG | ASN | B | 221 | 15.037 | 30.730 | 16.850 | 1.00 30.93 | B |
| ATOM | 4544 | OD1 | ASN | B | 221 | 15.890 | 31.585 | 17.095 | 1.00 35.31 | B |
| ATOM | 4545 | ND2 | ASN | B | 221 | 14.067 | 30.423 | 17.700 | 1.00 32.95 | B |
| ATOM | 4546 | C | ASN | B | 221 | 15.750 | 27.880 | 14.378 | 1.00 18.27 | B |
| ATOM | 4547 | O | ASN | B | 221 | 14.657 | 27.787 | 13.830 | 1.00 18.70 | B |
| ATOM | 4548 | N | ASN | B | 222 | 16.844 | 27.284 | 13.919 | 1.00 18.16 | B |
| ATOM | 4549 | CA | ASN | B | 222 | 16.822 | 26.555 | 12.653 | 1.00 16.52 | B |
| ATOM | 4550 | CB | ASN | B | 222 | 17.258 | 27.445 | 11.472 | 1.00 19.66 | B |
| ATOM | 4551 | CG | ASN | B | 222 | 16.359 | 28.636 | 11.258 | 1.00 21.30 | B |
| ATOM | 4552 | OD1 | ASN | B | 222 | 16.377 | 29.589 | 12.038 | 1.00 23.15 | B |
| ATOM | 4553 | ND2 | ASN | B | 222 | 15.570 | 28.607 | 10.172 | 1.00 22.47 | B |
| ATOM | 4554 | C | ASN | B | 222 | 17.820 | 25.447 | 12.674 | 1.00 15.05 | B |
| ATOM | 4555 | O | ASN | B | 222 | 18.762 | 25.461 | 13.464 | 1.00 15.87 | B |
| ATOM | 4556 | N | ILE | B | 223 | 17.571 | 24.457 | 11.836 | 1.00 14.78 | B |
| ATOM | 4557 | CA | ILE | B | 223 | 18.531 | 23.373 | 11.657 | 1.00 13.60 | B |
| ATOM | 4558 | CB | ILE | B | 223 | 18.077 | 22.036 | 12.294 | 1.00 13.56 | B |
| ATOM | 4559 | CG2 | ILE | B | 223 | 16.723 | 21.592 | 11.714 | 1.00 14.77 | B |
| ATOM | 4560 | CG1 | ILE | B | 223 | 19.172 | 20.962 | 12.069 | 1.00 15.05 | B |
| ATOM | 4561 | CD1 | ILE | B | 223 | 18.996 | 19.763 | 13.023 | 1.00 17.92 | B |
| ATOM | 4562 | C | ILE | B | 223 | 18.638 | 23.212 | 10.158 | 1.00 15.44 | B |
| ATOM | 4563 | O | ILE | B | 223 | 17.641 | 23.372 | 9.433 | 1.00 15.61 | B |
| ATOM | 4564 | N | ARG | B | 224 | 19.860 | 22.950 | 9.685 | 1.00 15.47 | B |
| ATOM | 4565 | CA | ARG | B | 224 | 20.103 | 22.744 | 8.267 | 1.00 14.89 | B |

Figure 1 (continued 46)

| ATOM | 4566 | CB | ARG | B | 224 | 20.845 | 23.962 | 7.665 | 1.00 | 15.96 | B |
| ATOM | 4567 | CG | ARG | B | 224 | 21.308 | 23.736 | 6.237 | 1.00 | 17.14 | B |
| ATOM | 4568 | CD | ARG | B | 224 | 21.764 | 25.058 | 5.624 | 1.00 | 19.60 | B |
| ATOM | 4569 | NE | ARG | B | 224 | 20.628 | 25.953 | 5.409 | 1.00 | 21.62 | B |
| ATOM | 4570 | CZ | ARG | B | 224 | 20.704 | 27.193 | 4.920 | 1.00 | 25.09 | B |
| ATOM | 4571 | NH1 | ARG | B | 224 | 21.882 | 27.726 | 4.589 | 1.00 | 26.00 | B |
| ATOM | 4572 | NH2 | ARG | B | 224 | 19.594 | 27.897 | 4.739 | 1.00 | 25.58 | B |
| ATOM | 4573 | C | ARG | B | 224 | 20.936 | 21.495 | 8.092 | 1.00 | 14.76 | B |
| ATOM | 4574 | O | ARG | B | 224 | 21.838 | 21.212 | 8.896 | 1.00 | 16.22 | B |
| ATOM | 4575 | N | ALA | B | 225 | 20.611 | 20.724 | 7.070 | 1.00 | 13.02 | B |
| ATOM | 4576 | CA | ALA | B | 225 | 21.362 | 19.518 | 6.742 | 1.00 | 15.06 | B |
| ATOM | 4577 | CB | ALA | B | 225 | 20.566 | 18.273 | 7.054 | 1.00 | 14.63 | B |
| ATOM | 4578 | C | ALA | B | 225 | 21.717 | 19.524 | 5.269 | 1.00 | 16.06 | B |
| ATOM | 4579 | O | ALA | B | 225 | 20.865 | 19.761 | 4.399 | 1.00 | 15.83 | B |
| ATOM | 4580 | N | HIS | B | 226 | 22.982 | 19.229 | 4.992 | 1.00 | 16.22 | B |
| ATOM | 4581 | CA | HIS | B | 226 | 23.470 | 19.183 | 3.609 | 1.00 | 16.96 | B |
| ATOM | 4582 | CB | HIS | B | 226 | 24.703 | 20.072 | 3.438 | 1.00 | 20.34 | B |
| ATOM | 4583 | CG | HIS | B | 226 | 24.570 | 21.455 | 3.984 | 1.00 | 22.82 | B |
| ATOM | 4584 | CD2 | HIS | B | 226 | 24.412 | 21.911 | 5.251 | 1.00 | 25.71 | B |
| ATOM | 4585 | ND1 | HIS | B | 226 | 24.731 | 22.573 | 3.193 | 1.00 | 26.34 | B |
| ATOM | 4586 | CE1 | HIS | B | 226 | 24.685 | 23.657 | 3.947 | 1.00 | 25.51 | B |
| ATOM | 4587 | NE2 | HIS | B | 226 | 24.494 | 23.283 | 5.199 | 1.00 | 26.67 | B |
| ATOM | 4588 | C | HIS | B | 226 | 23.928 | 17.756 | 3.288 | 1.00 | 17.69 | B |
| ATOM | 4589 | O | HIS | B | 226 | 24.739 | 17.195 | 4.031 | 1.00 | 18.01 | B |
| ATOM | 4590 | N | VAL | B | 227 | 23.420 | 17.177 | 2.203 | 1.00 | 16.43 | B |
| ATOM | 4591 | CA | VAL | B | 227 | 23.829 | 15.846 | 1.744 | 1.00 | 18.02 | B |
| ATOM | 4592 | CB | VAL | B | 227 | 22.774 | 14.737 | 2.032 | 1.00 | 21.51 | B |
| ATOM | 4593 | CG1 | VAL | B | 227 | 23.362 | 13.373 | 1.650 | 1.00 | 22.64 | B |
| ATOM | 4594 | CG2 | VAL | B | 227 | 22.335 | 14.777 | 3.508 | 1.00 | 24.44 | B |
| ATOM | 4595 | C | VAL | B | 227 | 23.944 | 15.953 | 0.236 | 1.00 | 18.76 | B |
| ATOM | 4596 | O | VAL | B | 227 | 22.966 | 16.286 | -0.433 | 1.00 | 17.98 | B |
| ATOM | 4597 | N | GLY | B | 228 | 25.117 | 15.673 | -0.323 | 1.00 | 18.52 | B |
| ATOM | 4598 | CA | GLY | B | 228 | 25.233 | 15.764 | -1.768 | 1.00 | 18.19 | B |
| ATOM | 4599 | C | GLY | B | 228 | 24.830 | 17.146 | -2.244 | 1.00 | 17.69 | B |
| ATOM | 4600 | O | GLY | B | 228 | 25.267 | 18.161 | -1.704 | 1.00 | 17.83 | B |
| ATOM | 4601 | N | ASP | B | 229 | 23.945 | 17.180 | -3.231 | 1.00 | 17.92 | B |
| ATOM | 4602 | CA | ASP | B | 229 | 23.548 | 18.464 | -3.754 | 1.00 | 17.89 | B |
| ATOM | 4603 | CB | ASP | B | 229 | 23.598 | 18.416 | -5.278 | 1.00 | 20.23 | B |
| ATOM | 4604 | CG | ASP | B | 229 | 25.018 | 18.203 | -5.796 | 1.00 | 24.39 | B |
| ATOM | 4605 | OD1 | ASP | B | 229 | 25.930 | 18.937 | -5.365 | 1.00 | 27.15 | B |
| ATOM | 4606 | OD2 | ASP | B | 229 | 25.218 | 17.308 | -6.638 | 1.00 | 28.68 | B |
| ATOM | 4607 | C | ASP | B | 229 | 22.202 | 18.935 | -3.259 | 1.00 | 17.01 | B |
| ATOM | 4608 | O | ASP | B | 229 | 21.532 | 19.734 | -3.937 | 1.00 | 16.40 | B |
| ATOM | 4609 | N | PHE | B | 230 | 21.841 | 18.485 | -2.052 | 1.00 | 15.16 | B |
| ATOM | 4610 | CA | PHE | B | 230 | 20.563 | 18.856 | -1.404 | 1.00 | 16.26 | B |
| ATOM | 4611 | CB | PHE | B | 230 | 19.715 | 17.622 | -1.099 | 1.00 | 15.55 | B |
| ATOM | 4612 | CG | PHE | B | 230 | 19.207 | 16.943 | -2.294 | 1.00 | 21.50 | B |
| ATOM | 4613 | CD1 | PHE | B | 230 | 18.078 | 17.408 | -2.938 | 1.00 | 21.49 | B |
| ATOM | 4614 | CD2 | PHE | B | 230 | 19.857 | 15.839 | -2.794 | 1.00 | 31.72 | B |
| ATOM | 4615 | CE1 | PHE | B | 230 | 17.605 | 16.756 | -4.093 | 1.00 | 22.44 | B |
| ATOM | 4616 | CE2 | PHE | B | 230 | 19.390 | 15.186 | -3.940 | 1.00 | 24.25 | B |
| ATOM | 4617 | CZ | PHE | B | 230 | 18.278 | 15.638 | -4.582 | 1.00 | 19.43 | B |
| ATOM | 4618 | C | PHE | B | 230 | 20.816 | 19.547 | -0.102 | 1.00 | 15.83 | B |
| ATOM | 4619 | O | PHE | B | 230 | 21.745 | 19.203 | 0.624 | 1.00 | 16.68 | B |
| ATOM | 4620 | N | ILE | B | 231 | 20.006 | 20.559 | 0.185 | 1.00 | 15.42 | B |
| ATOM | 4621 | CA | ILE | B | 231 | 20.125 | 21.288 | 1.419 | 1.00 | 15.06 | B |
| ATOM | 4622 | CB | ILE | B | 231 | 20.658 | 22.707 | 1.197 | 1.00 | 17.17 | B |
| ATOM | 4623 | CG2 | ILE | B | 231 | 20.842 | 23.403 | 2.547 | 1.00 | 17.21 | B |
| ATOM | 4624 | CG1 | ILE | B | 231 | 21.945 | 22.641 | 0.378 | 1.00 | 19.39 | B |
| ATOM | 4625 | CD1 | ILE | B | 231 | 23.020 | 21.819 | 0.992 | 1.00 | 27.13 | B |
| ATOM | 4626 | C | ILE | B | 231 | 18.737 | 21.413 | 2.019 | 1.00 | 16.11 | B |
| ATOM | 4627 | O | ILE | B | 231 | 17.839 | 22.016 | 1.414 | 1.00 | 16.41 | B |
| ATOM | 4628 | N | PHE | B | 232 | 18.564 | 20.830 | 3.196 | 1.00 | 13.24 | B |
| ATOM | 4629 | CA | PHE | B | 232 | 17.287 | 20.911 | 3.881 | 1.00 | 13.91 | B |
| ATOM | 4630 | CB | PHE | B | 232 | 16.906 | 19.529 | 4.423 | 1.00 | 13.73 | B |
| ATOM | 4631 | CG | PHE | B | 232 | 15.697 | 19.553 | 5.287 | 1.00 | 15.40 | B |
| ATOM | 4632 | CD1 | PHE | B | 232 | 14.469 | 19.868 | 4.725 | 1.00 | 15.78 | B |
| ATOM | 4633 | CD2 | PHE | B | 232 | 15.785 | 19.281 | 6.642 | 1.00 | 16.56 | B |
| ATOM | 4634 | CE1 | PHE | B | 232 | 13.307 | 19.911 | 5.522 | 1.00 | 18.04 | B |
| ATOM | 4635 | CE2 | PHE | B | 232 | 14.635 | 19.317 | 7.459 | 1.00 | 18.76 | B |
| ATOM | 4636 | CZ | PHE | B | 232 | 13.398 | 19.629 | 6.892 | 1.00 | 16.42 | B |
| ATOM | 4637 | C | PHE | B | 232 | 17.399 | 21.890 | 5.056 | 1.00 | 13.92 | B |
| ATOM | 4638 | O | PHE | B | 232 | 18.365 | 21.849 | 5.819 | 1.00 | 13.17 | B |
| ATOM | 4639 | N | THR | B | 233 | 16.421 | 22.790 | 5.219 | 1.00 | 12.41 | B |
| ATOM | 4640 | CA | THR | B | 233 | 16.459 | 23.718 | 6.340 | 1.00 | 12.88 | B |
| ATOM | 4641 | CB | THR | B | 233 | 16.768 | 25.163 | 5.894 | 1.00 | 14.92 | B |
| ATOM | 4642 | OG1 | THR | B | 233 | 17.997 | 25.186 | 5.150 | 1.00 | 16.97 | B |
| ATOM | 4643 | CG2 | THR | B | 233 | 16.957 | 26.045 | 7.122 | 1.00 | 15.17 | B |
| ATOM | 4644 | C | THR | B | 233 | 15.097 | 23.743 | 7.014 | 1.00 | 15.12 | B |
| ATOM | 4645 | O | THR | B | 233 | 14.086 | 23.800 | 6.338 | 1.00 | 15.11 | B |
| ATOM | 4646 | N | SER | B | 234 | 15.058 | 23.682 | 8.343 | 1.00 | 14.12 | B |
| ATOM | 4647 | CA | SER | B | 234 | 13.752 | 23.754 | 9.028 | 1.00 | 14.24 | B |
| ATOM | 4648 | CB | SER | B | 234 | 13.345 | 22.386 | 9.589 | 1.00 | 14.75 | B |
| ATOM | 4649 | OG | SER | B | 234 | 12.065 | 22.447 | 10.269 | 1.00 | 15.57 | B |
| ATOM | 4650 | C | SER | B | 234 | 13.799 | 24.697 | 10.218 | 1.00 | 15.61 | B |
| ATOM | 4651 | O | SER | B | 234 | 14.848 | 24.856 | 10.875 | 1.00 | 15.62 | B |
| ATOM | 4652 | N | LYS | B | 235 | 12.668 | 25.318 | 10.511 | 1.00 | 15.65 | B |
| ATOM | 4653 | CA | LYS | B | 235 | 12.614 | 26.103 | 11.724 | 1.00 | 16.12 | B |
| ATOM | 4654 | CB | LYS | B | 235 | 11.399 | 27.058 | 11.698 | 1.00 | 20.85 | B |
| ATOM | 4655 | CG | LYS | B | 235 | 11.492 | 28.066 | 10.551 | 1.00 | 22.12 | B |
| ATOM | 4656 | CD | LYS | B | 235 | 10.989 | 29.480 | 10.902 | 1.00 | 29.55 | B |
| ATOM | 4657 | CE | LYS | B | 235 | 9.573 | 29.464 | 11.445 | 1.00 | 31.45 | B |
| ATOM | 4658 | NZ | LYS | B | 235 | 8.906 | 30.815 | 11.360 | 1.00 | 30.18 | B |
| ATOM | 4659 | C | LYS | B | 235 | 12.482 | 25.057 | 12.855 | 1.00 | 14.05 | B |
| ATOM | 4660 | O | LYS | B | 235 | 11.991 | 23.940 | 12.643 | 1.00 | 16.41 | B |
| ATOM | 4661 | N | LEU | B | 236 | 12.945 | 25.430 | 14.044 | 1.00 | 15.37 | B |
| ATOM | 4662 | CA | LEU | B | 236 | 12.882 | 24.571 | 15.220 | 1.00 | 15.37 | B |
| ATOM | 4663 | CB | LEU | B | 236 | 14.087 | 24.837 | 16.110 | 1.00 | 15.88 | B |
| ATOM | 4664 | CG | LEU | B | 236 | 15.463 | 24.474 | 15.507 | 1.00 | 15.11 | B |
| ATOM | 4665 | CD1 | LEU | B | 236 | 16.608 | 24.944 | 16.431 | 1.00 | 16.66 | B |

Figure 1 (continued 47)

```
ATOM   4666  CD2 LEU B 236      15.474  22.974  15.228  1.00 16.38           B
ATOM   4667  C   LEU B 236      11.594  24.879  15.982  1.00 18.39           B
ATOM   4668  O   LEU B 236      10.986  25.947  15.802  1.00 19.38           B
ATOM   4669  N   VAL B 237      11.185  23.941  16.831  1.00 21.05           B
ATOM   4670  CA  VAL B 237       9.983  24.091  17.638  1.00 23.90           B
ATOM   4671  CB  VAL B 237       9.278  22.707  17.848  1.00 24.44           B
ATOM   4672  CG1 VAL B 237       8.085  22.831  18.837  1.00 25.05           B
ATOM   4673  CG2 VAL B 237       8.774  22.189  16.503  1.00 26.22           B
ATOM   4674  C   VAL B 237      10.380  24.655  19.000  1.00 26.41           B
ATOM   4675  O   VAL B 237      11.366  24.235  19.589  1.00 25.35           B
ATOM   4676  N   ASP B 238       9.639  25.636  19.496  1.00 32.01           B
ATOM   4677  CA  ASP B 238       9.975  26.158  20.816  1.00 37.53           B
ATOM   4678  CB  ASP B 238       9.528  27.603  20.977  1.00 40.37           B
ATOM   4679  CG  ASP B 238      10.234  28.530  20.022  1.00 42.20           B
ATOM   4680  OD1 ASP B 238      11.453  28.325  19.791  1.00 43.09           B
ATOM   4681  OD2 ASP B 238       9.571  29.466  19.514  1.00 45.01           B
ATOM   4682  C   ASP B 238       9.284  25.302  21.852  1.00 39.40           B
ATOM   4683  O   ASP B 238       8.449  24.457  21.519  1.00 41.81           B
ATOM   4684  N   GLY B 239       9.638  25.498  23.111  1.00 41.31           B
ATOM   4685  CA  GLY B 239       9.004  24.722  24.157  1.00 42.54           B
ATOM   4686  C   GLY B 239      10.019  24.022  25.019  1.00 43.17           B
ATOM   4687  O   GLY B 239      11.188  23.944  24.665  1.00 42.73           B
ATOM   4688  N   ARG B 240       9.572  23.506  26.156  1.00 44.77           B
ATOM   4689  CA  ARG B 240      10.473  22.812  27.062  1.00 45.41           B
ATOM   4690  CB  ARG B 240      10.215  23.250  28.497  1.00 47.67           B
ATOM   4691  CG  ARG B 240       8.807  22.985  28.997  1.00 50.38           B
ATOM   4692  CD  ARG B 240       8.662  23.521  30.408  1.00 52.39           B
ATOM   4693  NE  ARG B 240       8.988  24.942  30.464  1.00 53.18           B
ATOM   4694  CZ  ARG B 240       9.345  25.580  31.572  1.00 54.35           B
ATOM   4695  NH1 ARG B 240       9.422  24.925  32.727  1.00 53.83           B
ATOM   4696  NH2 ARG B 240       9.638  26.871  31.517  1.00 55.03           B
ATOM   4697  C   ARG B 240      10.277  21.306  26.942  1.00 44.25           B
ATOM   4698  O   ARG B 240       9.199  20.790  27.237  1.00 45.09           B
ATOM   4699  N   PHE B 241      11.331  20.615  26.520  1.00 42.31           B
ATOM   4700  CA  PHE B 241      11.290  19.167  26.326  1.00 40.40           B
ATOM   4701  CB  PHE B 241      12.024  18.818  25.019  1.00 37.04           B
ATOM   4702  CG  PHE B 241      11.584  17.518  24.380  1.00 33.05           B
ATOM   4703  CD1 PHE B 241      12.109  16.303  24.798  1.00 32.26           B
ATOM   4704  CD2 PHE B 241      10.666  17.529  23.338  1.00 30.96           B
ATOM   4705  CE1 PHE B 241      11.727  15.108  24.179  1.00 29.39           B
ATOM   4706  CE2 PHE B 241      10.276  16.347  22.714  1.00 29.62           B
ATOM   4707  CZ  PHE B 241      10.814  15.134  23.141  1.00 28.51           B
ATOM   4708  C   PHE B 241      11.892  18.398  27.511  1.00 39.78           B
ATOM   4709  O   PHE B 241      12.919  18.785  28.077  1.00 40.91           B
ATOM   4710  N   PRO B 242      11.254  17.279  27.890  1.00 38.82           B
ATOM   4711  CD  PRO B 242       9.987  16.826  27.286  1.00 37.70           B
ATOM   4712  CA  PRO B 242      11.660  16.404  28.997  1.00 37.16           B
ATOM   4713  CB  PRO B 242      10.688  15.230  28.874  1.00 37.98           B
ATOM   4714  CG  PRO B 242       9.448  15.869  28.336  1.00 37.43           B
ATOM   4715  C   PRO B 242      13.124  15.947  28.987  1.00 36.91           B
ATOM   4716  O   PRO B 242      13.728  15.748  27.925  1.00 35.36           B
ATOM   4717  N   ASP B 243      13.675  15.763  30.184  1.00 35.76           B
ATOM   4718  CA  ASP B 243      15.053  15.323  30.369  1.00 36.57           B
ATOM   4719  CB  ASP B 243      15.625  15.957  31.639  1.00 35.26           B
ATOM   4720  CG  ASP B 243      17.064  15.549  31.907  1.00 36.71           B
ATOM   4721  OD1 ASP B 243      17.556  14.587  31.281  1.00 36.01           B
ATOM   4722  OD2 ASP B 243      17.709  16.188  32.767  1.00 36.91           B
ATOM   4723  C   ASP B 243      15.114  13.796  30.495  1.00 36.45           B
ATOM   4724  O   ASP B 243      14.919  13.251  31.576  1.00 36.71           B
ATOM   4725  N   TYR B 244      15.419  13.103  29.407  1.00 36.69           B
ATOM   4726  CA  TYR B 244      15.477  11.638  29.446  1.00 36.02           B
ATOM   4727  CB  TYR B 244      16.148  11.089  28.186  1.00 34.53           B
ATOM   4728  CG  TYR B 244      17.657  10.998  28.255  1.00 34.00           B
ATOM   4729  CD1 TYR B 244      18.462  12.105  27.968  1.00 32.87           B
ATOM   4730  CE1 TYR B 244      19.858  12.000  27.984  1.00 34.13           B
ATOM   4731  CD2 TYR B 244      18.281   9.791  28.566  1.00 33.14           B
ATOM   4732  CE2 TYR B 244      19.665   9.672  28.581  1.00 34.72           B
ATOM   4733  CZ  TYR B 244      20.449  10.783  28.283  1.00 34.56           B
ATOM   4734  OH  TYR B 244      21.811  10.638  28.235  1.00 36.14           B
ATOM   4735  C   TYR B 244      16.199  11.060  30.673  1.00 37.56           B
ATOM   4736  O   TYR B 244      15.795  10.029  31.215  1.00 36.17           B
ATOM   4737  N   ARG B 245      17.269  11.728  31.092  1.00 38.21           B
ATOM   4738  CA  ARG B 245      18.074  11.296  32.231  1.00 40.14           B
ATOM   4739  CB  ARG B 245      19.166  12.333  32.518  1.00 40.81           B
ATOM   4740  CG  ARG B 245      20.029  12.665  31.319  1.00 43.08           B
ATOM   4741  CD  ARG B 245      21.075  13.731  31.631  1.00 43.61           B
ATOM   4742  NE  ARG B 245      21.787  14.137  30.420  1.00 45.10           B
ATOM   4743  CZ  ARG B 245      21.231  14.807  29.413  1.00 45.50           B
ATOM   4744  NH1 ARG B 245      19.952  15.157  29.464  1.00 44.89           B
ATOM   4745  NH2 ARG B 245      21.956  15.131  28.348  1.00 46.19           B
ATOM   4746  C   ARG B 245      17.233  11.102  33.486  1.00 40.09           B
ATOM   4747  O   ARG B 245      17.574  10.297  34.352  1.00 40.05           B
ATOM   4748  N   ARG B 246      16.133  11.840  33.560  1.00 39.85           B
ATOM   4749  CA  ARG B 246      15.239  11.808  34.707  1.00 40.96           B
ATOM   4750  CB  ARG B 246      14.755  13.227  34.984  1.00 43.17           B
ATOM   4751  CG  ARG B 246      15.880  14.252  35.113  1.00 46.06           B
ATOM   4752  CD  ARG B 246      16.443  14.295  36.529  1.00 47.96           B
ATOM   4753  NE  ARG B 246      15.374  14.318  37.524  1.00 49.96           B
ATOM   4754  CZ  ARG B 246      14.316  15.126  37.477  1.00 50.99           B
ATOM   4755  NH1 ARG B 246      14.169  15.992  36.481  1.00 51.52           B
ATOM   4756  NH2 ARG B 246      13.396  15.067  38.430  1.00 52.33           B
ATOM   4757  C   ARG B 246      14.022  10.889  34.566  1.00 40.13           B
ATOM   4758  O   ARG B 246      13.384  10.536  35.560  1.00 39.22           B
ATOM   4759  N   VAL B 247      13.695  10.532  33.327  1.00 38.72           B
ATOM   4760  CA  VAL B 247      12.553   9.675  33.018  1.00 36.88           B
ATOM   4761  CB  VAL B 247      12.061   9.942  31.585  1.00 37.39           B
ATOM   4762  CG1 VAL B 247      10.930   8.991  31.216  1.00 36.97           B
ATOM   4763  CG2 VAL B 247      11.624  11.391  31.462  1.00 37.68           B
ATOM   4764  C   VAL B 247      12.962   8.218  33.133  1.00 35.57           B
ATOM   4765  O   VAL B 247      12.125   7.334  33.308  1.00 36.36           B
```

Figure 1 (continued 48)

```
ATOM   4766  N   LEU B 248      14.260   7.974  33.019  1.00 34.36           B
ATOM   4767  CA  LEU B 248      14.797   6.627  33.124  1.00 34.03           B
ATOM   4768  CB  LEU B 248      16.296   6.621  32.855  1.00 33.66           B
ATOM   4769  CG  LEU B 248      16.785   7.109  31.499  1.00 33.85           B
ATOM   4770  CD1 LEU B 248      18.285   6.813  31.398  1.00 34.48           B
ATOM   4771  CD2 LEU B 248      16.017   6.403  30.386  1.00 33.89           B
ATOM   4772  C   LEU B 248      14.564   6.083  34.525  1.00 34.01           B
ATOM   4773  O   LEU B 248      14.860   6.756  35.519  1.00 32.99           B
ATOM   4774  N   PRO B 249      14.038   4.851  34.622  1.00 33.37           B
ATOM   4775  CD  PRO B 249      13.707   3.936  33.514  1.00 32.25           B
ATOM   4776  CA  PRO B 249      13.776   4.221  35.921  1.00 33.57           B
ATOM   4777  CB  PRO B 249      13.565   2.751  35.546  1.00 32.82           B
ATOM   4778  CG  PRO B 249      12.921   2.845  34.210  1.00 32.30           B
ATOM   4779  C   PRO B 249      14.965   4.423  36.875  1.00 33.81           B
ATOM   4780  O   PRO B 249      16.113   4.182  36.514  1.00 31.74           B
ATOM   4781  N   LYS B 250      14.672   4.869  38.091  1.00 36.30           B
ATOM   4782  CA  LYS B 250      15.695   5.128  39.102  1.00 39.83           B
ATOM   4783  CB  LYS B 250      15.024   5.653  40.370  1.00 41.65           B
ATOM   4784  CG  LYS B 250      13.622   6.224  40.144  1.00 44.53           B
ATOM   4785  CD  LYS B 250      12.980   6.637  41.466  1.00 46.40           B
ATOM   4786  CE  LYS B 250      11.562   7.139  41.267  1.00 47.75           B
ATOM   4787  NZ  LYS B 250      10.957   7.618  42.538  1.00 48.54           B
ATOM   4788  C   LYS B 250      16.562   3.912  39.454  1.00 40.80           B
ATOM   4789  O   LYS B 250      17.773   3.915  39.240  1.00 42.14           B
ATOM   4790  N   ASN B 251      15.944   2.881  40.016  1.00 40.30           B
ATOM   4791  CA  ASN B 251      16.687   1.686  40.388  1.00 41.84           B
ATOM   4792  CB  ASN B 251      16.907   1.661  41.899  1.00 43.14           B
ATOM   4793  CG  ASN B 251      17.875   2.734  42.365  1.00 44.47           B
ATOM   4794  OD1 ASN B 251      17.623   3.421  43.353  1.00 45.51           B
ATOM   4795  ND2 ASN B 251      18.996   2.873  41.662  1.00 45.61           B
ATOM   4796  C   ASN B 251      15.976   0.413  39.942  1.00 41.06           B
ATOM   4797  O   ASN B 251      15.388  -0.302  40.754  1.00 40.34           B
ATOM   4798  N   PRO B 252      16.020   0.121  38.634  1.00 40.93           B
ATOM   4799  CD  PRO B 252      16.646   0.951  37.592  1.00 40.87           B
ATOM   4800  CA  PRO B 252      15.384  -1.069  38.051  1.00 40.56           B
ATOM   4801  CB  PRO B 252      15.505  -0.839  36.539  1.00 40.95           B
ATOM   4802  CG  PRO B 252      15.797   0.628  36.393  1.00 41.84           B
ATOM   4803  C   PRO B 252      16.144  -2.323  38.481  1.00 40.59           B
ATOM   4804  O   PRO B 252      16.811  -2.953  37.666  1.00 41.49           B
ATOM   4805  N   ASP B 253      16.024  -2.681  39.754  1.00 39.23           B
ATOM   4806  CA  ASP B 253      16.725  -3.833  40.318  1.00 38.72           B
ATOM   4807  CB  ASP B 253      16.316  -4.011  41.799  1.00 40.83           B
ATOM   4808  CG  ASP B 253      14.803  -4.237  41.995  1.00 42.90           B
ATOM   4809  OD1 ASP B 253      13.992  -3.318  41.739  1.00 44.02           B
ATOM   4810  OD2 ASP B 253      14.412  -5.347  42.423  1.00 44.75           B
ATOM   4811  C   ASP B 253      16.616  -5.183  39.585  1.00 36.72           B
ATOM   4812  O   ASP B 253      17.601  -5.922  39.478  1.00 36.03           B
ATOM   4813  N   LYS B 254      15.432  -5.484  39.066  1.00 32.67           B
ATOM   4814  CA  LYS B 254      15.164  -6.751  38.403  1.00 30.08           B
ATOM   4815  CB  LYS B 254      13.688  -7.106  38.593  1.00 28.89           B
ATOM   4816  CG  LYS B 254      13.194  -7.092  40.049  1.00 29.78           B
ATOM   4817  CD  LYS B 254      11.661  -7.160  40.098  1.00 28.23           B
ATOM   4818  CE  LYS B 254      11.120  -7.160  41.515  1.00 33.00           B
ATOM   4819  NZ  LYS B 254      11.584  -5.968  42.297  1.00 33.49           B
ATOM   4820  C   LYS B 254      15.489  -6.736  36.912  1.00 29.93           B
ATOM   4821  O   LYS B 254      14.811  -6.060  36.135  1.00 30.36           B
ATOM   4822  N   HIS B 255      16.495  -7.501  36.519  1.00 27.24           B
ATOM   4823  CA  HIS B 255      16.897  -7.564  35.118  1.00 26.91           B
ATOM   4824  CB  HIS B 255      18.402  -7.339  34.966  1.00 30.35           B
ATOM   4825  CG  HIS B 255      18.876  -6.000  35.429  1.00 33.70           B
ATOM   4826  CD2 HIS B 255      20.129  -5.522  35.617  1.00 34.19           B
ATOM   4827  ND1 HIS B 255      18.021  -4.950  35.695  1.00 35.10           B
ATOM   4828  CE1 HIS B 255      18.730  -3.882  36.025  1.00 35.55           B
ATOM   4829  NE2 HIS B 255      20.011  -4.204  35.986  1.00 34.99           B
ATOM   4830  C   HIS B 255      16.587  -8.885  34.453  1.00 24.52           B
ATOM   4831  O   HIS B 255      16.979  -9.935  34.936  1.00 23.10           B
ATOM   4832  N   LEU B 256      15.923  -8.824  33.307  1.00 22.74           B
ATOM   4833  CA  LEU B 256      15.606 -10.014  32.551  1.00 21.40           B
ATOM   4834  CB  LEU B 256      14.080 -10.157  32.461  1.00 23.90           B
ATOM   4835  CG  LEU B 256      13.435 -11.154  31.508  1.00 24.90           B
ATOM   4836  CD1 LEU B 256      12.064 -11.555  32.033  1.00 26.89           B
ATOM   4837  CD2 LEU B 256      13.322 -10.514  30.136  1.00 23.55           B
ATOM   4838  C   LEU B 256      16.210  -9.867  31.154  1.00 19.61           B
ATOM   4839  O   LEU B 256      16.191  -8.768  30.581  1.00 19.32           B
ATOM   4840  N   GLU B 257      16.774 -10.955  30.641  1.00 18.29           B
ATOM   4841  CA  GLU B 257      17.329 -10.973  29.287  1.00 18.37           B
ATOM   4842  CB  GLU B 257      18.848 -11.229  29.318  1.00 18.54           B
ATOM   4843  CG  GLU B 257      19.681 -10.093  29.921  1.00 21.51           B
ATOM   4844  CD  GLU B 257      19.758 -10.132  31.460  1.00 27.65           B
ATOM   4845  OE1 GLU B 257      19.940 -11.236  32.023  1.00 31.19           B
ATOM   4846  OE2 GLU B 257      19.664  -9.056  32.108  1.00 33.27           B
ATOM   4847  C   GLU B 257      16.616 -12.085  28.510  1.00 17.69           B
ATOM   4848  O   GLU B 257      16.374 -13.182  29.042  1.00 18.75           B
ATOM   4849  N   ALA B 258      16.262 -11.808  27.256  1.00 17.24           B
ATOM   4850  CA  ALA B 258      15.558 -12.786  26.423  1.00 18.43           B
ATOM   4851  CB  ALA B 258      14.079 -12.680  26.654  1.00 22.18           B
ATOM   4852  C   ALA B 258      15.840 -12.507  24.966  1.00 19.20           B
ATOM   4853  O   ALA B 258      16.180 -11.370  24.609  1.00 19.32           B
ATOM   4854  N   GLY B 259      15.713 -13.539  24.130  1.00 18.97           B
ATOM   4855  CA  GLY B 259      15.917 -13.346  22.700  1.00 18.87           B
ATOM   4856  C   GLY B 259      14.894 -12.358  22.161  1.00 19.04           B
ATOM   4857  O   GLY B 259      13.693 -12.468  22.453  1.00 18.24           B
ATOM   4858  N   CYS B 260      15.356 -11.389  21.375  1.00 17.25           B
ATOM   4859  CA  CYS B 260      14.439 -10.387  20.846  1.00 18.30           B
ATOM   4860  CB  CYS B 260      15.216  -9.341  20.048  1.00 17.26           B
ATOM   4861  SG  CYS B 260      14.169  -7.950  19.540  1.00 23.04           B
ATOM   4862  C   CYS B 260      13.335 -10.980  19.981  1.00 17.67           B
ATOM   4863  O   CYS B 260      12.164 -10.678  20.188  1.00 18.38           B
ATOM   4864  N   ASP B 261      13.694 -11.811  19.006  1.00 18.04           B
ATOM   4865  CA  ASP B 261      12.666 -12.364  18.140  1.00 18.32           B
```

```
ATOM   4866  CB   ASP B 261      13.290 -13.046  16.919  1.00 21.68           B
ATOM   4867  CG   ASP B 261      12.334 -13.065  15.738  1.00 24.40           B
ATOM   4868  OD1  ASP B 261      11.951 -14.160  15.306  1.00 27.81           B
ATOM   4869  OD2  ASP B 261      11.957 -11.968  15.252  1.00 29.16           B
ATOM   4870  C    ASP B 261      11.685 -13.311  18.828  1.00 16.90           B
ATOM   4871  O    ASP B 261      10.480 -13.263  18.540  1.00 17.30           B
ATOM   4872  N    LEU B 262      12.154 -14.159  19.737  1.00 14.56           B
ATOM   4873  CA   LEU B 262      11.191 -15.037  20.413  1.00 17.35           B
ATOM   4874  CB   LEU B 262      11.872 -16.053  21.329  1.00 19.61           B
ATOM   4875  CG   LEU B 262      12.472 -17.269  20.618  1.00 19.99           B
ATOM   4876  CD1  LEU B 262      13.259 -18.057  21.656  1.00 21.84           B
ATOM   4877  CD2  LEU B 262      11.395 -18.129  19.939  1.00 21.69           B
ATOM   4878  C    LEU B 262      10.248 -14.170  21.243  1.00 15.38           B
ATOM   4879  O    LEU B 262       9.065 -14.433  21.311  1.00 15.79           B
ATOM   4880  N    LEU B 263      10.780 -13.136  21.892  1.00 15.25           B
ATOM   4881  CA   LEU B 263       9.923 -12.288  22.713  1.00 16.20           B
ATOM   4882  CB   LEU B 263      10.795 -11.293  23.487  1.00 18.03           B
ATOM   4883  CG   LEU B 263      10.111 -10.421  24.532  1.00 21.36           B
ATOM   4884  CD1  LEU B 263       9.540 -11.366  25.608  1.00 21.04           B
ATOM   4885  CD2  LEU B 263      11.103  -9.396  25.155  1.00 22.83           B
ATOM   4886  C    LEU B 263       8.916 -11.546  21.826  1.00 16.77           B
ATOM   4887  O    LEU B 263       7.735 -11.457  22.133  1.00 15.34           B
ATOM   4888  N    LYS B 264       9.395 -11.034  20.711  1.00 16.41           B
ATOM   4889  CA   LYS B 264       8.525 -10.302  19.806  1.00 16.03           B
ATOM   4890  CB   LYS B 264       9.335  -9.738  18.636  1.00 18.07           B
ATOM   4891  CG   LYS B 264       8.475  -9.099  17.595  1.00 22.20           B
ATOM   4892  CD   LYS B 264       9.281  -8.250  16.610  1.00 26.37           B
ATOM   4893  CE   LYS B 264      10.346  -9.023  15.870  1.00 28.03           B
ATOM   4894  NZ   LYS B 264      11.318  -8.076  15.214  1.00 31.01           B
ATOM   4895  C    LYS B 264       7.412 -11.191  19.262  1.00 15.79           B
ATOM   4896  O    LYS B 264       6.236 -10.796  19.245  1.00 14.64           B
ATOM   4897  N    GLN B 265       7.784 -12.391  18.817  1.00 15.72           B
ATOM   4898  CA   GLN B 265       6.779 -13.286  18.244  1.00 16.84           B
ATOM   4899  CB   GLN B 265       7.435 -14.519  17.598  1.00 17.09           B
ATOM   4900  CG   GLN B 265       8.320 -14.204  16.357  1.00 18.42           B
ATOM   4901  CD   GLN B 265       7.782 -13.068  15.479  1.00 22.54           B
ATOM   4902  OE1  GLN B 265       6.570 -12.890  15.303  1.00 26.47           B
ATOM   4903  NE2  GLN B 265       8.704 -12.294  14.913  1.00 25.44           B
ATOM   4904  C    GLN B 265       5.753 -13.721  19.293  1.00 14.97           B
ATOM   4905  O    GLN B 265       4.572 -13.896  18.984  1.00 15.81           B
ATOM   4906  N    ALA B 266       6.185 -13.892  20.535  1.00 15.47           B
ATOM   4907  CA   ALA B 266       5.255 -14.301  21.598  1.00 14.14           B
ATOM   4908  CB   ALA B 266       6.022 -14.664  22.883  1.00 15.40           B
ATOM   4909  C    ALA B 266       4.283 -13.174  21.879  1.00 15.29           B
ATOM   4910  O    ALA B 266       3.083 -13.405  22.019  1.00 13.58           B
ATOM   4911  N    PHE B 267       4.807 -11.951  21.974  1.00 13.20           B
ATOM   4912  CA   PHE B 267       3.921 -10.801  22.218  1.00 13.52           B
ATOM   4913  CB   PHE B 267       4.744  -9.513  22.439  1.00 13.38           B
ATOM   4914  CG   PHE B 267       5.198  -9.317  23.868  1.00 13.24           B
ATOM   4915  CD1  PHE B 267       4.271  -9.194  24.912  1.00 14.43           B
ATOM   4916  CD2  PHE B 267       6.565  -9.244  24.169  1.00 14.23           B
ATOM   4917  CE1  PHE B 267       4.694  -8.992  26.240  1.00 16.33           B
ATOM   4918  CE2  PHE B 267       6.986  -9.048  25.487  1.00 16.29           B
ATOM   4919  CZ   PHE B 267       6.051  -8.920  26.516  1.00 15.41           B
ATOM   4920  C    PHE B 267       2.960 -10.609  21.038  1.00 14.30           B
ATOM   4921  O    PHE B 267       1.788 -10.261  21.248  1.00 14.42           B
ATOM   4922  N    ALA B 268       3.446 -10.818  19.813  1.00 14.41           B
ATOM   4923  CA   ALA B 268       2.630 -10.628  18.615  1.00 15.14           B
ATOM   4924  CB   ALA B 268       3.504 -10.794  17.379  1.00 14.71           B
ATOM   4925  C    ALA B 268       1.480 -11.633  18.606  1.00 14.93           B
ATOM   4926  O    ALA B 268       0.329 -11.286  18.247  1.00 14.13           B
ATOM   4927  N    ARG B 269       1.757 -12.880  19.008  1.00 13.12           B
ATOM   4928  CA   ARG B 269       0.671 -13.840  19.015  1.00 13.27           B
ATOM   4929  CB   ARG B 269       1.214 -15.269  19.154  1.00 14.61           B
ATOM   4930  CG   ARG B 269       1.831 -15.845  17.872  1.00 13.63           B
ATOM   4931  CD   ARG B 269       2.204 -17.358  18.026  1.00 13.98           B
ATOM   4932  NE   ARG B 269       3.118 -17.555  19.133  1.00 13.12           B
ATOM   4933  CZ   ARG B 269       4.448 -17.518  19.033  1.00 15.76           B
ATOM   4934  NH1  ARG B 269       5.034 -17.313  17.853  1.00 14.76           B
ATOM   4935  NH2  ARG B 269       5.201 -17.683  20.114  1.00 14.02           B
ATOM   4936  C    ARG B 269      -0.324 -13.530  20.153  1.00 14.05           B
ATOM   4937  O    ARG B 269      -1.546 -13.617  19.952  1.00 14.17           B
ATOM   4938  N    ALA B 270       0.191 -13.167  21.338  1.00 13.89           B
ATOM   4939  CA   ALA B 270      -0.687 -12.886  22.471  1.00 14.30           B
ATOM   4940  CB   ALA B 270       0.141 -12.603  23.735  1.00 13.36           B
ATOM   4941  C    ALA B 270      -1.568 -11.682  22.159  1.00 13.96           B
ATOM   4942  O    ALA B 270      -2.748 -11.645  22.542  1.00 15.55           B
ATOM   4943  N    ALA B 271      -1.002 -10.720  21.438  1.00 14.27           B
ATOM   4944  CA   ALA B 271      -1.726  -9.500  21.096  1.00 13.67           B
ATOM   4945  CB   ALA B 271      -0.836  -8.599  20.291  1.00 15.13           B
ATOM   4946  C    ALA B 271      -3.002  -9.795  20.333  1.00 15.03           B
ATOM   4947  O    ALA B 271      -3.972  -9.041  20.421  1.00 15.64           B
ATOM   4948  N    ILE B 272      -3.016 -10.898  19.595  1.00 14.65           B
ATOM   4949  CA   ILE B 272      -4.196 -11.249  18.821  1.00 15.22           B
ATOM   4950  CB   ILE B 272      -3.974 -12.585  18.079  1.00 13.73           B
ATOM   4951  CG2  ILE B 272      -5.242 -13.018  17.334  1.00 15.77           B
ATOM   4952  CG1  ILE B 272      -2.854 -12.439  17.060  1.00 15.68           B
ATOM   4953  CD1  ILE B 272      -2.364 -13.817  16.555  1.00 16.71           B
ATOM   4954  C    ILE B 272      -5.430 -11.343  19.725  1.00 16.21           B
ATOM   4955  O    ILE B 272      -6.524 -10.941  19.311  1.00 16.96           B
ATOM   4956  N    LEU B 273      -5.277 -11.870  20.949  1.00 16.13           B
ATOM   4957  CA   LEU B 273      -6.425 -11.991  21.858  1.00 15.61           B
ATOM   4958  CB   LEU B 273      -6.508 -13.415  22.449  1.00 16.11           B
ATOM   4959  CG   LEU B 273      -6.563 -14.492  21.330  1.00 16.18           B
ATOM   4960  CD1  LEU B 273      -6.548 -15.891  21.960  1.00 16.52           B
ATOM   4961  CD2  LEU B 273      -7.847 -14.316  20.469  1.00 18.42           B
ATOM   4962  C    LEU B 273      -6.473 -10.946  22.968  1.00 17.30           B
ATOM   4963  O    LEU B 273      -7.106 -11.158  23.997  1.00 17.88           B
ATOM   4964  N    SER B 274      -5.811  -9.809  22.742  1.00 17.24           B
ATOM   4965  CA   SER B 274      -5.863  -8.708  23.702  1.00 18.02           B
```

Figure 1 (continued 50)

| ATOM | 4966 | CB | SER | B | 274 | -4.556 | -7.906 | 23.686 | 1.00 | 17.37 | B |
| --- | --- | --- | --- | --- | --- | --- | --- | --- | --- | --- | --- |
| ATOM | 4967 | OG | SER | B | 274 | -4.390 | -7.180 | 22.474 | 1.00 | 17.38 | B |
| ATOM | 4968 | C | SER | B | 274 | -7.033 | -7.796 | 23.318 | 1.00 | 17.71 | B |
| ATOM | 4969 | O | SER | B | 274 | -7.542 | -7.858 | 22.189 | 1.00 | 17.27 | B |
| ATOM | 4970 | N | ASN | B | 275 | -7.464 | -6.965 | 24.260 | 1.00 | 17.56 | B |
| ATOM | 4971 | CA | ASN | B | 275 | -8.550 | -6.014 | 24.026 | 1.00 | 18.55 | B |
| ATOM | 4972 | CB | ASN | B | 275 | -8.705 | -5.145 | 25.269 | 1.00 | 17.80 | B |
| ATOM | 4973 | CG | ASN | B | 275 | -9.904 | -4.223 | 25.180 | 1.00 | 19.42 | B |
| ATOM | 4974 | OD1 | ASN | B | 275 | -9.934 | -3.339 | 24.331 | 1.00 | 19.77 | B |
| ATOM | 4975 | ND2 | ASN | B | 275 | -10.898 | -4.431 | 26.063 | 1.00 | 22.03 | B |
| ATOM | 4976 | C | ASN | B | 275 | -8.184 | -5.166 | 22.792 | 1.00 | 20.76 | B |
| ATOM | 4977 | O | ASN | B | 275 | -7.090 | -4.585 | 22.723 | 1.00 | 17.98 | B |
| ATOM | 4978 | N | GLU | B | 276 | -9.091 | -5.093 | 21.816 | 1.00 | 21.76 | B |
| ATOM | 4979 | CA | GLU | B | 276 | -8.779 | -4.365 | 20.591 | 1.00 | 23.72 | B |
| ATOM | 4980 | CB | GLU | B | 276 | -9.897 | -4.556 | 19.554 | 1.00 | 25.43 | B |
| ATOM | 4981 | CG | GLU | B | 276 | -9.852 | -5.932 | 18.891 | 1.00 | 29.37 | B |
| ATOM | 4982 | CD | GLU | B | 276 | -11.021 | -6.196 | 17.960 | 1.00 | 32.27 | B |
| ATOM | 4983 | OE1 | GLU | B | 276 | -11.600 | -5.217 | 17.442 | 1.00 | 33.37 | B |
| ATOM | 4984 | OE2 | GLU | B | 276 | -11.348 | -7.390 | 17.745 | 1.00 | 32.65 | B |
| ATOM | 4985 | C | GLU | B | 276 | -8.481 | -2.888 | 20.782 | 1.00 | 23.01 | B |
| ATOM | 4986 | O | GLU | B | 276 | -7.749 | -2.292 | 19.986 | 1.00 | 23.94 | B |
| ATOM | 4987 | N | LYS | B | 277 | -9.034 | -2.310 | 21.837 | 1.00 | 23.05 | B |
| ATOM | 4988 | CA | LYS | B | 277 | -8.810 | -0.910 | 22.113 | 1.00 | 23.82 | B |
| ATOM | 4989 | CB | LYS | B | 277 | -10.085 | -0.230 | 22.638 | 1.00 | 25.13 | B |
| ATOM | 4990 | CG | LYS | B | 277 | -9.852 | 1.262 | 22.949 | 1.00 | 28.98 | B |
| ATOM | 4991 | CD | LYS | B | 277 | -11.084 | 2.016 | 23.463 | 1.00 | 31.73 | B |
| ATOM | 4992 | CE | LYS | B | 277 | -10.744 | 3.512 | 23.598 | 1.00 | 33.68 | B |
| ATOM | 4993 | NZ | LYS | B | 277 | -11.577 | 4.222 | 24.623 | 1.00 | 35.35 | B |
| ATOM | 4994 | C | LYS | B | 277 | -7.681 | -0.655 | 23.104 | 1.00 | 23.58 | B |
| ATOM | 4995 | O | LYS | B | 277 | -6.790 | 0.162 | 22.825 | 1.00 | 23.95 | B |
| ATOM | 4996 | N | PHE | B | 278 | -7.702 | -1.352 | 24.244 | 1.00 | 21.16 | B |
| ATOM | 4997 | CA | PHE | B | 278 | -6.698 | -1.155 | 25.300 | 1.00 | 20.62 | B |
| ATOM | 4998 | CB | PHE | B | 278 | -7.318 | -1.432 | 26.663 | 1.00 | 21.99 | B |
| ATOM | 4999 | CG | PHE | B | 278 | -8.431 | -0.459 | 27.021 | 1.00 | 26.60 | B |
| ATOM | 5000 | CD1 | PHE | B | 278 | -8.142 | 0.882 | 27.268 | 1.00 | 29.14 | B |
| ATOM | 5001 | CD2 | PHE | B | 278 | -9.760 | -0.869 | 27.021 | 1.00 | 28.88 | B |
| ATOM | 5002 | CE1 | PHE | B | 278 | -9.177 | 1.816 | 27.508 | 1.00 | 30.11 | B |
| ATOM | 5003 | CE2 | PHE | B | 278 | -10.795 | 0.052 | 27.258 | 1.00 | 30.65 | B |
| ATOM | 5004 | CZ | PHE | B | 278 | -10.496 | 1.391 | 27.500 | 1.00 | 30.56 | B |
| ATOM | 5005 | C | PHE | B | 278 | -5.403 | -1.957 | 25.131 | 1.00 | 19.25 | B |
| ATOM | 5006 | O | PHE | B | 278 | -4.356 | -1.582 | 25.677 | 1.00 | 18.94 | B |
| ATOM | 5007 | N | ARG | B | 279 | -5.484 | -3.045 | 24.371 | 1.00 | 19.60 | B |
| ATOM | 5008 | CA | ARG | B | 279 | -4.307 | -3.865 | 24.050 | 1.00 | 18.45 | B |
| ATOM | 5009 | CB | ARG | B | 279 | -3.404 | -3.067 | 23.088 | 1.00 | 19.81 | B |
| ATOM | 5010 | CG | ARG | B | 279 | -4.078 | -2.674 | 21.767 | 1.00 | 19.94 | B |
| ATOM | 5011 | CD | ARG | B | 279 | -4.097 | -3.843 | 20.776 | 1.00 | 21.13 | B |
| ATOM | 5012 | NE | ARG | B | 279 | -2.777 | -3.988 | 20.175 | 1.00 | 23.76 | B |
| ATOM | 5013 | CZ | ARG | B | 279 | -2.423 | -4.973 | 19.365 | 1.00 | 22.43 | B |
| ATOM | 5014 | NH1 | ARG | B | 279 | -3.297 | -5.921 | 19.058 | 1.00 | 25.01 | B |
| ATOM | 5015 | NH2 | ARG | B | 279 | -1.202 | -4.987 | 18.838 | 1.00 | 23.93 | B |
| ATOM | 5016 | C | ARG | B | 279 | -3.460 | -4.360 | 25.210 | 1.00 | 18.23 | B |
| ATOM | 5017 | O | ARG | B | 279 | -2.261 | -4.590 | 25.046 | 1.00 | 16.99 | B |
| ATOM | 5018 | N | GLY | B | 280 | -4.062 | -4.589 | 26.365 | 1.00 | 16.92 | B |
| ATOM | 5019 | CA | GLY | B | 280 | -3.260 | -5.011 | 27.491 | 1.00 | 15.52 | B |
| ATOM | 5020 | C | GLY | B | 280 | -2.864 | -6.477 | 27.534 | 1.00 | 14.43 | B |
| ATOM | 5021 | O | GLY | B | 280 | -3.652 | -7.360 | 27.199 | 1.00 | 15.18 | B |
| ATOM | 5022 | N | VAL | B | 281 | -1.623 | -6.709 | 27.942 | 1.00 | 15.08 | B |
| ATOM | 5023 | CA | VAL | B | 281 | -1.104 | -8.062 | 28.125 | 1.00 | 14.23 | B |
| ATOM | 5024 | CB | VAL | B | 281 | -0.046 | -8.473 | 27.057 | 1.00 | 12.60 | B |
| ATOM | 5025 | CG1 | VAL | B | 281 | -0.707 | -8.654 | 25.727 | 1.00 | 17.31 | B |
| ATOM | 5026 | CG2 | VAL | B | 281 | 1.061 | -7.440 | 26.981 | 1.00 | 15.23 | B |
| ATOM | 5027 | C | VAL | B | 281 | -0.450 | -8.059 | 29.497 | 1.00 | 13.94 | B |
| ATOM | 5028 | O | VAL | B | 281 | -0.049 | -7.000 | 30.034 | 1.00 | 14.27 | B |
| ATOM | 5029 | N | ARG | B | 282 | -0.387 | -9.241 | 30.091 | 1.00 | 12.68 | B |
| ATOM | 5030 | CA | ARG | B | 282 | 0.202 | -9.381 | 31.405 | 1.00 | 14.01 | B |
| ATOM | 5031 | CB | ARG | B | 282 | -0.753 | -10.142 | 32.337 | 1.00 | 18.49 | B |
| ATOM | 5032 | CG | ARG | B | 282 | -1.999 | -9.373 | 32.712 | 1.00 | 25.67 | B |
| ATOM | 5033 | CD | ARG | B | 282 | -2.770 | -10.154 | 33.784 | 1.00 | 31.13 | B |
| ATOM | 5034 | NE | ARG | B | 282 | -3.601 | -9.274 | 34.606 | 1.00 | 36.93 | B |
| ATOM | 5035 | CZ | ARG | B | 282 | -3.765 | -9.449 | 35.908 | 1.00 | 38.95 | B |
| ATOM | 5036 | NH1 | ARG | B | 282 | -3.154 | -10.470 | 36.510 | 1.00 | 41.34 | B |
| ATOM | 5037 | NH2 | ARG | B | 282 | -4.511 | -8.605 | 36.615 | 1.00 | 42.07 | B |
| ATOM | 5038 | C | ARG | B | 282 | 1.489 | -10.168 | 31.273 | 1.00 | 13.94 | B |
| ATOM | 5039 | O | ARG | B | 282 | 1.568 | -11.118 | 30.483 | 1.00 | 13.78 | B |
| ATOM | 5040 | N | LEU | B | 283 | 2.503 | -9.736 | 32.016 | 1.00 | 11.77 | B |
| ATOM | 5041 | CA | LEU | B | 283 | 3.784 | -10.427 | 32.050 | 1.00 | 12.94 | B |
| ATOM | 5042 | CB | LEU | B | 283 | 4.931 | -9.460 | 31.806 | 1.00 | 13.78 | B |
| ATOM | 5043 | CG | LEU | B | 283 | 5.246 | -9.059 | 30.376 | 1.00 | 16.55 | B |
| ATOM | 5044 | CD1 | LEU | B | 283 | 4.078 | -8.291 | 29.772 | 1.00 | 18.52 | B |
| ATOM | 5045 | CD2 | LEU | B | 283 | 6.512 | -8.199 | 30.417 | 1.00 | 15.82 | B |
| ATOM | 5046 | C | LEU | B | 283 | 3.989 | -10.979 | 33.454 | 1.00 | 13.65 | B |
| ATOM | 5047 | O | LEU | B | 283 | 3.832 | -10.232 | 34.422 | 1.00 | 15.26 | B |
| ATOM | 5048 | N | TYR | B | 284 | 4.281 | -12.271 | 33.584 | 1.00 | 13.05 | B |
| ATOM | 5049 | CA | TYR | B | 284 | 4.580 | -12.809 | 34.913 | 1.00 | 13.63 | B |
| ATOM | 5050 | CB | TYR | B | 284 | 3.686 | -14.004 | 35.283 | 1.00 | 13.56 | B |
| ATOM | 5051 | CG | TYR | B | 284 | 3.808 | -14.302 | 36.781 | 1.00 | 18.42 | B |
| ATOM | 5052 | CD1 | TYR | B | 284 | 2.898 | -13.778 | 37.698 | 1.00 | 20.54 | B |
| ATOM | 5053 | CE1 | TYR | B | 284 | 3.069 | -13.971 | 39.101 | 1.00 | 22.11 | B |
| ATOM | 5054 | CD2 | TYR | B | 284 | 4.890 | -15.024 | 37.260 | 1.00 | 19.69 | B |
| ATOM | 5055 | CE2 | TYR | B | 284 | 5.088 | -15.221 | 38.628 | 1.00 | 20.37 | B |
| ATOM | 5056 | CZ | TYR | B | 284 | 4.175 | -14.694 | 39.544 | 1.00 | 22.54 | B |
| ATOM | 5057 | OH | TYR | B | 284 | 4.412 | -14.897 | 40.889 | 1.00 | 21.81 | B |
| ATOM | 5058 | C | TYR | B | 284 | 6.027 | -13.271 | 34.818 | 1.00 | 12.58 | B |
| ATOM | 5059 | O | TYR | B | 284 | 6.357 | -14.144 | 34.026 | 1.00 | 13.78 | B |
| ATOM | 5060 | N | VAL | B | 285 | 6.898 | -12.675 | 35.635 | 1.00 | 12.36 | B |
| ATOM | 5061 | CA | VAL | B | 285 | 8.306 | -12.990 | 35.601 | 1.00 | 13.80 | B |
| ATOM | 5062 | CB | VAL | B | 285 | 9.106 | -11.669 | 35.724 | 1.00 | 16.86 | B |
| ATOM | 5063 | CG1 | VAL | B | 285 | 10.576 | -11.922 | 35.640 | 1.00 | 20.79 | B |
| ATOM | 5064 | CG2 | VAL | B | 285 | 8.675 | -10.718 | 34.599 | 1.00 | 19.51 | B |
| ATOM | 5065 | C | VAL | B | 285 | 8.656 | -13.928 | 36.761 | 1.00 | 12.81 | B |

```
ATOM   5066  O    VAL B 285       8.313 -13.643  37.889  1.00 14.44           B
ATOM   5067  N    SER B 286       9.318 -15.036  36.464  1.00 13.79           B
ATOM   5068  CA   SER B 286       9.730 -15.996  37.493  1.00 14.29           B
ATOM   5069  CB   SER B 286       8.716 -17.148  37.609  1.00 14.83           B
ATOM   5070  OG   SER B 286       8.623 -17.928  36.439  1.00 17.73           B
ATOM   5071  C    SER B 286      11.145 -16.492  37.139  1.00 14.68           B
ATOM   5072  O    SER B 286      11.712 -16.116  36.103  1.00 14.34           B
ATOM   5073  N    GLU B 287      11.732 -17.338  37.971  1.00 15.06           B
ATOM   5074  CA   GLU B 287      13.112 -17.732  37.692  1.00 16.29           B
ATOM   5075  CB   GLU B 287      13.621 -18.691  38.764  1.00 16.48           B
ATOM   5076  CG   GLU B 287      15.094 -19.065  38.591  1.00 20.87           B
ATOM   5077  CD   GLU B 287      15.613 -19.806  39.813  1.00 24.94           B
ATOM   5078  OE1  GLU B 287      15.225 -20.975  40.008  1.00 28.92           B
ATOM   5079  OE2  GLU B 287      16.400 -19.205  40.580  1.00 32.02           B
ATOM   5080  C    GLU B 287      13.278 -18.314  36.296  1.00 15.72           B
ATOM   5081  O    GLU B 287      12.644 -19.303  35.921  1.00 15.04           B
ATOM   5082  N    ASN B 288      14.134 -17.655  35.518  1.00 14.89           B
ATOM   5083  CA   ASN B 288      14.386 -18.021  34.127  1.00 15.81           B
ATOM   5084  CB   ASN B 288      15.363 -19.200  34.049  1.00 17.29           B
ATOM   5085  CG   ASN B 288      16.736 -18.812  34.607  1.00 19.00           B
ATOM   5086  OD1  ASN B 288      17.095 -17.642  34.575  1.00 18.60           B
ATOM   5087  ND2  ASN B 288      17.496 -19.779  35.122  1.00 22.68           B
ATOM   5088  C    ASN B 288      13.146 -18.280  33.271  1.00 14.61           B
ATOM   5089  O    ASN B 288      13.196 -19.064  32.325  1.00 15.72           B
ATOM   5090  N    GLN B 289      12.047 -17.592  33.589  1.00 12.93           B
ATOM   5091  CA   GLN B 289      10.834 -17.771  32.806  1.00 13.30           B
ATOM   5092  CB   GLN B 289       9.979 -18.907  33.380  1.00 14.55           B
ATOM   5093  CG   GLN B 289       8.664 -19.147  32.605  1.00 18.51           B
ATOM   5094  CD   GLN B 289       7.737 -20.171  33.274  1.00 20.33           B
ATOM   5095  OE1  GLN B 289       6.714 -19.820  33.913  1.00 24.66           B
ATOM   5096  NE2  GLN B 289       8.084 -21.430  33.128  1.00 20.90           B
ATOM   5097  C    GLN B 289       9.950 -16.543  32.706  1.00 13.31           B
ATOM   5098  O    GLN B 289       9.796 -15.783  33.648  1.00 11.95           B
ATOM   5099  N    LEU B 290       9.382 -16.347  31.513  1.00 12.64           B
ATOM   5100  CA   LEU B 290       8.438 -15.253  31.315  1.00 13.02           B
ATOM   5101  CB   LEU B 290       8.990 -14.220  30.294  1.00 14.05           B
ATOM   5102  CG   LEU B 290       7.961 -13.160  29.861  1.00 15.71           B
ATOM   5103  CD1  LEU B 290       7.482 -12.331  31.070  1.00 17.91           B
ATOM   5104  CD2  LEU B 290       8.586 -12.240  28.816  1.00 17.17           B
ATOM   5105  C    LEU B 290       7.155 -15.864  30.777  1.00 12.56           B
ATOM   5106  O    LEU B 290       7.201 -16.657  29.836  1.00 14.23           B
ATOM   5107  N    LYS B 291       6.022 -15.521  31.391  1.00 12.00           B
ATOM   5108  CA   LYS B 291       4.723 -15.991  30.909  1.00 12.78           B
ATOM   5109  CB   LYS B 291       3.958 -16.744  32.014  1.00 14.55           B
ATOM   5110  CG   LYS B 291       2.521 -17.061  31.604  1.00 17.33           B
ATOM   5111  CD   LYS B 291       1.794 -17.803  32.734  1.00 23.96           B
ATOM   5112  CE   LYS B 291       0.313 -17.910  32.428  1.00 28.19           B
ATOM   5113  NZ   LYS B 291      -0.532 -18.367  33.595  1.00 33.90           B
ATOM   5114  C    LYS B 291       3.975 -14.725  30.480  1.00 13.62           B
ATOM   5115  O    LYS B 291       3.869 -13.757  31.243  1.00 15.74           B
ATOM   5116  N    ILE B 292       3.487 -14.708  29.241  1.00 11.68           B
ATOM   5117  CA   ILE B 292       2.736 -13.572  28.712  1.00 12.10           B
ATOM   5118  CB   ILE B 292       3.318 -13.132  27.329  1.00 12.34           B
ATOM   5119  CG2  ILE B 292       2.448 -12.013  26.690  1.00 14.58           B
ATOM   5120  CG1  ILE B 292       4.739 -12.646  27.525  1.00 15.22           B
ATOM   5121  CD1  ILE B 292       5.529 -12.532  26.240  1.00 17.04           B
ATOM   5122  C    ILE B 292       1.303 -14.048  28.511  1.00 12.60           B
ATOM   5123  O    ILE B 292       1.075 -15.065  27.844  1.00 13.06           B
ATOM   5124  N    THR B 293       0.340 -13.316  29.072  1.00 12.37           B
ATOM   5125  CA   THR B 293      -1.050 -13.703  28.891  1.00 13.44           B
ATOM   5126  CB   THR B 293      -1.699 -14.182  30.200  1.00 14.23           B
ATOM   5127  OG1  THR B 293      -1.641 -13.160  31.179  1.00 18.90           B
ATOM   5128  CG2  THR B 293      -0.947 -15.366  30.766  1.00 15.88           B
ATOM   5129  C    THR B 293      -1.832 -12.525  28.372  1.00 14.34           B
ATOM   5130  O    THR B 293      -1.471 -11.362  28.600  1.00 13.84           B
ATOM   5131  N    ALA B 294      -2.883 -12.837  27.634  1.00 12.99           B
ATOM   5132  CA   ALA B 294      -3.746 -11.800  27.101  1.00 14.01           B
ATOM   5133  CB   ALA B 294      -3.325 -11.469  25.644  1.00 15.00           B
ATOM   5134  C    ALA B 294      -5.164 -12.333  27.116  1.00 15.21           B
ATOM   5135  O    ALA B 294      -5.383 -13.509  26.864  1.00 15.46           B
ATOM   5136  N    ASN B 295      -6.132 -11.486  27.461  1.00 15.97           B
ATOM   5137  CA   ASN B 295      -7.515 -11.907  27.367  1.00 17.95           B
ATOM   5138  CB   ASN B 295      -8.052 -12.461  28.700  1.00 23.39           B
ATOM   5139  CG   ASN B 295      -8.003 -11.480  29.817  1.00 25.82           B
ATOM   5140  OD1  ASN B 295      -8.523 -10.373  29.718  1.00 31.67           B
ATOM   5141  ND2  ASN B 295      -7.393 -11.888  30.939  1.00 32.50           B
ATOM   5142  C    ASN B 295      -8.325 -10.718  26.865  1.00 16.88           B
ATOM   5143  O    ASN B 295      -7.873  -9.568  26.935  1.00 17.31           B
ATOM   5144  N    ASN B 296      -9.499 -10.996  26.302  1.00 16.35           B
ATOM   5145  CA   ASN B 296     -10.311  -9.920  25.755  1.00 17.61           B
ATOM   5146  CB   ASN B 296     -10.294  -9.966  24.205  1.00 16.78           B
ATOM   5147  CG   ASN B 296     -10.835 -11.274  23.639  1.00 17.58           B
ATOM   5148  OD1  ASN B 296     -11.629 -11.955  24.285  1.00 19.52           B
ATOM   5149  ND2  ASN B 296     -10.438 -11.601  22.407  1.00 18.80           B
ATOM   5150  C    ASN B 296     -11.734 -10.022  26.306  1.00 18.87           B
ATOM   5151  O    ASN B 296     -12.049 -10.878  27.141  1.00 18.85           B
ATOM   5152  N    PRO B 297     -12.603  -9.111  25.877  1.00 22.70           B
ATOM   5153  CD   PRO B 297     -12.351  -7.873  25.120  1.00 23.09           B
ATOM   5154  CA   PRO B 297     -13.975  -9.157  26.373  1.00 25.09           B
ATOM   5155  CB   PRO B 297     -14.586  -7.858  25.842  1.00 25.02           B
ATOM   5156  CG   PRO B 297     -13.432  -6.952  25.666  1.00 23.49           B
ATOM   5157  C    PRO B 297     -14.773 -10.376  25.925  1.00 26.91           B
ATOM   5158  O    PRO B 297     -15.828 -10.638  26.490  1.00 29.58           B
ATOM   5159  N    GLU B 298     -14.317 -11.085  24.893  1.00 28.28           B
ATOM   5160  CA   GLU B 298     -15.033 -12.275  24.425  1.00 29.32           B
ATOM   5161  CB   GLU B 298     -14.805 -12.487  22.919  1.00 33.72           B
ATOM   5162  CG   GLU B 298     -15.968 -12.033  22.025  1.00 38.43           B
ATOM   5163  CD   GLU B 298     -16.282 -10.547  22.144  1.00 42.52           B
ATOM   5164  OE1  GLU B 298     -15.362  -9.730  21.889  1.00 43.73           B
ATOM   5165  OE2  GLU B 298     -17.449 -10.200  22.490  1.00 43.97           B
```

Figure 1 (continued 52)

```
ATOM   5166  C   GLU B 298    -14.606 -13.524  25.205  1.00 28.60      B
ATOM   5167  O   GLU B 298    -14.936 -14.643  24.817  1.00 27.81      B
ATOM   5168  N   GLN B 299    -13.870 -13.325  26.301  1.00 27.28      B
ATOM   5169  CA  GLN B 299    -13.431 -14.434  27.148  1.00 27.04      B
ATOM   5170  CB  GLN B 299    -14.615 -15.356  27.468  1.00 30.88      B
ATOM   5171  CG  GLN B 299    -15.432 -15.000  28.711  1.00 37.59      B
ATOM   5172  CD  GLN B 299    -15.844 -13.553  28.768  1.00 40.60      B
ATOM   5173  OE1 GLN B 299    -15.062 -12.682  29.185  1.00 42.63      B
ATOM   5174  NE2 GLN B 299    -17.080 -13.273  28.344  1.00 42.73      B
ATOM   5175  C   GLN B 299    -12.326 -15.273  26.516  1.00 22.97      B
ATOM   5176  O   GLN B 299    -12.014 -16.375  26.995  1.00 21.99      B
ATOM   5177  N   GLU B 300    -11.762 -14.769  25.428  1.00 19.48      B
ATOM   5178  CA  GLU B 300    -10.680 -15.479  24.756  1.00 15.67      B
ATOM   5179  CB  GLU B 300    -10.583 -15.026  23.291  1.00 15.71      B
ATOM   5180  CG  GLU B 300    -11.879 -15.412  22.546  1.00 16.99      B
ATOM   5181  CD  GLU B 300    -11.936 -14.867  21.148  1.00 17.62      B
ATOM   5182  OE1 GLU B 300    -11.425 -13.753  20.908  1.00 19.18      B
ATOM   5183  OE2 GLU B 300    -12.507 -15.566  20.289  1.00 18.81      B
ATOM   5184  C   GLU B 300     -9.395 -15.245  25.501  1.00 17.24      B
ATOM   5185  O   GLU B 300     -9.223 -14.200  26.160  1.00 15.99      B
ATOM   5186  N   GLU B 301     -8.487 -16.212  25.407  1.00 15.46      B
ATOM   5187  CA  GLU B 301     -7.239 -16.084  26.143  1.00 16.90      B
ATOM   5188  CB  GLU B 301     -7.305 -16.893  27.436  1.00 21.09      B
ATOM   5189  CG  GLU B 301     -8.146 -16.357  28.543  1.00 30.92      B
ATOM   5190  CD  GLU B 301     -7.962 -17.237  29.766  1.00 35.02      B
ATOM   5191  OE1 GLU B 301     -6.789 -17.389  30.212  1.00 38.01      B
ATOM   5192  OE2 GLU B 301     -8.979 -17.773  30.255  1.00 38.32      B
ATOM   5193  C   GLU B 301     -6.073 -16.632  25.401  1.00 15.82      B
ATOM   5194  O   GLU B 301     -6.198 -17.658  24.748  1.00 15.36      B
ATOM   5195  N   ALA B 302     -4.931 -15.953  25.537  1.00 14.54      B
ATOM   5196  CA  ALA B 302     -3.688 -16.427  24.943  1.00 14.01      B
ATOM   5197  CB  ALA B 302     -3.195 -15.479  23.876  1.00 15.13      B
ATOM   5198  C   ALA B 302     -2.644 -16.540  26.060  1.00 14.66      B
ATOM   5199  O   ALA B 302     -2.640 -15.741  27.006  1.00 16.02      B
ATOM   5200  N   GLU B 303     -1.782 -17.553  25.969  1.00 13.72      B
ATOM   5201  CA  GLU B 303     -0.691 -17.712  26.953  1.00 13.49      B
ATOM   5202  CB  GLU B 303     -1.021 -18.772  28.011  1.00 14.66      B
ATOM   5203  CG  GLU B 303      0.164 -19.059  28.960  1.00 18.75      B
ATOM   5204  CD  GLU B 303     -0.155 -20.148  29.970  1.00 23.21      B
ATOM   5205  OE1 GLU B 303     -0.967 -19.881  30.873  1.00 26.03      B
ATOM   5206  OE2 GLU B 303      0.387 -21.261  29.853  1.00 23.17      B
ATOM   5207  C   GLU B 303      0.559 -18.156  26.209  1.00 12.96      B
ATOM   5208  O   GLU B 303      0.502 -19.062  25.366  1.00 12.70      B
ATOM   5209  N   GLU B 304      1.667 -17.486  26.485  1.00 11.86      B
ATOM   5210  CA  GLU B 304      2.955 -17.833  25.880  1.00 12.51      B
ATOM   5211  CB  GLU B 304      3.474 -16.692  24.994  1.00 12.93      B
ATOM   5212  CG  GLU B 304      2.613 -16.412  23.768  1.00 13.88      B
ATOM   5213  CD  GLU B 304      2.846 -17.416  22.654  1.00 16.15      B
ATOM   5214  OE1 GLU B 304      3.836 -18.173  22.717  1.00 14.88      B
ATOM   5215  OE2 GLU B 304      2.029 -17.448  21.702  1.00 16.52      B
ATOM   5216  C   GLU B 304      3.958 -18.009  27.014  1.00 12.92      B
ATOM   5217  O   GLU B 304      4.033 -17.156  27.894  1.00 13.66      B
ATOM   5218  N   ILE B 305      4.718 -19.108  27.010  1.00 12.77      B
ATOM   5219  CA  ILE B 305      5.738 -19.283  28.037  1.00 11.99      B
ATOM   5220  CB  ILE B 305      5.549 -20.605  28.791  1.00 13.43      B
ATOM   5221  CG2 ILE B 305      6.730 -20.801  29.771  1.00 14.23      B
ATOM   5222  CG1 ILE B 305      4.211 -20.536  29.555  1.00 15.50      B
ATOM   5223  CD1 ILE B 305      3.773 -21.908  30.095  1.00 21.38      B
ATOM   5224  C   ILE B 305      7.074 -19.263  27.309  1.00 13.39      B
ATOM   5225  O   ILE B 305      7.206 -19.891  26.239  1.00 14.67      B
ATOM   5226  N   LEU B 306      8.033 -18.501  27.838  1.00 12.78      B
ATOM   5227  CA  LEU B 306      9.363 -18.388  27.201  1.00 13.06      B
ATOM   5228  CB  LEU B 306      9.567 -16.973  26.621  1.00 16.49      B
ATOM   5229  CG  LEU B 306      8.629 -16.459  25.530  1.00 19.31      B
ATOM   5230  CD1 LEU B 306      8.803 -14.943  25.356  1.00 22.78      B
ATOM   5231  CD2 LEU B 306      8.922 -17.216  24.223  1.00 21.99      B
ATOM   5232  C   LEU B 306     10.473 -18.598  28.221  1.00 13.14      B
ATOM   5233  O   LEU B 306     10.347 -18.191  29.368  1.00 13.66      B
ATOM   5234  N   ASP B 307     11.579 -19.197  27.784  1.00 14.05      B
ATOM   5235  CA  ASP B 307     12.724 -19.322  28.668  1.00 14.97      B
ATOM   5236  CB  ASP B 307     13.664 -20.441  28.216  1.00 17.59      B
ATOM   5237  CG  ASP B 307     13.064 -21.815  28.375  1.00 21.45      B
ATOM   5238  OD1 ASP B 307     12.257 -22.018  29.283  1.00 21.70      B
ATOM   5239  OD2 ASP B 307     13.415 -22.718  27.587  1.00 29.43      B
ATOM   5240  C   ASP B 307     13.472 -17.998  28.538  1.00 16.22      B
ATOM   5241  O   ASP B 307     13.683 -17.502  27.407  1.00 17.41      B
ATOM   5242  N   VAL B 308     13.856 -17.419  29.672  1.00 15.42      B
ATOM   5243  CA  VAL B 308     14.622 -16.170  29.691  1.00 16.59      B
ATOM   5244  CB  VAL B 308     13.719 -14.932  29.974  1.00 16.08      B
ATOM   5245  CG1 VAL B 308     12.596 -14.869  28.938  1.00 14.76      B
ATOM   5246  CG2 VAL B 308     13.156 -14.972  31.412  1.00 15.53      B
ATOM   5247  C   VAL B 308     15.661 -16.311  30.800  1.00 18.09      B
ATOM   5248  O   VAL B 308     15.705 -17.332  31.479  1.00 18.24      B
ATOM   5249  N   THR B 309     16.540 -15.320  30.928  1.00 17.26      B
ATOM   5250  CA  THR B 309     17.514 -15.322  32.010  1.00 19.28      B
ATOM   5251  CB  THR B 309     18.901 -14.815  31.545  1.00 19.61      B
ATOM   5252  OG1 THR B 309     19.416 -15.679  30.540  1.00 21.13      B
ATOM   5253  CG2 THR B 309     19.879 -14.794  32.712  1.00 23.93      B
ATOM   5254  C   THR B 309     16.944 -14.334  33.032  1.00 18.30      B
ATOM   5255  O   THR B 309     16.798 -13.147  32.747  1.00 20.11      B
ATOM   5256  N   TYR B 310     16.577 -14.826  34.215  1.00 18.66      B
ATOM   5257  CA  TYR B 310     16.037 -13.957  35.261  1.00 16.85      B
ATOM   5258  CB  TYR B 310     14.537 -13.655  35.065  1.00 17.90      B
ATOM   5259  CG  TYR B 310     13.993 -12.756  36.152  1.00 18.11      B
ATOM   5260  CD1 TYR B 310     14.389 -11.420  36.234  1.00 19.98      B
ATOM   5261  CE1 TYR B 310     13.958 -10.596  37.265  1.00 21.65      B
ATOM   5262  CD2 TYR B 310     13.135 -13.241  37.142  1.00 18.77      B
ATOM   5263  CE2 TYR B 310     12.694 -12.428  38.166  1.00 19.14      B
ATOM   5264  CZ  TYR B 310     13.100 -11.111  38.239  1.00 22.59      B
ATOM   5265  OH  TYR B 310     12.642 -10.325  39.276  1.00 23.29      B
```

Figure 1 (continued 53)

| | | | | | | | | | |
|---|---|---|---|---|---|---|---|---|---|
| ATOM | 5266 | C | | TYR | B | 310 | 16.202 | -14.605 | 36.635 | 1.00 | 20.33 | B |
| ATOM | 5267 | O | | TYR | B | 310 | 15.861 | -15.775 | 36.802 | 1.00 | 18.99 | B |
| ATOM | 5268 | N | | SER | B | 311 | 16.711 | -13.831 | 37.604 | 1.00 | 21.58 | B |
| ATOM | 5269 | CA | | SER | B | 311 | 16.890 | -14.340 | 38.973 | 1.00 | 25.75 | B |
| ATOM | 5270 | CB | | SER | B | 311 | 18.376 | -14.490 | 39.291 | 1.00 | 27.17 | B |
| ATOM | 5271 | OG | | SER | B | 311 | 18.819 | -15.761 | 38.877 | 1.00 | 32.61 | B |
| ATOM | 5272 | C | | SER | B | 311 | 16.229 | -13.539 | 40.094 | 1.00 | 27.05 | B |
| ATOM | 5273 | O | | SER | B | 311 | 16.370 | -13.876 | 41.264 | 1.00 | 31.83 | B |
| ATOM | 5274 | N | | GLY | B | 312 | 15.500 | -12.481 | 39.778 | 1.00 | 28.46 | B |
| ATOM | 5275 | CA | | GLY | B | 312 | 14.864 | -11.724 | 40.848 | 1.00 | 28.43 | B |
| ATOM | 5276 | C | | GLY | B | 312 | 13.588 | -12.299 | 41.478 | 1.00 | 27.94 | B |
| ATOM | 5277 | O | | GLY | B | 312 | 13.187 | -13.451 | 41.239 | 1.00 | 26.97 | B |
| ATOM | 5278 | N | | ALA | B | 313 | 12.957 | -11.478 | 42.310 | 1.00 | 26.88 | B |
| ATOM | 5279 | CA | | ALA | B | 313 | 11.711 | -11.848 | 42.966 | 1.00 | 24.05 | B |
| ATOM | 5280 | CB | | ALA | B | 313 | 11.312 | -10.763 | 43.966 | 1.00 | 24.56 | B |
| ATOM | 5281 | C | | ALA | B | 313 | 10.665 | -11.932 | 41.853 | 1.00 | 22.56 | B |
| ATOM | 5282 | O | | ALA | B | 313 | 10.806 | -11.298 | 40.799 | 1.00 | 20.08 | B |
| ATOM | 5283 | N | | GLU | B | 314 | 9.618 | -12.725 | 42.066 | 1.00 | 19.40 | B |
| ATOM | 5284 | CA | | GLU | B | 314 | 8.586 | -12.840 | 41.042 | 1.00 | 18.07 | B |
| ATOM | 5285 | CB | | GLU | B | 314 | 7.647 | -14.039 | 41.323 | 1.00 | 16.92 | B |
| ATOM | 5286 | CG | | GLU | B | 314 | 8.410 | -15.354 | 41.405 | 1.00 | 16.41 | B |
| ATOM | 5287 | CD | | GLU | B | 314 | 7.525 | -16.589 | 41.365 | 1.00 | 14.40 | B |
| ATOM | 5288 | OE1 | | GLU | B | 314 | 6.317 | -16.485 | 41.643 | 1.00 | 15.57 | B |
| ATOM | 5289 | OE2 | | GLU | B | 314 | 8.058 | -17.668 | 41.064 | 1.00 | 17.05 | B |
| ATOM | 5290 | C | | GLU | B | 314 | 7.772 | -11.565 | 41.032 | 1.00 | 17.69 | B |
| ATOM | 5291 | O | | GLU | B | 314 | 7.685 | -10.870 | 42.033 | 1.00 | 18.99 | B |
| ATOM | 5292 | N | | MET | B | 315 | 7.209 | -11.226 | 39.878 | 1.00 | 18.30 | B |
| ATOM | 5293 | CA | | MET | B | 315 | 6.352 | -10.044 | 39.793 | 1.00 | 16.99 | B |
| ATOM | 5294 | CB | | MET | B | 315 | 7.156 | -8.741 | 39.754 | 1.00 | 19.43 | B |
| ATOM | 5295 | CG | | MET | B | 315 | 8.052 | -8.587 | 38.571 | 1.00 | 18.90 | B |
| ATOM | 5296 | SD | | MET | B | 315 | 8.654 | -6.862 | 38.490 | 1.00 | 23.78 | B |
| ATOM | 5297 | CE | | MET | B | 315 | 7.247 | -6.033 | 37.765 | 1.00 | 21.20 | B |
| ATOM | 5298 | C | | MET | B | 315 | 5.509 | -10.144 | 38.542 | 1.00 | 18.24 | B |
| ATOM | 5299 | O | | MET | B | 315 | 5.833 | -10.890 | 37.618 | 1.00 | 16.64 | B |
| ATOM | 5300 | N | | GLU | B | 316 | 4.404 | -9.423 | 38.554 | 1.00 | 17.91 | B |
| ATOM | 5301 | CA | | GLU | B | 316 | 3.499 | -9.387 | 37.442 | 1.00 | 19.14 | B |
| ATOM | 5302 | CB | | GLU | B | 316 | 2.153 | -9.964 | 37.876 | 1.00 | 22.45 | B |
| ATOM | 5303 | CG | | GLU | B | 316 | 1.183 | -10.293 | 36.755 | 1.00 | 30.42 | B |
| ATOM | 5304 | CD | | GLU | B | 316 | -0.058 | -11.022 | 37.282 | 1.00 | 33.19 | B |
| ATOM | 5305 | OE1 | | GLU | B | 316 | -0.126 | -12.269 | 37.189 | 1.00 | 36.29 | B |
| ATOM | 5306 | OE2 | | GLU | B | 316 | -0.957 | -10.337 | 37.807 | 1.00 | 35.89 | B |
| ATOM | 5307 | C | | GLU | B | 316 | 3.374 | -7.916 | 37.058 | 1.00 | 18.61 | B |
| ATOM | 5308 | O | | GLU | B | 316 | 3.442 | -7.029 | 37.917 | 1.00 | 19.48 | B |
| ATOM | 5309 | N | | ILE | B | 317 | 3.202 | -7.651 | 35.770 | 1.00 | 17.17 | B |
| ATOM | 5310 | CA | | ILE | B | 317 | 3.090 | -6.281 | 35.317 | 1.00 | 14.40 | B |
| ATOM | 5311 | CB | | ILE | B | 317 | 4.500 | -5.648 | 35.163 | 1.00 | 14.99 | B |
| ATOM | 5312 | CG2 | | ILE | B | 317 | 5.382 | -6.449 | 34.166 | 1.00 | 15.39 | B |
| ATOM | 5313 | CG1 | | ILE | B | 317 | 4.373 | -4.195 | 34.724 | 1.00 | 16.07 | B |
| ATOM | 5314 | CD1 | | ILE | B | 317 | 5.731 | -3.450 | 34.830 | 1.00 | 16.39 | B |
| ATOM | 5315 | C | | ILE | B | 317 | 2.319 | -6.249 | 34.003 | 1.00 | 15.91 | B |
| ATOM | 5316 | O | | ILE | B | 317 | 2.484 | -7.144 | 33.166 | 1.00 | 15.36 | B |
| ATOM | 5317 | N | | GLY | B | 318 | 1.489 | -5.225 | 33.826 | 1.00 | 15.37 | B |
| ATOM | 5318 | CA | | GLY | B | 318 | 0.701 | -5.121 | 32.611 | 1.00 | 13.91 | B |
| ATOM | 5319 | C | | GLY | B | 318 | 1.261 | -4.061 | 31.670 | 1.00 | 15.48 | B |
| ATOM | 5320 | O | | GLY | B | 318 | 1.888 | -3.115 | 32.135 | 1.00 | 14.18 | B |
| ATOM | 5321 | N | | PHE | B | 319 | 1.072 | -4.255 | 30.363 | 1.00 | 15.89 | B |
| ATOM | 5322 | CA | | PHE | B | 319 | 1.513 | -3.311 | 29.331 | 1.00 | 16.03 | B |
| ATOM | 5323 | CB | | PHE | B | 319 | 2.897 | -3.692 | 28.777 | 1.00 | 17.13 | B |
| ATOM | 5324 | CG | | PHE | B | 319 | 4.022 | -3.383 | 29.686 | 1.00 | 18.79 | B |
| ATOM | 5325 | CD1 | | PHE | B | 319 | 4.434 | -2.073 | 29.877 | 1.00 | 21.89 | B |
| ATOM | 5326 | CD2 | | PHE | B | 319 | 4.673 | -4.401 | 30.368 | 1.00 | 21.55 | B |
| ATOM | 5327 | CE1 | | PHE | B | 319 | 5.481 | -1.786 | 30.740 | 1.00 | 22.47 | B |
| ATOM | 5328 | CE2 | | PHE | B | 319 | 5.716 | -4.122 | 31.236 | 1.00 | 21.80 | B |
| ATOM | 5329 | CZ | | PHE | B | 319 | 6.121 | -2.820 | 31.423 | 1.00 | 23.74 | B |
| ATOM | 5330 | C | | PHE | B | 319 | 0.602 | -3.282 | 28.129 | 1.00 | 16.79 | B |
| ATOM | 5331 | O | | PHE | B | 319 | -0.122 | -4.242 | 27.846 | 1.00 | 16.37 | B |
| ATOM | 5332 | N | | ASN | B | 320 | 0.635 | -2.143 | 27.431 | 1.00 | 16.27 | B |
| ATOM | 5333 | CA | | ASN | B | 320 | -0.051 | -1.983 | 26.158 | 1.00 | 16.46 | B |
| ATOM | 5334 | CB | | ASN | B | 320 | -0.055 | -0.504 | 25.796 | 1.00 | 18.69 | B |
| ATOM | 5335 | CG | | ASN | B | 320 | -0.561 | -0.259 | 24.407 | 1.00 | 18.32 | B |
| ATOM | 5336 | OD1 | | ASN | B | 320 | -0.226 | -0.997 | 23.481 | 1.00 | 18.44 | B |
| ATOM | 5337 | ND2 | | ASN | B | 320 | -1.362 | 0.791 | 24.242 | 1.00 | 18.81 | B |
| ATOM | 5338 | C | | ASN | B | 320 | 0.927 | -2.745 | 25.249 | 1.00 | 17.08 | B |
| ATOM | 5339 | O | | ASN | B | 320 | 2.093 | -2.350 | 25.102 | 1.00 | 16.27 | B |
| ATOM | 5340 | N | | VAL | B | 321 | 0.478 | -3.843 | 24.645 | 1.00 | 15.94 | B |
| ATOM | 5341 | CA | | VAL | B | 321 | 1.379 | -4.662 | 23.845 | 1.00 | 16.35 | B |
| ATOM | 5342 | CB | | VAL | B | 321 | 0.703 | -6.027 | 23.464 | 1.00 | 16.49 | B |
| ATOM | 5343 | CG1 | | VAL | B | 321 | -0.409 | -5.817 | 22.450 | 1.00 | 17.69 | B |
| ATOM | 5344 | CG2 | | VAL | B | 321 | 1.743 | -7.004 | 22.956 | 1.00 | 14.64 | B |
| ATOM | 5345 | C | | VAL | B | 321 | 1.891 | -3.939 | 22.610 | 1.00 | 17.10 | B |
| ATOM | 5346 | O | | VAL | B | 321 | 2.977 | -4.245 | 22.119 | 1.00 | 15.35 | B |
| ATOM | 5347 | N | | SER | B | 322 | 1.146 | -2.961 | 22.109 | 1.00 | 16.12 | B |
| ATOM | 5348 | CA | | SER | B | 322 | 1.657 | -2.257 | 20.925 | 1.00 | 17.12 | B |
| ATOM | 5349 | CB | | SER | B | 322 | 0.587 | -1.352 | 20.311 | 1.00 | 18.39 | B |
| ATOM | 5350 | OG | | SER | B | 322 | -0.513 | -2.129 | 19.863 | 1.00 | 22.65 | B |
| ATOM | 5351 | C | | SER | B | 322 | 2.899 | -1.436 | 21.276 | 1.00 | 15.98 | B |
| ATOM | 5352 | O | | SER | B | 322 | 3.837 | -1.353 | 20.468 | 1.00 | 15.16 | B |
| ATOM | 5353 | N | | TYR | B | 323 | 2.932 | -0.853 | 22.482 | 1.00 | 14.24 | B |
| ATOM | 5354 | CA | | TYR | B | 323 | 4.110 | -0.088 | 22.908 | 1.00 | 15.80 | B |
| ATOM | 5355 | CB | | TYR | B | 323 | 3.878 | 0.590 | 24.259 | 1.00 | 15.47 | B |
| ATOM | 5356 | CG | | TYR | B | 323 | 2.813 | 1.668 | 24.294 | 1.00 | 16.25 | B |
| ATOM | 5357 | CD1 | | TYR | B | 323 | 2.397 | 2.314 | 23.127 | 1.00 | 19.59 | B |
| ATOM | 5358 | CE1 | | TYR | B | 323 | 1.458 | 3.374 | 23.170 | 1.00 | 20.04 | B |
| ATOM | 5359 | CD2 | | TYR | B | 323 | 2.284 | 2.093 | 25.509 | 1.00 | 18.22 | B |
| ATOM | 5360 | CE2 | | TYR | B | 323 | 1.354 | 3.166 | 25.567 | 1.00 | 19.75 | B |
| ATOM | 5361 | CZ | | TYR | B | 323 | 0.957 | 3.790 | 24.399 | 1.00 | 21.19 | B |
| ATOM | 5362 | OH | | TYR | B | 323 | 0.112 | 4.886 | 24.453 | 1.00 | 23.64 | B |
| ATOM | 5363 | C | | TYR | B | 323 | 5.327 | -1.018 | 23.041 | 1.00 | 15.80 | B |
| ATOM | 5364 | O | | TYR | B | 323 | 6.468 | -0.646 | 22.726 | 1.00 | 15.87 | B |
| ATOM | 5365 | N | | VAL | B | 324 | 5.101 | -2.226 | 23.563 | 1.00 | 14.85 | B |

Figure 1 (continued 54)

```
ATOM   5366  CA  VAL B 324       6.193  -3.182  23.687  1.00 14.69           B
ATOM   5367  CB  VAL B 324       5.776  -4.387  24.550  1.00 14.90           B
ATOM   5368  CG1 VAL B 324       6.913  -5.422  24.610  1.00 16.80           B
ATOM   5369  CG2 VAL B 324       5.440  -3.896  25.952  1.00 16.82           B
ATOM   5370  C   VAL B 324       6.674  -3.670  22.301  1.00 13.75           B
ATOM   5371  O   VAL B 324       7.885  -3.761  22.039  1.00 14.44           B
ATOM   5372  N   LEU B 325       5.737  -3.984  21.410  1.00 14.44           B
ATOM   5373  CA  LEU B 325       6.105  -4.424  20.085  1.00 13.52           B
ATOM   5374  CB  LEU B 325       4.852  -4.870  19.317  1.00 14.38           B
ATOM   5375  CG  LEU B 325       4.339  -6.244  19.774  1.00 14.30           B
ATOM   5376  CD1 LEU B 325       2.953  -6.506  19.170  1.00 15.19           B
ATOM   5377  CD2 LEU B 325       5.338  -7.346  19.363  1.00 14.63           B
ATOM   5378  C   LEU B 325       6.848  -3.319  19.334  1.00 14.06           B
ATOM   5379  O   LEU B 325       7.801  -3.603  18.606  1.00 15.63           B
ATOM   5380  N   ASP B 326       6.420  -2.074  19.503  1.00 14.14           B
ATOM   5381  CA  ASP B 326       7.113  -0.960  18.843  1.00 14.45           B
ATOM   5382  CB  ASP B 326       6.505   0.385  19.217  1.00 15.89           B
ATOM   5383  CG  ASP B 326       5.168   0.634  18.556  1.00 16.26           B
ATOM   5384  OD1 ASP B 326       4.803  -0.036  17.556  1.00 17.26           B
ATOM   5385  OD2 ASP B 326       4.471   1.551  19.018  1.00 18.69           B
ATOM   5386  C   ASP B 326       8.588  -0.952  19.255  1.00 14.86           B
ATOM   5387  O   ASP B 326       9.454  -0.768  18.416  1.00 15.93           B
ATOM   5388  N   VAL B 327       8.871  -1.163  20.542  1.00 15.32           B
ATOM   5389  CA  VAL B 327      10.246  -1.175  20.989  1.00 15.55           B
ATOM   5390  CB  VAL B 327      10.301  -1.226  22.534  1.00 16.32           B
ATOM   5391  CG1 VAL B 327      11.715  -1.474  22.996  1.00 15.81           B
ATOM   5392  CG2 VAL B 327       9.783   0.086  23.085  1.00 15.65           B
ATOM   5393  C   VAL B 327      11.039  -2.352  20.422  1.00 16.20           B
ATOM   5394  O   VAL B 327      12.179  -2.184  19.974  1.00 15.94           B
ATOM   5395  N   LEU B 328      10.437  -3.547  20.435  1.00 14.84           B
ATOM   5396  CA  LEU B 328      11.150  -4.726  19.961  1.00 15.54           B
ATOM   5397  CB  LEU B 328      10.347  -5.985  20.295  1.00 14.62           B
ATOM   5398  CG  LEU B 328      10.130  -6.193  21.808  1.00 15.10           B
ATOM   5399  CD1 LEU B 328       9.295  -7.460  22.024  1.00 14.68           B
ATOM   5400  CD2 LEU B 328      11.503  -6.337  22.497  1.00 16.58           B
ATOM   5401  C   LEU B 328      11.416  -4.600  18.480  1.00 16.34           B
ATOM   5402  O   LEU B 328      12.455  -5.042  17.998  1.00 17.56           B
ATOM   5403  N   ASN B 329      10.491  -3.970  17.758  1.00 17.06           B
ATOM   5404  CA  ASN B 329      10.680  -3.755  16.332  1.00 20.23           B
ATOM   5405  CB  ASN B 329       9.371  -3.285  15.675  1.00 20.68           B
ATOM   5406  CG  ASN B 329       8.414  -4.440  15.381  1.00 25.15           B
ATOM   5407  OD1 ASN B 329       7.193  -4.308  15.536  1.00 29.33           B
ATOM   5408  ND2 ASN B 329       8.961  -5.571  14.932  1.00 25.44           B
ATOM   5409  C   ASN B 329      11.790  -2.743  16.076  1.00 20.26           B
ATOM   5410  O   ASN B 329      12.504  -2.875  15.074  1.00 21.57           B
ATOM   5411  N   ALA B 330      11.958  -1.754  16.963  1.00 19.54           B
ATOM   5412  CA  ALA B 330      13.007  -0.741  16.795  1.00 20.36           B
ATOM   5413  CB  ALA B 330      12.703   0.488  17.630  1.00 19.00           B
ATOM   5414  C   ALA B 330      14.392  -1.275  17.151  1.00 22.18           B
ATOM   5415  O   ALA B 330      15.410  -0.786  16.652  1.00 22.02           B
ATOM   5416  N   LEU B 331      14.425  -2.269  18.031  1.00 22.79           B
ATOM   5417  CA  LEU B 331      15.675  -2.900  18.445  1.00 26.40           B
ATOM   5418  CB  LEU B 331      15.542  -3.459  19.876  1.00 24.34           B
ATOM   5419  CG  LEU B 331      15.521  -2.496  21.077  1.00 23.11           B
ATOM   5420  CD1 LEU B 331      15.059  -3.251  22.320  1.00 23.07           B
ATOM   5421  CD2 LEU B 331      16.904  -1.904  21.324  1.00 22.88           B
ATOM   5422  C   LEU B 331      15.953  -4.042  17.466  1.00 29.87           B
ATOM   5423  O   LEU B 331      15.346  -5.118  17.543  1.00 32.92           B
ATOM   5424  N   LYS B 332      16.871  -3.831  16.540  1.00 32.35           B
ATOM   5425  CA  LYS B 332      17.157  -4.892  15.576  1.00 34.77           B
ATOM   5426  CB  LYS B 332      17.447  -4.281  14.205  1.00 37.40           B
ATOM   5427  CG  LYS B 332      18.504  -3.195  14.249  1.00 41.60           B
ATOM   5428  CD  LYS B 332      18.968  -2.812  12.865  1.00 44.04           B
ATOM   5429  CE  LYS B 332      20.404  -2.327  12.925  1.00 46.03           B
ATOM   5430  NZ  LYS B 332      21.304  -3.408  13.449  1.00 46.84           B
ATOM   5431  C   LYS B 332      18.364  -5.647  16.110  1.00 34.26           B
ATOM   5432  O   LYS B 332      19.478  -5.520  15.583  1.00 36.38           B
ATOM   5433  N   CYS B 333      18.139  -6.428  17.167  1.00 31.45           B
ATOM   5434  CA  CYS B 333      19.227  -7.147  17.809  1.00 28.74           B
ATOM   5435  CB  CYS B 333      19.682  -6.364  19.040  1.00 26.65           B
ATOM   5436  SG  CYS B 333      18.382  -6.128  20.301  1.00 24.29           B
ATOM   5437  C   CYS B 333      18.900  -8.582  18.201  1.00 27.77           B
ATOM   5438  O   CYS B 333      17.771  -9.039  18.057  1.00 27.74           B
ATOM   5439  N   GLU B 334      19.891  -9.292  18.722  1.00 24.94           B
ATOM   5440  CA  GLU B 334      19.651 -10.671  19.072  1.00 25.13           B
ATOM   5441  CB  GLU B 334      20.940 -11.490  19.059  1.00 28.75           B
ATOM   5442  CG  GLU B 334      20.639 -12.973  18.832  1.00 33.58           B
ATOM   5443  CD  GLU B 334      21.798 -13.903  19.171  1.00 37.85           B
ATOM   5444  OE1 GLU B 334      22.835 -13.880  18.469  1.00 38.76           B
ATOM   5445  OE2 GLU B 334      21.656 -14.670  20.151  1.00 39.90           B
ATOM   5446  C   GLU B 334      18.977 -10.831  20.420  1.00 22.72           B
ATOM   5447  O   GLU B 334      18.060 -11.628  20.559  1.00 22.05           B
ATOM   5448  N   ASN B 335      19.449 -10.089  21.410  1.00 21.54           B
ATOM   5449  CA  ASN B 335      18.873 -10.202  22.751  1.00 21.37           B
ATOM   5450  CB  ASN B 335      19.841 -10.945  23.673  1.00 22.21           B
ATOM   5451  CG  ASN B 335      20.230 -12.327  23.127  1.00 23.10           B
ATOM   5452  OD1 ASN B 335      21.320 -12.515  22.569  1.00 27.23           B
ATOM   5453  ND2 ASN B 335      19.349 -13.283  23.283  1.00 20.66           B
ATOM   5454  C   ASN B 335      18.540  -8.849  23.347  1.00 21.05           B
ATOM   5455  O   ASN B 335      19.193  -7.848  23.057  1.00 19.95           B
ATOM   5456  N   VAL B 336      17.499  -8.824  24.174  1.00 18.30           B
ATOM   5457  CA  VAL B 336      17.074  -7.600  24.817  1.00 18.62           B
ATOM   5458  CB  VAL B 336      15.629  -7.224  24.418  1.00 19.11           B
ATOM   5459  CG1 VAL B 336      15.564  -6.941  22.908  1.00 19.33           B
ATOM   5460  CG2 VAL B 336      14.681  -8.367  24.762  1.00 23.69           B
ATOM   5461  C   VAL B 336      17.118  -7.770  26.331  1.00 19.78           B
ATOM   5462  O   VAL B 336      17.054  -8.896  26.846  1.00 20.30           B
ATOM   5463  N   ARG B 337      17.243  -6.644  27.022  1.00 18.96           B
ATOM   5464  CA  ARG B 337      17.259  -6.617  28.482  1.00 19.16           B
ATOM   5465  CB  ARG B 337      18.589  -6.071  29.016  1.00 20.68           B
```

Figure 1 (continued 55)

```
ATOM   5466  CG   ARG B 337      18.600  -5.938  30.554  1.00 23.91           B
ATOM   5467  CD   ARG B 337      19.995  -5.583  31.102  1.00 23.98           B
ATOM   5468  NE   ARG B 337      21.011  -6.545  30.668  1.00 27.10           B
ATOM   5469  CZ   ARG B 337      21.895  -6.313  29.704  1.00 26.89           B
ATOM   5470  NH1  ARG B 337      21.898  -5.149  29.068  1.00 28.48           B
ATOM   5471  NH2  ARG B 337      22.773  -7.244  29.371  1.00 28.51           B
ATOM   5472  C    ARG B 337      16.134  -5.715  28.938  1.00 19.09           B
ATOM   5473  O    ARG B 337      15.996  -4.586  28.465  1.00 18.29           B
ATOM   5474  N    MET B 338      15.293  -6.223  29.835  1.00 18.31           B
ATOM   5475  CA   MET B 338      14.197  -5.456  30.392  1.00 19.62           B
ATOM   5476  CB   MET B 338      12.884  -6.241  30.331  1.00 20.28           B
ATOM   5477  CG   MET B 338      12.410  -6.552  28.924  1.00 23.02           B
ATOM   5478  SD   MET B 338      10.698  -7.188  28.918  1.00 30.58           B
ATOM   5479  CE   MET B 338      10.105  -6.371  30.539  1.00 23.41           B
ATOM   5480  C    MET B 338      14.585  -5.245  31.843  1.00 19.01           B
ATOM   5481  O    MET B 338      14.968  -6.203  32.527  1.00 19.47           B
ATOM   5482  N    MET B 339      14.491  -4.008  32.302  1.00 20.01           B
ATOM   5483  CA   MET B 339      14.840  -3.658  33.682  1.00 19.93           B
ATOM   5484  CB   MET B 339      15.951  -2.600  33.651  1.00 23.82           B
ATOM   5485  CG   MET B 339      17.044  -3.049  32.682  1.00 28.37           B
ATOM   5486  SD   MET B 339      18.055  -1.714  32.046  1.00 39.00           B
ATOM   5487  CE   MET B 339      19.307  -1.887  33.240  1.00 33.07           B
ATOM   5488  C    MET B 339      13.570  -3.191  34.385  1.00 18.83           B
ATOM   5489  O    MET B 339      12.958  -2.204  34.009  1.00 16.91           B
ATOM   5490  N    LEU B 340      13.174  -3.940  35.420  1.00 18.32           B
ATOM   5491  CA   LEU B 340      11.927  -3.673  36.114  1.00 20.68           B
ATOM   5492  CB   LEU B 340      11.036  -4.916  36.055  1.00 23.79           B
ATOM   5493  CG   LEU B 340      10.657  -5.377  34.649  1.00 25.40           B
ATOM   5494  CD1  LEU B 340      11.509  -6.576  34.276  1.00 29.66           B
ATOM   5495  CD2  LEU B 340       9.190  -5.735  34.630  1.00 28.50           B
ATOM   5496  C    LEU B 340      12.104  -3.309  37.555  1.00 19.92           B
ATOM   5497  O    LEU B 340      13.150  -3.553  38.135  1.00 21.79           B
ATOM   5498  N    THR B 341      11.055  -2.720  38.116  1.00 23.10           B
ATOM   5499  CA   THR B 341      11.045  -2.310  39.509  1.00 25.27           B
ATOM   5500  CB   THR B 341      10.910  -0.789  39.596  1.00 26.79           B
ATOM   5501  OG1  THR B 341      12.026  -0.190  38.911  1.00 28.07           B
ATOM   5502  CG2  THR B 341      10.904  -0.337  41.053  1.00 26.69           B
ATOM   5503  C    THR B 341       9.863  -3.015  40.164  1.00 25.85           B
ATOM   5504  O    THR B 341      10.041  -3.872  41.028  1.00 28.86           B
ATOM   5505  N    ASP B 342       8.653  -2.670  39.735  1.00 25.54           B
ATOM   5506  CA   ASP B 342       7.466  -3.300  40.266  1.00 25.04           B
ATOM   5507  CB   ASP B 342       7.138  -2.742  41.651  1.00 25.70           B
ATOM   5508  CG   ASP B 342       6.999  -1.236  41.650  1.00 27.01           B
ATOM   5509  OD1  ASP B 342       6.409  -0.692  40.701  1.00 23.85           B
ATOM   5510  OD2  ASP B 342       7.474  -0.587  42.615  1.00 29.24           B
ATOM   5511  C    ASP B 342       6.309  -3.091  39.312  1.00 26.03           B
ATOM   5512  O    ASP B 342       6.469  -2.510  38.235  1.00 23.30           B
ATOM   5513  N    SER B 343       5.140  -3.581  39.700  1.00 24.63           B
ATOM   5514  CA   SER B 343       3.954  -3.490  38.866  1.00 26.73           B
ATOM   5515  CB   SER B 343       2.814  -4.253  39.519  1.00 27.90           B
ATOM   5516  OG   SER B 343       3.278  -5.495  39.991  1.00 33.35           B
ATOM   5517  C    SER B 343       3.445  -2.107  38.522  1.00 25.46           B
ATOM   5518  O    SER B 343       2.683  -1.947  37.568  1.00 27.08           B
ATOM   5519  N    VAL B 344       3.837  -1.100  39.291  1.00 25.08           B
ATOM   5520  CA   VAL B 344       3.324   0.227  39.030  1.00 23.51           B
ATOM   5521  CB   VAL B 344       2.676   0.818  40.318  1.00 24.60           B
ATOM   5522  CG1  VAL B 344       1.474  -0.026  40.725  1.00 27.19           B
ATOM   5523  CG2  VAL B 344       3.687   0.847  41.456  1.00 24.67           B
ATOM   5524  C    VAL B 344       4.405   1.163  38.512  1.00 23.49           B
ATOM   5525  O    VAL B 344       4.199   2.365  38.405  1.00 23.89           B
ATOM   5526  N    SER B 345       5.550   0.607  38.151  1.00 21.31           B
ATOM   5527  CA   SER B 345       6.617   1.467  37.691  1.00 20.87           B
ATOM   5528  CB   SER B 345       7.810   1.318  38.627  1.00 23.30           B
ATOM   5529  OG   SER B 345       7.409   1.696  39.946  1.00 21.45           B
ATOM   5530  C    SER B 345       7.012   1.166  36.260  1.00 21.79           B
ATOM   5531  O    SER B 345       6.770   0.077  35.761  1.00 21.63           B
ATOM   5532  N    SER B 346       7.618   2.153  35.615  1.00 21.53           B
ATOM   5533  CA   SER B 346       8.060   2.002  34.239  1.00 21.50           B
ATOM   5534  CB   SER B 346       8.655   3.320  33.722  1.00 21.47           B
ATOM   5535  OG   SER B 346       9.793   3.703  34.474  1.00 26.08           B
ATOM   5536  C    SER B 346       9.107   0.914  34.106  1.00 20.70           B
ATOM   5537  O    SER B 346       9.755   0.521  35.078  1.00 21.55           B
ATOM   5538  N    VAL B 347       9.255   0.411  32.890  1.00 21.06           B
ATOM   5539  CA   VAL B 347      10.254  -0.589  32.610  1.00 19.47           B
ATOM   5540  CB   VAL B 347       9.667  -1.886  31.960  1.00 21.64           B
ATOM   5541  CG1  VAL B 347       9.016  -1.578  30.636  1.00 22.58           B
ATOM   5542  CG2  VAL B 347      10.767  -2.905  31.746  1.00 22.90           B
ATOM   5543  C    VAL B 347      11.171   0.054  31.582  1.00 19.98           B
ATOM   5544  O    VAL B 347      10.705   0.845  30.758  1.00 19.77           B
ATOM   5545  N    GLN B 348      12.447  -0.270  31.667  1.00 18.29           B
ATOM   5546  CA   GLN B 348      13.421   0.211  30.694  1.00 19.12           B
ATOM   5547  CB   GLN B 348      14.667   0.811  31.375  1.00 21.07           B
ATOM   5548  CG   GLN B 348      15.791   1.231  30.385  1.00 24.52           B
ATOM   5549  CD   GLN B 348      16.826   2.140  31.039  1.00 25.62           B
ATOM   5550  OE1  GLN B 348      18.017   2.109  30.692  1.00 29.04           B
ATOM   5551  NE2  GLN B 348      16.378   2.944  31.980  1.00 25.26           B
ATOM   5552  C    GLN B 348      13.827  -0.987  29.863  1.00 18.81           B
ATOM   5553  O    GLN B 348      14.128  -2.070  30.398  1.00 19.57           B
ATOM   5554  N    ILE B 349      13.828  -0.811  28.539  1.00 16.48           B
ATOM   5555  CA   ILE B 349      14.216  -1.893  27.640  1.00 16.69           B
ATOM   5556  CB   ILE B 349      13.043  -2.317  26.739  1.00 15.20           B
ATOM   5557  CG2  ILE B 349      13.450  -3.542  25.886  1.00 15.51           B
ATOM   5558  CG1  ILE B 349      11.814  -2.594  27.628  1.00 14.39           B
ATOM   5559  CD1  ILE B 349      10.543  -2.916  26.841  1.00 16.74           B
ATOM   5560  C    ILE B 349      15.354  -1.434  26.757  1.00 16.84           B
ATOM   5561  O    ILE B 349      15.342  -0.309  26.258  1.00 17.09           B
ATOM   5562  N    GLU B 350      16.316  -2.315  26.555  1.00 18.33           B
ATOM   5563  CA   GLU B 350      17.477  -2.012  25.717  1.00 20.07           B
ATOM   5564  CB   GLU B 350      18.606  -1.403  26.573  1.00 22.27           B
ATOM   5565  CG   GLU B 350      18.629  -1.904  28.009  1.00 27.54           B
```

Figure 1 (continued 56)

```
ATOM   5566  CD   GLU B 350      19.768  -1.317  28.861  1.00 28.87           B
ATOM   5567  OE1  GLU B 350      19.985  -0.085  28.838  1.00 30.71           B
ATOM   5568  OE2  GLU B 350      20.435  -2.111  29.569  1.00 32.23           B
ATOM   5569  C    GLU B 350      18.018  -3.247  25.033  1.00 20.43           B
ATOM   5570  O    GLU B 350      17.663  -4.385  25.373  1.00 19.39           B
ATOM   5571  N    ASP B 351      18.864  -3.023  24.030  1.00 18.78           B
ATOM   5572  CA   ASP B 351      19.556  -4.127  23.383  1.00 20.40           B
ATOM   5573  CB   ASP B 351      20.393  -3.559  22.216  1.00 20.92           B
ATOM   5574  CG   ASP B 351      21.276  -4.593  21.540  1.00 24.22           B
ATOM   5575  OD1  ASP B 351      21.520  -5.668  22.122  1.00 23.24           B
ATOM   5576  OD2  ASP B 351      21.747  -4.326  20.399  1.00 24.36           B
ATOM   5577  C    ASP B 351      20.480  -4.641  24.519  1.00 20.22           B
ATOM   5578  O    ASP B 351      21.154  -3.837  25.166  1.00 19.94           B
ATOM   5579  N    ALA B 352      20.513  -5.955  24.767  1.00 20.14           B
ATOM   5580  CA   ALA B 352      21.371  -6.512  25.828  1.00 22.88           B
ATOM   5581  CB   ALA B 352      21.102  -8.023  25.989  1.00 23.61           B
ATOM   5582  C    ALA B 352      22.856  -6.282  25.541  1.00 25.05           B
ATOM   5583  O    ALA B 352      23.687  -6.298  26.459  1.00 25.32           B
ATOM   5584  N    ALA B 353      23.187  -6.059  24.272  1.00 25.32           B
ATOM   5585  CA   ALA B 353      24.583  -5.871  23.874  1.00 27.92           B
ATOM   5586  CB   ALA B 353      24.888  -6.727  22.622  1.00 28.12           B
ATOM   5587  C    ALA B 353      25.008  -4.429  23.628  1.00 29.48           B
ATOM   5588  O    ALA B 353      26.134  -4.185  23.189  1.00 30.65           B
ATOM   5589  N    SER B 354      24.130  -3.471  23.895  1.00 28.82           B
ATOM   5590  CA   SER B 354      24.491  -2.068  23.695  1.00 30.09           B
ATOM   5591  CB   SER B 354      24.439  -1.695  22.213  1.00 30.87           B
ATOM   5592  OG   SER B 354      24.378  -0.282  22.073  1.00 30.83           B
ATOM   5593  C    SER B 354      23.612  -1.097  24.458  1.00 29.65           B
ATOM   5594  O    SER B 354      22.382  -1.233  24.488  1.00 29.50           B
ATOM   5595  N    GLN B 355      24.236  -0.096  25.064  1.00 29.47           B
ATOM   5596  CA   GLN B 355      23.475   0.900  25.794  1.00 29.78           B
ATOM   5597  CB   GLN B 355      24.227   1.337  27.057  1.00 33.08           B
ATOM   5598  CG   GLN B 355      24.449   0.245  28.091  1.00 37.90           B
ATOM   5599  CD   GLN B 355      25.421   0.691  29.180  1.00 41.35           B
ATOM   5600  OE1  GLN B 355      26.640   0.756  28.959  1.00 42.13           B
ATOM   5601  NE2  GLN B 355      24.883   1.026  30.355  1.00 42.11           B
ATOM   5602  C    GLN B 355      23.230   2.117  24.896  1.00 29.04           B
ATOM   5603  O    GLN B 355      22.833   3.167  25.389  1.00 29.11           B
ATOM   5604  N    SER B 356      23.439   1.963  23.586  1.00 28.20           B
ATOM   5605  CA   SER B 356      23.247   3.072  22.630  1.00 28.53           B
ATOM   5606  CB   SER B 356      23.499   2.600  21.187  1.00 29.22           B
ATOM   5607  OG   SER B 356      24.878   2.462  20.908  1.00 33.92           B
ATOM   5608  C    SER B 356      21.839   3.659  22.699  1.00 26.91           B
ATOM   5609  O    SER B 356      21.636   4.883  22.644  1.00 26.04           B
ATOM   5610  N    ALA B 357      20.849   2.782  22.801  1.00 24.78           B
ATOM   5611  CA   ALA B 357      19.476   3.240  22.852  1.00 23.09           B
ATOM   5612  CB   ALA B 357      18.707   2.773  21.599  1.00 23.03           B
ATOM   5613  C    ALA B 357      18.795   2.702  24.099  1.00 23.24           B
ATOM   5614  O    ALA B 357      19.167   1.646  24.625  1.00 25.22           B
ATOM   5615  N    ALA B 358      17.825   3.457  24.587  1.00 21.13           B
ATOM   5616  CA   ALA B 358      17.055   3.030  25.747  1.00 21.52           B
ATOM   5617  CB   ALA B 358      17.643   3.649  27.031  1.00 22.50           B
ATOM   5618  C    ALA B 358      15.585   3.402  25.566  1.00 19.54           B
ATOM   5619  O    ALA B 358      15.257   4.451  25.037  1.00 18.37           B
ATOM   5620  N    TYR B 359      14.683   2.527  26.017  1.00 18.21           B
ATOM   5621  CA   TYR B 359      13.259   2.747  25.886  1.00 18.06           B
ATOM   5622  CB   TYR B 359      12.642   1.724  24.919  1.00 17.72           B
ATOM   5623  CG   TYR B 359      13.303   1.776  23.558  1.00 15.03           B
ATOM   5624  CD1  TYR B 359      14.473   1.076  23.300  1.00 16.16           B
ATOM   5625  CE1  TYR B 359      15.151   1.242  22.104  1.00 14.13           B
ATOM   5626  CD2  TYR B 359      12.812   2.648  22.573  1.00 15.69           B
ATOM   5627  CE2  TYR B 359      13.485   2.819  21.379  1.00 13.85           B
ATOM   5628  CZ   TYR B 359      14.633   2.127  21.145  1.00 15.70           B
ATOM   5629  OH   TYR B 359      15.265   2.315  19.935  1.00 16.11           B
ATOM   5630  C    TYR B 359      12.597   2.609  27.235  1.00 19.04           B
ATOM   5631  O    TYR B 359      12.908   1.686  27.992  1.00 19.57           B
ATOM   5632  N    VAL B 360      11.730   3.546  27.545  1.00 17.94           B
ATOM   5633  CA   VAL B 360      11.023   3.501  28.812  1.00 19.18           B
ATOM   5634  CB   VAL B 360      11.276   4.794  29.641  1.00 18.75           B
ATOM   5635  CG1  VAL B 360      10.448   4.742  30.934  1.00 20.25           B
ATOM   5636  CG2  VAL B 360      12.753   4.923  29.937  1.00 19.41           B
ATOM   5637  C    VAL B 360       9.562   3.381  28.501  1.00 19.10           B
ATOM   5638  O    VAL B 360       9.008   4.188  27.753  1.00 19.90           B
ATOM   5639  N    VAL B 361       8.905   2.372  29.069  1.00 19.72           B
ATOM   5640  CA   VAL B 361       7.488   2.188  28.831  1.00 18.92           B
ATOM   5641  CB   VAL B 361       7.216   0.872  28.069  1.00 18.99           B
ATOM   5642  CG1  VAL B 361       5.743   0.769  27.716  1.00 18.31           B
ATOM   5643  CG2  VAL B 361       8.065   0.839  26.786  1.00 17.76           B
ATOM   5644  C    VAL B 361       6.793   2.100  30.167  1.00 19.47           B
ATOM   5645  O    VAL B 361       7.232   1.362  31.038  1.00 16.90           B
ATOM   5646  N    MET B 362       5.737   2.885  30.318  1.00 20.10           B
ATOM   5647  CA   MET B 362       4.962   2.882  31.540  1.00 21.78           B
ATOM   5648  CB   MET B 362       4.226   4.206  31.682  1.00 24.19           B
ATOM   5649  CG   MET B 362       3.918   4.589  33.122  1.00 27.23           B
ATOM   5650  SD   MET B 362       5.405   4.806  34.163  1.00 29.11           B
ATOM   5651  CE   MET B 362       4.575   4.880  35.731  1.00 30.05           B
ATOM   5652  C    MET B 362       3.949   1.731  31.471  1.00 20.28           B
ATOM   5653  O    MET B 362       3.385   1.438  30.410  1.00 19.68           B
ATOM   5654  N    PRO B 363       3.698   1.069  32.599  1.00 20.71           B
ATOM   5655  CD   PRO B 363       4.521   1.025  33.818  1.00 21.21           B
ATOM   5656  CA   PRO B 363       2.729  -0.038  32.579  1.00 20.67           B
ATOM   5657  CB   PRO B 363       3.155  -0.883  33.776  1.00 22.57           B
ATOM   5658  CG   PRO B 363       3.665   0.160  34.754  1.00 22.37           B
ATOM   5659  C    PRO B 363       1.272   0.395  32.672  1.00 22.28           B
ATOM   5660  O    PRO B 363       0.959   1.574  32.811  1.00 18.47           B
ATOM   5661  N    MET B 364       0.368  -0.568  32.537  1.00 23.87           B
ATOM   5662  CA   MET B 364      -1.037  -0.272  32.674  1.00 26.94           B
ATOM   5663  CB   MET B 364      -1.780  -0.391  31.332  1.00 29.59           B
ATOM   5664  CG   MET B 364      -1.636  -1.670  30.568  1.00 31.24           B
ATOM   5665  SD   MET B 364      -2.386  -1.510  28.872  1.00 31.43           B
```

Figure 1 (continued 57)

```
ATOM  5666  CE   MET B 364    -4.155  -1.253  29.308  1.00  32.24  B
ATOM  5667  C    MET B 364    -1.602  -1.218  33.725  1.00  30.19  B
ATOM  5668  O    MET B 364    -0.999  -2.251  34.035  1.00  29.20  B
ATOM  5669  N    ARG B 365    -2.732  -0.836  34.307  1.00  32.96  B
ATOM  5670  CA   ARG B 365    -3.383  -1.655  35.324  1.00  36.74  B
ATOM  5671  CB   ARG B 365    -4.029  -0.756  36.394  1.00  37.59  B
ATOM  5672  CG   ARG B 365    -4.785  -1.490  37.505  1.00  39.77  B
ATOM  5673  CD   ARG B 365    -3.859  -2.316  38.398  1.00  40.23  B
ATOM  5674  NE   ARG B 365    -4.571  -2.956  39.505  1.00  40.59  B
ATOM  5675  CZ   ARG B 365    -3.984  -3.707  40.434  1.00  40.64  B
ATOM  5676  NH1  ARG B 365    -2.678  -3.913  40.385  1.00  41.51  B
ATOM  5677  NH2  ARG B 365    -4.698  -4.247  41.418  1.00  41.53  B
ATOM  5678  C    ARG B 365    -4.459  -2.492  34.648  1.00  39.32  B
ATOM  5679  O    ARG B 365    -5.449  -1.961  34.150  1.00  39.51  B
ATOM  5680  N    LEU B 366    -4.267  -3.801  34.609  1.00  41.59  B
ATOM  5681  CA   LEU B 366    -5.272  -4.665  33.996  1.00  44.25  B
ATOM  5682  CB   LEU B 366    -4.615  -5.908  33.366  1.00  45.24  B
ATOM  5683  CG   LEU B 366    -3.640  -5.701  32.202  1.00  45.46  B
ATOM  5684  CD1  LEU B 366    -4.331  -5.029  31.031  1.00  47.09  B
ATOM  5685  CD2  LEU B 366    -2.489  -4.856  32.678  1.00  46.71  B
ATOM  5686  C    LEU B 366    -6.263  -5.080  35.092  1.00  45.55  B
ATOM  5687  O    LEU B 366    -6.424  -6.296  35.333  1.00  46.32  B
ATOM  5688  OXT  LEU B 366    -6.868  -4.169  35.704  1.00  46.33  B
ATOM  5689  CB   ARG C  10    -5.663   0.205  32.737  0.76  34.47  C
ATOM  5690  CG   ARG C  10    -7.073  -0.397  32.771  0.76  36.85  C
ATOM  5691  CD   ARG C  10    -7.748  -0.383  31.408  0.76  39.56  C
ATOM  5692  NE   ARG C  10    -8.728  -1.462  31.268  0.76  41.14  C
ATOM  5693  CZ   ARG C  10    -9.992  -1.301  30.875  0.76  41.65  C
ATOM  5694  NH1  ARG C  10   -10.464  -0.093  30.582  0.76  41.65  C
ATOM  5695  NH2  ARG C  10   -10.779  -2.365  30.749  0.76  42.22  C
ATOM  5696  C    ARG C  10    -4.106   2.152  32.497  0.76  29.83  C
ATOM  5697  O    ARG C  10    -3.278   1.863  33.369  0.76  26.71  C
ATOM  5698  N    ARG C  10    -6.417   2.186  31.464  0.76  33.45  C
ATOM  5699  CA   ARG C  10    -5.587   1.727  32.625  0.76  31.94  C
ATOM  5700  N    GLN C  11    -3.805   2.853  31.408  0.76  28.04  C
ATOM  5701  CA   GLN C  11    -2.458   3.321  31.094  0.76  25.66  C
ATOM  5702  CB   GLN C  11    -2.423   3.866  29.662  0.76  24.07  C
ATOM  5703  CG   GLN C  11    -1.047   4.361  29.231  0.76  21.39  C
ATOM  5704  CD   GLN C  11    -0.039   3.245  29.174  0.76  22.59  C
ATOM  5705  OE1  GLN C  11    -0.263   2.232  28.494  0.76  19.54  C
ATOM  5706  NE2  GLN C  11     1.082   3.415  29.876  0.76  21.15  C
ATOM  5707  C    GLN C  11    -1.895   4.396  32.038  0.76  25.33  C
ATOM  5708  O    GLN C  11    -2.494   5.467  32.217  0.76  25.97  C
ATOM  5709  N    LEU C  12    -0.732   4.111  32.618  0.76  24.73  C
ATOM  5710  CA   LEU C  12    -0.065   5.046  33.519  0.76  25.25  C
ATOM  5711  CB   LEU C  12     0.754   4.277  34.561  0.76  24.93  C
ATOM  5712  CG   LEU C  12    -0.036   3.305  35.450  0.76  23.68  C
ATOM  5713  CD1  LEU C  12     0.907   2.681  36.468  0.76  25.75  C
ATOM  5714  CD2  LEU C  12    -1.184   4.040  36.153  0.76  25.66  C
ATOM  5715  C    LEU C  12     0.845   5.948  32.680  0.76  25.12  C
ATOM  5716  O    LEU C  12     1.111   5.653  31.510  0.76  25.73  C
ATOM  5717  N    VAL C  13     1.317   7.044  33.273  0.76  25.64  C
ATOM  5718  CA   VAL C  13     2.166   7.987  32.543  0.76  25.65  C
ATOM  5719  CB   VAL C  13     1.473   9.371  32.386  0.76  26.39  C
ATOM  5720  CG1  VAL C  13     0.217   9.239  31.523  0.76  26.34  C
ATOM  5721  CG2  VAL C  13     1.113   9.929  33.750  0.76  26.38  C
ATOM  5722  C    VAL C  13     3.542   8.211  33.174  0.76  26.02  C
ATOM  5723  O    VAL C  13     3.740   8.050  34.381  0.76  24.85  C
ATOM  5724  N    LEU C  14     4.498   8.596  32.339  0.76  26.90  C
ATOM  5725  CA   LEU C  14     5.860   8.846  32.803  0.76  28.40  C
ATOM  5726  CB   LEU C  14     6.836   8.819  31.619  0.76  28.31  C
ATOM  5727  CG   LEU C  14     6.972   7.481  30.889  0.76  29.36  C
ATOM  5728  CD1  LEU C  14     7.666   7.705  29.557  0.76  30.19  C
ATOM  5729  CD2  LEU C  14     7.744   6.495  31.769  0.76  29.17  C
ATOM  5730  C    LEU C  14     6.010  10.186  33.517  0.76  29.12  C
ATOM  5731  O    LEU C  14     5.238  11.126  33.284  0.76  29.91  C
ATOM  5732  N    GLY C  15     7.000  10.263  34.396  0.76  29.70  C
ATOM  5733  CA   GLY C  15     7.264  11.510  35.090  0.76  32.11  C
ATOM  5734  C    GLY C  15     8.263  12.275  34.234  0.76  33.78  C
ATOM  5735  O    GLY C  15     9.472  12.210  34.462  0.76  35.30  C
ATOM  5736  N    LEU C  16     7.750  12.995  33.241  0.76  34.34  C
ATOM  5737  CA   LEU C  16     8.576  13.756  32.306  0.76  34.95  C
ATOM  5738  CB   LEU C  16     7.732  14.157  31.094  0.76  33.39  C
ATOM  5739  CG   LEU C  16     7.258  12.955  30.269  0.76  30.69  C
ATOM  5740  CD1  LEU C  16     6.303  13.411  29.171  0.76  30.83  C
ATOM  5741  CD2  LEU C  16     8.467  12.233  29.690  0.76  31.29  C
ATOM  5742  C    LEU C  16     9.263  14.982  32.898  0.76  35.04  C
ATOM  5743  O    LEU C  16    10.182  15.515  32.231  0.76  36.84  C
ATOM  5744  OXT  LEU C  16     8.870  15.398  34.009  0.76  37.64  C
ATOM  5745  OH2  TIP S   1     4.929 -23.609  18.052  1.00  15.99  S
ATOM  5746  OH2  TIP S   2     4.228  -8.274 -26.027  1.00  13.10  S
ATOM  5747  OH2  TIP S   3    10.558  12.623 -25.084  1.00  15.30  S
ATOM  5748  OH2  TIP S   4     5.227 -21.550  19.916  1.00  15.79  S
ATOM  5749  OH2  TIP S   5     8.098  19.305 -28.222  1.00  16.24  S
ATOM  5750  OH2  TIP S   6    15.241  27.169  -6.212  1.00  15.04  S
ATOM  5751  OH2  TIP S   7    20.667  23.747 -19.701  1.00  12.11  S
ATOM  5752  OH2  TIP S   8     8.057 -16.814  20.553  1.00  18.56  S
ATOM  5753  OH2  TIP S   9    -8.202  -7.752 -28.805  1.00  15.40  S
ATOM  5754  OH2  TIP S  10    -3.188  14.555 -36.202  1.00  15.80  S
ATOM  5755  OH2  TIP S  11    -8.735  18.253 -21.735  1.00  16.46  S
ATOM  5756  OH2  TIP S  12     1.707   0.243  28.691  1.00  19.43  S
ATOM  5757  OH2  TIP S  13    21.827  20.941 -18.878  1.00  15.07  S
ATOM  5758  OH2  TIP S  14   -12.919   1.529 -20.565  1.00  14.60  S
ATOM  5759  OH2  TIP S  15     6.506   7.845 -24.491  1.00  14.11  S
ATOM  5760  OH2  TIP S  16   -16.095 -26.586   6.640  1.00  18.29  S
ATOM  5761  OH2  TIP S  17   -20.810  -5.324 -15.729  1.00  15.06  S
ATOM  5762  OH2  TIP S  18     6.790 -16.969  34.740  1.00  14.72  S
ATOM  5763  OH2  TIP S  19   -28.633 -22.763  -9.122  1.00  19.48  S
ATOM  5764  OH2  TIP S  20    -4.575  19.633 -14.656  1.00  16.85  S
ATOM  5765  OH2  TIP S  21     6.941   2.131  23.109  1.00  18.16  S
```

Figure 1 (continued 58)

```
ATOM   5766  OH2 TIP S  22     -27.660 -14.486 -13.561  1.00 17.12      S
ATOM   5767  OH2 TIP S  23     -13.962  -0.925 -21.605  1.00 14.22      S
ATOM   5768  OH2 TIP S  24       1.435  28.503 -10.938  1.00 18.48      S
ATOM   5769  OH2 TIP S  25       9.366   3.813  23.519  1.00 16.22      S
ATOM   5770  OH2 TIP S  26       6.434 -22.228  22.332  1.00 19.93      S
ATOM   5771  OH2 TIP S  27       7.890 -18.056  18.119  1.00 19.57      S
ATOM   5772  OH2 TIP S  28     -15.000   8.720 -22.814  1.00 14.68      S
ATOM   5773  OH2 TIP S  29      10.776  24.804 -24.045  1.00 16.80      S
ATOM   5774  OH2 TIP S  30       1.778  20.791  -6.653  1.00 17.56      S
ATOM   5775  OH2 TIP S  31       0.621  20.501  -9.333  1.00 18.49      S
ATOM   5776  OH2 TIP S  32       4.572   1.385 -28.353  1.00 18.53      S
ATOM   5777  OH2 TIP S  33       8.530  13.438  21.012  1.00 18.38      S
ATOM   5778  OH2 TIP S  34      -5.364 -34.951  13.172  1.00 16.54      S
ATOM   5779  OH2 TIP S  35      -0.215  -6.534 -30.846  1.00 17.23      S
ATOM   5780  OH2 TIP S  36       3.783  18.454 -29.707  1.00 19.51      S
ATOM   5781  OH2 TIP S  37       3.591  -1.199 -27.445  1.00 19.45      S
ATOM   5782  OH2 TIP S  38       9.369  34.981 -11.888  1.00 20.02      S
ATOM   5783  OH2 TIP S  39      10.133 -20.154  36.900  1.00 17.90      S
ATOM   5784  OH2 TIP S  40       3.793   8.403 -19.080  1.00 16.65      S
ATOM   5785  OH2 TIP S  41      10.939   4.680  14.536  1.00 18.20      S
ATOM   5786  OH2 TIP S  42       8.076  12.297 -25.798  1.00 16.16      S
ATOM   5787  OH2 TIP S  43     -14.372 -32.728   6.563  1.00 18.38      S
ATOM   5788  OH2 TIP S  44     -23.715  -9.227 -23.646  1.00 21.11      S
ATOM   5789  OH2 TIP S  45      20.825  28.255  -9.159  1.00 15.67      S
ATOM   5790  OH2 TIP S  46      -1.109  13.957 -40.824  1.00 17.50      S
ATOM   5791  OH2 TIP S  47       5.330 -27.571  17.233  1.00 20.27      S
ATOM   5792  OH2 TIP S  48      -6.283  -7.101  26.866  1.00 19.83      S
ATOM   5793  OH2 TIP S  49      -4.904  -9.220  29.033  1.00 18.63      S
ATOM   5794  OH2 TIP S  50       6.596  25.027  -2.197  1.00 18.25      S
ATOM   5795  OH2 TIP S  51       3.946 -28.513  19.328  1.00 22.98      S
ATOM   5796  OH2 TIP S  52      18.496  30.057  13.872  1.00 21.35      S
ATOM   5797  OH2 TIP S  53      14.476  13.406 -26.031  1.00 20.88      S
ATOM   5798  OH2 TIP S  54      -5.854  17.119 -30.322  1.00 18.67      S
ATOM   5799  OH2 TIP S  55     -11.444 -12.723  13.885  1.00 21.78      S
ATOM   5800  OH2 TIP S  56     -18.531 -23.945  -2.069  1.00 20.92      S
ATOM   5801  OH2 TIP S  57       8.793  -1.749  36.685  1.00 23.51      S
ATOM   5802  OH2 TIP S  58     -10.518  17.199 -18.634  1.00 19.66      S
ATOM   5803  OH2 TIP S  59      18.320  33.650 -11.778  1.00 23.35      S
ATOM   5804  OH2 TIP S  60       3.811  10.767 -14.624  1.00 21.33      S
ATOM   5805  OH2 TIP S  61      10.630 -17.965  40.549  1.00 20.18      S
ATOM   5806  OH2 TIP S  62       7.563  12.545 -28.560  1.00 22.05      S
ATOM   5807  OH2 TIP S  63      17.504  24.804   2.515  1.00 17.88      S
ATOM   5808  OH2 TIP S  64      11.187   4.750 -21.381  1.00 18.39      S
ATOM   5809  OH2 TIP S  65       3.669  23.465   0.736  1.00 20.78      S
ATOM   5810  OH2 TIP S  66       0.642 -25.439  24.271  1.00 19.92      S
ATOM   5811  OH2 TIP S  67      -5.697 -28.454  21.972  1.00 20.88      S
ATOM   5812  OH2 TIP S  68       4.514  12.181 -28.340  1.00 18.14      S
ATOM   5813  OH2 TIP S  69     -20.340 -23.019  19.925  1.00 21.76      S
ATOM   5814  OH2 TIP S  70       1.000  -3.521  35.944  1.00 23.02      S
ATOM   5815  OH2 TIP S  71       4.561  34.315 -12.922  1.00 19.38      S
ATOM   5816  OH2 TIP S  72     -20.556   2.785 -36.420  1.00 27.46      S
ATOM   5817  OH2 TIP S  73       4.764  -1.117 -32.012  1.00 27.35      S
ATOM   5818  OH2 TIP S  74     -20.786 -26.799  16.978  1.00 21.37      S
ATOM   5819  OH2 TIP S  75      30.429  23.473  16.248  1.00 26.87      S
ATOM   5820  OH2 TIP S  76     -14.593  15.544 -36.291  1.00 26.66      S
ATOM   5821  OH2 TIP S  77      27.307  15.098   1.258  1.00 25.86      S
ATOM   5822  OH2 TIP S  78       5.319   7.976 -32.697  1.00 23.44      S
ATOM   5823  OH2 TIP S  79       8.457 -24.862  15.056  1.00 27.61      S
ATOM   5824  OH2 TIP S  80      -0.400  -9.335  16.470  1.00 23.64      S
ATOM   5825  OH2 TIP S  81     -30.824 -24.685  -8.816  1.00 23.87      S
ATOM   5826  OH2 TIP S  82      -2.412  16.657 -12.786  1.00 22.67      S
ATOM   5827  OH2 TIP S  83     -16.348   6.876 -33.518  1.00 20.01      S
ATOM   5828  OH2 TIP S  84      -4.781  13.922 -43.086  1.00 19.96      S
ATOM   5829  OH2 TIP S  85      22.867  14.713  -4.352  1.00 27.67      S
ATOM   5830  OH2 TIP S  86      14.019  34.958 -17.016  1.00 24.03      S
ATOM   5831  OH2 TIP S  87     -22.863  -7.339  -7.089  1.00 30.51      S
ATOM   5832  OH2 TIP S  88       0.014 -13.197  13.132  1.00 24.07      S
ATOM   5833  OH2 TIP S  89      -0.477 -26.421  26.641  1.00 22.63      S
ATOM   5834  OH2 TIP S  90       8.749   0.467  15.868  1.00 29.65      S
ATOM   5835  OH2 TIP S  91      -6.197  -6.594  19.747  1.00 23.37      S
ATOM   5836  OH2 TIP S  92       7.703   5.467 -24.148  1.00 20.70      S
ATOM   5837  OH2 TIP S  93       1.486 -22.220  27.625  1.00 23.06      S
ATOM   5838  OH2 TIP S  94      -8.748  -9.800  20.699  1.00 22.04      S
ATOM   5839  OH2 TIP S  95     -16.624   1.189 -13.898  1.00 21.62      S
ATOM   5840  OH2 TIP S  96     -17.781  -3.404 -34.492  1.00 24.71      S
ATOM   5841  OH2 TIP S  97      22.028  14.095 -22.382  1.00 22.03      S
ATOM   5842  OH2 TIP S  98       0.850  24.987 -25.136  1.00 29.29      S
ATOM   5843  OH2 TIP S  99       3.761  -8.089  41.138  1.00 24.22      S
ATOM   5844  OH2 TIP S 100       6.060 -19.622  23.723  1.00 20.71      S
ATOM   5845  OH2 TIP S 101     -20.830  -8.439  -5.124  1.00 25.02      S
ATOM   5846  OH2 TIP S 102     -23.978 -22.857 -27.649  1.00 27.37      S
ATOM   5847  OH2 TIP S 103     -19.110 -26.350   4.119  1.00 28.04      S
ATOM   5848  OH2 TIP S 104     -10.419  10.168 -16.512  1.00 20.89      S
ATOM   5849  OH2 TIP S 105      26.620   6.278   5.868  1.00 26.84      S
ATOM   5850  OH2 TIP S 106      15.079 -16.710  41.044  1.00 31.49      S
ATOM   5851  OH2 TIP S 107      -6.608  -4.481  27.748  1.00 21.60      S
ATOM   5852  OH2 TIP S 108     -10.514  -6.785  27.903  1.00 28.76      S
ATOM   5853  OH2 TIP S 109       7.483  34.057 -13.520  1.00 20.71      S
ATOM   5854  OH2 TIP S 110      -6.501 -31.759  -5.806  1.00 31.23      S
ATOM   5855  OH2 TIP S 111      -2.508  -7.957  17.238  1.00 28.35      S
ATOM   5856  OH2 TIP S 112     -16.554   3.360 -34.130  1.00 19.83      S
ATOM   5857  OH2 TIP S 113      -1.472  10.711 -15.764  1.00 27.87      S
ATOM   5858  OH2 TIP S 114     -22.960 -28.887 -19.727  1.00 25.60      S
ATOM   5859  OH2 TIP S 115      15.115 -14.901  19.731  1.00 24.51      S
ATOM   5860  OH2 TIP S 116      -5.148 -33.100  -3.606  1.00 25.41      S
ATOM   5861  OH2 TIP S 117      20.099  -0.396  23.402  1.00 22.68      S
ATOM   5862  OH2 TIP S 118      -7.111  -2.117 -16.703  1.00 24.27      S
ATOM   5863  OH2 TIP S 119     -11.193  -9.224  19.755  1.00 25.30      S
ATOM   5864  OH2 TIP S 120      18.193 -11.449  36.973  1.00 27.57      S
ATOM   5865  OH2 TIP S 121     -22.357   2.771 -13.647  1.00 25.49      S
```

Figure 1 (continued 59)

```
ATOM   5866  OH2 TIP S 123      20.077  32.381  13.831  1.00 28.68    S
ATOM   5867  OH2 TIP S 124     -17.741   4.784 -15.367  1.00 27.89    S
ATOM   5868  OH2 TIP S 125       4.106 -14.005  15.492  1.00 25.37    S
ATOM   5869  OH2 TIP S 126      13.838  16.125 -26.991  1.00 25.20    S
ATOM   5870  OH2 TIP S 127      -2.287 -34.498   8.522  1.00 26.09    S
ATOM   5871  OH2 TIP S 128     -11.663  -6.092  22.298  1.00 28.13    S
ATOM   5872  OH2 TIP S 129      11.561  18.821 -28.755  1.00 36.46    S
ATOM   5873  OH2 TIP S 130       7.031   1.863 -26.963  1.00 26.76    S
ATOM   5874  OH2 TIP S 131       6.205 -28.726   8.902  1.00 29.30    S
ATOM   5875  OH2 TIP S 132     -10.559  19.568 -19.983  1.00 20.77    S
ATOM   5876  OH2 TIP S 133      22.972  19.220 -17.034  1.00 20.45    S
ATOM   5877  OH2 TIP S 134       5.249  21.787   8.628  1.00 29.10    S
ATOM   5878  OH2 TIP S 135      16.410  14.232  27.045  1.00 27.03    S
ATOM   5879  OH2 TIP S 136      -3.218 -34.687  11.046  1.00 24.07    S
ATOM   5880  OH2 TIP S 137      24.833  28.261 -21.884  1.00 22.96    S
ATOM   5881  OH2 TIP S 138      13.264  35.476 -14.774  1.00 30.23    S
ATOM   5882  OH2 TIP S 139      -2.053   2.392  26.549  1.00 25.03    S
ATOM   5883  OH2 TIP S 140      11.605  15.067   0.133  1.00 34.22    S
ATOM   5884  OH2 TIP S 141      13.972  24.010  19.832  1.00 25.81    S
ATOM   5885  OH2 TIP S 142     -19.355 -25.503  19.026  1.00 29.46    S
ATOM   5886  OH2 TIP S 143      -4.006 -31.965   2.763  1.00 26.41    S
ATOM   5887  OH2 TIP S 144      15.901  28.652  -2.514  1.00 25.23    S
ATOM   5888  OH2 TIP S 145     -17.355 -32.497  18.572  1.00 25.07    S
ATOM   5889  OH2 TIP S 146       0.958 -13.688  32.466  1.00 22.13    S
ATOM   5890  OH2 TIP S 147      -6.459  12.128 -44.255  1.00 32.10    S
ATOM   5891  OH2 TIP S 148      -0.707 -24.653   2.977  1.00 26.54    S
ATOM   5892  OH2 TIP S 149     -12.838 -12.951  11.427  1.00 23.90    S
ATOM   5893  OH2 TIP S 150     -24.404 -11.780 -24.495  1.00 25.54    S
ATOM   5894  OH2 TIP S 151       0.539  -6.289 -33.601  1.00 29.88    S
ATOM   5895  OH2 TIP S 152     -13.161 -28.396  -0.606  1.00 27.46    S
ATOM   5896  OH2 TIP S 153      10.877   9.824   5.701  1.00 24.98    S
ATOM   5897  OH2 TIP S 154     -24.429 -25.832   1.552  1.00 29.48    S
ATOM   5898  OH2 TIP S 155       9.976  29.261   3.159  1.00 26.39    S
ATOM   5899  OH2 TIP S 156      -8.594  -7.245 -13.161  1.00 38.12    S
ATOM   5900  OH2 TIP S 157       2.066  24.920   5.025  1.00 22.77    S
ATOM   5901  OH2 TIP S 158     -15.909  14.296 -28.353  1.00 25.22    S
ATOM   5902  OH2 TIP S 159       0.091  16.467 -11.319  1.00 24.31    S
ATOM   5903  OH2 TIP S 160      16.526 -12.797  18.583  1.00 26.81    S
ATOM   5904  OH2 TIP S 161       3.049   7.864  19.831  1.00 24.57    S
ATOM   5905  OH2 TIP S 162      21.865  -8.253  21.271  1.00 23.66    S
ATOM   5906  OH2 TIP S 163      -7.960  -6.892 -33.834  1.00 30.32    S
ATOM   5907  OH2 TIP S 164      19.362 -16.854  36.055  1.00 31.05    S
ATOM   5908  OH2 TIP S 165      -5.308 -32.390  18.952  1.00 29.57    S
ATOM   5909  OH2 TIP S 166     -11.933 -29.026  -5.229  1.00 26.58    S
ATOM   5910  OH2 TIP S 167     -19.093 -31.089  17.480  1.00 33.54    S
ATOM   5911  OH2 TIP S 168      14.092  18.448 -25.956  1.00 29.46    S
ATOM   5912  OH2 TIP S 169      10.876   5.438  12.054  1.00 32.82    S
ATOM   5913  OH2 TIP S 170      -6.890  -9.072 -26.532  1.00 25.62    S
ATOM   5914  OH2 TIP S 171      29.867  28.203  18.182  1.00 30.29    S
ATOM   5915  OH2 TIP S 172      16.406  39.004   9.209  1.00 28.96    S
ATOM   5916  OH2 TIP S 173      -4.013 -11.245  30.748  1.00 25.90    S
ATOM   5917  OH2 TIP S 174     -26.979 -31.890  -8.368  1.00 36.88    S
ATOM   5918  OH2 TIP S 175     -23.390   1.597 -33.916  1.00 36.95    S
ATOM   5919  OH2 TIP S 176     -21.827 -20.068  21.374  1.00 28.64    S
ATOM   5920  OH2 TIP S 177     -17.123 -16.612   7.118  1.00 25.01    S
ATOM   5921  OH2 TIP S 178      -0.586  30.510 -11.769  1.00 23.24    S
ATOM   5922  OH2 TIP S 179       6.159  20.259  17.337  1.00 30.73    S
ATOM   5923  OH2 TIP S 180      21.260  -1.762  19.163  1.00 34.09    S
ATOM   5924  OH2 TIP S 181      -2.864 -28.282   2.753  1.00 27.53    S
ATOM   5925  OH2 TIP S 182      -8.835 -11.179  -6.743  1.00 29.61    S
ATOM   5926  OH2 TIP S 183      15.829  24.884 -23.368  1.00 31.33    S
ATOM   5927  OH2 TIP S 184      24.002  17.831 -10.733  1.00 29.65    S
ATOM   5928  OH2 TIP S 185     -29.401   5.440 -14.949  1.00 32.48    S
ATOM   5929  OH2 TIP S 186      -1.383 -33.459  19.317  1.00 29.25    S
ATOM   5930  OH2 TIP S 187      12.063 -19.966  25.080  1.00 25.65    S
ATOM   5931  OH2 TIP S 188      -4.351  -9.679 -26.788  1.00 27.17    S
ATOM   5932  OH2 TIP S 189       3.729   5.832  16.486  1.00 34.24    S
ATOM   5933  OH2 TIP S 190       9.565  37.434  -9.975  1.00 27.30    S
ATOM   5934  OH2 TIP S 191       1.483  14.975 -40.508  1.00 31.36    S
ATOM   5935  OH2 TIP S 192      -6.648 -10.961 -20.165  1.00 32.28    S
ATOM   5936  OH2 TIP S 193       3.745  12.221  31.113  1.00 29.48    S
ATOM   5937  OH2 TIP S 194       2.400 -29.701 -15.849  1.00 26.51    S
ATOM   5938  OH2 TIP S 195       1.145 -29.287  18.977  1.00 27.97    S
ATOM   5939  OH2 TIP S 196       1.173  24.321 -30.127  1.00 37.69    S
ATOM   5940  OH2 TIP S 197     -28.254 -20.580   5.716  1.00 43.95    S
ATOM   5941  OH2 TIP S 198      22.283  20.039  25.715  1.00 34.76    S
ATOM   5942  OH2 TIP S 199      -1.895   4.664 -43.775  1.00 27.75    S
ATOM   5943  OH2 TIP S 200      23.429  31.198 -15.860  1.00 32.99    S
ATOM   5944  OH2 TIP S 201      -9.479  -5.901 -15.419  1.00 21.16    S
ATOM   5945  OH2 TIP S 202     -12.878   0.162 -12.723  1.00 33.84    S
ATOM   5946  OH2 TIP S 203       5.581  19.187  14.793  1.00 27.97    S
ATOM   5947  OH2 TIP S 204     -23.954 -24.578  -2.262  1.00 30.51    S
ATOM   5948  OH2 TIP S 205       3.457  33.211 -23.268  1.00 31.98    S
ATOM   5949  OH2 TIP S 206     -17.263   0.457 -42.268  1.00 31.49    S
ATOM   5950  OH2 TIP S 207      16.260  31.888   2.413  1.00 23.24    S
ATOM   5951  OH2 TIP S 208      -4.320   1.145  26.565  1.00 29.33    S
ATOM   5952  OH2 TIP S 209     -19.947   2.160 -11.744  1.00 38.41    S
ATOM   5953  OH2 TIP S 210       1.872  26.689 -27.041  1.00 29.78    S
ATOM   5954  OH2 TIP S 211     -13.714  23.099 -13.845  1.00 33.77    S
ATOM   5955  OH2 TIP S 212       9.218  35.580 -19.331  1.00 29.22    S
ATOM   5956  OH2 TIP S 213      -0.219  26.259   5.173  1.00 31.76    S
ATOM   5957  OH2 TIP S 214      -8.272   3.938 -13.966  1.00 35.25    S
ATOM   5958  OH2 TIP S 215       9.984 -22.548  31.867  1.00 33.85    S
ATOM   5959  OH2 TIP S 216     -30.386 -28.425   2.476  1.00 30.05    S
ATOM   5960  OH2 TIP S 217       5.272  16.545 -36.105  1.00 33.30    S
ATOM   5961  OH2 TIP S 218     -14.957  -2.170 -39.231  1.00 30.96    S
ATOM   5962  OH2 TIP S 219       2.136 -28.546  23.097  1.00 39.83    S
ATOM   5963  OH2 TIP S 220       0.866  11.873  23.871  1.00 32.14    S
ATOM   5964  OH2 TIP S 221      -7.469  -8.003 -23.367  1.00 24.79    S
ATOM   5965  OH2 TIP S 222      10.219   6.251  34.646  1.00 37.06    S
```

Figure 1 (continued 60)

```
ATOM  5966  OH2 TIP S 223    9.603 -19.191  12.099  1.00 30.03  S
ATOM  5967  OH2 TIP S 224   15.592   1.270  14.898  1.00 29.33  S
ATOM  5968  OH2 TIP S 225   -7.625 -22.611 -22.802  1.00 32.63  S
ATOM  5969  OH2 TIP S 226  -30.236 -24.968 -11.543  1.00 24.51  S
ATOM  5970  OH2 TIP S 227  -11.748 -27.136  28.999  1.00 35.80  S
ATOM  5971  OH2 TIP S 228  -17.912 -19.364  23.072  1.00 31.69  S
ATOM  5972  OH2 TIP S 229  -12.001   4.279 -15.335  1.00 28.59  S
ATOM  5973  OH2 TIP S 230   27.573  31.316  11.831  1.00 32.14  S
ATOM  5974  OH2 TIP S 231  -25.350   3.037 -21.957  1.00 30.50  S
ATOM  5975  OH2 TIP S 232   -9.948  19.698 -27.138  1.00 32.26  S
ATOM  5976  OH2 TIP S 233   31.351  11.309  12.566  1.00 40.60  S
ATOM  5977  OH2 TIP S 234    7.345   8.147  -8.973  1.00 40.15  S
ATOM  5978  OH2 TIP S 235   13.323  25.650 -24.378  1.00 28.39  S
ATOM  5979  OH2 TIP S 236   14.326 -23.002  38.347  1.00 44.20  S
ATOM  5980  OH2 TIP S 237   18.205  35.226 -19.376  1.00 36.69  S
ATOM  5981  OH2 TIP S 238    7.073   7.343 -21.458  1.00 26.18  S
ATOM  5982  OH2 TIP S 239    6.134 -17.380  11.852  1.00 34.32  S
ATOM  5983  OH2 TIP S 240   -6.807   3.536 -42.001  1.00 25.28  S
ATOM  5984  OH2 TIP S 241  -24.937 -17.863 -25.603  1.00 32.04  S
ATOM  5985  OH2 TIP S 242  -17.088 -21.664 -30.797  1.00 30.50  S
ATOM  5986  OH2 TIP S 243    6.771  -7.663  14.406  1.00 36.01  S
ATOM  5987  OH2 TIP S 244  -27.706 -30.578  -5.708  1.00 47.96  S
ATOM  5988  OH2 TIP S 245  -21.059  10.316 -25.562  1.00 35.65  S
ATOM  5989  OH2 TIP S 246   10.606  28.216 -25.525  1.00 29.43  S
ATOM  5990  OH2 TIP S 247    1.528   5.171  -7.593  1.00 27.85  S
ATOM  5991  OH2 TIP S 248  -29.012 -18.667 -20.134  1.00 33.27  S
ATOM  5992  OH2 TIP S 249  -21.413 -24.799   4.888  1.00 34.44  S
ATOM  5993  OH2 TIP S 250    1.196  -8.297 -29.245  1.00 27.57  S
ATOM  5994  OH2 TIP S 251   -0.162 -13.772  35.108  1.00 36.60  S
ATOM  5995  OH2 TIP S 252   19.156 -15.454  21.696  1.00 29.04  S
ATOM  5996  OH2 TIP S 253   21.723  17.101 -18.745  1.00  9.13  S
ATOM  5997  OH2 TIP S 254    7.667   9.573 -26.321  1.00 15.05  S
ATOM  5998  OH2 TIP S 255    5.459   9.537 -28.155  1.00 14.20  S
ATOM  5999  OH2 TIP S 256    7.583 -20.372  19.535  1.00 17.45  S
ATOM  6000  OH2 TIP S 257    8.434   5.091 -21.601  1.00 20.19  S
ATOM  6001  OH2 TIP S 258   10.303 -20.727  39.479  1.00 21.19  S
ATOM  6002  OH2 TIP S 259   23.351  15.777 -20.932  1.00 24.25  S
ATOM  6003  OH2 TIP S 260    8.255 -19.223  21.937  1.00 16.91  S
ATOM  6004  OH2 TIP S 261    7.407  21.555 -29.683  1.00 18.42  S
ATOM  6005  OH2 TIP S 262    0.133 -33.614   9.571  1.00 23.67  S
ATOM  6006  OH2 TIP S 263    1.067  23.311 -27.412  1.00 26.04  S
ATOM  6007  OH2 TIP S 264   10.172 -20.657  23.070  1.00 20.75  S
ATOM  6008  OH2 TIP S 265    5.434   1.347 -31.078  1.00 25.19  S
ATOM  6009  OH2 TIP S 266    6.473   8.791 -30.462  1.00 22.73  S
ATOM  6010  OH2 TIP S 267   16.690 -16.534  21.428  1.00 23.86  S
ATOM  6011  OH2 TIP S 268   -7.886  21.056 -13.245  1.00 26.88  S
ATOM  6012  OH2 TIP S 269   12.771  20.121 -27.176  1.00 33.96  S
ATOM  6013  OH2 TIP S 270  -17.226   9.555 -21.614  1.00 26.62  S
ATOM  6014  OH2 TIP S 271   -2.213  14.948 -43.167  1.00 24.56  S
ATOM  6015  OH2 TIP S 272    9.664   5.525 -25.968  1.00 25.69  S
ATOM  6016  OH2 TIP S 273    6.917 -25.402  17.512  1.00 27.80  S
ATOM  6017  OH2 TIP S 274   -4.242 -20.885  28.965  1.00 32.23  S
ATOM  6018  OH2 TIP S 275  -17.221 -17.062  17.975  1.00 28.09  S
ATOM  6019  OH2 TIP S 276   12.668  11.417 -26.228  1.00 27.75  S
ATOM  6020  OH2 TIP S 277   10.299   1.950  14.305  1.00 27.65  S
ATOM  6021  OH2 TIP S 278  -31.806 -30.359  -6.948  1.00 57.47  S
ATOM  6022  OH2 TIP S 279  -26.463   4.339  -9.507  1.00 29.65  S
ATOM  6023  OH2 TIP S 280  -26.015 -34.574  -7.677  1.00 26.06  S
ATOM  6024  OH2 TIP S 281  -31.347   5.379 -17.218  1.00 33.42  S
ATOM  6025  OH2 TIP S 282   14.453 -16.744  17.668  1.00 30.41  S
ATOM  6026  OH2 TIP S 283   27.710   8.976   5.055  1.00 26.81  S
ATOM  6027  OH2 TIP S 284    2.896   8.795 -16.720  1.00 27.99  S
ATOM  6028  OH2 TIP S 285   -9.100  19.482 -24.203  1.00 25.80  S
ATOM  6029  OH2 TIP S 286   -2.579   1.667  21.500  1.00 29.60  S
ATOM  6030  OH2 TIP S 287    6.335  11.378 -31.555  1.00 29.71  S
ATOM  6031  OH2 TIP S 288   12.371 -16.564  41.802  1.00 31.26  S
ATOM  6032  OH2 TIP S 289    0.360 -29.275  21.468  1.00 31.50  S
ATOM  6033  OH2 TIP S 290   -2.645   4.725  26.240  1.00 33.72  S
ATOM  6034  OH2 TIP S 291   19.718  -0.267  20.338  1.00 32.39  S
ATOM  6035  OH2 TIP S 292    7.034  29.199   9.979  1.00 29.78  S
ATOM  6036  OH2 TIP S 293   -4.995  20.991 -12.507  1.00 34.58  S
ATOM  6037  OH2 TIP S 294  -28.086 -24.068 -26.481  1.00 30.52  S
ATOM  6038  OH2 TIP S 295    4.690  32.380 -25.768  1.00 32.16  S
ATOM  6039  OH2 TIP S 296   12.183  37.736  -9.852  1.00 32.44  S
ATOM  6040  OH2 TIP S 297   -0.897  -9.935 -28.834  1.00 28.74  S
ATOM  6041  OH2 TIP S 298   -5.666 -26.946  -3.776  1.00 35.30  S
ATOM  6042  OH2 TIP S 299  -19.121 -17.609  23.997  1.00 30.20  S
ATOM  6043  OH2 TIP S 300   11.846   2.521 -20.488  1.00 34.76  S
ATOM  6044  OH2 TIP S 301   21.299   6.735  24.995  1.00 37.00  S
ATOM  6045  OH2 TIP S 302  -23.638 -27.161  16.432  1.00 29.19  S
ATOM  6046  OH2 TIP S 303    1.556  -0.845 -22.820  1.00 34.60  S
ATOM  6047  OH2 TIP S 304  -12.057 -30.800  -2.592  1.00 30.84  S
ATOM  6048  OH2 TIP S 305   16.694 -19.967  30.452  1.00 32.66  S
ATOM  6049  OH2 TIP S 306    0.157  25.634  -7.191  1.00 32.17  S
ATOM  6050  OH2 TIP S 307   -0.449  27.840 -20.073  1.00 29.18  S
ATOM  6051  OH2 TIP S 308   21.819   3.025   9.910  1.00 41.68  S
ATOM  6052  OH2 TIP S 309  -15.005 -11.439 -28.535  1.00 38.02  S
ATOM  6053  OH2 TIP S 310  -21.942 -31.716  -8.240  1.00 33.01  S
ATOM  6054  OH2 TIP S 311   -8.284 -25.125 -23.593  1.00 41.18  S
ATOM  6055  OH2 TIP S 312    2.515   4.002 -33.125  1.00 26.47  S
ATOM  6056  OH2 TIP S 313  -18.335  13.849 -29.235  1.00 30.43  S
ATOM  6057  OH2 TIP S 314  -12.912  -8.449  21.566  1.00 30.42  S
ATOM  6058  OH2 TIP S 315   -1.397 -26.362   1.310  1.00 33.91  S
ATOM  6059  OH2 TIP S 316    9.366 -22.526  35.732  1.00 30.66  S
ATOM  6060  OH2 TIP S 317  -25.401 -30.023  -8.998  1.00 29.44  S
ATOM  6061  OH2 TIP S 318  -21.887   3.702 -34.234  1.00 36.98  S
ATOM  6062  OH2 TIP S 319   -8.700 -20.782 -24.886  1.00 32.89  S
ATOM  6063  OH2 TIP S 320  -20.333 -29.925  -6.872  1.00 34.64  S
ATOM  6064  OH2 TIP S 321   -7.827 -13.241 -33.387  1.00 32.71  S
ATOM  6065  OH2 TIP S 322   14.750  31.182   9.293  1.00 31.66  S
```

```
ATOM   6066  OH2 TIP S 323    -24.400 -19.167  20.554  1.00 30.46   S
ATOM   6067  OH2 TIP S 324     -9.584   3.692 -42.248  1.00 33.30   S
ATOM   6068  OH2 TIP S 325      6.014  19.032 -31.179  1.00 40.38   S
ATOM   6069  OH2 TIP S 326    -13.974 -30.622  -5.965  1.00 32.26   S
ATOM   6070  OH2 TIP S 327    -29.857 -10.593  -7.579  1.00 34.80   S
ATOM   6071  OH2 TIP S 328     12.690  33.497 -20.379  1.00 34.07   S
ATOM   6072  OH2 TIP S 329      7.069   2.658 -20.988  1.00 28.88   S
ATOM   6073  OH2 TIP S 330     12.019  -0.360  36.086  1.00 26.34   S
ATOM   6074  OH2 TIP S 331    -22.705   5.938 -14.330  1.00 34.70   S
ATOM   6075  OH2 TIP S 332      8.097  14.122  -2.649  1.00 39.46   S
ATOM   6076  OH2 TIP S 333    -21.898 -21.927   4.044  1.00 37.81   S
ATOM   6077  OH2 TIP S 334      9.937 -17.771  16.216  1.00 29.70   S
ATOM   6078  OH2 TIP S 335    -16.221  -6.845 -33.678  1.00 33.31   S
ATOM   6079  OH2 TIP S 336     -3.494 -22.898 -17.063  1.00 31.83   S
ATOM   6080  OH2 TIP S 337    -22.157   5.573 -30.240  1.00 39.35   S
ATOM   6081  OH2 TIP S 338     -7.617 -32.398  -8.188  1.00 30.34   S
ATOM   6082  OH2 TIP S 339     23.475  29.150  -8.430  1.00 36.32   S
ATOM   6083  OH2 TIP S 340     -7.276  -9.187 -35.186  1.00 41.69   S
ATOM   6084  OH2 TIP S 341     26.845  32.870   8.481  1.00 37.63   S
ATOM   6085  OH2 TIP S 342    -12.192  21.236 -21.321  1.00 30.21   S
ATOM   6086  OH2 TIP S 343    -14.628 -35.461  19.832  1.00 35.16   S
ATOM   6087  OH2 TIP S 344     -5.653 -31.128  21.101  1.00 34.25   S
ATOM   6088  OH2 TIP S 345     -6.084  -8.172 -19.496  1.00 36.21   S
ATOM   6089  OH2 TIP S 346     27.089  28.347   6.056  1.00 42.19   S
ATOM   6090  OH2 TIP S 347     17.043  22.284 -26.012  1.00 32.12   S
ATOM   6091  OH2 TIP S 348    -21.277   2.842 -26.424  1.00 36.86   S
ATOM   6092  OH2 TIP S 349    -23.886 -14.574 -31.320  1.00 39.26   S
ATOM   6093  OH2 TIP S 350      5.980  19.532  10.965  1.00 26.13   S
ATOM   6094  OH2 TIP S 351     15.574  -9.666  16.201  1.00 35.41   S
ATOM   6095  OH2 TIP S 352    -20.467 -13.308  -4.732  1.00 35.05   S
ATOM   6096  OH2 TIP S 353      3.368  14.285  32.732  1.00 36.22   S
ATOM   6097  OH2 TIP S 354     -7.181  18.881 -31.723  1.00 38.24   S
ATOM   6098  OH2 TIP S 355    -28.089 -22.839 -28.744  1.00 37.10   S
ATOM   6099  OH2 TIP S 356     20.976  15.824 -10.665  1.00 30.49   S
ATOM   6100  OH2 TIP S 357    -28.758 -11.680 -18.762  1.00 30.24   S
ATOM   6101  OH2 TIP S 358      7.259  27.237  24.216  1.00 43.84   S
ATOM   6102  OH2 TIP S 359     -1.640  22.549  -9.537  1.00 31.98   S
ATOM   6103  OH2 TIP S 360     -4.918 -24.935 -15.685  1.00 38.37   S
ATOM   6104  OH2 TIP S 361      4.941  -2.575  16.309  1.00 33.12   S
ATOM   6105  OH2 TIP S 362      9.096 -17.304  13.805  1.00 34.53   S
ATOM   6106  OH2 TIP S 363     -5.045  -8.870  15.785  1.00 34.10   S
ATOM   6107  OH2 TIP S 364     17.874   2.521  14.615  1.00 31.53   S
ATOM   6108  OH2 TIP S 365    -10.159 -16.244 -28.446  1.00 34.86   S
ATOM   6109  OH2 TIP S 366      4.946   7.818 -15.134  1.00 36.25   S
ATOM   6110  OH2 TIP S 367     -6.685 -11.153  14.460  1.00 34.00   S
ATOM   6111  OH2 TIP S 368     14.487 -20.336  24.009  1.00 40.57   S
ATOM   6112  OH2 TIP S 369     -1.563   6.524 -45.958  1.00 34.28   S
ATOM   6113  OH2 TIP S 370      0.375   7.077  23.000  1.00 39.83   S
ATOM   6114  OH2 TIP S 371     17.591  31.139   0.347  1.00 42.33   S
ATOM   6115  OH2 TIP S 372    -16.867  13.392 -37.376  1.00 41.73   S
ATOM   6116  OH2 TIP S 373    -12.567   7.824 -44.159  1.00 41.23   S
ATOM   6117  OH2 TIP S 374     26.381  23.140 -10.721  1.00 31.69   S
ATOM   6118  OH2 TIP S 375      9.272  35.080   2.703  1.00 40.85   S
ATOM   6119  OH2 TIP S 376      9.264   3.347  41.197  1.00 40.96   S
ATOM   6120  OH2 TIP S 377     25.188  14.056  27.610  1.00 34.17   S
ATOM   6121  OH2 TIP S 378      5.411  -5.742  41.987  1.00 42.27   S
ATOM   6122  OH2 TIP S 379    -11.338  22.385 -17.862  1.00 32.59   S
ATOM   6123  OH2 TIP S 380    -20.579  13.226 -28.071  1.00 32.84   S
ATOM   6124  OH2 TIP S 381      8.683   9.553   3.945  1.00 34.93   S
ATOM   6125  OH2 TIP S 382      0.828  11.135 -13.934  1.00 42.23   S
ATOM   6126  OH2 TIP S 383    -21.600 -31.698 -19.564  1.00 38.49   S
ATOM   6127  OH2 TIP S 384     21.597  31.274  15.485  1.00 35.82   S
ATOM   6128  OH2 TIP S 385     12.268  35.903   4.587  1.00 31.57   S
ATOM   6129  OH2 TIP S 386    -10.826  21.324 -11.527  1.00 38.64   S
ATOM   6130  OH2 TIP S 387     20.994  17.489  -8.086  1.00 40.11   S
ATOM   6131  OH2 TIP S 388    -18.148  20.285 -26.433  1.00 31.64   S
ATOM   6132  OH2 TIP S 389     18.469  17.950  25.908  1.00 38.40   S
ATOM   6133  OH2 TIP S 390    -17.756   2.318 -44.136  1.00 37.68   S
ATOM   6134  OH2 TIP S 391     23.292  -5.751  18.962  1.00 37.56   S
ATOM   6135  OH2 TIP S 392     -5.798   2.354 -16.069  1.00 37.13   S
ATOM   6136  OH2 TIP S 393      2.260  -2.829 -24.110  1.00 34.35   S
ATOM   6137  OH2 TIP S 394     -1.341   7.648 -15.393  1.00 33.61   S
ATOM   6138  OH2 TIP S 395     14.575   6.039 -16.208  1.00 33.64   S
ATOM   6139  OH2 TIP S 396     21.269  15.381  -6.817  1.00 40.16   S
ATOM   6140  OH2 TIP S 397     11.903  28.956   0.420  1.00 35.70   S
ATOM   6141  OH2 TIP S 398      8.524 -21.963  24.816  1.00 30.69   S
ATOM   6142  OH2 TIP S 399    -19.214 -17.096  20.987  1.00 39.79   S
ATOM   6143  OH2 TIP S 400    -30.167 -21.541  -5.640  1.00 38.19   S
ATOM   6144  OH2 TIP S 401      9.901   9.176   7.979  1.00 37.49   S
ATOM   6145  OH2 TIP S 402     -4.981 -29.566   1.767  1.00 34.27   S
ATOM   6146  OH2 TIP S 403     22.136  13.679  -1.917  1.00 36.13   S
ATOM   6147  OH2 TIP S 404    -13.420  -2.821  26.291  1.00 31.35   S
ATOM   6148  OH2 TIP S 405    -21.015 -10.324  -1.067  1.00 35.17   S
ATOM   6149  OH2 TIP S 406      4.107 -17.741  35.320  1.00 29.07   S
ATOM   6150  OH2 TIP S 407     20.599  24.525  23.153  1.00 39.40   S
ATOM   6151  OH2 TIP S 408    -29.430  -5.137 -24.806  1.00 31.71   S
ATOM   6152  OH2 TIP S 409      6.574  17.571  29.465  1.00 37.78   S
ATOM   6153  OH2 TIP S 410     25.806  21.628  -4.370  1.00 39.24   S
ATOM   6154  OH2 TIP S 411    -18.143 -31.597 -26.039  1.00 38.21   S
ATOM   6155  OH2 TIP S 412     -1.328  25.281 -12.054  1.00 31.58   S
ATOM   6156  OH2 TIP S 413      0.344  10.818  20.777  1.00 42.29   S
ATOM   6157  OH2 TIP S 414    -18.150 -29.804 -21.191  1.00 35.29   S
ATOM   6158  OH2 TIP S 415    -23.823  -3.528 -33.040  1.00 40.40   S
ATOM   6159  OH2 TIP S 416      1.739   1.943  19.314  1.00 36.07   S
ATOM   6160  OH2 TIP S 417    -27.131 -17.300 -23.592  1.00 38.57   S
ATOM   6161  OH2 TIP S 418     17.275   0.759  18.671  1.00 31.62   S
ATOM   6162  OH2 TIP S 419      0.007  26.223  -9.446  1.00 41.38   S
ATOM   6163  OH2 TIP S 420    -13.181 -10.416  10.475  1.00 37.29   S
ATOM   6164  OH2 TIP S 421    -18.110  16.629 -32.614  1.00 36.54   S
ATOM   6165  OH2 TIP S 422      7.358  26.526  17.628  1.00 39.18   S
```

Figure 1 (continued 62)

```
ATOM   6166  OH2 TIP S 423      17.448 -14.531  17.011  1.00 35.91      S
ATOM   6167  OH2 TIP S 424     -10.700 -26.518  31.162  1.00 35.06      S
ATOM   6168  OH2 TIP S 425      -9.328  -9.491  -8.639  1.00 37.90      S
ATOM   6169  OH2 TIP S 426     -17.105 -29.156 -14.203  1.00 24.63      S
ATOM   6170  OH2 TIP S 427       5.332  11.493  13.731  1.00 37.93      S
ATOM   6171  OH2 TIP S 428       6.050   9.224  14.792  1.00 30.75      S
ATOM   6172  OH2 TIP S 429       4.345  13.808  15.393  1.00 29.44      S
ATOM   6173  OH2 TIP S 430       8.193  12.380  12.091  1.00 21.45      S
ATOM   6174  OH2 TIP S 431     -28.556 -20.447 -15.197  1.00 37.37      S
ATOM   6175  OH2 TIP S 432      12.135  28.679  16.661  1.00 40.91      S
ATOM   6176  OH2 TIP S 433       6.265  25.002  26.462  1.00 33.19      S
ATOM   6177  OH2 TIP S 434      -2.131 -25.697  31.299  1.00 31.13      S
ATOM   6178  OH2 TIP S 435      -5.343 -20.243  26.687  1.00 32.69      S
ATOM   6179  OH2 TIP S 436     -24.850 -28.762  -6.570  1.00 37.97      S
ATOM   6180  OH2 TIP S 437     -22.436   0.184 -22.971  1.00 44.02      S
ATOM   6181  OH2 TIP S 438       1.275  22.882 -25.085  1.00 48.03      S
ATOM   6182  OH2 TIP S 439       7.058  13.884  -6.158  1.00 31.71      S
ATOM   6183  OH2 TIP S 440      13.032  24.424  22.464  1.00 39.78      S
ATOM   6184  OH2 TIP S 441      20.078  26.105  19.324  1.00 31.16      S
ATOM   6185  OH2 TIP S 442       4.931 -19.598  38.096  1.00 32.92      S
ATOM   6186  OH2 TIP S 443      -5.576 -22.456  27.255  1.00 65.54      S
ATOM   6187  OH2 TIP S 444      22.214  -2.644  27.541  1.00 35.37      S
ATOM   6188  OH2 TIP S 445      20.892   5.709  27.304  1.00 39.35      S
END
```

Figure 1 (continued 63)

SEQUENCE LISTING

```
<160> NUMBER OF SEQ ID NOS: 4

<210> SEQ ID NO 1
<211> LENGTH: 16
<212> TYPE: PRT
<213> ORGANISM: Escherichia coli

<400> SEQUENCE: 1

Val Thr Leu Leu Asp Pro Gln Met Glu Arg Gln Leu Val Leu Gly Leu
1               5                   10                  15

<210> SEQ ID NO 2
<211> LENGTH: 22
<212> TYPE: PRT
<213> ORGANISM: Artificial sequence
<220> FEATURE:
<223> OTHER INFORMATION: Control peptide

<400> SEQUENCE: 2

Arg Pro Val Lys Val Thr Pro Asn Gly Ala Glu Asp Glu Ser Ala Glu
1               5                   10                  15

Ala Phe Pro Leu Glu Phe
            20
```

```
<210> SEQ ID NO 3
<211> LENGTH: 30
<212> TYPE: DNA
<213> ORGANISM: Artificial sequence
<220> FEATURE:
<223> OTHER INFORMATION: Primer for replication assay

<400> SEQUENCE: 3
gtaaaacgac ggccagtgcc aagcttagtc                                              30

<210> SEQ ID NO 4
<211> LENGTH: 90
<212> TYPE: DNA
<213> ORGANISM: Artificial sequence
<220> FEATURE:
<223> OTHER INFORMATION: Template for replication assay

<400> SEQUENCE: 4
ccatgattac gaattcagtc atcaccggcg ccacagacta agcttggcac tggccgtcgt             60
tttacaacgt cgtgactggg aaaaccctgg                                              90
```

PROTEIN CRYSTAL COMPRISING THE PROCESSIVITY CLAMP FACTOR OF DNA POLYMERASE AND A LIGAND, AND ITS USES

BACKGROUND OF THE INVENTION

1. Field of the Invention

The present invention relates to a protein crystal comprising the processivity clamp factor of DNA polymerase and a peptide comprising all or part of the processivity clamp factor binding sequence of a processivity clamp factor interacting protein, and its uses, in particular for the screening, the design or the modification of ligands of the processivity clamp factor of DNA polymerase.

2. Description of the Related Art

The presence of lesions on DNA may severely impair its replication and have dramatic consequences on cells survival. Beside the activity of efficient repair processes, which remove most of the lesions from DNA before replication occurs, the replisome is able to cope with replication blocking DNA lesions, thanks to specialized biochemical processes referred to as damaged DNA tolerance pathways. Translesion synthesis (TLS) is one of these mechanisms which requires the incorporation of a nucleotide opposite and past the lesion. Depending on the nature of the incorporated nucleotide relative to the parental sequence, the TLS process is error-free or mutagenic. TLS has recently gained much understanding, with the discovery of specialized DNA polymerases, which are able to replicate through lesions which otherwise impede the progression of DNA polymerases involved in replication. These new polymerases have been found in both prokaryotes and eukaryotes and most of them have been classified in the Y superfamily (Ohmori et al., 2001). In *Escherichia coli*, two such polymerases have been identified, Pol IV (DinB) (Wagner et al., 1999) and Pol V (Tang et al., 1999; Reuven et al., 1999), whereas Pol II polymerase has also been shown to perform TLS, although it belongs to the B family (Napolitano et al., 2000; Becherel et al., 2001; Fuchs et al, 2001). Interestingly, all these three polymerase genes are part of the SOS network and are induced upon the arrest of replication due to the presence of replicase blocking lesions onto DNA.

The discovery of translesional polymerases (Ohmori et al., 2001) resulted in a major modification of the molecular model of TLS and resulting lesion induced mutagenesis. The previous model, essentially built on genetic experiments in *E. coli* (Bridges and Woodgates, 1985) suggested that the replicative polymerase stalled at blocking lesions was assisted by SOS induced proteins, whose functions were expected to facilitate the polymerase progression through the lesion by increasing its anchoring onto modified DNA or by reducing its fidelity either by alteration of the correct nucleotide selection process and/or by inhibition of its proofreading activity. The current new model (Cordonnier et al., 1999) proposes that the blocked replicative polymerase is replaced by one or several TLS polymerases that cooperate at different steps of the translesional process, namely incorporation opposite the lesion and elongation of the lesion terminus, to ensure an efficient bypass of the lesion. These polymerases further dissociate from the DNA substrate and the replicative enzyme resumes its synthesis function.

It was demonstrated that prokaryotic and eukaryotic replicative polymerases (Pol III holoenzyme of *E. coli*, pol C, eukaryotic pol δ and pol ε) physically interact with their respective processivity clamp factor, also called sliding clamp. Moreover, all prokaryotic and most eukaryotic TLS polymerases also interact with their processivity clamp factor (Lenne-Samuel et al., 2002; Wagner et al., 2000; Becherel et al., 2002; Haracska et al., 2002; Haracska et al., 2001a; Haracska et al., 2001b). These clamps, which act by increasing the replicative polymerase processivity (Bruck and O'Donnel, 2001), are homodimeric (β of *E. coli*) or homotrimeric (gp45 of T4/RB69 or PCNA in eukaryotes) toroid-shape molecules that are loaded onto DNA near primer-template junctions, by specific clamp loader complexes (e.g. the so-called γ complex in *E. coli* and RFC in eukaryotes). The β and PCNA monomers fold into structurally similar subdomains (3 and 2, respectively), despite a lack of internal homology in their amino acids sequences, so that the ring presents a pseudo-six-fold symmetry. A consensus pentapeptidic sequence, QL(SD)LF, conserved among eubacteria, was identified in most of the β-binding proteins as the motif mediating their connection with the clamp, through hydrophobic interactions (Dalrymple et al., 2001). Similarly, a eukaryotic PCNA (or alternative sliding clamps) consensus binding sequence has been identified. A recent study in *E. coli* demonstrated that the integrity of this motif is absolutely required for the inducible polymerases to perform TLS: Pol IV and Pol II mutant proteins deleted for their β-clamp binding motif retain their polymerase activity, but loose their functions in the TLS process in vivo, highlightening the fact that their functional interaction with β is crucial for translesion DNA synthesis and mutagenesis (Becherel et al., 2002; Lenne-Samuel et al., 2002).

The presence of several TLS polymerases within a single organism has remained a puzzling question. Analysis of the TLS process in *E. coli* indicated that, depending on both the nature of the lesion and the local DNA sequence, one or several TLS polymerases may participate to a single TLS event (Napolitano et al., 2000; Wagner et al., 2002). TLS appears as a complex process where a pool of low fidelity polymerases replace the highly stringent replisome and eventually exchange mutually to accommodate the large variety of DNA lesions and to ensure ultimately the completion of DNA replication. Whether this polymerase switching process is somehow coordinated or simply occurs on the basis of competition between the different TLS polymerases is not yet known.

BRIEF SUMMARY OF THE INVENTION

An object of the invention is to provide a method to obtain ligands of the processivity clamp factor which would impair the interaction between the sliding clamp and its interacting proteins.

Such ligands might be useful for the preparation of drugs for the treatment of bacterial diseases or of proliferative disorders.

The invention follows on from the solving by the Inventors of the structure of a co-crystal obtained between the β clamp of *E. coli* and the 16 residues C-terminal peptide of Pol IV DNA polymerase (P16) of *E. coli* containing its β-binding sequence, from the identification of the peptide binding site on β and from the description of the interactions between P16 and β residues.

The Invention also follows on from the results of experiments carried out by the Inventors showing that P16 competes with Pol IV, but also with the α subunit of the *E. coli* replicative Pol III holoenzyme, for binding to β, thus inhibiting their β dependent polymerase activity.

The present invention relates to a protein crystal comprising the processivity clamp factor of DNA polymerase and a peptide of about 3 to about 30 amino acids, in particular of about 16 amino acids, said peptide comprising all or part of the processivity clamp factor binding sequence of a processivity clamp factor interacting protein, such as prokaryotic Pol I, Pol II, Pol III, Pol IV, Pol V, MutS, ligase I, α subunit of DNA polymerase, UmuD or UmuD', or eukaryotic pol ε, pol δ, pol η, pol ι, pol κ.

Other processivity clamp factor interacting proteins are notably described in Tsurimoto et al. (1999).

The expression "processivity clamp factor of DNA polymerase" refers to dnaN genes products and their functional analogs in prokaryotes, and PCNA genes products and their functional analogs and orthologs in eukaryotes. It can also be referred to as a sliding clamp. It is notably described in Kong et al. (1992) and Gulbis et al. (1996).

"Pol I", "Pol II", "Pol III", "Pol IV", "Pol V" respectively refer to DNA polymerase I, II, III, IV and V, in bacteria, such as E. coli, as reviewed in Friedberg et al. (2000a), and Friedberg et al. (2000b).

"MutS" refers to the product of the mutS gene in E. coli, and functional analogs and orthologs thereof, involved in mismatch repair.

"Ligase I" refers to the product of the lig gene in E. coli, and functional analogs and orthologs thereof.

"α subunit of DNA polymerase" refers to the product of the dnaE gene in E. coli, and functional analogs and orthologs thereof.

"UmuD" refers to the product of the umuD gene in E. coli, and functional analogs and orthologs thereof.

"Pol ε", "pol δ", "pol η", "pol ι", "pol κ" refer to eukaryotic polymerases as reviewed in Friedberg et al. (2000a), and Friedberg et al. (2000b).

The invention more particularly relates to a protein crystal as defined above, wherein the processivity clamp factor of DNA polymerase is the β subunit of DNA polymerase, in particular the β subunit of DNA polymerase III of Escherichia coli, and the peptide has the following sequence:

VTLLDPQMERQLVLGL (SEQ ID NO: 1)

The β subunit of DNA polymerase III of Escherichia coli is in particular described in Kong et al. (1992).

The invention more particularly relates to a protein crystal as defined above, comprising the β subunit of DNA polymerase III of Escherichia coli and the peptide of SEQ ID NO: 1, said crystal belonging to the triclinic space group P1 and its cell dimensions being approximately a=41.23 Å, b=65.22 Å, c=73.38 Å, α=73.11°, β=85.58°, γ=85.80°.

The expression "triclinic space group P1" refers to a nomenclature well known to the man skilled in the art, it is in particular described in "International tables for X-ray crystallography", Vol. 1 (The Kynoch press, Birmingham, England, 1968)

The expression "cell dimensions" refers to the geometrical description of the smallest volume being repeated in the three dimensions to build the crystal.

The invention more particularly relates to a protein crystal as defined above, characterized by the atomic coordinates such as obtained by the X-ray diffraction of said crystal, said atomic coordinates being represented in FIG. 1.

The expression "atomic coordinates" refers to the three coordinates X, Y, Z (given in Å, 1 Å=10$^{-10}$ m) necessary to describe the exact position of each atom in the molecule.

The expression "X-ray diffraction" refers to the phenomenon following which X-rays are scattered in a specific way by a crystal.

Two major X-ray sources can be used: a rotating anode, which is a usual laboratory equipment and/or a synchrotron which is a large-scale equipment, such as the European Synchrotron Radiation Facility (ESRF) in Grenoble, France.

The general methodology to obtain atomic coordinates from X-ray diffraction of a crystal is well known to man skilled in the art, briefly it consists in measuring the intensities of the numerous secondary X-rays beams resulting from the diffraction by the crystal of an incident X-ray beam.

The invention more particularly relates to a protein crystal as defined above, characterized by the atomic coordinates representing the peptide and the peptide binding site of the β subunit of DNA polymerase III of Escherichia coli, and being as follows:

| ATOM | 4045 | N   | LEU | B | 155 | 5.874  | 17.816 | 22.109 | 1.00 | 1.00 B |
|------|------|-----|-----|---|-----|--------|--------|--------|------|--------|
| ATOM | 4046 | CA  | LEU | B | 155 | 6.029  | 16.359 | 22.087 | 1.00 | 1.00 B |
| ATOM | 4047 | CB  | LEU | B | 155 | 5.055  | 15.686 | 23.064 | 1.00 | 1.00 B |
| ATOM | 4048 | CG  | LEU | B | 155 | 5.260  | 16.046 | 24.536 | 1.00 | 1.00 B |
| ATOM | 4049 | CD1 | LEU | B | 155 | 4.256  | 15.237 | 25.360 | 1.00 | 1.00 B |
| ATOM | 4050 | CD2 | LEU | B | 155 | 6.686  | 15.757 | 24.980 | 1.00 | 1.00 B |
| ATOM | 4051 | C   | LEU | B | 155 | 5.808  | 15.776 | 20.682 | 1.00 | 1.00 B |
| ATOM | 4052 | O   | LEU | B | 155 | 6.177  | 14.613 | 20.431 | 1.00 | 1.00 B |
| ATOM | 4177 | N   | THR | B | 172 | 9.112  | 11.246 | 22.902 | 1.00 | 1.00 B |
| ATOM | 4178 | CA  | THR | B | 172 | 8.212  | 10.730 | 23.917 | 1.00 | 1.00 B |
| ATOM | 4179 | CB  | THR | B | 172 | 8.776  | 11.014 | 25.344 | 1.00 | 1.00 B |
| ATOM | 4180 | OG1 | THR | B | 172 | 7.931  | 10.400 | 26.328 | 1.00 | 1.00 B |
| ATOM | 4181 | CG2 | THR | B | 172 | 8.870  | 12.532 | 25.619 | 1.00 | 1.00 B |
| ATOM | 4182 | C   | THR | B | 172 | 6.805  | 11.269 | 23.709 | 1.00 | 1.00 B |
| ATOM | 4183 | O   | THR | B | 172 | 6.588  | 12.352 | 23.145 | 1.00 | 1.00 B |
| ATOM | 4192 | N   | GLY | B | 174 | 4.562  | 10.770 | 26.397 | 1.00 | 1.00 B |
| ATOM | 4193 | CA  | GLY | B | 174 | 3.992  | 10.745 | 27.737 | 1.00 | 1.00 B |
| ATOM | 4194 | C   | GLY | B | 174 | 3.762  | 9.337  | 28.266 | 1.00 | 1.00 B |
| ATOM | 4195 | O   | GLY | B | 174 | 3.667  | 9.141  | 29.489 | 1.00 | 1.00 B |
| ATOM | 4196 | N   | HIS | B | 175 | 3.650  | 8.349  | 27.375 | 1.00 | 1.00 B |
| ATOM | 4197 | CA  | HIS | B | 175 | 3.440  | 6.953  | 27.796 | 1.00 | 1.00 B |
| ATOM | 4198 | CB  | HIS | B | 175 | 2.313  | 6.309  | 26.977 | 1.00 | 1.00 B |
| ATOM | 4199 | CG  | HIS | B | 175 | 0.992  | 6.997  | 27.119 | 1.00 | 1.00 B |
| ATOM | 4200 | CD2 | HIS | B | 175 | 0.106  | 7.435  | 26.193 | 1.00 | 1.00 B |
| ATOM | 4201 | ND1 | HIS | B | 175 | 0.420  | 7.255  | 28.345 | 1.00 | 1.00 B |
| ATOM | 4202 | CE1 | HIS | B | 175 | -0.763 | 7.817  | 28.170 | 1.00 | 1.00 B |
| ATOM | 4203 | NE2 | HIS | B | 175 | -0.977 | 7.938  | 26.875 | 1.00 | 1.00 B |
| ATOM | 4204 | C   | HIS | B | 175 | 4.706  | 6.135  | 27.641 | 1.00 | 1.00 B |
| ATOM | 4205 | O   | HIS | B | 175 | 4.990  | 5.212  | 28.403 | 1.00 | 1.00 B |

-continued

| | | | | | | | | | | |
|---|---|---|---|---|---|---|---|---|---|---|
| ATOM | 4207 | CA | ARG | B | 176 | 6.711 | 5.768 | 26.422 | 1.00 | 18.30 B |
| ATOM | 4208 | CB | ARG | B | 176 | 6.575 | 4.633 | 25.398 | 1.00 | 19.53 B |
| ATOM | 4209 | CG | ARG | B | 176 | 6.329 | 5.094 | 23.954 | 1.00 | 22.88 B |
| ATOM | 4210 | CD | ARG | B | 176 | 4.876 | 4.888 | 23.657 | 1.00 | 22.11 B |
| ATOM | 4211 | NE | ARG | B | 176 | 4.435 | 5.312 | 22.314 | 1.00 | 22.09 B |
| ATOM | 4212 | CZ | ARG | B | 176 | 4.555 | 4.591 | 21.202 | 1.00 | 20.17 B |
| ATOM | 4213 | NH1 | ARG | B | 176 | 5.159 | 3.403 | 21.213 | 1.00 | 17.04 B |
| ATOM | 4214 | NH2 | ARG | B | 176 | 3.914 | 4.977 | 20.120 | 1.00 | 20.02 B |
| ATOM | 4215 | C | ARG | B | 176 | 7.684 | 6.807 | 25.902 | 1.00 | 17.30 B |
| ATOM | 4216 | O | ARG | B | 176 | 7.255 | 7.860 | 25.374 | 1.00 | 18.10 B |
| ATOM | 4217 | N | LEU | B | 177 | 8.957 | 6.504 | 26.080 | 1.00 | 17.97 B |
| ATOM | 4218 | CA | LEU | B | 177 | 10.049 | 7.360 | 25.633 | 1.00 | 17.85 B |
| ATOM | 4219 | CB | LEU | B | 177 | 10.664 | 8.095 | 26.827 | 1.00 | 18.29 B |
| ATOM | 4220 | CG | LEU | B | 177 | 11.921 | 8.955 | 26.611 | 1.00 | 16.28 B |
| ATOM | 4221 | CD1 | LEU | B | 177 | 11.819 | 10.163 | 27.559 | 1.00 | 19.52 B |
| ATOM | 4222 | CD2 | LEU | B | 177 | 13.191 | 8.172 | 26.839 | 1.00 | 19.12 B |
| ATOM | 4223 | C | LEU | B | 177 | 11.110 | 6.517 | 24.964 | 1.00 | 18.45 B |
| ATOM | 4224 | O | LEU | B | 177 | 11.291 | 5.329 | 25.281 | 1.00 | 18.33 B |
| ATOM | 4710 | N | PRO | B | 242 | 11.254 | 17.279 | 27.890 | 1.00 | 1.00 B |
| ATOM | 4711 | CD | PRO | B | 242 | 9.987 | 16.826 | 27.286 | 1.00 | 1.00 B |
| ATOM | 4712 | CA | PRO | B | 242 | 11.660 | 16.404 | 28.997 | 1.00 | 1.00 B |
| ATOM | 4713 | CB | PRO | B | 242 | 10.688 | 15.230 | 28.874 | 1.00 | 1.00 B |
| ATOM | 4714 | CG | PRO | B | 242 | 9.448 | 15.869 | 28.336 | 1.00 | 1.00 B |
| ATOM | 4715 | C | PRO | B | 242 | 13.124 | 15.947 | 28.987 | 1.00 | 1.00 B |
| ATOM | 4716 | O | PRO | B | 242 | 13.728 | 15.748 | 27.925 | 1.00 | 1.00 B |
| ATOM | 4748 | N | ARG | B | 246 | 16.133 | 11.840 | 33.560 | 1.00 | 1.00 B |
| ATOM | 4749 | CA | ARG | B | 246 | 15.239 | 11.808 | 34.707 | 1.00 | 1.00 B |
| ATOM | 4750 | CB | ARG | B | 246 | 14.755 | 13.227 | 34.984 | 1.00 | 1.00 B |
| ATOM | 4751 | CG | ARG | B | 246 | 15.880 | 14.252 | 35.113 | 1.00 | 1.00 B |
| ATOM | 4752 | CD | ARG | B | 246 | 16.443 | 14.295 | 36.529 | 1.00 | 1.00 B |
| ATOM | 4753 | NE | ARG | B | 246 | 15.374 | 14.318 | 37.524 | 1.00 | 1.00 B |
| ATOM | 4754 | CZ | ARG | B | 246 | 14.316 | 15.126 | 37.477 | 1.00 | 1.00 B |
| ATOM | 4755 | NH1 | ARG | B | 246 | 14.169 | 15.992 | 36.481 | 1.00 | 1.00 B |
| ATOM | 4756 | NH2 | ARG | B | 246 | 13.396 | 15.067 | 38.430 | 1.00 | 1.00 B |
| ATOM | 4757 | C | ARG | B | 246 | 14.022 | 10.889 | 34.566 | 1.00 | 1.00 B |
| ATOM | 4758 | O | ARG | B | 246 | 13.384 | 10.536 | 35.560 | 1.00 | 1.00 B |
| ATOM | 4759 | N | VAL | B | 247 | 13.695 | 10.532 | 33.327 | 1.00 | 1.00 B |
| ATOM | 4760 | CA | VAL | B | 247 | 12.553 | 9.675 | 33.018 | 1.00 | 1.00 B |
| ATOM | 4761 | CB | VAL | B | 247 | 12.061 | 9.942 | 31.585 | 1.00 | 1.00 B |
| ATOM | 4762 | CG1 | VAL | B | 247 | 10.930 | 8.991 | 31.216 | 1.00 | 1.00 B |
| ATOM | 4763 | CG2 | VAL | B | 247 | 11.624 | 11.391 | 31.462 | 1.00 | 1.00 B |
| ATOM | 4764 | C | VAL | B | 247 | 12.962 | 8.218 | 33.133 | 1.00 | 1.00 B |
| ATOM | 4765 | O | VAL | B | 247 | 12.125 | 7.334 | 33.308 | 1.00 | 1.00 B |
| ATOM | 4996 | M | PHE | B | 278 | −7.702 | −1.352 | 24.244 | 1.00 | 1.00 B |
| ATOM | 4997 | CA | PHE | B | 278 | −6.698 | −1.155 | 25.300 | 1.00 | 1.00 B |
| ATOM | 4998 | CB | PHE | B | 278 | −7.318 | −1.432 | 26.663 | 1.00 | 1.00 B |
| ATOM | 4999 | CG | PHE | B | 278 | −8.431 | −0.459 | 27.021 | 1.00 | 1.00 B |
| ATOM | 5000 | CD1 | PHE | B | 278 | −8.142 | 0.882 | 27.268 | 1.00 | 1.00 B |
| ATOM | 5001 | CD2 | PHE | B | 276 | −9.760 | −0.869 | 27.021 | 1.00 | 1.00 B |
| ATOM | 5002 | CE1 | PHE | B | 278 | −9.177 | 1.816 | 27.508 | 1.00 | 1.00 B |
| ATOM | 5003 | CE2 | PHE | B | 278 | −10.795 | 0.052 | 27.258 | 1.00 | 1.00 B |
| ATOM | 5004 | CZ | PHE | B | 278 | −10.496 | 1.391 | 27.500 | 1.00 | 1.00 B |
| ATOM | 5005 | C | PHE | B | 278 | −5.403 | −1.957 | 25.131 | 1.00 | 1.00 B |
| ATOM | 5006 | O | PHE | B | 278 | −4.356 | −1.582 | 25.677 | 1.00 | 1.00 B |
| ATOM | 5332 | N | ASN | B | 320 | 0.635 | −2.143 | 27.431 | 1.00 | 1.00 B |
| ATOM | 5333 | CA | ASN | B | 320 | −0.051 | −1.983 | 26.158 | 1.00 | 1.00 B |
| ATOM | 5334 | CB | ASN | B | 320 | −0.055 | −0.504 | 25.796 | 1.00 | 1.00 B |
| ATOM | 5335 | CG | ASN | B | 320 | −0.561 | −0.259 | 24.407 | 1.00 | 1.00 B |
| ATOM | 5336 | OD1 | ASN | B | 320 | −0.226 | −0.997 | 23.481 | 1.00 | 1.00 B |
| ATOM | 5337 | ND2 | ASN | B | 320 | −1.362 | 0.791 | 24.242 | 1.00 | 1.00 B |
| ATOM | 5338 | C | ASN | B | 320 | 0.927 | −2.745 | 25.249 | 1.00 | 1.00 B |
| ATOM | 5339 | O | ASN | B | 320 | 2.093 | −2.350 | 25.102 | 1.00 | 1.00 B |
| ATOM | 5353 | N | TYR | B | 323 | 2.932 | −0.853 | 22.482 | 1.00 | 1.00 B |
| ATOM | 5354 | CA | TYR | B | 323 | 4.110 | −0.088 | 22.908 | 1.00 | 1.00 B |
| ATOM | 5355 | CB | TYR | B | 323 | 3.878 | 0.590 | 24.259 | 1.00 | 1.00 B |
| ATOM | 5356 | CG | TYR | B | 323 | 2.813 | 1.668 | 24.294 | 1.00 | 1.00 B |
| ATOM | 5357 | CD1 | TYR | B | 323 | 2.397 | 2.314 | 23.127 | 1.00 | 1.00 B |
| ATOM | 5358 | CE1 | TYR | B | 323 | 1.458 | 3.374 | 23.170 | 1.00 | 1.00 B |
| ATOM | 5359 | CD2 | TYR | B | 323 | 2.284 | 2.093 | 25.509 | 1.00 | 1.00 B |
| ATOM | 5360 | CE2 | TYR | B | 323 | 1.354 | 3.166 | 25.567 | 1.00 | 1.00 B |
| ATOM | 5361 | CZ | TYR | B | 323 | 0.957 | 3.790 | 24.399 | 1.00 | 1.00 B |
| ATOM | 5362 | OH | TYR | B | 323 | 0.112 | 4.886 | 24.453 | 1.00 | 1.00 B |
| ATOM | 5363 | C | TYR | B | 323 | 5.327 | −1.018 | 23.041 | 1.00 | 1.00 B |
| ATOM | 5364 | O | TYR | B | 323 | 6.468 | −0.646 | 22.726 | 1.00 | 1.00 B |
| ATOM | 5519 | N | VAL | B | 344 | 3.837 | −1.100 | 39.291 | 1.00 | 1.00 B |
| ATOM | 5520 | CA | VAL | B | 344 | 3.324 | 0.227 | 39.030 | 1.00 | 1.00 B |
| ATOM | 5521 | CB | VAL | B | 344 | 2.676 | 0.818 | 40.318 | 1.00 | 1.00 B |
| ATOM | 5522 | CG1 | VAL | B | 344 | 1.474 | −0.026 | 40.725 | 1.00 | 1.00 B |
| ATOM | 5523 | CG2 | VAL | B | 344 | 3.687 | 0.847 | 41.456 | 1.00 | 1.00 B |

-continued

| | | | | | | | | | | |
|---|---|---|---|---|---|---|---|---|---|---|
| ATOM | 5524 | C | VAL | B | 344 | 4.405 | 1.163 | 38.512 | 1.00 | 1.00 B |
| ATOM | 5525 | O | VAL | B | 344 | 4.199 | 2.365 | 38.405 | 1.00 | 1.00 B |
| ATOM | 5532 | N | SER | B | 346 | 7.618 | 2.151 | 35.615 | 1.00 | 21.53 B |
| ATOM | 5533 | CA | SER | B | 346 | 8.060 | 2.002 | 34.239 | 1.00 | 21.50 B |
| ATOM | 5534 | CB | SER | B | 346 | 8.655 | 3.320 | 33.722 | 1.00 | 21.47 B |
| ATOM | 5535 | OG | SER | B | 346 | 9.793 | 3.703 | 34.474 | 1.00 | 26.08 B |
| ATOM | 5536 | C | SER | B | 346 | 9.107 | 0.914 | 34.106 | 1.00 | 20.70 B |
| ATOM | 5537 | O | SER | B | 346 | 9.755 | 0.521 | 35.078 | 1.00 | 21.55 B |
| ATOM | 5632 | N | VAL | B | 360 | 11.730 | 3.546 | 27.545 | 1.00 | 1.00 B |
| ATOM | 5633 | CA | VAL | B | 360 | 11.023 | 3.501 | 28.812 | 1.00 | 1.00 B |
| ATOM | 5634 | CB | VAL | B | 360 | 11.276 | 4.794 | 29.641 | 1.00 | 1.00 B |
| ATOM | 5635 | CG1 | VAL | B | 360 | 10.448 | 4.742 | 30.934 | 1.00 | 1.00 B |
| ATOM | 5636 | CG2 | VAL | B | 360 | 12.753 | 4.923 | 29.937 | 1.00 | 1.00 B |
| ATOM | 5637 | C | VAL | B | 360 | 9.562 | 3.381 | 28.501 | 1.00 | 1.00 B |
| ATOM | 5638 | O | VAL | B | 360 | 9.008 | 4.188 | 27.753 | 1.00 | 1.00 B |
| ATOM | 5639 | N | VAL | B | 361 | 8.905 | 2.372 | 29.069 | 1.00 | 19.72 B |
| ATOM | 5640 | CA | VAL | B | 361 | 7.488 | 2.188 | 28.831 | 1.00 | 18.92 B |
| ATOM | 5641 | CB | VAL | B | 361 | 7.216 | 0.872 | 28.069 | 1.00 | 18.99 B |
| ATOM | 5642 | CG1 | VAL | B | 361 | 5.743 | 0.769 | 27.716 | 1.00 | 18.31 B |
| ATOM | 5643 | CG2 | VAL | B | 361 | 8.065 | 0.839 | 26.786 | 1.00 | 17.76 B |
| ATOM | 5644 | C | VAL | B | 361 | 6.793 | 2.100 | 30.167 | 1.00 | 19.47 B |
| ATOM | 5645 | O | VAL | B | 361 | 7.232 | 1.362 | 31.038 | 1.00 | 16.90 B |
| ATOM | 5646 | N | MET | B | 362 | 5.737 | 2.885 | 30.316 | 1.00 | 1.00 B |
| ATOM | 5647 | CA | MET | B | 362 | 4.962 | 2.882 | 31.540 | 1.00 | 1.00 B |
| ATOM | 5648 | CB | MET | B | 362 | 4.226 | 4.206 | 31.682 | 1.00 | 1.00 B |
| ATOM | 5649 | CG | MET | B | 362 | 3.918 | 4.589 | 33.122 | 1.00 | 1.00 B |
| ATOM | 5650 | SD | MET | B | 362 | 5.405 | 4.806 | 34.163 | 1.00 | 1.00 B |
| ATOM | 5651 | CE | MET | B | 362 | 4.575 | 4.880 | 35.731 | 1.00 | 1.00 B |
| ATOM | 5652 | C | MET | B | 362 | 3.949 | 1.731 | 31.471 | 1.00 | 1.00 B |
| ATOM | 5653 | O | MET | B | 362 | 3.385 | 1.438 | 30.410 | 1.00 | 1.00 B |
| ATOM | 5654 | N | PRO | B | 363 | 3.698 | 1.069 | 32.599 | 1.00 | 1.00 B |
| ATOM | 5655 | CD | PRO | B | 363 | 4.521 | 1.025 | 33.818 | 1.00 | 1.00 B |
| ATOM | 5656 | CA | PRO | B | 363 | 2.729 | −0.038 | 32.579 | 1.00 | 1.00 B |
| ATOM | 5657 | CB | PRO | B | 363 | 3.155 | −0.883 | 33.776 | 1.00 | 1.00 B |
| ATOM | 5658 | CG | PRO | B | 363 | 3.665 | 0.160 | 34.754 | 1.00 | 1.00 B |
| ATOM | 5659 | C | PRO | B | 363 | 1.272 | 0.395 | 32.672 | 1.00 | 1.00 B |
| ATOM | 5660 | O | PRO | B | 363 | 0.959 | 1.574 | 32.311 | 1.00 | 1.00 B |
| ATOM | 5661 | N | MET | B | 364 | 0.368 | −0.568 | 32.537 | 1.00 | 1.00 B |
| ATOM | 5662 | CA | MET | B | 364 | −1.037 | −0.272 | 32.674 | 1.00 | 1.00 B |
| ATOM | 5663 | CB | MET | B | 364 | −1.780 | −0.391 | 31.332 | 1.00 | 1.00 B |
| ATOM | 5664 | CG | MET | B | 364 | −1.636 | −1.670 | 30.568 | 1.00 | 1.00 B |
| ATOM | 5665 | SD | MET | B | 364 | −2.386 | −1.510 | 28.872 | 1.00 | 1.00 B |
| ATOM | 5666 | CE | MET | B | 364 | −4.155 | −1.253 | 29.308 | 1.00 | 1.00 B |
| ATOM | 5667 | C | MET | B | 364 | −1.602 | −1.218 | 33.725 | 1.00 | 1.00 B |
| ATOM | 5668 | O | MET | B | 364 | −0.999 | −2.251 | 34.035 | 1.00 | 1.00 B |
| ATOM | 5669 | N | ARG | B | 365 | −2.732 | −0.836 | 34.307 | 1.00 | 1.00 B |
| ATOM | 5670 | CA | ARG | B | 365 | −3.383 | −1.655 | 35.324 | 1.00 | 1.00 B |
| ATOM | 5671 | CB | ARG | B | 365 | −4.029 | −0.756 | 36.394 | 1.00 | 1.00 B |
| ATOM | 5672 | CG | ARG | B | 365 | −4.785 | −1.490 | 37.505 | 1.00 | 1.00 B |
| ATOM | 5673 | CD | ARG | B | 365 | −3.859 | −2.316 | 38.398 | 1.00 | 1.00 B |
| ATOM | 5674 | NE | ARG | B | 365 | −4.571 | −2.956 | 39.505 | 1.00 | 1.00 B |
| ATOM | 5675 | CZ | ARG | B | 365 | −3.984 | −3.707 | 40.434 | 1.00 | 1.00 B |
| ATOM | 5676 | NH1 | ARG | B | 365 | −2.678 | −3.913 | 40.385 | 1.00 | 1.00 B |
| ATOM | 5677 | NH2 | ARG | B | 365 | −4.698 | −4.247 | 41.418 | 1.00 | 1.00 B |
| ATOM | 5678 | C | ARG | B | 365 | −4.459 | −2.492 | 34.648 | 1.00 | 1.00 B |
| ATOM | 5679 | O | ARG | B | 365 | −5.449 | −1.961 | 34.150 | 1.00 | 1.00 B |
| ATOM | 5680 | N | LEU | B | 366 | −4.267 | −3.801 | 34.609 | 1.00 | 41.59 B |
| ATOM | 5681 | CA | LEU | B | 366 | −5.272 | −4.665 | 33.996 | 1.00 | 44.25 B |
| ATOM | 5682 | CB | LEU | B | 366 | −4.615 | −5.908 | 33.366 | 1.00 | 45.24 B |
| ATOM | 5683 | CG | LEU | B | 366 | −3.640 | −5.701 | 32.202 | 1.00 | 45.46 B |
| ATOM | 5684 | CD1 | LEU | B | 366 | −4.331 | −5.029 | 31.031 | 1.00 | 47.09 B |
| ATOM | 5685 | CD2 | LEU | B | 366 | −2.489 | −4.856 | 32.678 | 1.00 | 46.71 B |
| ATOM | 5686 | C | LEU | B | 366 | −6.263 | −5.080 | 35.092 | 1.00 | 45.55 B |
| ATOM | 5687 | O | LEU | B | 366 | −6.424 | −6.296 | 35.333 | 1.00 | 46.32 B |
| ATOM | 5688 | OXT | LEU | B | 366 | −6.868 | −4.169 | 35.704 | 1.00 | 46.33 B |
| ATOM | 5689 | CB | ARG | C | 10 | −5.663 | 0.205 | 32.737 | 0.76 | 1.00 C |
| ATOM | 5690 | CG | ARG | C | 10 | −7.073 | −0.397 | 32.771 | 0.76 | 1.00 C |
| ATOM | 5691 | CD | ARG | C | 10 | −7.748 | −0.383 | 31.408 | 0.76 | 1.00 C |
| ATOM | 5692 | NE | ARG | C | 10 | −8.728 | −1.462 | 31.268 | 0.76 | 1.00 C |
| ATOM | 5693 | CZ | ARG | C | 10 | −9.992 | −1.301 | 30.875 | 0.76 | 1.00 C |
| ATOM | 5694 | NH1 | ARG | C | 10 | −10.464 | −0.093 | 30.582 | 0.76 | 1.00 C |
| ATOM | 5695 | NH2 | ARG | C | 10 | −10.779 | −2.365 | 30.749 | 0.76 | 1.00 C |
| ATOM | 5696 | C | ARG | C | 10 | −4.106 | 2.152 | 32.497 | 0.76 | 1.00 C |
| ATOM | 5697 | O | ARG | C | 10 | −3.278 | 1.863 | 33.369 | 0.76 | 1.00 C |
| ATOM | 5698 | N | ARG | C | 10 | −6.417 | 2.186 | 31.464 | 0.76 | 1.00 C |
| ATOM | 5699 | CA | ARG | C | 10 | −5.587 | 1.727 | 32.625 | 0.76 | 1.00 C |
| ATOM | 5700 | N | GLN | C | 11 | −3.805 | 2.853 | 31.408 | 0.76 | 1.00 C |
| ATOM | 5701 | CA | GLN | C | 11 | −2.458 | 3.321 | 31.094 | 0.76 | 1.00 C |
| ATOM | 5702 | CB | GLN | C | 11 | −2.423 | 3.866 | 29.662 | 0.76 | 1.00 C |

-continued

| ATOM | 5703 | CG | GLN | C | 11 | −1.047 | 4.361 | 29.231 | 0.76 | 1.00 | C |
| ATOM | 5704 | CD | GLN | C | 11 | −0.039 | 3.245 | 29.174 | 0.76 | 1.00 | C |
| ATOM | 5705 | OE1 | GLN | C | 11 | −0.263 | 2.232 | 28.494 | 0.76 | 1.00 | C |
| ATOM | 5706 | NE2 | GLN | C | 11 | 1.082 | 3.415 | 29.876 | 0.76 | 1.00 | C |
| ATOM | 5707 | C | GLN | C | 11 | −1.895 | 4.396 | 32.038 | 0.76 | 1.00 | C |
| ATOM | 5708 | O | GLN | C | 11 | −2.494 | 5.467 | 32.217 | 0.76 | 1.00 | C |
| ATOM | 5709 | N | LEU | C | 12 | −0.732 | 4.111 | 32.618 | 0.76 | 1.00 | C |
| ATOM | 5710 | CA | LEU | C | 12 | −0.065 | 5.046 | 33.519 | 0.76 | 1.00 | C |
| ATOM | 5711 | CB | LEU | C | 12 | 0.754 | 4.277 | 34.561 | 0.76 | 1.00 | C |
| ATOM | 5712 | CG | LEU | C | 12 | −0.036 | 3.305 | 35.450 | 0.76 | 1.00 | C |
| ATOM | 5713 | CD1 | LEU | C | 12 | 0.907 | 2.681 | 36.468 | 0.76 | 1.00 | C |
| ATOM | 5714 | CD2 | LEU | C | 12 | −1.184 | 4.040 | 36.153 | 0.76 | 1.00 | C |
| ATOM | 5715 | C | LEU | C | 12 | 0.845 | 5.948 | 32.680 | 0.76 | 1.00 | C |
| ATOM | 5716 | O | LEU | C | 12 | 1.111 | 5.653 | 31.510 | 0.76 | 1.00 | C |
| ATOM | 5717 | N | VAL | C | 13 | 1.317 | 7.044 | 33.273 | 0.76 | 1.00 | C |
| ATOM | 5718 | CA | VAL | C | 13 | 2.166 | 7.987 | 32.543 | 0.76 | 1.00 | C |
| ATOM | 5719 | CB | VAL | C | 13 | 1.473 | 9.371 | 32.386 | 0.76 | 1.00 | C |
| ATOM | 5720 | CG1 | VAL | C | 13 | 0.217 | 9.239 | 31.523 | 0.76 | 1.00 | C |
| ATOM | 5721 | CG2 | VAL | C | 13 | 1.113 | 9.929 | 33.750 | 0.76 | 1.00 | C |
| ATOM | 5722 | C | VAL | C | 13 | 3.542 | 8.211 | 33.174 | 0.76 | 1.00 | C |
| ATOM | 5723 | O | VAL | C | 13 | 3.740 | 8.050 | 34.381 | 0.76 | 1.00 | C |
| ATOM | 5724 | N | LEU | C | 14 | 4.498 | 8.595 | 32.339 | 0.76 | 1.00 | C |
| ATOM | 5725 | CA | LEU | C | 14 | 5.860 | 8.846 | 32.803 | 0.76 | 1.00 | C |
| ATOM | 5726 | CB | LEU | C | 14 | 6.836 | 8.819 | 31.619 | 0.76 | 1.00 | C |
| ATOM | 5727 | CG | LEU | C | 14 | 6.972 | 7.481 | 30.889 | 0.76 | 1.00 | C |
| ATOM | 5728 | CD1 | LEU | C | 14 | 7.666 | 7.705 | 29.557 | 0.76 | 1.00 | C |
| ATOM | 5729 | CD2 | LEU | C | 14 | 7.744 | 6.495 | 31.769 | 0.76 | 1.00 | C |
| ATOM | 5730 | C | LEU | C | 14 | 6.010 | 10.186 | 33.517 | 0.76 | 1.00 | C |
| ATOM | 5731 | O | LEU | C | 14 | 5.238 | 11.126 | 33.284 | 0.76 | 1.00 | C |
| ATOM | 5732 | N | GLY | C | 15 | 7.000 | 10.263 | 34.396 | 0.76 | 1.00 | C |
| ATOM | 5733 | CA | GLY | C | 15 | 7.264 | 11.510 | 35.090 | 0.76 | 1.00 | C |
| ATOM | 5734 | C | GLY | C | 15 | 8.263 | 12.275 | 34.234 | 0.76 | 1.00 | C |
| ATOM | 5735 | O | GLY | C | 15 | 9.472 | 12.210 | 34.462 | 0.76 | 1.00 | C |
| ATOM | 5736 | N | LEU | C | 16 | 7.750 | 12.995 | 33.241 | 0.76 | 1.00 | C |
| ATOM | 5737 | CA | LEU | C | 16 | 8.576 | 13.756 | 32.306 | 0.76 | 1.00 | C |
| ATOM | 5738 | CB | LEU | C | 16 | 7.732 | 14.157 | 31.094 | 0.76 | 1.00 | C |
| ATOM | 5739 | CG | LEU | C | 16 | 7.258 | 12.955 | 30.269 | 0.76 | 1.00 | C |
| ATOM | 5740 | CD1 | LEU | C | 16 | 6.303 | 13.411 | 29.171 | 0.76 | 1.00 | C |
| ATOM | 5741 | CD2 | LEU | C | 16 | 8.467 | 12.233 | 29.690 | 0.76 | 1.00 | C |
| ATOM | 5742 | C | LEU | C | 16 | 9.263 | 14.982 | 32.898 | 0.76 | 1.00 | C |
| ATOM | 5743 | O | LEU | C | 16 | 10.182 | 15.515 | 32.231 | 0.76 | 1.00 | C |
| ATOM | 5744 | OXT | LEU | C | 16 | 8.870 | 15.398 | 34.009 | 0.76 | 1.00 | C |
| END | | | | | | | | | | | | wherein atoms 4045 to 5688 represent the peptide binding site and atoms 5689 to 5748 represent the peptide.

The atomic coordinates are represented in protein data bank (pdb) format. Such a format is well known to the man skilled in the art.

According to another embodiment, the invention relates to a method to purify the processivity clamp factor of DNA polymerase, in particular the β subunit of DNA polymerase III of *Escherichia coli*, comprising the following steps:

elution of a solution containing the processivity clamp factor of DNA polymerase, in particular the β subunit of DNA polymerase III of *Escherichia coli*, through a cation exchange column, in particular a SP sepharose column;

elution of a solution containing the processivity clamp factor of DNA polymerase, in particular the β subunit of DNA polymerase III of *Escherichia coli*, in particular as obtained by the preceding step, through an anion exchange column, in particular a Mono Q column;

elution of a solution containing the processivity clamp factor of DNA polymerase, in particular the β subunit of DNA polymerase III of *Escherichia coli*, in particular as obtained by the preceding step, through a cation exchange column, in particular a Mono S column.

The expression "purify" relates to the process of separating a protein of interest from substantially all the other components of a solution containing said protein of interest, such as a bacterial extract.

Assessment of the purity of the protein of interest can be carried out by methods well known to the man skilled in the art, such as polyacrylamide gel electrophoresis analysis and Coomassie Blue staining or other type of protein staining (e.g. silver staining), mass spectrometry, protein sequencing, HPLC (high performance liquid chromatography). Quantification can be measured by absorbance spectroscopy, Bradford colorimetric assay, or protein sequencing.

The SP sepharose column, Mono Q column and Mono S column are obtained from Pharmacia (Uppsala, Sweden).

Alternatively, columns carrying ion exchange groups with properties similar to those of the SP sepharose column, Mono Q column and Mono S column can also be used.

The above mentioned column can be used with a FPLC system (Pharmacia), and possesses a high protein binding capacity. Advantageously, the SP sepharose column is used during the initial steps of the purification process because it is usually not clogged by dirty samples. The Mono Q and Mono S column are used during the last steps of the purification process, they are highly resolutive columns, but they are easily clogged by dirty samples.

The invention also relates to a method to obtain a protein crystal as defined above, comprising the following steps:

mixing a solution of processivity clamp factor of DNA polymerase, with a solution of a peptide of about 3 to about 30 amino acids, in particular of about 16 amino acids, said peptide comprising all or part of the processivity clamp factor binding sequence of a processivity clamp factor interacting protein, such as prokaryotic Pol I, Pol II, Pol III, Pol IV, Pol V, MutS, ligase I, α subunit of DNA polymerase, UmuD or UmuD', or eukaryotic pol ε, pol δ, pol η, pol τ, pot κ, and with a solution of MES pH 6.0 0.2 M, CaCl$_2$ 0.2 M, PEG 400 60%, to obtain a crystallisation drop, letting the crystallisation drop concentrate against a solution of MES pH 6.0 0.1 M, CaCl$_2$ 0.1 M, PEG 400 30%, by vapour diffusion, to obtain a protein crystal.

The expression "vapour diffusion" refers to a crystallization method for macromolecules well known to the man skilled in the art, it is in particular described in "Crystallization of nucleic acids and proteins", pp. 130-145. A. Ducruix & R. Giegé eds., 1999, Oxford University Press.

MES refers to 2-(N-morpholino)-ethane sulfonic acid.

PEG 400 refers to polyethylene glycol 400.

Advantageously MES, PEG and CaCl$_2$ can be obtained from Hampton Research, (Laguna Niguel, USA).

The invention more particularly relates to a method to obtain a protein crystal as defined above, wherein the processivity clamp factor of DNA polymerase is the β subunit of DNA polymerase, in particular the β subunit of DNA polymerase III of *Escherichia coli*, in particular as purified according the abovementioned methods of purification, and the peptide has the following sequence:

VTLLDPQMERQLVLGL         (SEQ ID NO: 1)

According to a preferred embodiment the β subunit of DNA polymerase III of *Escherichia coli* and the peptide of SEQ ID NO: 1 are mixed in a molar ratio of about 1:1 to about 1:3 in particular about 1:1.5

According to another preferred embodiment the concentration of the β subunit of DNA polymerase III of *Escherichia coli* is from about 8 mg/ml to about 50 mg/ml, in particular about 34 mg/ml.

According to another preferred embodiment the concentration of the peptide of SEQ ID NO: 1 is from about 0.5 mg/ml to about 1.2 mg/ml, in particular about 1.1 mg/ml.

According to another embodiment, the invention relates to the use of the atomic coordinates as defined above, for the screening, the design or the modification of ligands of the processivity clamp factor of DNA polymerase, in particular of the β subunit of DNA polymerase III of *Escherichia coli*.

The expression "ligand" refers to a compound which is liable to bind to the processivity clamp factor of DNA polymerase.

The invention also relates to the use as defined above, for the screening, the design or the modification of ligands liable to be used for the preparation of pharmaceutical compositions useful for the treatment of bacterial diseases or diseases originating from DNA synthesis processes, such as fragile X syndrome, or proliferative disorders, such as cancers.

The expression "bacterial diseases" refers to diseases which are caused by bacterial influences, such as infections.

The expression "proliferative disorders" refers to disorders which are linked to abnormal cell multiplication, such as cancers.

The invention also relates to a method to screen ligands of the processivity clamp factor of DNA polymerase, said method comprising the step of assessing the interaction of tridimensional models of the ligands to screen with the structure of the β subunit of DNA polymerase as defined by the atomic coordinates as defined above, and in particular with the structure of the peptide binding site as defined by the atomic coordinates defined above, and more particularly with at least nine of the following amino acids: Leu 155, Thr 172, Gly 174, His 175, Arg 176, Leu 177, Pro 242, Arg 246, Val 247, Phe 278, Asn 320, Tyr 323, Val 344, Ser 346, Val 360, Val 361, Met 362, Pro 363, Met 364, Arg 365, Leu 366.

Assessing the interaction can be done by methods such as molecular dynamics, energy calculation, continuum electrostatics, semi-empirical free energy functions and other related methods well known to the man skilled in the art. Several packages and softwares are available for these purposes such as CHARM, UHBD, or SYBILL.

The invention more particularly relates to a method as defined above, to screen ligands liable to be used for the preparation of pharmaceutical compositions useful for the treatment of bacterial diseases or diseases originating from DNA synthesis processes, such as fragile X syndrome, or proliferative disorders, such as cancers.

The invention also relates to a method to design or to modify compounds liable to bind to the processivity clamp factor of DNA polymerase, said method comprising the step of designing or modifying a compound, so that the tridimensional model of said compound is liable to interact with the structure of the β subunit of DNA polymerase as defined by the atomic coordinates as defined above, and in particular with the structure of the peptide binding site as defined by the atomic coordinates as defined above, and more particularly with at least nine of the following amino acids: Leu 155, Thr 172, Gly 174, His 175, Arg 176, Leu 177, Pro 242, Arg 246, Val 247, Phe 278, Asn 320, Tyr 323, Val 344, Ser 346, Val 360, Val 361, Met 362, Pro 363, Met 364, Arg 365, Leu 366.

The invention more particularly relates to a method as defined above, to design or to modify ligands liable to be used for the preparation of pharmaceutical compositions useful for the treatment of bacterial diseases or diseases originating from DNA synthesis processes, such as fragile X syndrome, or proliferative disorders, such as cancers.

According to another embodiment, the invention relates to a peptide of the following sequence:

VTLLDPQMERQLVLGL.         (SEQ ID NO: 1)

According to a preferred embodiment, said peptide comprises non-hydrolysable bonds between amino-acids and/or non-amide bonds between amino-acids.

The invention also relates to a pharmaceutical composition comprising as active substance the peptide of SEQ ID NO: 1, in association with a pharmaceutically acceptable carrier.

Examples of pharmaceutically acceptable carrier are well known to the man skilled in the art.

According to a preferred embodiment, said peptide comprises non-hydrolysable bonds between amino-acids and/or non-amide bonds between amino-acids.

According to another embodiment the invention relates to the use of the peptide of SEQ ID NO: 1, as an anti-bacterial compound.

The expression "anti-bacterial compound" refers to a compound which has bactericidal or bacteriostatic properties, such as an antibiotic.

According to a preferred embodiment, said peptide comprises non-hydrolysable bonds between amino-acids and/or non-amide bonds between amino-acids.

The invention more particularly relates to the use of the peptide of SEQ ID NO: 1 for the manufacture of a medicament for the treatment of bacterial diseases or diseases originating from DNA synthesis processes, such as fragile X syndrome, or proliferative disorders, such as cancers.

According to another embodiment the invention relates to a method to test in vitro the inhibitory effect of compounds on the processivity clamp factor-dependant activity of DNA polymerase, in particular of Pol IV DNA polymerase of *Escherichia coli*, or of the α subunit of Pol III DNA polymerase of *Escherichia coli*, comprising the following steps:
  adding to assay solutions comprising a labelled nucleotidic primer, a template DNA, and DNA polymerase, in particular Pol IV DNA polymerase of *Escherichia coli*, or the α subunit of Pol III DNA polymerase of *Escherichia coli*, a compound to test at a given concentration for each assay solution, in the presence or the absence of the processivity clamp factor of DNA polymerase, in particular the β subunit of DNA polymerase in particular the β subunit of DNA polymerase III of *Escherichia coli*,
  electrophoretically migrating the abovementioned assay solutions,
  comparing the migration pattern of each assay solutions in the presence or the absence of the processivity clamp factor of DNA polymerase, in particular the β subunit of DNA polymerase, in particular the β subunit of DNA polymerase III of *Escherichia coli*.

According to a preferred embodiment of the above defined in vitro test method, the assay solutions also comprise a clamp loader, in particular the γ complex of *E. coli*, adenosine triphosphate (ATP), the divalent cation $Mg^{2+}$ and single strand binding protein (SSB) of *E. coli*.

According to another preferred embodiment of the above mentioned in vitro test method, the compounds to be tested are such that their tridimensional models have been screened, modified or designed with respect to, the structure of the β subunit of DNA polymerase, according to the corresponding above defined screening, modifying or designing methods.

The invention also relates to the use of the in vitro test method defined above, for the screening of compounds liable to be used for the preparation of pharmaceutical compositions useful for the treatment of bacterial diseases or diseases originating from DNA synthesis processes, such as fragile X syndrome, or proliferative disorders, such as cancers.

BRIEF DESCRIPTION OF THE DRAWING FIGURES

FIG. 1

FIG. 1 represents the atomic coordinates in protein databank (pdb) format of the crystallographic structure of the complex between *Escherichia coli* β subunit of DNA polymerase III and the 16 C-terminal residues of the β binding peptide of *E. coli* Pol IV DNA polymerase (P16)

FIG. 2

FIG. 2 represents a ribbon representation of the β subunit of DNA polymerase III of *E. coli* complexed with the P16 peptide (boxed) as obtained from the crystallographic structure of the complex.

FIG. 3A, FIG. 3B, FIG. 3C and FIG. 3D

Figure 3A:
FIG. 3A and FIG. 3B represent the inhibition of β dependant activity of Pol IV by the Pol IV β binding peptide, P16
Figure 3B:
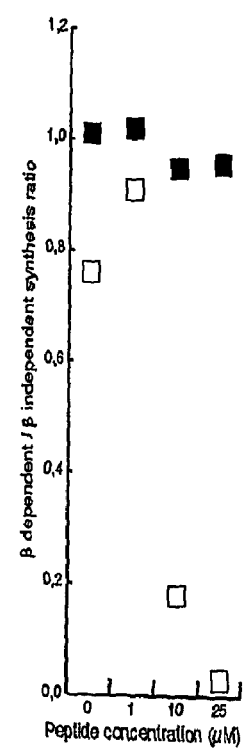

FIG. 3A represents the migration pattern of an electrophoresis gel. β free (lanes 1-4 and 9-12) or β loaded (lanes 5-8 and 13-16) labelled primer/template hybrids are incubated with increasing amounts of control peptide (CLIP) (lanes 1-8) or P16 peptide (lanes 9-16). Concentrations of peptides are as follows: 0 µM, lanes 1, 5, 9 and 13; 1 µM, lanes 2, 6, 10 and 14; 10 µM, lanes 3, 7, 11 and 15; 25 µM, lanes 4, 8, 12 and 16. This mixture is then submitted to the enzymatic activity of Pol IV (1.5 nM) in the presence of each four dNTPs for 1 minute at room temperature. Beside the overall increase in DNA synthesis activity, the β-dependent activity of the polymerase is characterised by the apparition of synthesis products longer than 12 nucleotides (β dependent synthesis), β independent synthesis is characterised by products shorter than 12 nucleotides. The broader band at the bottom of the gel corresponds to the primer. FIG. 3B represents the quantitative analysis of the relative amounts of each β-independent (incorporation of 1 up to 12 nucleotides) and β-dependent (12 and more nucleotides incorporation) activities observed in lanes 5-8 and 13-16. Black and white rectangles represent the ratio of β-dependent to β-independent polymerase activities (vertical axis) in the presence of specified amounts of CLIP and P16 peptides (horizontal axis), respectively. Decrease in this ratio value actually indicates a specific inhibition of the β-dependent polymerase activity.

Figure 3C:
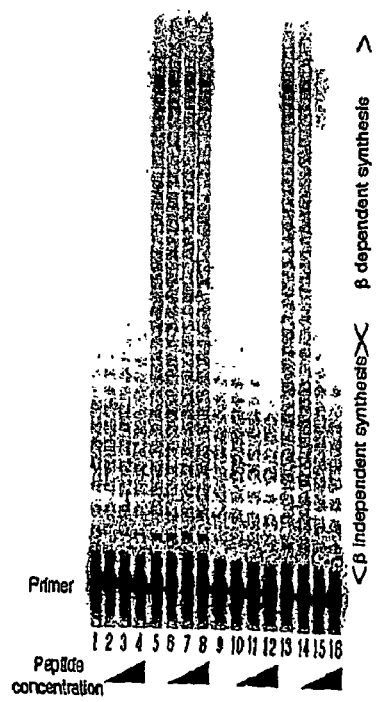
FIG. 3C and FIG. 3D represent the inhibition of β dependant activity of Pol III α subunit by the Pol IV β binding peptide, P16.
Figure 3D:
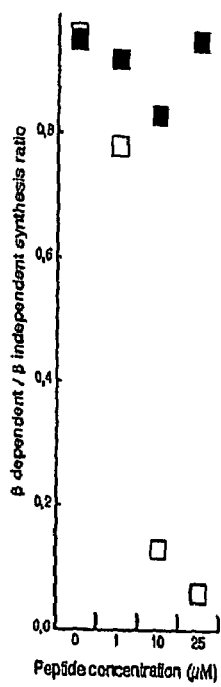

FIGS. 3C and 3D respectively correspond to the same experiments than those represented in FIGS. 3A and 3B, except that the polymerase used is the purified α subunit of Pol III (6 nM).

FIG. 4

Figure 4:
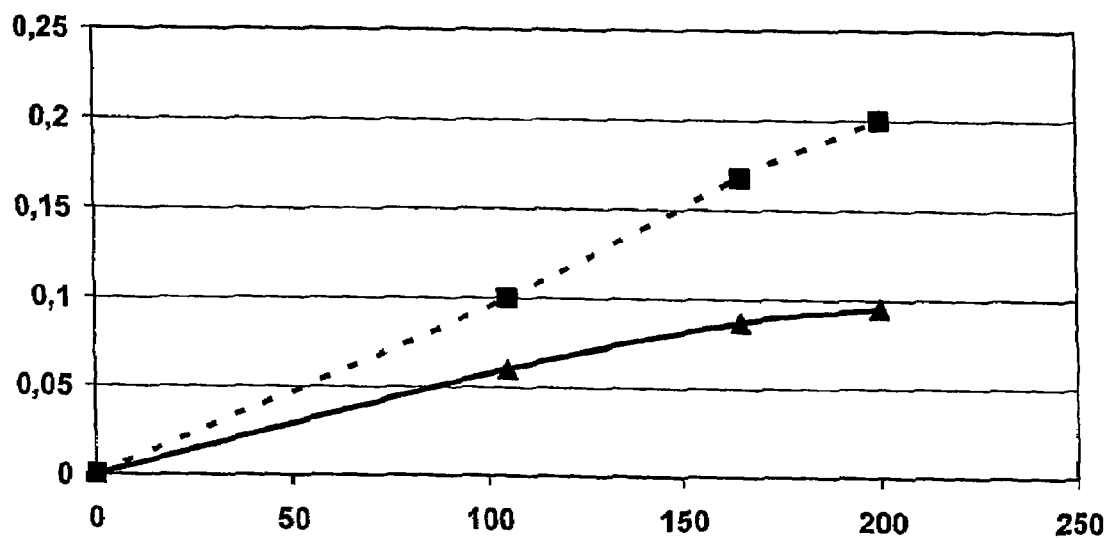

FIG. 4 represents the growth rate of *E. coli* transformed by IPTG inducible plasmids expressing either the wild type Pol IV (pWp4) (triangles) or the Pol IVD5 mutant of Pol IV lacking the 5 C-terminal amino-acids (pD5p4) (squares, dotted line) in the presence of IPTG. The vertical axis represents the OD at 600 nm and the horizontal axis the time in minutes.

Figure 5A:
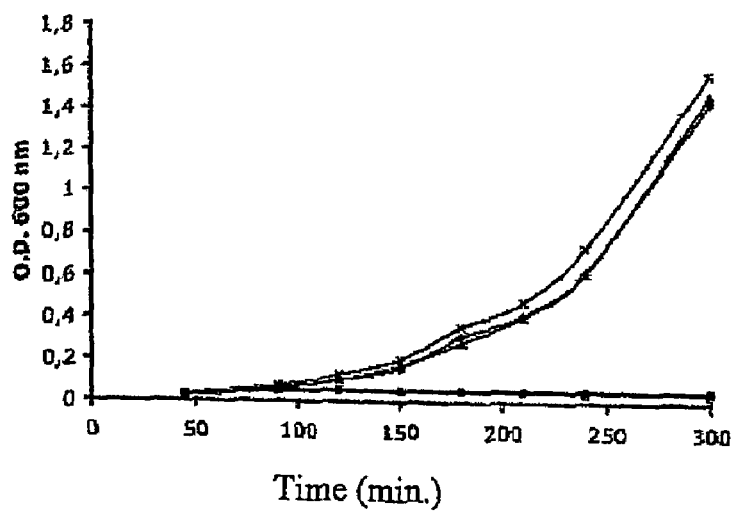
Figure 5B:
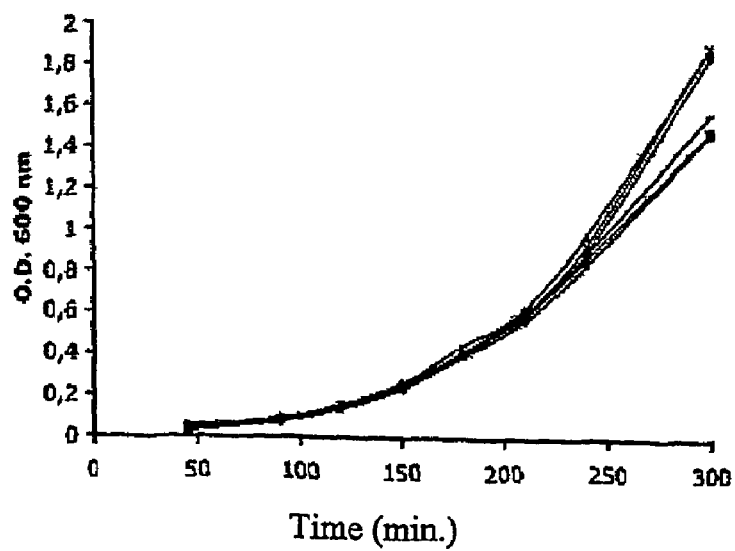

FIG. 5A and FIG. 5B

FIG. 5A represents the growth rate of independent *E. coli* clones harbouring the P403FL vector in the absence (diamonds, triangles, crosses) or the presence (squares, dashes, circles) of 0.1 mM IPTG.

FIG. 5B represents the growth rate of independent *E. coli* clones harbouring the P403D5 vector in the absence (diamonds, triangles, crosses) or the presence (squares, dashes, circles) of 0.1 mM IPTG.

The vertical axis represents the O.D. at 600 nm and the horizontal axis represents the time (in minutes).

FIG. 6

Figure 6:
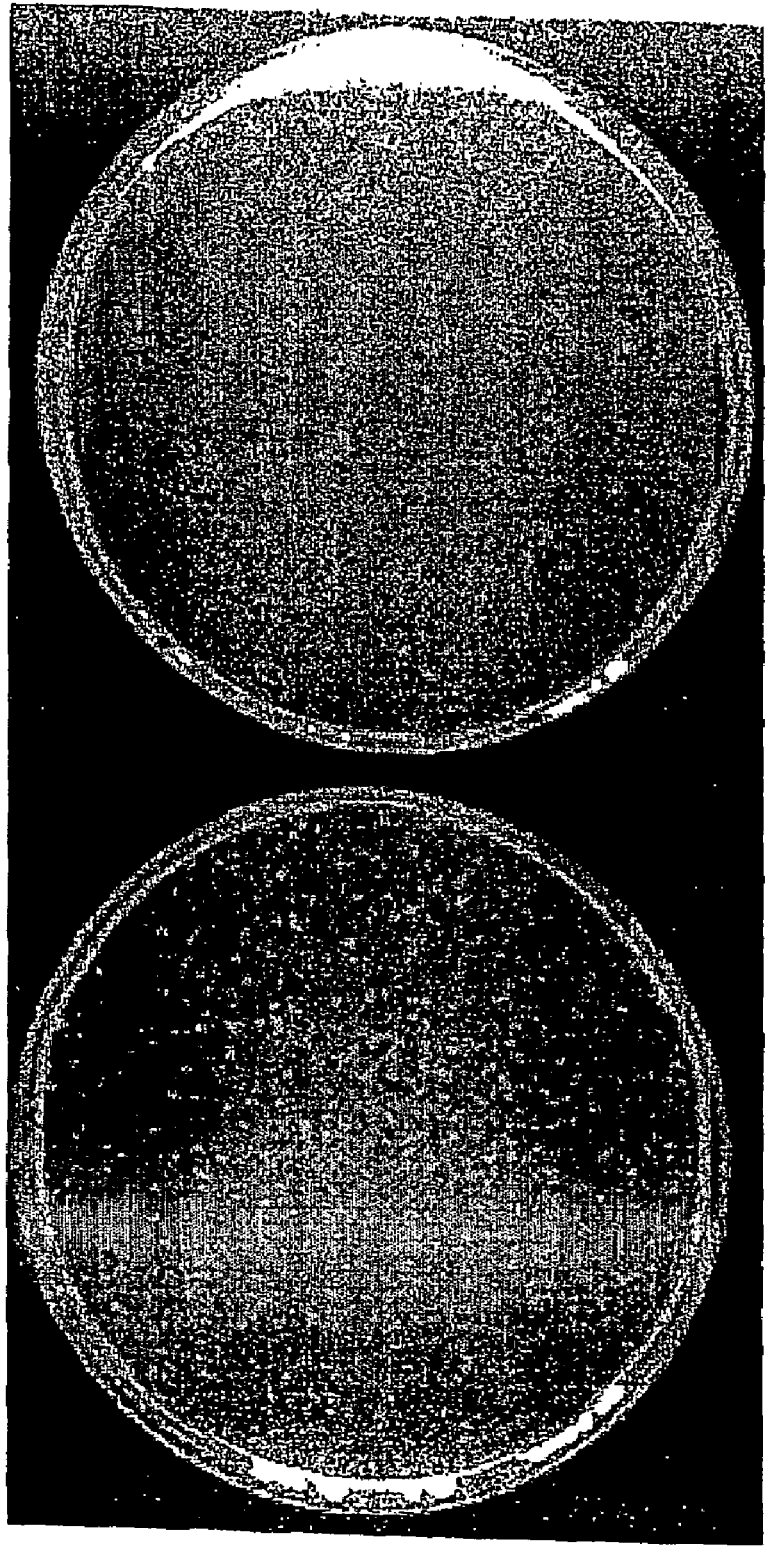

FIG. 6 represents Petri dishes containing an agarose-based nutritive medium supplemented with 0.05 mM IPTG and plated with *E. coli* cells harbouring P403FL (top) or with *E. coli* cells harbouring P403D5 (bottom).

DETAILED DESCRIPTION OF THE PREFERRED EMBODIMENTS

Examples

Example 1

Crystallographic Study of the *Escherichia coli* β Sliding Clamp Complexed with the β Binding Peptide of Pol IV DNA Polymerase of *E. coli*.

1. β Binding Peptide Synthesis and Purification

The 16-mer peptide sequence VTLLDPQMERQLVLGL (P16) (SEQ ID NO: 1), representing the 16 last residues of Pol IV DNA polymerase of *E. coli*, was obtained purified from Neosystem (Illkirch, France) and the 22-mer control peptide. RPVKVTPNGAEDESAEAFPLEF (CLIP) (SEQ ID NO: 2) was a gift from Dr J. P. Briand (Strasbourg, France). P16 was resuspended at 1.1 mg/ml in a buffer containing Tris HCl 20 mM, pH 7.5, 5 mM EDTA, 20% glycerol, and kept at −80° C. CLIP was resuspended in 20 mM NaHCO$_3$ buffer, pH 9, at concentrations of 250, 100 and 10 pmoles/µl

2. β Protein Purification

The dnaN gene encoding *E. coli* β sliding clamp (hereafter referred to as β protein) was cloned into the pET15b plasmid (Invitrogen). The β protein was expressed in a transformed *E. coli* BL21(DE3)pLysS/(pET15b-dnaN) and was purified as described (Johanson et al., 1986) with the following modifications. A SP Sepharose column (Pharmacia, Upsalla, Sweden) was used instead of the SP Sephadex column. A Mono Q column (Pharmacia, Upsalla, Sweden) followed by a Mono S column (Pharmacia, Upsalla, Sweden) were performed after the SP Sepharose column step. The β protein was purified to >99% purity, as judged by Coomassie gel analysis, and concentrated using Centriplus YM-30 concentrators (Amicon) to 34.2 mg/ml in a buffer containing 20 mM Tris-HCl pH 7.5, 0.5 mM EDTA and 20% (v/v) glycerol, as determined by Bradford assay, using BSA as a standard.

3. Crystalization Conditions

Drops were obtained by mixing 0.92 µL of β protein at 34.2 mg/ml (775 pmoles) with 1.89 µl of P16 at 1.1 mg/ml (1136 pmoles) and 1 µl of 2× reservoir solution. Reservoir solution contains 0.1 M MES pH 6.0, 0.1M CaCl$_2$ and 30% PEG 400 (Hampton Research, Laguna Niguel, Calif., USA). The peptide/β monomer molar ratio was 1.46. Co-crystals were grown by vapour diffusion in hanging drops at 20° C. They typically grew within three days and reached 200×100×40 µm$^3$. Crystals were mounted in loops (Hampton Research, Laguna Niguel, Calif., USA), frozen in liquid ethane and kept in liquid nitrogen before collection of crystallographic data.

4. Data Collection and Structure Determination

Diffraction data were collected at beam line ID 14-EH4 (ESRF, Grenoble, France). The data were integrated with DENZO and normalized with SCALEPACK (Z. Otwinowski and W. Minor "Processing of X-ray Diffraction Data Collected in Oscillation Mode", Methods in Enzymology, Volume 276; Macromolecular Crystallography, part A, p. 307-326, 1997, C. W. Carter, Jr. and R. M. Sweet, Eds., Academic Press (New York)). The structure was solved by molecular replacement with MOLREP (CCP4, COLLABORATIVE COMPUTATIONAL PROJECT, NUMBER 4. (1994) "The CCP4 Suite: Programs for Protein Crystallography". Acta Cryst. D50, 760-763.), using the known β protein structure as a search model (Kong et al., 1992). The peptide was built with the graphics program O (Copyright 1990 by Alwyn Jones, DatOno AB, Blueberry Hill, S-75591 Uppsala, Sweden) and the model was refined with O and CNS (Brunger et al., 1998) (Copyright© 1997-2001 Yale University).

The results are summarized in following Table 1:

TABLE 1

Crystal structure data and refinement statistics

| Data collection | |
| --- | --- |
| Space group | P1 |
| Cell parameters | a = 41.23 Å; b = 65.22 Å; c = 73.38 Å; α = 73.11°; β = 85.58°; γ = 85.80° |
| X-ray source | ID14eh4 |
| Wavelength (Å) | 0.93922 |
| Asymmetric unit | 1 dimer |
| Resolution (Å) | 1.65 |

TABLE 1-continued

Crystal structure data and refinement statistics

| Number of observations | |
| --- | --- |
| Unique | 85999 |
| Total | 231008 |
| Completeness (%) | 96.7 (95.4)$^a$ |
| Rsym | 0.051 (0.254)$^a$ |
| Mean I/σ | 15.5 (4.3)$^a$ |
| Refinement | |
| Resolution range (Å) | 500-1.65 |
| R-factor, reflections | 20.87, 80566 |
| Rfree, reflexions | 23.71, 4226 |
| Number of atoms | |
| Protein | 5744 |
| Water | 443 |
| R.m.s deviation | |
| Bond angles (°) | 1.59 |
| Bond lenghts (Å) | 0.013 |
| Average atomic B-value (Å$^2$) | |
| Protein | |
| β | 22.8 |
| Peptide | 29.7 |
| Water | 29.1 |
| Ramachandran plot$^b$ (%) | |
| residues in core, | 92.4 |
| allowed, | 6.9 |
| generously allowed regions | 0.8 |

$^a$Number in parentheses is for the last shell (1.71-1.65)
$^b$Statistics from PROCHECK (Laskowski et al., 1993)

The results obtained indicate that the crystal is triclinic, with cell dimensions a=41.23 Å, b=65.22 Å, c=73.38 Å, α=73.11°, β=85.58°, γ85.79°. These cell parameters lead to a quite usual value of 2.36 Å$^3$/Dalton for two molecules (i.e. one ring) per asymmetric unit. The present structure was solved by molecular replacement with the program MOLREP and was refined up to 1.65 Å resolution, which represents an important improvement in comparison to the 2.5 Å resolution obtained for the structure published previously (Kong et al., 1992). The atomic coordinates of the structure solved by the Inventors are given in FIG. 1 in pdb format. The superposition of the present structure onto the previous one yields an overall rmsd of 1.22 Å for the Cα chain, which indicates that both structures are very similar, although numerous side chains and several mobile loops were rebuilt and a better description of the solvent was achieved. A more sensible superposition, systematically downweighting too distant residues (as those in the rebuilt loops), yields a weighted rmsd of 0.78 Å, which is more significant than the former value.

Figure 2:
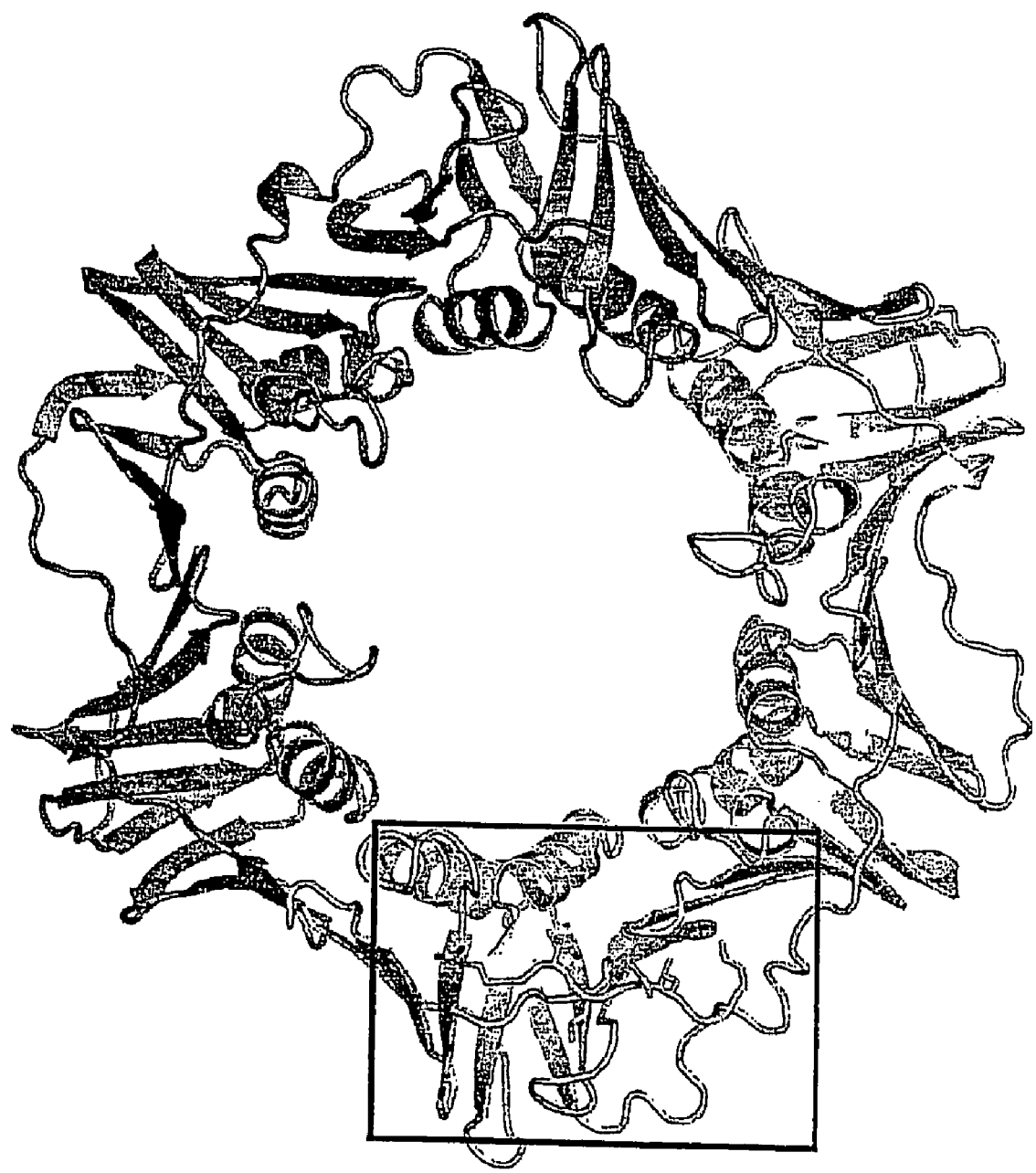

A density related to the presence of the peptide could be located after several rounds of refinement in a "simulated annealing composite omit map" (Brunger et al., 1998). The seven C-terminal residues of the P16 peptide, $R_{10}Q_{11}L_{12}V_{13}L_{14}G_{15}L_{16}$ (SEQ ID NO: 6) encompassing the β binding sequence were built into the density map (FIG. 2). This map extended slightly toward the N-terminus of the peptide but rapidly faded, so that the $Q_{11}$ residue was still easily seen while the $R_{10}$ was built in a poor density region. The rest of the peptide, probably disordered, was not visible. The seven C-terminal amino acids of the P16 peptide bind onto the β surface within two distinct but adjacent domains: one deep crevice, located between sub-domains 2 and 3 (area 1), and a second area which extends over the third β subdomain, close to the C-terminal extremity of the β chain (area 2) (FIG. 2).

In the first area (area 1) of the peptide P16 binding site, two β strands of the clamp (β$^{4'}$ of domain 2 and β$^{8''}$ of domain 3) align. Some of their residues (L177 and V360, respectively), along with residues of the subdomain connecting loop (P242 and V247), form a hydrophobic pocket at the surface of the β monomer. The P16 residues L16 and L14 bind in this crevice. The hydrophobic nature of the interactions is revealed by the removal, upon peptide binding, of water molecules nested inside the free pocket. However, L14 and L16 are also involved in interactions with other adjacent residues like L155, T172, H175, R176, S346 and M362 (Table 2). The residue G15 has no interaction with any residues of the pocket and serves as a connector between L14 and L16. Consequently, the L16 residue which, according to the pentapeptidic consensus motif ($Q_1L_2(SD)_3L_4F_5$) (Dalrymple et al., 2001), was not considered to belong to the β-binding sequence, actually fully participates to the interaction.

In the second binding area (area 2), the four other P16 residues, V13, L12, Q11 and R10 establish mostly hydrophobic interactions with residues H175, N320, Y323, V344, M362, P363 and M364 of the β monomer (Table 2). Among the four P16 residues located within this region, the Q residue is highly conserved within the binding motifs of the various β ligands, to the same extent as residues that bind into the hydrophobic crevice (L14 and L16) (Dalrymple et al., 2001). Particularly, it forms interactions, directly or mediated by two water molecules with β residues M362 and E320. These contacts might prime the binding of the peptide with the β surface and facilitate the formation of interactions of the C-terminal residues within the hydrophobic pocket of area 1. Thus the peptide would be anchored on the β surface by two points located on each extremity of the binding sequence.

TABLE 2

| β residues | Interacting P16 residues |
|---|---|
| M364 | R10, Q11, L12 |
| P363 | Q11, L12 |
| M362 | Q11, L12, V13, L14 |
| V361 | L14 |
| V344 | L12 |
| Y323 | Q11 |
| N320 | Q11 |
| V360 | L14 |
| S346 | L14 |
| V247 | L14, L16 |
| P242 | L16 |
| L177 | L14, L16 |
| R176 | L14 |
| H175 | Q11, L12, V13, L14 |
| T172 | L14, L16 |
| L155 | L16 |

Interactions between the β residues and the peptide P16 residues. All considered distances between β and peptide P16 residues are between 3 and 3.8 Å, except those (P16 residues in bold) between L155: L16, T172: L14, L177: L16 and V361: L14 which are larger than 4 Å.

5. N-Terminal Sequencing of the Protein

The crystal was recovered after data collection, washed several times in the well solution, and dissolved in 10 µl water. The proteins contained within the crystal were derivatized and sequenced by automated Edman's degradation using a PE Applied Biosystems 492 cLC Protein Sequencer allowing the identification and precise quantitative analysis of the amino acids released at each step of degradation.

6. Improvement of the P16-β Clamp Interaction

Preliminary in silico docking experiments carried out with modified versions of the P16 peptide suggest that its interaction with the β clamp could be strengthened by replacing Leu 12 and Leu 14 by aromatic amino acids, or by extending the lateral chain of Gln 11. Thus, these modifications show the way to designing new high affinity β clamp interaction inhibitors.

Example 2

In vitro Study of the β Clamp-β Binding Peptide of Pol IV Interaction by Competition Assays In order to ascertain the biological relevance of the P16 peptide-β clamp interaction observed in the crystallographic structure, an in vitro assay based on the activity of Pol IV DNA polymerase was designed. This assay relies on the observation that the in vitro activity of Pol IV is greatly enhanced by the presence of the β subunit loaded onto a primer/template DNA substrate (Wagner et al., 2000) (FIG. 3A, compare lanes 1 and 5 or 9 and 13), while the enzyme alone incorporates nucleotides in a distributive mode (Wagner et al, 1999).

Briefly, P16 peptide and a control peptide (CLIP) were diluted in 20 mM NaHCO$_3$ at concentrations of 250, 100 and 10 pmol/µl. 5' end radiolabelling, purification and annealing of synthetic primers were performed as previously described (Wagner et al., 1999). The 30/90 nucleotide synthetic construct (Wagner et al., 2000) was obtained by annealing the 30 nucleotide primer (5'GTAAAACGACGGCCAGTGC-CAAGCTTAGTC) (SEQ ID NO: 3) with the 90 nucleotide template (5'CCATGATTACGAATTCAGTCATCACCG-GCGC CACAGACTAAGCTTGGCACTGGC-CGTCGTTTTACAACGTCGTGACTGGGAAAACC CTGG) (SEQ ID NO: 4) to form a double stranded structure with 5' and 3' single stranded DNA overhangs of 25 and 35 nucleotides, respectively.

All replication experiments (10 µl final volume) were carried out in buffer E (40 mM HEPES pH 7.5, 80 mM potassium glutamate, 160 µg/ml BSA, 16% glycerol, 0.016% NP40, 8 mM DTT). The 30/90 nucleotide hybrid was first incubated with single strand binding proteins (SSB; Sigma; 90 nM final concentration) in the presence of ATP (200 µM) and MgCl$_2$ (7.5 mM) at 37° C. for 10 min. When specified, the γ complex (1 nM final concentration) (gift from Dr. C. S. McHenry, Denver, USA), and the β clamp (5 nM as dimer final concentration) were added at that stage, and incubation was carried out at 37° C. for 10 min. Then, 7 µl of the mixture was added to 1 µl of either 20 mM NaHCO$_3$ or 1 µl of peptide solution (1, 10 or 25 µM final concentration), incubated 20 min. at room temperature and farther 2 hours at 4° C. 1 µl of polymerase was then added (1.5 nM of Pol IV or 6 nM of α subunit (gift from Dr. H. Maki, Nara, Japan) final concentrations), incubated 5 min. at room temperature and finally, the whole reaction was mixed with 1 µl of a dNTPs solution (200 µM each dNTP final concentration) and let to react for 1 min. at room temperature. Reactions were quenched by the addition of 20 µl of 95% formamide/dyes solution containing 7.5 mM EDTA, heat-denatured and analysed by chromatography on 12% denaturing polyacrylamide gels. Radiolabelled products were visualised and quantified using a PhosphorImager 445 SI (Molecular Dynamics) and the ImageQuant software.

As shown in FIG. 3A and FIG. 3B, increasing amounts of P16 inhibits the β-dependent activity of Pol IV (lane 13 to 16). At the highest P16 concentration tested (25 µM), the β-dependent Pol IV activity is decreased by a factor around 30, as indicated on the graphic. On the other hand, the control peptide (CLIP) has no effect on this activity even at the highest concentration tested (FIG. 3A, lane 8). Also, neither P16 nor CLIP peptides do affect the intrinsic activity of Pol IV characterised by the distributive incorporation of one to up to 12 nucleotides (FIG. 3A, lanes 1-4, 9-12, FIG. 3B). Thus P16 specifically inhibits the β-Pol IV DNA polymerase interaction in solution, which demonstrate that the site we identified actually corresponds to the Pol IV DNA polymerase binding site on β.

The polymerase activity of the α subunit of the replicative DNA Polymerase III of *E. coli* is greatly enhanced by its interaction with the β clamp (Marians et al., 1998) (FIG. 3C, compare lanes 1 and 5 or 9 and 13), and the putative β binding peptide of the α subunit has been identified through bioinformatics analysis (Dalrymple et al., 2001) and is a variant of the pentapeptide consensus motif. In order to determine if the replicative DNA polymerase interact with the β monomer within the same site than Pol IV, the ability of P16 peptide to inhibit the β-dependent activity of the α subunit was tested. The dose dependent inhibition of the α subunit β-dependent activity (FIG. 3C, lane 13 to 16, FIG. 3D) strongly suggest that this is the case. To achieve a high level of inhibition, the concentration of P16 peptide should exceed the polymerase concentration by a factor of 4 to $16.10^3$. The need for such a high excess of peptide may reflect a higher affinity of the whole protein for the DNA-β substrate, mediated by other polymerase-β and/or polymerase-DNA interactions, but also a high entropic factor of the free peptide as opposed to the same fragment folded in the whole protein. Therefore, the lower peptide affinity would result from a lower kinetic constant $k_{on}$, and not from an increased $k_{off}$. Overall, this biochemical analysis indicates that (i) the P16-β structure we solved is of biological significance as indicated by the competitive inhibition of the β dependent activity of Pol IV DNA polymerase by peptide P16 and (ii) that peptide P16 also competes with and inhibits the β dependent activity of the α subunit of the DNA Polymerase III of *E. coli* which suggests that (iii) if not identical, the Pol IV and α subunit interaction sites on β subunit overlap.

Example 3

In vivo Study of the Inhibition of Bacterial Growth by the β Binding Peptide of Pol IV Plasmids bearing either the wild type Pol IV (pWp4) or the Pol IV mutant deleted for the 5 last C-terminal residues (pD5p4) coding sequences under the IPTG inducible lac promoter were transformed into recipient *E. coli* cells (BL21 (DE3, pLys)). These transformed cells were then allowed to grow in LB medium at 37° C. with aeration and without or with (FIG. 4) addition of the protein expression inducer IPTG (0.1 mM). Growth rates were monitored by measuring the optical density of the cultures (OD 600 nm) at different time points.

The growth rates of both cultures without artificial protein expression were identical whether the cells contain the wild type Pol IV expression plasmid (pWp4) or the Pol IVD5 mutant (pD5p4). On the other hand, when protein expression was induced by the adjunction of low IPTG concentration in the culture medium (FIG. 4), a clear growth inhibition was observed for the culture expressing the wild type Pol IV protein compared to the one expressing the mutant protein. As the mutant protein (expressed from pD5p4) lacks essential amino acids for the interaction with the β-clamp, the observed cytotoxicity may be rationalised by the fact that the wild type Pol IV protein interacts with the β clamp and, because of its relative high concentration, interfere and/or compete with the β binding of the replicative DNA polymerase, thereby inhibiting chromosome replication and culture growth.

In other words, these preliminary results indicate that site-specific β binding molecules (such as the Pol IV β binding motif) may serve as antimicrobial agents.

Example 4

In vivo Study of the Inhibition of Bacterial Growth by the β Binding Peptide of Pol IV A DNA sequence encoding a catalytically inactive version of DNA polymerase IV of *E. coli* has been cloned into a vector to form P403FL which enable the IPTG inducible expression of the corresponding inactive enzyme. Similarly, a DNA sequence encoding the catalytically inactive version of DNA polymerase IV of *E. coli* depleted of the 5 last C-terminal residues (which are essential residues for the interaction with the β clamp) has been cloned into the same IPTG inducible vector to form P403D5.

Three independently isolated clones of *E. coli* containing either P403FL or P403D5 were cultured in a selective medium until an optical density (O.D.) of 0.2 at 600 nm was reached, 15 ml of a selective medium containing 0 or 0.1 mM IPTG were then inoculated with a quantity corresponding to 0.02 O.D. unit of the culture and bacterial growth was followed by the measure of the optical density at 600 nm during 5 hours.

The results indicate that in the absence of IPTG the three cultures of the independent clones carrying P403FL grow normally, however, in the presence of 0.1 mM IPTG the growth of these clones is completely halted (FIG. 5A). Conversely, the three independent clones carrying P403D5 grow normally, irrespective of the presence or not of IPTG (FIG. 5B).

Furthermore, about 1000 *E. coli* cells harbouring either P403FL or P403D5 were plated on nutritive agarose dishes containing 0.05 mM IPTG. The results shown in FIG. 6 indicate that, whereas essentially no P403FL carrying cells are growing, essentially all P403D5 carrying cells are growing.

As in Example 3, those results confirm that site-specific β binding molecules (such as the Pol IV β binding motif) may serve as antimicrobial agents.

REFERENCES

Becherel O. et al. (2002) "Pivotal role of the b-clamp in translesion DNA synthesis and mutagenesis in *E. coli* cells." *DNA Repair* 68: 1_6.

Becherel O. and Fuchs R. P. (2001) "mechanism of DNA polymerase II-mediated frameshift mutagenesis." *Proc Natl Acad Sci USA* 98(15): 8566-71.

Bridges B. A. and Woodgate R. (1985). "The two-step model of bacterial UV mutagenesis." *Mutat Res* 150(1-2): 133-9.

Bruck, I. and O'Donnell M. (2001). "The ring-type polymerase sliding clamp family." *Genome Biol.* 2(1): 3001.1-3000.3.

Brunger A. T. et al., (1998) "Crystallography and NMR system (CNS) a new software system for macromolecular structure determination." *Acta Cryst.* D54: 905-921.

Cordonnier A. M. et al. (1999) "Impaired translesion synthesis in xeroderma is pigmentosum variant extracts." *Mol Cell Biol* 19(3): 2206-11.

Dalrymple B. P. et al. (2001) "A universal protein-protein interaction motif in the eubacterial DNA replication and repair systems." *Proc Natl Acad Sci USA* 98(20): 11627-32.

Friedberg et al. (2000a) "The many faces of DNA polymerases: strategies for mutagenesis or for mutational avoidance." *Proc Natl Acad Sci USA* 97:5681-5683.

Friedberg et al. (2000b), "Specialized DNA polymerases, cellular survival, and the genesis of mutations." *Science* 296:1627-1630.

Fuchs R. P. et al. (2001) "DNA polymerases II and V mediate respectively mutagenic (-2 frameshift) and error-free bypass of a single N-2-acetylaminofluorene adduct." *Biochem Soc Trans* 29(Pt 2): 191-5.

Gulbis J. M. et al. (1996) "Structure of the C-terminal region of p21 complexed with human PCNA." *Cell* 87:297-306.

Haracska L. et al. (2001a) "Physical and functional interactions of human DNA polymerase eta with PCNA." *Mol Cell Biol* 21(21): 7199-206.

Haracska L. et al. (2001b) "Targeting of human DNA polymerase iota to the replication machinery via interaction with PCNA." *Proc Natl Acad Sci USA* 98(25): 14256-61.

Haracska L. et al. (2002) "Stimulation of DNA synthesis activity of human DNA polymerase kappa by PCNA." *Mol Cell Biol* 22(3): 784-91.

Jeruzalmi D. et al. (2001) "Mechanism of processivity clamp opening by the delta subunit wrench of the clamp loader complex of *E. coli* DNA polymerase III." *Cell* 106(4): 417-28.

Kong, X. P. et al. (1992) "Three-dimensional structure of the beta subunit of *E. coli* DNA polymerase III holoenzyme: a sliding DNA clamp." *Cell* 69(3): 425-37.

Laskowski R A et al. (1993) "PROCHECK: a program to check the stereochemical quality of protein structures." *J. Appl. Cryst.* 26: 283-291.)

Lenne-Samuel N. et al. (2002) "The processivity factor beta controls DNA polymerase IV traffic during spontaneous mutagenesis and translesion synthesis in vivo." *EMBO Rep* 3(1): 45-9.

Marians K. J. et al. (1998) "Role of the core DNA polymerase III subunits at the replication fork." *The Journal of biological Chemistry* 273(4): 2452-2457.

Napolitano R. et al. (2000) "All three SOS-inducible DNA polymerases (Pol II, Pol IV and Pol V) are involved in induced mutagenesis." *Embo J* 19(22): 6259-65.

Ohmori H. et al. (2001). "The Y family of DNA polymerases", Mol Cell, 8: 7-8.

Reuven N. B. et al. (1999) "The mutagenesis protein UmuC is a DNA polymerase activated by UmuD', RecA, and SSB and is specialized for translesion replication." *J Biol Chem.* 274(45): 31763-6.

Shamoo Y. and Steitz T. A. (1999) "Building a replisome from interacting pieces: sliding clamp complexed to a peptide from DNA polymerase and a polymerase editing complex." *Cell* 99(2): 155-66.

Tang M. et al. (1999) "UmuD'(2)C is an error-prone DNA polymerase, *Escherichia coli* pol V." *Proc Natl Acad Sci USA* 96(16): 8919-24.

Thompson J. D. et al. (2000) "DbClustal: rapid and reliable global multiple alignments of protein sequences detected by database searches." *Nucleic Acids Research* 28(15): 2919-2926.

Tsurimoto T. (1999) "PCNA binding proteins." in *Front Biosci.* vol 4:D 849-858.

Wagner J. et al. (2002) "Genetics of mutagenesis in *E. coli*: various combinations of translesion polymerases (Pol II, IV and V) deal with lesion/sequence context diversity." *DNA Repair* 1: 159-167.

Wagner J. et al. (2000) "The beta clamp targets DNA polymerase IV to DNA and strongly increases its processivity." *EMBO Rep* 1(6): 484-8.

Wagner J. et al. (1999) "The dinB gene encodes a novel *E. coli* DNA polymerase, DNA pol IV, involved in mutagenesis." *Mol Cell* 4(2): 281-6.

Willcox B. E. (1999) "TCR binding to peptide-MHC stabilizes a flexible recognition interface." *Immunity* 10: 357-65.

---

The invention claimed is:

1. A protein crystal comprising a processivity clamp factor of DNA polymerase that is the subunit of DNA polymerase III of *Escherichia coli* which has the amino acid sequence of SEQ ID NO: 5; and a peptide of 16 amino acids having the amino acid sequence of VTLLDPQMERQLVLGL (SEQ ID NO: 1), wherein said protein crystal is in triclinic space group P1 and has cell dimensions of: a=41.23 Å, b=65.22 Å, c=73.38 Å, α=73.11°, β=85.58°, and γ=85.80°.

2. The protein crystal according to claim 1 having a three-dimensional structure represented by atomic coordinates obtained by X-ray diffraction of said protein crystal, wherein said atomic coordinates are shown in FIG. 1.

3. The protein crystal according to claim 1, wherein the three-dimensional structure of the peptide of SEQ ID NO: 1 is defined by atoms 5689-5744 as shown in FIG. 1, and the peptide binding site of the β subunit of DNA polymerase III is defined by amino acid residues Leu 155, Thr 172, Gly 174, His 175, Arg 176, Leu 177, Pro 242, Arg 246, Val 247, Phe 278, Asn 320, Tyr 323, Val 344, Ser 346, Val 360, Val 361, Met 362, Pro 363, Met 364, Arg 365 and Leu 366 having the atomic coordinates as shown in FIG. 1.

4. A method to obtain the protein crystal of claim 1, said method comprising:
(a) mixing a solution comprising the β subunit of DNA polymerase III of *Escherichia coli* having the amino acid sequence of SEQ ID NO: 5, with a solution of the peptide of 16 amino acids having the amino acid sequence of VTLLDPQMERQLVLGL (SEQ ID NO: 1), and with a solution of 0.2 M 2-(N-morpholino)ethane sulfonic acid (MES) at pH 6.0, 0.2 M $CaCl_2$, 60% PEG 400, to obtain a crystallization drop; and
(b) allowing the crystallization drop to concentrate against a solution of 0.1 M MES pH 6.0, 0.1M $CaCl_2$, 30% PEG 400, by vapor diffusion, to obtain the protein crystal.

* * * * *